US007999107B2

(12) United States Patent
Debenham et al.

(10) Patent No.: US 7,999,107 B2
(45) Date of Patent: Aug. 16, 2011

(54) SUBSTITUTED PYRANO[2,3-B]PYRIDINE DERIVATIVES AS CANNABINOID-1 RECEPTOR MODULATORS

(75) Inventors: John S. Debenham, Scotch Plains, NJ (US); Jeffrey J. Hale, Westfield, NJ (US); Pei Huo, Millburn, NJ (US); Christina B. Madsen-Duggan, Scotch Plains, NJ (US); Thomas F. Walsh, Watchung, NJ (US); Lin Yan, East Brunswick, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 768 days.

(21) Appl. No.: 12/009,114

(22) Filed: Jan. 16, 2008

(65) Prior Publication Data

US 2008/0207666 A1 Aug. 28, 2008

Related U.S. Application Data

(60) Provisional application No. 60/898,602, filed on Jan. 31, 2007, provisional application No. 60/905,690, filed on Mar. 8, 2007.

(51) Int. Cl.
*C07D 491/052* (2006.01)
*A61K 31/436* (2006.01)

(52) U.S. Cl. ......................... 546/115; 546/116; 514/302

(58) Field of Classification Search .................... 546/83, 546/115, 116; 514/302
See application file for complete search history.

(56) References Cited

U.S. PATENT DOCUMENTS

| | | | |
|---|---|---|---|
| 5,140,031 | A | 8/1992 | Atwal et al. |
| 5,563,170 | A | 10/1996 | Atwal |
| 2004/0209902 | A1 | 10/2004 | Lin et al. |
| 2005/0010050 | A1 | 1/2005 | Rogier et al. |
| 2005/0272763 | A1 | 12/2005 | Toupence et al. |

FOREIGN PATENT DOCUMENTS

| | | |
|---|---|---|
| EP | 0499414 | 8/1992 |
| EP | 0624589 | 5/1994 |
| EP | 0600617 | 6/1994 |
| EP | 0895994 | 7/1998 |
| EP | 1357111 | 10/2003 |
| JP | 4282353 | 10/1992 |
| JP | 5032655 | 2/1993 |
| WO | WO 95/34547 | 12/1995 |
| WO | WO 98/09969 | 3/1998 |
| WO | WO 99/03859 | 1/1999 |
| WO | WO 00/78724 | 12/2000 |
| WO | WO 01/49675 | 7/2001 |
| WO | WO 01/98306 | 12/2001 |
| WO | WO 03/011872 | 2/2003 |
| WO | WO 03/032897 | 4/2003 |
| WO | WO 03/055876 | 7/2003 |
| WO | WO 2004/106493 | 12/2004 |
| WO | WO 2005/000250 | 1/2005 |
| WO | WO 2005/042697 | 5/2005 |
| WO | WO 2005/047285 | 5/2005 |
| WO | WO 2006/045096 | 4/2006 |

OTHER PUBLICATIONS

P. H. Reggio "Endocannabinoid structure—activity relationships for interaction at the cannabinoid receptors" Prostaglandins, Leukotrienes and Essential Fatty Acids 2002, 66, 143-160.*
Lea W. Padgett "Recent developments in cannabinoid ligands" Life Sciences 2005, 77, 1767-1798.*
Meurer et. al. "Synthesis and SAR of 5,6-diarylpyridines as human CB1 inverse agonists" Bioorganic & Medicinal Chemistry Letters 15 (2005) 645-651.*
Simiand et al., Behavioural Pharmacol., vol. 9 (1998), pp. 179-181, "SR 141716, a CB1 cannabinoid reeptor antagonist, selectively reduces sweet food intake . . . ".
Debenham et al., Bioorg. & Med. Chem. Lett., vol. 16 (2006), pp. 681-685, "Synthesis of functionalized 1,8-naphthyridinones and their evaluation as novel, . . . ".
Arnone et al., Psychopharmacology, vol. 132 (1997), pp. 104-106, "Selective inhibition of sucrose and ethanol intake by SR 141716, . . . ".
Ledent et al., Science, vol. 283 (1999), pp. 401-404, "Unresponsiveness to cannabinoids and reduced addictive effects of opiates . . . ".
Cheer et al., Psychopharmacol., vol. 151 (2000), pp. 25-30, "Cannabinoid receptors and reward in the rat . . . ".
Milne et al, Eur. J. Pharmacol., vol. 282 (1995), pp. 243-249, "Role of the VLA-4 integrin in leucocyte recruitment and bronchial . . . ".
Chaperon et al., Psychopharmacol., vol. 135 (1998), pp. 324-332, "Involvement of central cannabinoid (CB1) receptors . . . ".
Feng et al., Life Sciences, vol. 63 (1998), pp. 111-119,"Lactation increases prolactin receptor expression . . . ".
Batkai et al., Nature Medicine, vol. 7 (2001), pp. 827-832, "Endocannabinoids acting at vascular CB1 receptors mediate the vasodilated state . . . ".
Abraham et al., J.-Clin. Invest., vol. 93 (1994), pp. 776-787, "α4-integrins mediate antigen-induced late bronchial responses . . . ".

(Continued)

*Primary Examiner* — Janet Andres
*Assistant Examiner* — David K O Dell
(74) *Attorney, Agent, or Firm* — Baerbel R. Brown; John C. Todaro

(57) ABSTRACT

Novel compounds of the structural formula (I) are antagonists and/or inverse agonists of the Cannabinoid-1 (CB1) receptor and are useful in the treatment, prevention and suppression of diseases mediated by the CB1 receptor. The compounds of the present invention are useful as centrally acting drugs in the treatment of psychosis, memory deficits, cognitive disorders, Alzheimer's disease, migraine, neuropathy, neuro-inflammatory disorders including multiple sclerosis and Guillain-Barre syndrome and the inflammatory sequelae of viral encephalitis, cerebral vascular accidents, and head trauma, anxiety disorders, stress, epilepsy, Parkinson's disease, Huntington's disease movement disorders, and schizophrenia. The compounds are also useful for the treatment of substance abuse disorders, the treatment of obesity or eating disorders, as well as the treatment of asthma, constipation, chronic intestinal pseudo-obstruction, cirrhosis of the liver, non-alcoholic fatty liver disease (NAFLD), non-alcoholic steatohepatitis (NASH), and the promotion of wakefulness.

16 Claims, No Drawings

OTHER PUBLICATIONS

Kapur, J. of Pathology, vol. 194 (2001), pp. 277-288, "Neuropathology of paediatric chronic intestinal pseudo-obstruction . . . ".
Compton et al., J. Pharmacol. & Exper. Ther., vol. 277 (1996), pp. 586-594, "In vivo characterization of a specific cannabinoid receptor antagonist (SR141716A): . . . ".
Tsusumi et al., Biol. Pharm. Bull. (abstract), vol. 23 (2000), pp. 657-659, "Amitripytline-induced constipation in Cynomolgus monkeys . . . ".
Seitz et al., Tetrahedron Letters, vol. 26 (1985), pp. 4355-4358, Intramolecular Diels-Alder reactions of substituted 1,2,4,5-tetrazines and 1,2,4-triazines.

* cited by examiner

SUBSTITUTED PYRANO[2,3-B]PYRIDINE DERIVATIVES AS CANNABINOID-1 RECEPTOR MODULATORS

CROSS-REFERENCE TO RELATED APPLICATIONS

This application claims priority from and the benefit of U.S. Provisional Application Nos. 60/898,602, filed Jan. 31, 2007, and 60/905,690, filed Mar. 8, 2007.

BACKGROUND OF THE INVENTION

Marijuana (*Cannabis sativa* L.) and its derivatives have been used for centuries for medicinal and recreational purposes. A major active ingredient in marijuana and hashish has been determined to be $\Delta^9$-tetrahydrocannabinol ($\Delta^9$-THC). Detailed research has revealed that the biological action of $\Delta^9$-THC and other members of the cannabinoid family occurs through two G-protein coupled receptors termed CB1 and CB2. The CB1 receptor is primarily found in the central and peripheral nervous systems and to a lesser extent in several peripheral organs. The CB2 receptor is found primarily in lymphoid tissues and cells. Three endogenous ligands for the cannabinoid receptors derived from arachidonic acid have been identified (anandamide, 2-arachidonoyl glycerol, and 2-arachidonyl glycerol ether). Each is an agonist with activities similar to $\Delta^9$-THC, including sedation, hypothermia, intestinal immobility, antinociception, analgesia, catalepsy, anti-emesis, and appetite stimulation.

There are at least three CB1 modulators characterized as inverse agonists/antagonists, ACOMPLIA (rimonabant, N-(1-piperidinyl)-5-(4-chlorophenyl)-1-(2,4-dichlorophenyl)-4-methylpyrazole-3-carboxamide, SR141716A), and 3-(4-chlorophenyl-N'-(4-chlorophenyl)sulfonyl-N-methyl-4-phenyl-4,5-dihydro-1H-pyrazole-1-carboxamide (SLV-319), and taranabant, N-[(1S,2S)-3-(4-Chlorophenyl)-2-(3-cyanophenyl)-1-methylpropyl]-2-methyl-2-[[5-(trifluoromethyl)-2-pyridinyl]oxy]propanamide, in clinical development for treatment of eating disorders and/or smoking cessation at this time. There still remains a need for potent low molecular weight CB1 modulators that have pharmacokinetic and pharmacodynamic properties suitable for use as human pharmaceuticals.

Naphthyridone CB1 antagonists/inverse agonists are described in Debenham, et al., Bioorg. Med. Chem. Lett. 16: 681-685 (2006) and in WO 05/047285. Pyranopyridine derivatives are described in the following publications: EP 895994, WO 98/09969, WO 99/03859, WO 01/98306, WO 03/032897, WO 05/000250, WO 05/042697, and WO 06/045096.

SUMMARY OF THE INVENTION

The present invention is concerned with novel pyrano[2,3-b]pyridines of structural Formula I:

I

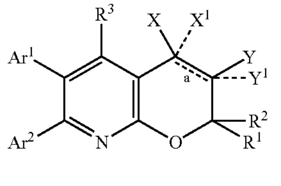

and pharmaceutically acceptable salts thereof which are modulators of and, in particular, antagonists and/or inverse agonists of the Cannabinoid-1 (CB1) receptor and are useful in the treatment, prevention or suppression of diseases mediated by the Cannabinoid-1 (CB1) receptor. In one aspect, the invention is concerned with the use of these novel compounds to selectively antagonize the Cannabinoid-1 (CB1) receptor. As such, compounds of the present invention are useful as centrally acting drugs in the treatment of psychosis, memory deficits, cognitive disorders, Alzheimer's disease, migraine, neuropathy, neuro-inflammatory disorders including multiple sclerosis and Guillain-Barre syndrome and the inflammatory sequelae of viral encephalitis, cerebral vascular accidents, and head trauma, anxiety disorders, stress, epilepsy, Parkinson's disease, Huntington's disease, movement disorders, and schizophrenia. The compounds are also useful for the treatment of substance abuse disorders, the treatment of obesity or eating disorders, and complications associated therewith, including left ventricular hypertrophy, as well as the treatment of asthma, constipation, chronic intestinal pseudo-obstruction, and cirrhosis of the liver.

The present invention is also concerned with treatment of these conditions, and the use of compounds of the present invention for manufacture of a medicament useful in treating these conditions. The present invention is also concerned with treatment of these conditions through a combination of compounds of formula I and other currently available pharmaceuticals.

The invention is also concerned with pharmaceutical formulations comprising one of the compounds as an active ingredient, as well as processes for preparing the compounds of this invention.

DETAILED DESCRIPTION OF THE INVENTION

The compounds of the present invention are represented by the compound of structural formula I:

I

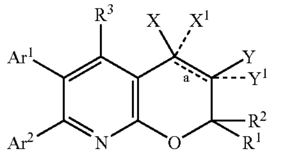

or a pharmaceutically acceptable salt thereof, wherein:

"a" is:

(1) a single bond and $X^1$ and $Y^1$ are present, or (2) a double bond and $X^1$ and $Y^1$ are absent;

X is selected from:

(1) hydrogen, (2) halogen, (3) —$C_{1-6}$alkyl, unsubstituted or substituted with one, two or three substituents independently selected from $R^a$, (4) aryl-, unsubstituted or substituted with one, two or three substituents independently selected from $R^b$, (5) cycloalkyl, unsubstituted or substituted with one, two or three substituents independently selected from $R^b$, (6) heteroaryl-, unsubstituted or substituted with one, two, or three substituents independently selected from $R^b$, (7) heterocycloalkyl-, unsubstituted or substituted with one, two or three substituents independently selected from $R^b$, (8) heteroaryl-$C_{1-3}$alkyl, unsubstituted or substituted on heteroaryl with one, two, or three substituents independently selected from $R^b$, (9) —$CO_2R^d$,

(10) —CO—$NR^cR^d$,

(11) —CN,

(12) —$OR^d$,

(13) —O—C(O)$R^d$,

(14) —$NR^cR^d$,

(15) —$NR^c$C(═O)$R^d$,

(16) —$NR^c$C(═O)$OR^d$,

(17) —$NR^c$C(═O)—C(═O)$NR^cR^d$,

(18) —NH—$SO_2$—$R^f$, and

(19) —S—$C_{1-6}$alkyl, $X^1$, when present, is selected from hydrogen, halogen and $C_{1-6}$alkyl, or together X and $X^1$ together form ═O, ═$NR^g$, or ═CH—C(O)—O—$R^d$;

Y is selected from: hydrogen, halogen, $C_{1-6}$alkyl, and —C(O)—$R^e$;

$Y^1$, when present, is selected from: hydrogen, halogen, and $C_{1-6}$alkyl;

or when "a" is a double bond, "a", X, and Y together form a pyrazole ring:

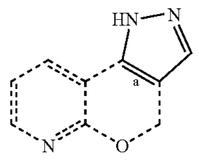

PROVIDED THAT, when "a" is a double bond, X and Y are not simultaneously hydrogen;

PROVIDED THAT: when "a" is a single bond, X, $X^1$, Y, and $Y^1$ are not simultaneously hydrogen;

$Ar^1$ is selected from:

(1) aryl, and (2) heteroaryl, wherein aryl and heteroaryl are unsubstituted or substituted with one, two, three or four substituents selected from $R^4$ and $R^5$;

$Ar^2$ is selected from:

(1) aryl, and (2) heteroaryl, wherein aryl and heteroaryl are unsubstituted or substituted with one, two, three or four substituents independently selected from $R^6$ and $R^7$;

$R^1$ is selected from:

(1) hydrogen, (2) $C_{1-10}$alkyl, (3) $C_{3-10}$cycloalkyl, (4) $C_{3-10}$cycloalkenyl, (5) $C_{3-10}$cycloalkyl-$C_{1-4}$alkyl, (6) $C_{3-10}$cycloalkenyl-$C_{1-4}$alkyl, (7) cycloheteroalkyl, (8) cycloheteroalkyl-$C_{1-4}$alkyl, (9) aryl,

(10) aryl-$C_{1-4}$alkyl,

(11) heteroaryl,

(12) heteroaryl-$C_{1-4}$alkyl,

(13) —C(O)O—$R^e$,

(14) —$OR^e$,

(15) —$NR^cR^d$,

(16) —C(O)NH—$S(O)_2$—$R^e$, wherein each alkyl is unsubstituted or substituted with one to four substituents independently selected from $R^a$, and each cycloalkyl, and cycloheteroalkyl, aryl and heteroaryl is optionally substituted with one to four substituents independently selected from $R^b$;

$R^2$ is selected from:

(1) $C_{1-10}$alkyl, (2) $C_{3-10}$cycloalkyl, (3) $C_{3-10}$cycloalkenyl, (4) $C_{3-10}$cycloalkyl-$C_{1-4}$alkyl, (5) $C_{3-10}$cycloalkenyl-$C_{1-4}$alkyl, (6) cycloheteroalkyl, (7) cycloheteroalkyl-$C_{1-4}$alkyl, (8) aryl, (9) aryl-$C_{1-4}$alkyl,

(10) heteroaryl,

(11) heteroaryl-$C_{1-4}$alkyl,

(12) —C(O)O—$R^e$,

(13) —$OR^e$,

(14) —$NR^cR^d$,

(15) —C(O)—NH—$S(O)_2$—$R^e$, wherein each alkyl is unsubstituted or substituted with one to four substituents independently selected from $R^a$, and each cycloalkyl, cycloalkenyl, cycloheteroalkyl, aryl and heteroaryl is optionally substituted with one to four substituents independently selected from $R^b$;

or $R^1$ and $R^2$ together with the carbon to which they are attached form a carbonyl group (C═O) or a spiroannulated ring system of 3 to 10 members containing 0, 1, or 2 heteroatoms independently selected from —O—, —S—, and —N($R^d$)—, optionally substituted with one to four substituents independently selected from $R^b$;

$R^3$ is selected from:

(1) hydrogen, (2) $C_{1-6}$alkyl, (3) $C_{1-6}$alkyloxy, (4) trifluoromethyl, (5) trifluoromethoxy, (6) halo, and (7) $C_{3-7}$cycloalkyl, wherein alkyl, and cycloalkyl are optionally substituted with one, two, or three substituents independently selected from $R^a$;

each $R^4$, $R^5$, $R^6$, and $R^7$ is independently selected from:

(1) —H, (2) halo-, (3) —CN, (4) $C_{1-6}$alkyl-, unsubstituted or substituted with one, two or three $R^h$ substitutents, (5) —$CF_3$, (6) $C_{2-6}$alkenyl-, unsubstituted or substituted with one, two or three $R^h$ substitutents, (7) cycloalkyl, unsubstituted or substituted with one, two or three $R^h$ substitutents, (8) cycloalkyl-$C_{1-3}$alkyl, unsubstituted or substituted with one, two or three $R^h$ substitutents, (9) cycloheteroalkyl, unsubstituted or substituted with one, two or three $R^h$ substitutents,

(10) cycloheteroalkyl-$C_{1-3}$ alkyl, unsubstituted or substituted with one, two or three $R^h$ substitutents,

(11) aryl, unsubstituted or substituted with one, two or three $R^k$ substitutents,

(12) aryl-$C_{1-3}$alkyl, unsubstituted or substituted on aryl with one, two or three $R^k$ substitutents,

(13) heteroaryl, unsubstituted or substituted with one, two or three $R^k$ substitutents,

(14) heteroaryl-$C_{1-3}$alkyl, -, unsubstituted or substituted with one, two or three $R^k$ substitutents,
(15) —$OR^d$,
(16) —$OCF_3$
(17) —$C(O)R^d$,
(18) —$CO_2R^d$,
(19) —$C(O)NR^cR^d$,
(20) —$SR^d$,
(21) —$S(O)_mNR^cR^d$,
(22) —$NR^cR^d$,
(23) —$NR^cC(O)R^d$,
(24) —$NR^cC(O)OR^d$,
(25) —$NR^cC(O)NR^cR^d$, and
(26) —$NR^cS(O)_mR^d$;

each $R^a$ is independently selected from:
(1) —$OR^d$,
(2) —$NR^cS(O)_mR^d$,
(3) halogen,
(4) —$SR^d$,
(5) —$S(O)_mNR^cR^d$
(6) —$S(O)_mNR^cR^d$,
(7) —$NR^cR^d$,
(8) —$C(O)R^d$,
(9) —$CO_2R^d$,
(10) —CN,
(11) —$C(O)NR^cR^d$,
(12) —$NR^cC(O)R^d$,
(13) —$NR^cC(O)OR^d$,
(14) —$NR^cC(O)NR^cR^d$,
(15) —$CF_3$, and
(16) —$OCF_3$, each $R^b$ is independently selected from:
(1) $R^a$,
(2) oxo,
(3) $C_{1-10}$alkyl,
(4) $C_{2-10}$ alkenyl,
(5) cycloalkyl,
(6) cycloalkyl-$C_{1-10}$ alkyl;
(7) cycloheteroalkyl,
(8) cycloheteroalkyl-$C_{1-10}$alkyl,
(9) aryl,
(10) heteroaryl,
(11) aryl-$C_{1-10}$alkyl, and
(12) heteroaryl-$C_{1-10}$alkyl, wherein alkyl and alkenyl moieties are unsubstituted or substituted with one, two, three or four $R^k$ substituents, and cycloalkyl, cycloheteroalkyl, aryl and heteroaryl moieties are unsubstituted or substituted with one, two or three $R^k$ substituents;

$R^c$ and $R^d$ are each independently selected from:
(1) hydrogen,
(2) $C_{1-10}$alkyl,
(3) $C_{2-10}$ alkenyl,
(4) cycloalkyl,
(5) cycloalkyl-$C_{1-10}$alkyl-,
(6) cycloheteroalkyl,
(7) cycloheteroalkyl-$C_{1-10}$alkyl-,
(8) aryl,
(9) heteroaryl,
(10) aryl-$C_{1-10}$alkyl-, and
(11) heteroaryl-$C_{1-10}$alkyl-, wherein each $R^c$ and $R^d$ moiety, other than hydrogen, may be unsubstituted or substituted with one to three substituents selected from $R^h$;

each $R^e$ is independently selected from:
(1) $C_{1-10}$alkyl,
(2) aryl,
(3) heteroaryl,
(4) cycloalkyl,
(5) cycloheteroaryl;

wherein alkyl and aryl are unsubstituted or substituted with one, two, or three substituents independently selected from $R^h$;

each $R^f$ is independently selected from:
(1) halogen,
(2) $C_{1-6}$alkyl, unsubstituted or substituted with one, two, or three $R^i$ substituents,
(3) $C_{2-6}$ alkenyl, unsubstituted or substituted with one, two, or three $R^i$ substituents,
(4) cycloalkyl, unsubstituted or substituted with one, two, or three $R^h$ substituents,
(5) cycloalkyl-$C_{1-4}$alkyl-, unsubstituted or substituted with one, two, or three $R^h$ substituents,
(6) cycloheteroalkyl, unsubstituted or substituted with one, two, or three $R^h$ substituents,
(7) cycloheteroalkyl-$C_{1-4}$alkyl-, unsubstituted or substituted with one, two, or three $R^h$ substituents,
(8) aryl, unsubstituted or substituted with one, two, or three $R^h$ substituents,
(9) heteroaryl, unsubstituted or substituted with one, two, or three $R^h$ substituents,
(10) aryl-$C_{1-4}$alkyl-, unsubstituted or substituted with one, two, or three $R^h$ substituents,
(11) heteroaryl-$C_{1-4}$alkyl-, unsubstituted or substituted with one, two, or three $R^h$ substituents, and
(12) —$N(CH_3)_2$;

each $R^g$ is independently selected from:
(1) hydrogen,
(2) —OH,
(3) $C_{1-3}$alkyl,
(4) aryl,
(5) heteroaryl,
(6) cycloalkyl,
(7) cycloheteroaryl;

wherein alkyl and aryl are unsubstituted or substituted with one, two, or three substituents independently selected from $R^h$;

each $R^h$ is independently selected from:
(1) halogen,
(2) $C_{1-6}$alkyl,
(3) 4-methylbenzyl-,
(4) —OH,
(5) —O—$C_{1-4}$alkyl,
(6) benzyloxy-,
(7) -oxo,
(8) —OC(O)—$C_{1-6}$alkyl,
(9) —C(O)O—$C_{1-6}$alkyl,
(10) —S—$C_{1-4}$alkyl,
(11) —$NH_2$,
(12) —$NH(CH_3)$,
(13) —$N(CH_3)_2$,
(14) —$NO_2$,
(15) —CN,
(16) —$CF_3$, and
(17) —$OCF_3$, wherein alkyl may be unsubstituted or substituted with one, two or three substituents selected from $R^i$;

each $R^i$ is independently selected from:
(1) halogen,
(2) —O—$C_{1-4}$alkyl,
(3) —OH,
(4) —S—$C_{1-14}$alkyl,
(5) —CN, (6) —$CF_3$, and
(7) —$OCF_3$;

each $R^k$ is independently selected from:
(1) halogen,
(2) oxo,
(3) amino,
(4) hydroxy,
(5) $C_{1-4}$alkyl,
(6) —O—$C_{1-4}$alkyl,
(7) —S—$C_{1-4}$alkyl,
(8) —CN,
(9) —$CF_3$, and
(10) —$OCF_3$, each m is independently selected from 1 and 2.

In one embodiment of the present invention, "a" is a single bond and X is selected from:
(1) hydrogen,
(2) halogen,
(3) —$C_{1-6}$alkyl, unsubstituted or substituted with one, two or three substituents independently selected from $R^a$,
(4) aryl-, unsubstituted or substituted with one, two or three substituents independently selected from $R^b$,
(5) cycloalkyl, unsubstituted or substituted with one, two or three substituents independently selected from $R^b$,
(6) heteroaryl-, unsubstituted or substituted with one, two, or three substituents independently selected from $R^b$,
(7) heterocycloalkyl-, unsubstituted or substituted with one, two or three substituents independently selected from $R^b$,
(8) heteroaryl-$C_{1-3}$alkyl, unsubstituted or substituted on heteroaryl with one, two, or three substituents independently selected from $R^b$,
(9) $C_{1-6}$alkyloxycarbonyl-$C_{1-6}$alkyl-,
(10) —$CO_2R^d$,
(11) —CO—$NR^cR^d$,
(12) —CN,
(13) —$OR^d$,
(14) —O—C(O)$R^d$,
(15) —$NR^cR^d$,
(16) —$NR^cC$(═O)$R^d$,
(17) —$NR^cC$(═O)—C(═O)$NR^cR^d$,
(18) —NH—$SO_2$—$R^d$, and
(19) —S—$C_{1-16}$alkyl, $X^1$, when present, is selected from hydrogen, halogen and $C_{1-16}$alkyl, or together X and $X^1$ form ═O, ═$NR^g$, or ═CH—C(O)—O—$R^d$.

In one class of this embodiment, "a" is a single bond and X is selected from:
(1) hydrogen,
(2) halogen,
(3) —$C_{1-6}$alkyl, unsubstituted or substituted with one, two or three substituents independently selected from $R^a$,
(4) aryl-, unsubstituted or substituted with one, two or three substituents independently selected from $R^b$,
(5) cycloalkyl, unsubstituted or substituted with one, two or three substituents independently selected from $R^b$,
(6) heteroaryl-, unsubstituted or substituted with one, two, or three substituents independently selected from $R^b$,
(7) heterocycloalkyl-, unsubstituted or substituted with one, two or three substituents independently selected from $R^b$,
(8) heteroaryl-$C_{1-13}$alkyl, unsubstituted or substituted on heteroaryl with one, two, or three substituents independently selected from $R^b$,
(9) $C_{1-6}$alkyloxycarbonyl-$C_{1-6}$alkyl-,
(10) —$CO_2R^d$,
(11) —CO—$NR^cR^d$,
(12) —CN,
(13) —$OR^d$,
(14) —O—C(O)$R^d$,
(15) —$NR^cR^d$,
(16) —$NR^cC$(═O)$R^d$,
(17) —$NR^cC$(═O)$OR^d$,
(18) —$NR^cC$(═O)—C(═O)$NR^cR^d$,
(19) —NH—$SO_2$—$R^d$, and
(20) —S—$C_{1-6}$alkyl, $X^1$, when present, is selected from hydrogen, halogen and $C_{1-6}$alkyl, or together X and $X^1$ form ═O, ═$NR^g$, or ═CH—C(O)—O—$R^d$.

In another class, X is selected from:
(1) halogen,
(2) —$C_{1-6}$alkyl, unsubstituted or substituted with one, two or three substituents independently selected from $R^a$,
(3) aryl-, unsubstituted or substituted with one, two or three substituents independently selected from $R^b$,
(4) cycloalkyl, unsubstituted or substituted with one, two or three substituents independently selected from $R^b$,
(5) heteroaryl-, unsubstituted or substituted with one, two, or three substituents independently selected from $R^b$,
(6) heterocycloalkyl-, unsubstituted or substituted with one, two or three substituents independently selected from $R^b$,
(7) heteroaryl-$C_{1-3}$alkyl, unsubstituted or substituted on heteroaryl with one, two, or three substituents independently selected from $R^b$,
(8) —$CO_2R^d$,
(9) —CO—$NR^cR^d$,
(10) —CN,
(11) —$OR^d$,
(12) —O—C(O)$R^d$,
(13) —$NR^cR^d$,
(14) —$NR^cC$(═O)$R^d$,
(15) —$NR^cC$(═O)$OR^d$,
(16) —$NR^cC$(═O)—C(═O)$NR^cR^d$,
(17) —NH—$SO_2$—$R^f$, and
(18) —S—$C_{1-6}$alkyl, $X^1$, when present, is selected from hydrogen, halogen and $C_{1-6}$alkyl, or together X and $X^1$ form ═O, ═$NR^g$, or ═CH—C(O)—O—$R^d$.

In one class of the present invention, "a" is a single bond, and X is selected from:
(1) methyl, ethyl, isopropyl or t-butyl, substituted with one, two or three substituents independently selected from $R^a$,
(2) phenyl-, unsubstituted or substituted with one, two or three substituents independently selected from $R^b$,
(3) heteroaryl-, unsubstituted or substituted with one, two, or three substituents independently selected from $R^b$,
(4) heterocycloalkyl-, unsubstituted or substituted with one, two or three substituents independently selected from $R^b$,
(5) heteroaryl-methyl-, unsubstituted or substituted on heteroaryl with one, two, or three substituents independently selected from $R^b$,
(6) —$CO_2R^d$,
(7) —CO—$NR^cR^d$.
(8) —$OR^d$,
(9) —O—C(O)$R^d$,
(10) —$NR^cR^d$,
(11) —$NR^cC$(═O)$R^d$,
(12) —NHC(═O)$OR^d$,
(13) —NHC(═O)—C(═O)$NHR^d$, and
(14) —NH—$SO_2$—$R^f$, $X^1$ is hydrogen, or X and $X^1$ together form =O, =N—OH, or =CH—C(O)—O—$CH_2CH_3$.

In one embodiment of the present invention, "a" is a double bond, $X^1$ is absent, and X is selected from:

(1) hydrogen, (2) $C_{1-6}$alkyl, substituted with one, two or three substituents independently selected from $R^a$, (3) phenyl-, unsubstituted or substituted with one, two or three substituents independently selected from $R^b$, (4) heteroaryl-, unsubstituted or substituted with one, two, or three substituents independently selected from $R^b$, (5) heterocycloalkyl-, unsubstituted or substituted with one, two or three substituents independently selected from $R^b$, (6) —$CO_2R^d$, (7) —$NHR^d$, (8) —NHC(=O)$R^d$, and (9) —NHC(=O)$OR^d$.

In one class of this embodiment, "a" is a double bond, $X^1$ is absent, and X is selected from:

(1) —H, (2) —$CH_2$—C(O)—$OCH_2CH_3$, (3) —$C(CH_3)_2$—C(O)—$CH_2CH_3$, (4) phenyl-, substituted with one or two halogen substituents, (5) pyridyl, (6) 1-methyl-1H-pyrazolyl, (7) 1H-pyrazolyl, (8) —$CO_2CH_3$, (9) —$CO_2H$,

(10) —$NH_2$,

(11) —NH—C(O)—$CH_3$,

(12) —NH—C(O)—$CH_2$—O—C(O)—$CH_3$, and

(13) —NH—C(O)—$CH_2$—OH.

In one embodiment of the present invention, Y is selected from: hydrogen, halogen, $C_{1-6}$alkyl, and —C(O)—$R^e$; and $Y^1$, when present, is selected from: hydrogen, halogen, and $C_{1-6}$alkyl.

In one embodiment of the present invention, "a" is a single bond, $Y^1$ is hydrogen, and Y is selected from: hydrogen, halogen, $C_{1-6}$alkyl, and —C(O)—$R^e$.

In one class of this embodiment, "a" is a single bond, $Y^1$ is hydrogen, and Y is selected from: hydrogen, chloro, bromo, iodo, $C_{1-3}$alkyl, methylcarbonyl-, and —C(O)-cycloheteroalkyl.

In a subclass of this class, "a" is a single bond, $Y^1$ is hydrogen, and Y is selected from: hydrogen, bromo, methyl, and piperidinyl-1-carbonyl-. In still another subclass, "a" is a single bond, $Y^1$ is hydrogen, and Y is hydrogen, bromo or methyl. In yet another subclass, "a" is a single bond, $Y^1$ is hydrogen, and Y is hydrogen.

In one embodiment of the present invention, "a" is a single bond and $Y^1$ is selected from: hydrogen, halogen, and $C_{1-6}$alkyl. In one class of this embodiment, "a" is a single bond and $Y^1$ is selected from: hydrogen and methyl. In a subclass of this embodiment, "a" is a single bond and $Y^1$ is hydrogen.

In one embodiment of the present invention, "a" is a double bond, $Y^1$ is absent, and Y is selected from: hydrogen, halogen, $C_{1-6}$alkyl, and —C(O)—$R^e$.

In one class of this embodiment, "a" is a double bond, $Y^1$ is absent, and Y is selected from: hydrogen, chloro, bromo, iodo, $C_{1-3}$alkyl, methylcarbonyl-, and —C(O)-cycloheteroalkyl. In a subclass of this class, "a" is a double bond, $Y^1$ is absent, and Y is selected from: hydrogen, bromo, methyl, and piperidinyl-1-carbonyl-. In still another subclass, "a" is a double bond, $Y^1$ is absent, and Y is hydrogen or piperidinyl-1-carbonyl. In yet another subclass, "a" is a double bond, $Y^1$ is absent, and Y is hydrogen.

In one embodiment of the present invention, $Ar^1$ is selected from:

(1) aryl, and (2) heteroaryl, wherein aryl and heteroaryl are substituted with $R^4$ and $R^5$.

In one class of this embodiment, $Ar^1$ is selected from:

(1) phenyl, (2) pyridyl, (3) 1H-indazolyl, and (4) benzo[d]isoxazolyl, wherein the phenyl and heteroaryl moieties are substituted with $R^4$ and $R^5$.

In a subclass of this class, $Ar^1$ is selected from:

(1)

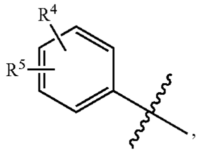

(2)

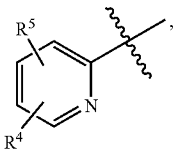

(3)

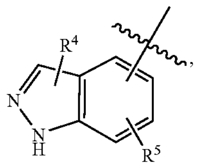

and (4)

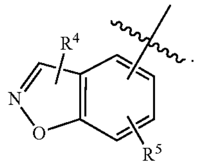

In a subclass of this class, $Ar^1$ is selected from:

(5)

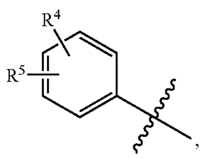

(6) 1H-indazolyl, (7) benzo[d]isoxazol-3-ol-yl, and (8) 1H-indazol-ol-yl.

In another class, $Ar^1$ is:

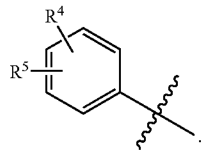

In a subclass of this class, $Ar^1$ is:

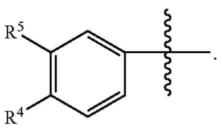

In another subclass, $Ar^1$ is selected from: 4-chlorophenyl, 4-bromophenyl, 4-cyanophenyl, 4-methylphenyl, 4-trifluoromethylphenyl, 4-methoxyphenyl, 3-methoxy-4-chlorophenyl, 4-trifluoromethyloxyphenyl, and 4-(2,2,2-trifluoroethyloxy)-phenyl.

In yet another subclass, $Ar^1$ is 4-chlorophenyl.

In one embodiment of the present invention, $Ar^2$ is selected from:

(1) aryl, and (2) heteroaryl, wherein aryl and heteroaryl are substituted with $R^6$ and $R^7$.

In one class of this embodiment, $Ar^2$ is selected from:

(1)

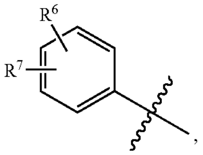

(2)

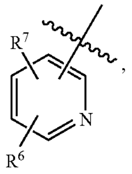

(3)

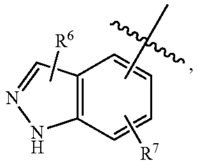

and (4)

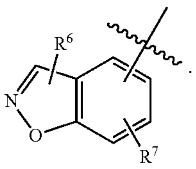

In another class of this embodiment, $Ar^2$ is selected from:

(1)

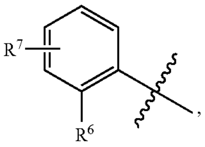

(2)

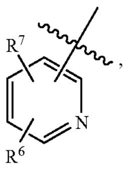

(3)

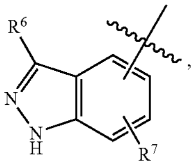

and (4)

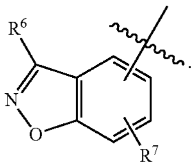

In a subclass of this class, $Ar^2$ is selected from:

(1)

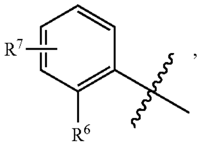

(2) 1H-indazolyl, (3) benzo[d]isoxazol-3-ol-yl, and (4) 1H-indazol-ol-yl.

In a subclass of this class. $Ar^2$ is:

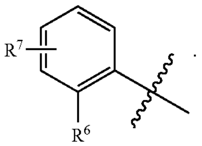

In another subclass, $Ar^2$ is selected from: and

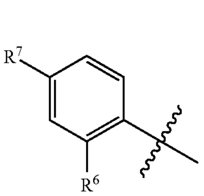

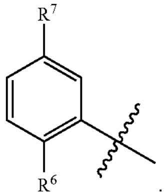

In yet another subclass of this class, $Ar^2$ is selected from: 2-chlorophenyl, 2-bromophenyl, 2-cyanophenyl, 2,4-dichlorophenyl, 4-bromo-2-chlorophenyl, 4-cyano-2-chlorophenyl, 4-methyl-2-chlorophenyl, 4-methoxy-2-chlorophenyl, 4-hydroxy-2-chlorophenyl, 4-trifluoromethoxy-2-chlorophenyl, 4-methoxycarbonyl-2-chlorophenyl, 4-(2,2,2-trifluoroethoxy)-2-chlorophenyl, 4-(5-oxo-4,5-dihydro-1,3,4-oxadiazol-2-yl)-2-chlorophenyl, 4-(1,2,4-oxadiazol-3-yl)-2-chlorophenyl, 4-(5-methyl-1,2,4-oxadiazol-3-yl)-2-chlorophenyl, 4-(1,3,4-oxadiazol-2-yl)-2-chlorophenyl, 4-(1H-pyrazol-1-yl)-2-chlorophenyl, 4-(1H-pyrazol-4-yl)-2-chlorophenyl, 4-(5-methyl-thien-2-yl)-2-chlorophenyl, 4-(thien-3-yl)-2-chlorophenyl, 4-(1-methyl-pyrazol-4-yl)-2-chlorophenyl, 4-(pyrazol-4-yl)-2-chlorophenyl, 4-(pyrazol-5-yl)-2-chlorophenyl, 4-(fury-2-yl)-2-chlorophenyl, 4-(fury-3-yl)-2-chlorophenyl, 4-(1,3-oxazol-2-yl)-2-chlorophenyl, 4-chloro-2-bromophenyl, 4-chloro-2-cyanophenyl, 4-chloro-2-methylphenyl, 2,4-di-trifluoromethylphenyl, 2,4-dicyanophenyl, 2,5-chlorophenyl, 5-bromo-2-chlorophenyl, 5-cyano-2-chlorophenyl, 5-methyl-2-chlorophenyl, 5-trifluoromethyl-2-chlorophenyl, 5-chloro-2-bromophenyl, 5-chloro-2-cyanophenyl, 5-chloro-2-trifluoromethylphenyl, 5-chloro-2-(1,2,4-oxadiazol-3-yl)-phenyl.

In still another subclass, $Ar^2$ is selected from 2-chlorophenyl and 2,4-dichlorophenyl. In yet another subclass, $Ar^2$ is 2,4-dichlorophenyl.

In one embodiment of the present invention, $R^1$ is selected from:

(1) hydrogen,
(2) $C_{1-10}$ alkyl,
(3) $C_{3-10}$cycloalkyl,
(4) $C_{3-10}$cycloalkenyl,
(5) $C_{3-10}$cycloalkyl-$C_{1-4}$alkyl,
(6) $C_{3-10}$cycloalkenyl-$C_{1-4}$alkyl,
(7) cycloheteroalkyl,
(8) cycloheteroalkyl-$C_{1-4}$alkyl,
(9) aryl,
(10) aryl-$C_{1-4}$alkyl,
(11) heteroaryl,
(12) heteroaryl-$C_{1-4}$alkyl,
(13) —C(O)O—$R^e$,
(14) —$OR^e$,
(15) —$NR^cR^d$,
(16) —C(O)NH—$S(O)_2$—$R^e$, wherein each alkyl is unsubstituted or substituted with one to four substituents independently selected from $R^a$, and each cycloalkyl, and cycloheteroalkyl, aryl and heteroaryl is optionally substituted with one to four substituents independently selected from $R^b$;

$R^2$ is selected from:

(1) $C_{1-10}$alkyl,
(2) $C_{3-10}$cycloalkyl,
(3) $C_{3-10}$cycloalkenyl,
(4) $C_{3-10}$cycloalkyl-$C_{1-4}$alkyl,
(5) $C_{3-10}$cycloalkenyl-$C_{1-4}$alkyl,
(6) cycloheteroalkyl,
(7) cycloheteroalkyl-$C_{1-4}$alkyl,
(8) aryl,
(9) aryl-$C_{1-4}$alkyl,
(10) heteroaryl,
(11) heteroaryl-$C_{1-4}$alkyl,
(12) —C(O)O—$R^e$,
(13) —$OR^e$,
(14) —$NR^cR^d$,
(15) —C(O)—NH—$S(O)_2$—$R^e$, wherein each alkyl is unsubstituted or substituted with one to four substituents independently selected from $R^a$, and each cycloalkyl, cycloalkenyl, cycloheteroalkyl, aryl and heteroaryl is optionally substituted with one to four substituents independently selected from $R^b$;

or $R^1$ and $R^2$ together with the carbon to which they are attached form a carbonyl group (C═O) or a spiroannulated ring system of 3 to 10 members containing 0, 1, or 2 heteroatoms independently selected from —O—, —S—, and —N($R^d$)—, optionally substituted with one to four substituents independently selected from $R^b$.

In another embodiment of the present invention, $R^i$ is selected from:

(1) hydrogen,
(2) $C_{1-10}$alkyl,
(3) $C_{3-10}$cycloalkyl,
(4) $C_{3-10}$cycloalkenyl,
(5) $C_{3-10}$cycloalkyl-$C_{1-4}$alkyl,
(6) $C_{3-10}$cycloalkenyl-$C_{1-4}$alkyl,
(7) cycloheteroalkyl,
(8) cycloheteroalkyl-$C_{1-4}$alkyl,
(9) aryl,
(10) aryl-$C_{1-4}$alkyl,
(11) heteroaryl,
(12) heteroaryl-$C_{1-4}$alkyl,
(13) —C(O)O—$R^e$,
(14) —$OR^e$,
(15) —$NR^cR^d$,
(16) —C(O)NH—$S(O)_2$—$R^e$, wherein each alkyl is unsubstituted or substituted with one to four substituents independently selected from $R^a$, and each cycloalkyl, and cycloheteroalkyl, aryl and heteroaryl is optionally substituted with one to four substituents independently selected from $R^b$;

$R^2$ is selected from:

(1) $C_{1-10}$alkyl,
(2) $C_{3-10}$cycloalkyl,
(3) $C_{3-10}$cycloalkenyl,
(4) $C_{3-10}$cycloalkyl-$C_{1-4}$alkyl,
(5) $C_{3-10}$cycloalkenyl-$C_{1-4}$alkyl,
(6) cycloheteroalkyl,
(7) cycloheteroalkyl-$C_{1-4}$alkyl,
(8) aryl,
(9) aryl-$C_{1-4}$alkyl,
(10) heteroaryl,
(11) heteroaryl-$C_{1-4}$alkyl,
(12) —C(O)O—$R^e$,
(13) —$OR^e$,
(14) —$NR^cR^d$,
(15) —C(O)—NH—$S(O)_2$—$R^e$, wherein each alkyl is unsubstituted or substituted with one to four substituents independently selected from $R^a$, and each cycloalkyl, cycloalkenyl, cycloheteroalkyl, aryl and heteroaryl is optionally substituted with one to four substituents independently selected from $R^b$;

or $R^1$ and $R^2$ together with the carbon to which they are attached form a carbonyl group (C═O) or a spiroannulated ring system of 3 to 10 members containing 0, 1, or 2 heteroatoms independently selected from —O—, —S—, and —N($R^d$)—, optionally substituted with one to four substituents independently selected from $R^b$.

In one class of the present invention, $R^i$ is selected from:

(1) hydrogen,
(2) $C_{1-6}$alkyl,
(3) $C_{3-7}$cycloalkyl,
(4) $C_{3-8}$cycloalkenyl,
(5) $C_{3-7}$cycloalkyl-$C_{1-4}$alkyl,
(6) $C_{3-8}$cycloalkenyl-$C_{1-4}$alkyl,
(7) cycloheteroalkyl,
(8) cycloheteroalkyl-$C_{1-4}$alkyl,
(9) phenyl,
(10) benzyl,

(11) heteroaryl,

(12) heteroaryl-$C_{1-4}$alkyl,

(13) —C(O)NH—$S(O)_2$—$CH_3$, wherein each alkyl is unsubstituted or substituted with one to four substituents independently selected from $R^a$, and each cycloalkyl, and cycloheteroalkyl, aryl and heteroaryl is optionally substituted with one to four substituents independently selected from $R^b$;

$R^2$ is selected from:

(1) $C_{1-6}$alkyl, (2) $C_{3-7}$cycloalkyl, (3) $C_{3-8}$cycloalkenyl, (4) $C_{3-7}$cycloalkyl-$C_{1-4}$alkyl, (5) $C_{3-8}$cycloalkenyl-$C_{1-4}$alkyl, (6) cycloheteroalkyl, (7) cycloheteroalkyl-$C_{1-4}$alkyl, (8) phenyl, (9) benzyl,

(10) heteroaryl,

(11) heteroaryl-$C_{1-4}$alkyl,

(12) —C(O)NH—$S(O)_2$—$CH_3$, wherein each alkyl is unsubstituted or substituted with one to four substituents independently selected from $R^a$, and each cycloalkyl, cycloalkenyl, cycloheteroalkyl, aryl and heteroaryl is optionally substituted with one to four substituents independently selected from $R^b$;

or $R^1$ and $R^2$ together with the carbon to which they are attached form a carbonyl group (C═O) or a spiroannulated ring system of 5 to 10 members containing 0, 1, or 2 heteroatoms independently selected from —O—, and —S, optionally substituted with an $R^b$ substituent.

In another class of the present invention, $R^1$ is selected from:

(1) hydrogen, (2) $C_{1-6}$alkyl, unsubstituted or substituted with hydroxy, fluoro, or methylsulfonylmethyl, (3) bicyclo[2.2.1]hept-5-en-2-yl, (4) cycloheteroalkyl, (5) cycloheteroalkyl-$C_{1-4}$alkyl, and (6) phenyl, unsubstituted or substituted with fluoro;

$R^2$ is selected from:

(1) $C_{1-6}$alkyl, unsubstituted or substituted with hydroxy, fluoro, or methylsulfonyl, (2) bicyclo[2.2.1]hept-5-en-2-yl, (3) cycloheteroalkyl, (4) cycloheteroalkyl-$C_{1-4}$alkyl, and (5) phenyl, unsubstituted or substituted with fluoro;

or $R^1$ and $R^2$ together with the carbon to which they are attached form a carbonyl group (C═O) or a spiroannulated ring system selected from:

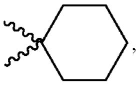, 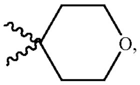, 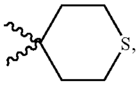,
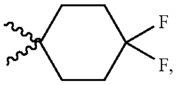, 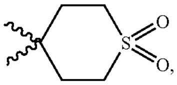, 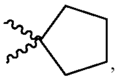, and
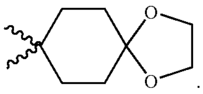.

In still another class of the present invention, $R^1$ is selected from:

(1) hydrogen, (2) methyl, (3) hydroxymethyl-, (4) methylsulfonylmethyl-, (5) ethyl, (6) isopropyl, (7) t-butyl, (8) bicyclo[2.2.1]hept-5-en-2-yl-, and (9) 3-fluoro-phenyl-, $R^2$ is selected from:

(1) methyl, (2) hydroxymethyl-, (3) methylsulfonylmethyl-, (4) ethyl, (5) isopropyl, (6) t-butyl, (7) bicyclo[2.2.1]hept-5-en-2-yl-, and (8) 3-fluoro-phenyl-, or $R^1$ and $R^2$ together with the carbon to which they are attached form a carbonyl group (C═O) or a spiroannulated ring system selected from:

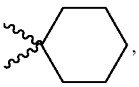, 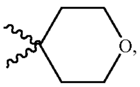, 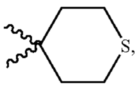,
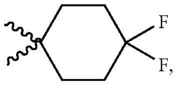, 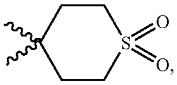, 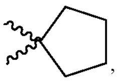, and
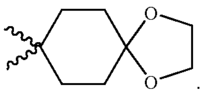.

In yet another class of the present invention, $R^1$ is selected from: hydrogen, methyl, and ethyl; $R^2$ is selected from: methyl, hydroxymethyl-, methylsulfonylmethyl-, ethyl, isopropyl, t-butyl, bicyclo[2.2.1]hept-5-en-2-yl-, and 3-fluoro-phenyl-;

or $R^1$ and $R^2$ together with the carbon to which they are attached form a carbonyl group (C═O) or a spiroannulated ring system selected from:

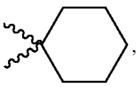, 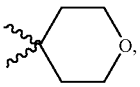, 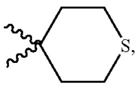,
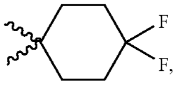, 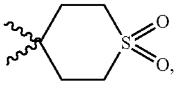, 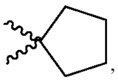, and
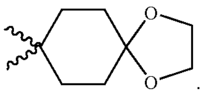.

In a subclass of the present invention, $R^1$ is selected from: hydrogen, methyl, and ethyl; $R^2$ is selected from: methyl, ethyl, isopropyl, and t-butyl;

or $R^1$ and $R^2$ together with the carbon to which they are attached form the spiroannulated ring system:

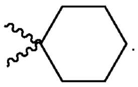.

In another subclass of the present invention, $R^1$ and $R^2$ are each methyl or together form:

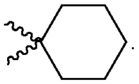

In yet another subclass of the present invention, $R^1$ and $R^2$ are each methyl. In still another subclass of the present invention, $R^1$ and $R^2$ together form:

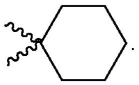

In another embodiment of the present invention, $R^3$ is selected from: hydrogen, methyl, ethyl, propyl, t-butyl, methoxy, ethyloxy, propyloxy, t-butyloxy, trifluoromethyloxy, trifluoromethyl, halo, and cyclopropyl, wherein the alkyl and cycloalkyl moieties are optionally substituted with one or two substituents independently selected from $R^a$.

In one class of this embodiment, the alkyl and cycloalkyl moieties are optionally substituted with one or two substituents independently selected from: halo, trifluoromethyl, methoxy, ethyloxy, methoxycarbonyl, and carboxyl.

In another class, $R^3$ is selected from: hydrogen, methyl, trifluoromethyl, methoxy, trifluoromethyloxy, chloro, and fluoro.

In a subclass of this class, $R^3$ is hydrogen.

In one embodiment of the present invention, $R^4$ is selected from:

(1) —H,
(2) halo-,
(3) —CN,
(4) $C_{1-6}$alkyl-, unsubstituted or substituted with one, two or three $R^h$ substitutents,
(5) —$CF_3$,
(6) cycloalkyl, unsubstituted or substituted with one, two or three $R^h$ substitutents,
(7) cycloheteroalkyl, unsubstituted or substituted with one, two or three $R^h$ substitutents,
(8) aryl, unsubstituted or substituted with one, two or three $R^k$ substitutents,
(9) heteroaryl, unsubstituted or substituted with one, two or three $R^k$ substitutents,
(10) —$OR^d$,
(11) —$OCF_3$
(12) —$C(O)R^d$,
(13) —$CO_2R^d$,
(14) —$C(O)NR^cR^d$,
(15) —$SR^d$,
(16) —$S(O)_mNR^cR^d$,
(17) —$NR^cR^d$,
(18) —$NR^cC(O)R^d$, and
(19) —$NR^cC(O)OR^d$.

In one class, $R^4$ is selected from:

(1) —H,
(2) halo-,
(3) —CN,
(4) $C_{1-3}$alkyl-, unsubstituted or substituted with one, two or three $R^h$ substitutents,
(5) —$CF_3$,
(6) —$OR^d$, and
(7) —$OCF_3$.

In another class, $R^4$ is selected from:

(1) halo-,
(2) —CN,
(3) $C_{1-3}$alkyl-, unsubstituted or substituted with one, two or three $R^h$ substitutents,
(4) —$CF_3$,
(5) —$OR^d$, and
(6) —$OCF_3$.

In one subclass, $R^4$ is selected from: halo-, —CN, —$CH_3$, —$CF_3$, —$OCH_3$, —$OCH_2CF_3$, and —$OCF_3$.

In another subclass, $R^4$ is chloro-.

In one embodiment of the present invention, $R^5$ is selected from:

(1) —H,
(2) halo-,
(3) —CN,
(4) $C_{1-6}$alkyl-, unsubstituted or substituted with one, two or three $R^h$ substitutents,
(5) —$CF_3$,
(6) cycloalkyl, unsubstituted or substituted with one, two or three $R^h$ substitutents,
(7) cycloheteroalkyl, unsubstituted or substituted with one, two or three $R^h$ substitutents,
(8) aryl, unsubstituted or substituted with one, two or three $R^k$ substitutents,
(9) heteroaryl, unsubstituted or substituted with one, two or three $R^k$ substitutents,
(10) —$OR^d$,
(11) —$OCF_3$
(12) —$C(O)R^d$,
(13) —$CO_2R^d$,
(14) —$C(O)NR^cR^d$,
(15) —$SR^d$,
(16) —$S(O)_mNR^cR^d$,
(17) —$NR^cR^d$,
(18) —$NR^cC(O)R^d$, and
(19) —$NR^cC(O)OR^d$.

In one class of this embodiment, $R^5$ is selected from:

(1) —H,
(2) halo-,
(3) —CN,
(4) $C_{1-6}$alkyl-, unsubstituted or substituted with one, two or three $R^h$ substitutents,
(5) —$CF_3$,
(6) —$OR^d$,
(7) —$OCF_3$.

In another class, $R^5$ is selected from: —H, halo-, —CN, —$CH_3$, —$CF_3$, —$OCH_3$, —$OCH_2CF_3$, and —$OCF_3$.

In one subclass, $R^5$ is hydrogen.

In one embodiment of the present invention, $R^6$ is selected from:

(1) —H,
(2) halo-,
(3) —CN,
(4) $C_{1-6}$alkyl-, unsubstituted or substituted with one, two or three $R^h$ substitutents,
(5) —$CF_3$,
(6) cycloalkyl, unsubstituted or substituted with one, two or three $R^h$ substitutents,
(7) cycloheteroalkyl, unsubstituted or substituted with one, two or three $R^h$ substitutents,
(8) aryl, unsubstituted or substituted with one, two or three $R^k$ substitutents,
(9) heteroaryl, unsubstituted or substituted with one, two or three $R^k$ substitutents,
(10) —$OR^d$,
(11) —$OCF_3$
(12) —$C(O)R^d$,

(13) —$CO_2R^d$,

(14) —$C(O)NR^cR^d$,

(15) —$SR^d$,

(16) —$S(O)_mNR^cR^d$,

(17) —$NR^cR^d$,

(18) —$NR^cC(O)R^d$, and

(19) —$NR^cC(O)OR^d$.

In one embodiment, when $Ar^2$ is phenyl and $R^7$ is hydrogen, $R^6$ is other than hydrogen.

In one class, $R^6$ is selected from:

(1) —H, (2) halo-, (3) —CN, (4) $C_{1-3}$alkyl-, unsubstituted or substituted with one, two, or three $R^h$ substitutents, (5) —$CF_3$, (6) cycloalkyl, unsubstituted or substituted with one or two $R^h$ substitutents, (7) cycloheteroalkyl, unsubstituted or substituted with one or two $R^h$ substitutents, (8) aryl, unsubstituted or substituted with one or two $R^k$ substitutents, (9) heteroaryl, unsubstituted or substituted with one or two $R^k$ substitutents,

(10) —OH,

(11) —$OCH_3$,

(12) —$OCF_3$,

(13) —$OCH_2CF_3$,

(14) —$C(O)R^d$,

(15) —$CO_2R^d$,

(16) —$C(O)NR^cR^d$, and

(17) —$NR^cR^d$;

PROVIDED THAT, if $Ar^2$ is phenyl and $R^7$ is hydrogen, $R^6$ is other than hydrogen.

In another class, $R^6$ is selected from:

(1) halo-, (2) —CN, (3) —$C_{1-13}$alkyl-, unsubstituted or substituted with one, two, or three $R^h$ substitutents, (4) —$CF_3$, (5) cycloheteroalkyl, unsubstituted or substituted with one or two $R^h$ substitutents, (6) heteroaryl, unsubstituted or substituted with one or two $R^k$ substitutents, (7) —OH, (8) —$OCH_3$, (9) —$OCF_3$,

(10) —$OCH_2CF_3$, and

(11) —$CO_2R^d$.

In another class, $R^6$ is selected from:

(1) —F, (2) —Cl, (3) —Br, (4) —I, (5) —CN, (6) —$CH_3$, (7) —$CF_3$, (8) oxadiazolyl, unsubstituted or substituted with one or two $R^h$ substitutents, (9) pyrazolyl,

(10) thienyl,

(11) furyl,

(12) oxazolyl,

(13) —OH,

(14) —$OCH_3$,

(15) —$OCF_3$,

(16) —$OCH_2CF_3$, and

(17) —$CO_2CH_3$.

In another class, $R^6$ is selected from: —Cl, —Br, —CN, —$CH_3$, —$CF_3$, and 1,2,4-oxadiazolyl.

In a subclass, $R^6$ is chloro.

In one embodiment of the present invention, $R^7$ is selected from:

(1) —H, (2) halo-, (3) —CN, (4) $C_{1-6}$alkyl-, unsubstituted or substituted with one, two or three $R^h$ substitutents, (5) —$CF_3$, (6) cycloalkyl, unsubstituted or substituted with one, two or three $R^h$ substitutents, (7) cycloheteroalkyl, unsubstituted or substituted with one, two or three $R^h$ substitutents, (8) aryl, unsubstituted or substituted with one, two or three $R^k$ substitutents, (9) heteroaryl, unsubstituted or substituted with one, two or three $R^k$ substitutents,

(10) —$OR^d$,

(11) —$OCF_3$

(12) —$C(O)R^d$,

(13) —$CO_2R^d$,

(14) —$C(O)NR^cR^d$,

(15) —$SR^d$,

(16) —$S(O)_mNR^cR^d$,

(17) —$NR^cR^d$,

(18) —$NR^cC(O)R^d$, and

(19) —$NR^cC(O)OR^d$.

In one embodiment, when $Ar^2$ is phenyl and $R^6$ is hydrogen, $R^7$ is other than hydrogen.

In one class, $R^7$ is selected from:

(1) —H, (2) halo-, (3) —CN, (4) $C_{1-3}$alkyl-, unsubstituted or substituted with one, two, or three $R^h$ substitutents, (5) —$CF_3$, (6) cycloalkyl, unsubstituted or substituted with one or two $R^h$ substitutents, (7) cycloheteroalkyl, unsubstituted or substituted with one or two $R^h$ substitutents, (8) aryl, unsubstituted or substituted with one or two $R^k$ substitutents, (9) heteroaryl, unsubstituted or substituted with one or two $R^k$ substitutents,

(10) —OH,

(11) —$OCH_3$,

(12) —$OCF_3$,

(13) —$OCH_2CF_3$,

(14) —$C(O)R^d$,

(15) —$CO_2R^d$,

(16) —$C(O)NR^cR^d$, and

(17) —$NR^cR^d$.

In another class, $R^7$ is selected from:

(1) —H, (2) halo-, (3) —CN, (4) —$C_{1-3}$alkyl-, unsubstituted or substituted with one, two, or three $R^h$ substitutents, (5) —$CF_3$, (6) cycloheteroalkyl, unsubstituted or substituted with one or two $R^h$ substitutents, (7) heteroaryl, unsubstituted or substituted with one or two $R^k$ substitutents, (8) —OH, (9) —$OCH_3$,
(10) —$OCF_3$,
(11) —$OCH_2CF_3$, and
(12) —$CO_2R^d$.

In still another class, $R^7$ is selected from:
(1) —H,
(2) halo-,
(3) —CN,
(4) —$C_{1-3}$alkyl-, unsubstituted or substituted with one, two, or three $R^h$ substitutents,
(5) —$CF_3$,
(6) cycloheteroalkyl, unsubstituted or substituted with one or two $R^h$ substitutents,
(7) heteroaryl, unsubstituted or substituted with one or two $R^k$ substitutents,
(8) —OH,
(9) —$OCH_3$,
(10) —$OCF_3$,
(11) —$OCH_2CF_3$, and
(12) —$CO_2R^d$.

In another class, $R^7$ is selected from: —H, —F; —Cl; —Br; —I; —CN; —$CH_3$; —$CF_3$; oxadiazolyl, unsubstituted or substituted with one or two $R^h$ substitutents; pyrazolyl; thienyl; furyl; oxazolyl; —OH; —$OCH_3$; —$OCF_3$; —$OCH_2CF_3$; and —$CO_2CH_3$.

In a subclass, $R^7$ is selected from: —F; —Cl; —Br; —I; —CN; —$CH_3$; —$CF_3$; oxadiazolyl, unsubstituted or substituted with one or two $R^h$ substitutents; pyrazolyl; thienyl; furyl; oxazolyl; —OH; —$OCH_3$; —$OCF_3$; —$OCH_2CF_3$; and —$CO_2CH_3$.

In a subclass, $R^7$ is selected from hydrogen and chloro.

In one embodiment, when $Ar^1$ is phenyl and $Ar^2$ is phenyl, at least one of $R^4$, $R^5$, $R^6$ and $R^7$ is other than hydrogen, In one embodiment of the present invention, each $R^a$ is independently selected from: —$OR^d$, —$NR^cS(O)_mR^d$, halogen, —$SR^d$, —$S(O)_mNR^d$, —$S(O)_mNR^cR^d$, —$NR^cR^d$, —$C(O)R^d$, —$CO_2R^d$, —CN, —$C(O)NR^cR^d$, —$NR^cC(O)R^d$, —$NR^cC(O)OR^d$, —$NR^cC(O)NR^cR^d$, —$CF_3$, and —$OCF_3$.

In one class of this embodiment, each $R^a$ is independently selected from: —OH, —$OCH_3$, halogen, —SH, —$SO_2R^d$, —$NH_2$, —CN, —$CO_2R^d$, —$C(O)NR^cR^d$, —$CF_3$, and —$OCF_3$.

In one subclass, each $R^a$ is independently selected from: —OH, —F, —$SO_2CH_3$, —$CO_2$—$C_{1-6}$alkyl, and —$CF_3$.

In another subclass, each $R^a$ is independently selected from: —OH, —F, and —$CF_3$.

In one embodiment, $R^b$ is independently selected from:
(1) —$OR^d$,
(2) —$NR^cS(O)_mR^d$,
(3) halogen,
(4) —$SR^d$,
(5) —$S(O)_mNR^cR^d$
(6) —$S(O)_mNR^cR^d$,
(7) —$NR^cR^d$,
(8) —$C(O)R^d$,
(9) —$CO_2R^d$,
(10) —CN,
(11) —$C(O)NR^cR^d$,
(12) —$NR^cC(O)R^d$,
(13) —$NR^cC(O)OR^d$,
(14) —$NR^cC(O)NR^cR^d$,
(15) —$CF_3$,
(16) —$OCF_3$,
(17) oxo,
(18) $C_{1-10}$alkyl,
(19) $C_{2-10}$alkenyl,
(20) cycloalkyl,

(21) cycloalkyl-$C_{1-10}$alkyl,
(22) cycloheteroalkyl,
(23) cycloheteroalkyl-$C_{1-10}$ alkyl,
(24) aryl,
(25) heteroaryl,
(26) aryl-$C_{1-10}$alkyl, and
(27) heteroaryl-$C_{1-10}$alkyl, wherein alkyl and alkenyl moieties are unsubstituted or substituted with one, two, three or four $R^k$ substituents, and cycloalkyl, cycloheteroalkyl, aryl and heteroaryl moieties are unsubstituted or substituted with one, two or three $R^k$ substituents.

In one class of this embodiment, each $R^b$ is independently selected from:
(1) —$OR^d$,
(2) halogen,
(3) —$SCH_3$,
(4) —$NR^cR^d$,
(5) —$C(O)R^d$,
(6) —$CO_2R^d$,
(7) —CN,
(8) —$C(O)NR^cR^d$,
(9) —$CF_3$,
(10) —$OCF_3$,
(11) oxo,
(12) $C_{1-10}$alkyl,
(13) $C_{2-10}$alkenyl,
(14) cycloalkyl,
(15) cycloalkyl-methyl,
(16) cycloheteroalkyl,
(17) cycloheteroalkyl-methyl,
(18) aryl,
(19) heteroaryl,
(20) aryl-methyl,
(21) heteroaryl-methyl, wherein alkyl and alkenyl moieties are unsubstituted or substituted with one, two, or three $R^k$ substituents, and cycloalkyl, cycloheteroalkyl, aryl and heteroaryl moieties are unsubstituted or substituted with one, two or three $R^k$ substituents.

In another class of this embodiment, each $R^b$ is independently selected from:
(1) —OH,
(2) —$OCH_3$,
(3) halogen,
(4) —$N(CH_3)_2$,
(5) —CH(O)
(6) —$C(O)R^d$,
(7) —$CO_2CH_3$,
(8) —$CO_2CH_2C_6H_5$,
(9) —CN,
(10) —$CF_3$,
(11) —$OCF_3$,
(12) oxo,
(13) $C_{1-3}$alkyl,
(14) $C_{2-3}$ alkenyl,
(15) cyclopropyl,
(16) oxadiazolyl,
(17) pyrazolyl,
(18) tetrazolyl, and
(19) phenyl, wherein alkyl and alkenyl moieties are unsubstituted or substituted with one, two, or three $R^k$ substituents, and cycloalkyl, cycloheteroalkyl, aryl and heteroaryl moieties are unsubstituted or substituted with one, two or three $R^k$ substituents.

In another class of this embodiment, $R^b$ is independently selected from:

(1) —OH,
(2) —$OCH_3$,
(3) halogen,
(4) —$C(O)CH_3$,
(5) —$CO_2CH_3$,
(6) —CN,
(7) —$CF_3$,
(8) —$OCF_3$,
(9) oxo,
(10) methyl,
(11) ethyl,
(12) isopropyl, and
(13) $C_{2-3}$ alkenyl, wherein alkyl and alkenyl moieties are unsubstituted or substituted with one, two, or three $R^k$ substituents.

In a subclass, each $R^b$ is independently selected from: —OH, fluoro, —$C(O)CH_3$, —$CO_2CH_3$, —CN, —$CF_3$, —$OCF_3$, oxo, methyl, ethyl, isopropyl, and $C_{2-3}$ alkenyl, wherein alkyl and alkenyl moieties are unsubstituted or substituted with one, two, or three $R^k$ substituents.

In a another subclass, each $R^b$ is independently selected from: —OH, fluoro, oxo, methyl, ethyl, isopropyl, and $C_{2-3}$ alkenyl, wherein alkyl and alkenyl moieties are unsubstituted or substituted with one, two, or three $R^k$ substituents.

In one embodiment of the present invention, $R^c$ and $R^d$ are each independently selected from:

(1) hydrogen,
(2) $C_{1-10}$ alkyl,
(3) $C_{2-10}$alkenyl,
(4) cycloalkyl,
(5) cycloalkyl-$C_{1-10}$ alkyl-,
(6) cycloheteroalkyl,
(7) cycloheteroalkyl-$C_{1-10}$ alkyl-,
(8) aryl,
(9) heteroaryl,
(10) aryl-$C_{1-10}$alkyl-, and
(11) heteroaryl-$C_{1-10}$alkyl-, wherein each $R^c$ and $R^d$ moiety, other than hydrogen, may be unsubstituted or substituted with one to three substituents selected from $R^h$.

In one class of this embodiment, each $R^c$ is independently selected from: hydrogen, and $C_{1-3}$alkyl, unsubstituted or substituted with one to three substituents selected from $R^h$.

In a subclass, each $R^c$ is independently selected from: hydrogen, and methyl.

In one class, each $R^d$ is independently selected from:

(1) hydrogen,
(2) $C_{1-16}$alkyl,
(3) $C_{2-6}$alkenyl,
(4) cycloalkyl,
(5) cycloalkyl-$C_{1-10}$alkyl-,
(6) cycloheteroalkyl,
(7) cycloheteroalkyl-$C_{1-10}$alkyl-,
(8) aryl,
(9) heteroaryl,
(10) aryl-$C_{1-3}$alkyl-, and
(11) heteroaryl-$C_{1-3}$alkyl-, wherein each $R^d$ moiety, other than hydrogen, may be unsubstituted or substituted with one, two or three substituents selected from $R^h$.

In one embodiment of the present invention, each $R^e$ is independently selected from: $C_{1-10}$alkyl, aryl, heteroaryl, cycloalkyl, and cycloheteroaryl; wherein alkyl and aryl are unsubstituted or substituted with one, two, or three substituents independently selected from $R^h$.

In one embodiment of the present invention, each $R^f$ is independently selected from:

(1) halogen,
(2) $C_{1-6}$alkyl, unsubstituted or substituted with one, two, or three $R^i$ substituents,
(3) $C_{2-6}$ alkenyl, unsubstituted or substituted with one, two, or three $R^i$ substituents,
(4) cycloalkyl, unsubstituted or substituted with one, two, or three $R^h$ substituents,
(5) cycloalkyl-$C_{1-4}$alkyl-, unsubstituted or substituted with one, two, or three $R^h$ substituents,
(6) cycloheteroalkyl, unsubstituted or substituted with one, two, or three $R^h$ substituents,
(7) cycloheteroalkyl-$C_{1-4}$alkyl-, unsubstituted or substituted with one, two, or three $R^h$ substituents,
(8) aryl, unsubstituted or substituted with one, two, or three $R^h$ substituents,
(9) heteroaryl, unsubstituted or substituted with one, two, or three $R^h$ substituents,
(10) aryl-$C_{1-4}$alkyl-, unsubstituted or substituted with one, two, or three $R^h$ substituents,
(11) heteroaryl-$C_{1-4}$alkyl-, unsubstituted or substituted with one, two, or three $R^h$ substituents, and
(12) —$N(CH_3)_2$.

In one class of this embodiment, each $R^f$ is independently selected from: halogen; $C_{1-6}$alkyl, unsubstituted or substituted with one or two $R^i$ substituents; and —$N(CH_3)_2$.

In another class, each $R^f$ is independently selected from: chloro, ethyl, n-propyl, chloropropyl, and —$N(CH_3)_2$.

In one embodiment of the present invention, each $R^g$ is independently selected from: hydrogen, —OH, $C_{1-3}$alkyl, aryl, heteroaryl, cycloalkyl, cycloheteroaryl; wherein alkyl and aryl are unsubstituted or substituted with one, two, or three substituents independently selected from $R^h$.

In one class of this embodiment, each $R^g$ is independently selected from: hydrogen, —OH, and methyl.

In one embodiment of the present invention, each $R^h$ is independently selected from: halogen, $C_{1-6}$alkyl, 4-methylbenzyl-, —OH, —O—$C_{1-4}$alkyl, benzyloxy-, -oxo, —OC(O)—$C_{1-6}$alkyl, —C(O)O—$C_{1-6}$alkyl, —S—$C_{1-4}$alkyl, —$NH_2$, —$NH(CH_3)$, —$N(CH_3)_2$, —$NO_2$, —CN, —$CF_3$, and —$OCF_3$;

wherein alkyl may be unsubstituted or substituted with one, two or three substituents selected from $R^i$.

In one embodiment of the present invention, each $R^i$ is independently selected from: halogen, —O—$C_{1-4}$alkyl, —OH, —S—$C_{1-4}$alkyl, —CN, —$CF_3$, and —$OCF_3$.

In one class, each $R^i$ is independently selected from: halogen, methoxy, —OH, —S—$CH_3$, —CN, —$CF_3$, and —$OCF_3$.

In one embodiment of the present invention, each $R^k$ is independently selected from: halogen, oxo, amino, hydroxy, $C_{1-4}$alkyl, —O—$C_{1-4}$alkyl, —S—$C_{1-4}$alkyl, —CN, —$CF_3$, and —$OCF_3$.

In one class, each $R^k$ is independently selected from: halogen, oxo, amino, hydroxy, $C_{1-4}$alkyl, —O—$CH_3$, —S—$CH_3$, —CN, —$CF_3$, and —$OCF_3$.

In one embodiment of the present invention, each m is selected from 1 and 2. In one class, m is 1. In another, m is 2.

One embodiment of the present invention comprises a compound of structural formula IA:

IA

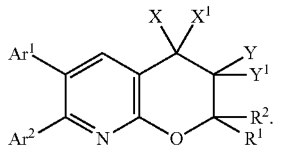

Another embodiment comprises a compound of structural formula IB:

IB

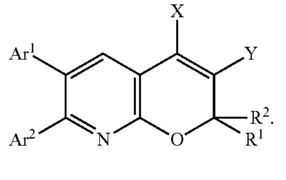

One class of the compounds of structural formula IB are those compounds of structural formula IC:

IC

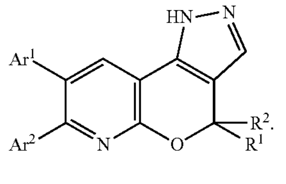

In another embodiment of the present invention are compounds of structural formula ID:

ID

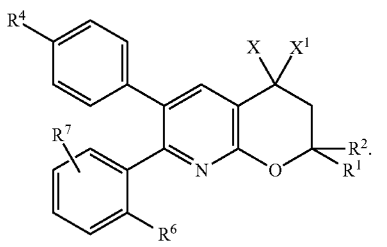

In a class of this embodiment, are compounds of structural formula ID-1:

ID-1

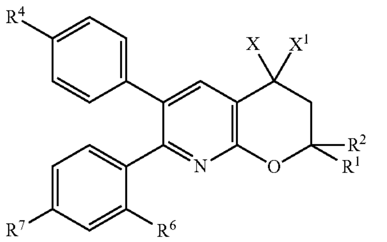

"Alkyl", as well as other groups having the prefix "alk", such as alkoxy, alkanoyl, means carbon chains which may be linear or branched or combinations thereof. Examples of alkyl groups include methyl, ethyl, n-propyl, isopropyl, butyl, isobutyl, sec- and tert-butyl, pentyl, hexyl, heptyl, octyl, nonyl, and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means mono- or bicyclic or bridged saturated carbocyclic rings, each having from 3 to 10 carbon atoms. Examples of cycloalkyl include cyclopropyl, cyclobutyl, cyclopentyl, cyclohexyl, cycloheptyl, cyclooxtyl, tetrahydronaphthyl, decahydronaphthyl, bicyclo and the like. In one embodiment of the present invention, cycloalkyl is selected from cyclopropyl, cyclobutyl, cyclopentyl, cyclohexyl, and 1,2,3,4-tetrahydronaphthyl.

"Cycloalkenyl" means nonaromatic, mono- or bicyclic or bridged carbocyclic rings, each having from 3 to 10 carbon atoms and at least one degree of unsaturation. Examples of cycloalkyl include cyclopropenyl, cyclobutenyl, cyclopentenyl, cyclohexenyl, cycloheptenyl, cyclooxtenyl, decahydronaphthyl, bicyclo[2.2.1]hept-5-en-2-yl, and the like. In one embodiment of the present invention, cycloalkenyl is selected from cyclopropenyl, cyclobutenyl, cyclopentenyl, cyclohexenyl, and bicyclo[2.2.1]hept-5-en-2-yl, and the like.

"Aryl" means mono- or bicyclic aromatic rings containing only carbon atoms. Examples of aryl include phenyl, naphthyl, and the like.

"Heteroaryl" means an aromatic or partially aromatic heterocycle that contains at least one ring heteroatom selected from O, S, and N. Heteroaryls thus include heteroaryls fused to other kinds of rings, such as aryls, cycloalkyls, and cycloheteroalkyls that are not aromatic. Examples of heteroaryl groups include: pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furyl, triazinyl, thienyl, pyrimidyl, pyridazinyl, pyrazinyl, benzoxazolyl, benzothiazolyl, benzimidazolyl, benzofuranyl, dibenzylfuranyl, isobenzylfuranyl, benzopyrazolyl, benzothienyl, benzothiazolyl, furo(2,3-b)pyridyl, quinolyl, indolyl, isoquinolyl, oxazolidinyl, imidazothiathiazolyl, pyrazolylpyridyl, benzotriazolyl, methylenedioxyphenyl, hexahydrothieno-pyridinyl, thienopyridinyl, and the like. In one embodiment of the present invention, heteroaryl is selected from pyridyl, furyl, thienyl, pyrazolyl, oxazolyl, isoxazolyl, oxadiazolyl, indazolyl, oxadiazolyl, tetrazolyl, imidazolyl, indolyl, benzimidazolyl, triazolyl, and benzopyrazolyl.

"Cycloheteroalkyl" refers to a saturated or unsaturated non-aromatic ring or ring system containing at least one heteroatom selected from O, S and N, further including the oxidized forms of sulfur, namely SO and $SO_2$, in which the point of attachment may be carbon or nitrogen. Examples of heterocycloalkyl include tetrahydrofuranyl, azetidinyl, perhydroazepinyl, dihydrofuranyl, dioxanyl, oxanyl, morpholinyl, 1,4-dithianyl, piperazinyl, piperidinyl, 1,3-dioxolanyl, imidazolidinyl, imidazolinyl, pyrrolinyl, pyrrolidinyl, pyranyl, tetrahydropyranyl, dihydropyranyl, oxathiolanyl, dithiolanyl, 1,3-dithianyl, oxathianyl, thiomorpholinyl, dioxidoisothiazolidinyl, azacycloheptyl, diazobicyclo[3.2.1]-octane, and hexahydroindazolyl. The cycloheteroalkyl ring may be substituted on the ring carbons and/or the ring nitrogens. In one embodiment of the present invention, cycloheteroalkyl is selected from tetrahydrofuranyl, imidazolidinyl, piperidinyl, pyrrolidinyl, isothiazolidinyl morpholinyl and thiomorpholinyl.

"Halogen" includes fluorine, chlorine, bromine and iodine.

When any variable (e.g., $R^1$, $R^d$, etc.) occurs more than one time in any constituent or in formula I, its definition on each occurrence is independent of its definition at every other occurrence. Also, combinations of substituents and/or variables are permissible only if such combinations result in stable compounds. A squiggly line across a bond in a substituent variable represents the point of attachment.

Under standard nomenclature used throughout this disclosure, the terminal portion of the designated side chain is described first, followed by the adjacent functionality toward the point of attachment. For example, a $C_{1-5}$ alkylcarbonylamino $C_{1-6}$ alkyl substituent is equivalent to:

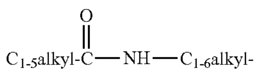

In choosing compounds of the present invention, one of ordinary skill in the art will recognize that the various substituents, i.e. $R^1$, $R^2$, etc., are to be chosen in conformity with well-known principles of chemical structure connectivity and stability.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

Compounds of Formula I may contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Tautomers are defined as compounds that undergo rapid proton shifts from one atom of the compound to another atom of the compound. Some of the compounds described herein may exist as tautomers with different points of attachment of hydrogen. Such an example may be a ketone and its enol form known as keto-enol tautomers. The individual tautomers as well as mixture thereof are encompassed with compounds of Formula I.

Compounds of the Formula I may be separated into diastereoisomeric pairs of enantiomers by, for example, fractional crystallization from a suitable solvent, for example MeOH or ethyl acetate or a mixture thereof. The pair of enantiomers thus obtained may be separated into individual stereoisomers by conventional means, for example by the use of an optically active amine as a resolving agent or on a chiral HPLC column.

Alternatively, any enantiomer of a compound of the general Formula I may be obtained by stereospecific synthesis using optically pure starting materials or reagents of known configuration.

Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

It is generally preferable to administer compounds of the present invention as enantiomerically pure formulations. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. The term "pharmaceutically acceptable salt" further includes all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or pro-drug formulations.

It will be understood that, as used herein, references to the compounds of Formula I are meant to also include the pharmaceutically acceptable salts.

Compounds of the present invention are modulators of the CB1 receptor. In particular, the compounds of structural formula I are antagonists or inverse agonists of the CB1 receptor.

An "agonist" is a compound (hormone, neurotransmitter or synthetic compound) which binds to a receptor and mimics the effects of the endogenous regulatory compound, such as contraction, relaxation, secretion, change in enzyme activity, etc. An "antagonist" is a compound, devoid of intrinsic regulatory activity, which produces effects by interfering with the binding of the endogenous agonist or inhibiting the action of an agonist. An "inverse agonist" is a compound which acts on a receptor but produces the opposite effect produced by the agonist of the particular receptor.

Compounds of this invention are modulators of the CB1 receptor and as such are useful as centrally acting drugs in the treatment of psychosis, memory deficits, cognitive disorders, Alzheimer's disease, migraine, neuropathy, neuro-inflammatory disorders including multiple sclerosis and Guillain-Barre syndrome and the inflammatory sequelae of viral encephalitis, cerebral vascular accidents, and head trauma, anxiety disorders, stress, epilepsy, Parkinson's disease, Huntington's disease, movement disorders, and schizophrenia. In particular, the compounds of this invention are antagonists/inverse agonists of the CB1 receptor. The compounds are also useful for the treatment of substance abuse disorders, particularly to opiates, alcohol, marijuana, and nicotine. In particular, the compounds of the invention are useful for smoking cessation. The compounds are also useful for the treatment of obesity or eating disorders associated with excessive food intake and complications associated therewith, including left ventricular hypertrophy, as well as treating or preventing obesity in other mammalian species, including canines and felines. The compounds are also useful for the treatment of constipation and chronic intestinal pseudo-obstruction. The compounds are also useful for the treatment of cirrhosis of the liver, non-alcoholic fatty liver disease (NAFLD), non-alcoholic steatohepatitis (NASH), promotion of wakefulness and treatment of asthma.

The terms "administration of" and or "administering a" compound should be understood to mean providing a compound of the invention or a prodrug of a compound of the invention to the individual in need of treatment.

The administration of the compound of structural formula I in order to practice the present methods of therapy is carried out by administering an effective amount of the compound of structural formula I to the mammalian patient in need of such treatment or prophylaxis. The need for a prophylactic administration according to the methods of the present invention is determined via the use of well known risk factors. The effective amount of an individual compound is determined, in the final analysis, by the physician or veterinarian in charge of the case, but depends on factors such as the exact disease to be treated, the severity of the disease and other diseases or conditions from which the patient suffers, the chosen route of administration other drugs and treatments which the patient may concomitantly require, and other factors in the physician's judgment.

The usefulness of the present compounds in these diseases or disorders may be demonstrated in animal disease models that have been reported in the literature. The following are examples of such animal disease models: a) suppression of food intake and resultant weight loss in rats (Life Sciences 1998, 63, 113-117); b) reduction of sweet food intake in marmosets (Behavioural Pharm. 1998, 9, 179-181); c) reduction of sucrose and ethanol intake in mice (Psychopharm. 1997, 132, 104-106); d) increased motor activity and place conditioning in rats (Psychopharm. 1998, 135, 324-332; Psychopharmacol 2000, 151: 25-30); e) spontaneous locomotor activity in mice (J. Pharm. Exp. Ther. 1996, 277, 586-594); f) reduction in opiate self-administration in mice (Sci. 1999, 283, 401-404); g) bronchial hyperresponsiveness in sheep and guinea pigs as models for the various phases of asthma (for example, see W. M. Abraham et al., "$\alpha_4$-Integrins mediate antigen-induced late bronchial responses and prolonged airway hyperresponsiveness in sheep." J. Clin. Invest. 93, 776 (1993) and A. A. Y. Milne and P. P. Piper, "Role of VLA-4 integrin in leucocyte recruitment and bronchial hyperresponsiveness in the guinea-pig." Eur. J. Pharmacol., 282, 243 (1995)); h) mediation of the vasodilated state in advanced liver cirrhosis induced by carbon tetrachloride (Nature Medicine, 2001, 7 (7), 827-832); i) amitriptyline-induced constipation in cynomolgus monkeys is beneficial for the evaluation of laxatives (Biol. Pharm. Bulletin (Japan), 2000, 23(5), 657-9); j) neuropathology of paediatric chronic intestinal pseudo-obstruction and animal models related to the neuropathology of paediatric chronic intestinal pseudo-obstruction (Journal of Pathology (England), 2001, 194 (3), 277-88).

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases.

For use where a composition for intravenous administration is employed, a suitable dosage range is from about 0.001 mg to about 100 mg in one embodiment from about 0.01 mg to about 50 mg, and in another embodiment from 0.1 mg to 10 mg of a compound of Formula I per kg of body weight per day.

In the case where an oral composition is employed, a suitable dosage range is, e.g. from about 0.01 mg to about 1000 mg of a compound of Formula I per day. In one embodiment, the range is from about 0.1 mg to about 10 mg per day. For oral administration, the compositions are preferably provided in the form of tablets containing from 0.01 to 1,000 mg, preferably 0.01, 0.05, 0.1, 0.5, 1, 2, 2.5, 3, 4, 5, 6, 7, 8, 9, 10, 12, 12.5, 15, 20, 25, 30, 40, 50, 100, 250, 500, 750 or 1000 milligrams of the active ingredient for the symptomatic adjustment of the dosage to the patient to be treated.

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

Any suitable route of administration may be employed for providing a mammal, particularly a human or companion animal such as a dog or cat, with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. By "pharmaceutically acceptable" it is meant the carrier, diluent or excipient must be compatible with the other ingredients of the formulation and not deleterious to the recipient thereof. The compositions include compositions suitable for oral, rectal, topical, parenteral (including subcutaneous, intramuscular, and intravenous), ocular (ophthalmic), pulmonary (aerosol inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulizers, or as powders which may be formulated and the powder composition may be inhaled with the aid of an insufflation powder inhaler device. The preferred delivery systems for inhalation are metered dose inhalation (MDI) aerosol, which may be formulated as a suspension or solution of a compound of Formula I in suitable propellants, such as fluorocarbons or hydrocarbons and dry powder inhalation (DPI) aerosol, which may be formulated as a dry powder of a compound of Formula I with or without additional excipients.

Suitable topical formulations of a compound of formula I include transdermal devices, aerosols, creams, solutions, ointments, gels, lotions, dusting powders, and the like. The topical pharmaceutical compositions containing the compounds of the present invention ordinarily include about 0.005% to 5% by weight of the active compound in admixture with a pharmaceutically acceptable vehicle. Transdermal skin patches useful for administering the compounds of the present invention include those well known to those of ordinary skill in that art.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules (including timed release and sustained release formulations), pills, cachets, powders, granules or tablets each containing a predetermined amount of the active ingredient, as a powder or granules or as a solution or a suspension in an aqueous liquid, a non-aqueous liquid, an oil-in-water emulsion or a water-in-oil liquid emulsion, including elixirs, tinctures, solutions, suspensions, syrups and emulsions. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet cachet or capsule contains from about 0.01 to 1,000 mg, particularly 0.01, 0.05, 0.1, 0.5, 1.0, 2, 2.5, 3, 4, 5, 6, 7, 8, 9, 10, 12, 15, 25, 30, 40, 50, 75, 100, 125, 150, 175, 180, 200, 225, 250, 500, 750 and 1,000 milligrams of the active ingredient for the symptomatic adjustment of the dosage to the patient to be treated.

Additional suitable means of administration of the compounds of the present invention include injection, intravenous bolus or infusion, intraperitoneal, subcutaneous, intramuscular, intranasal, and topical, with or without occlusion.

Exemplifying the invention is a pharmaceutical composition comprising any of the compounds described above and a pharmaceutically acceptable carrier. Also exemplifying the invention is a pharmaceutical composition made by combining any of the compounds described above and a pharmaceutically acceptable carrier. An illustration of the invention is a process for making a pharmaceutical composition comprising combining any of the compounds described above and a pharmaceutically acceptable carrier.

The dose may be administered in a single daily dose or the total daily dosage may be administered in divided doses of two, three or four times daily. Furthermore, based on the properties of the individual compound selected for administration, the dose may be administered less frequently, e.g., weekly, twice weekly, monthly, etc. The unit dosage will, of course, be correspondingly larger for the less frequent administration.

When administered via intranasal routes, transdermal routes, by rectal or vaginal suppositories, or through a continual intravenous solution, the dosage administration will, of course, be continuous rather than intermittent throughout the dosage regimen.

The following are examples of representative pharmaceutical dosage forms for the compounds of Formula I:

| Injectable Suspension (I.M.) | mg/mL |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |

Water for injection to a total volume of 1 mL

| Capsule | mg/capsule |
|---|---|
| Compound of Formula I | 25 |
| Lactose Powder | 573.5 |
| Magnesium Stearate | 1.5 |
| | 600 |

| Tablet | mg/tablet |
|---|---|
| Compound of Formula I | 25 |
| Microcrystalline Cellulose | 415 |

-continued

| | |
|---|---|
| Povidone | 14.0 |
| Pregelatinized Starch | 43.5 |
| Magnesium Stearate | 2.5 |
| | 500 |

| Aerosol | Per canister |
|---|---|
| Compound of Formula I | 24 mg |
| Lecithin, NF Liq. Conc. | 1.2 mg |
| Trichlorofluoromethane, NF | 4.025 g |
| Dichlorodifluoromethane, NF | 12.15 g |

Compounds of formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I include, but are not limited to: antipsychotic agents, cognition enhancing agents, anti-migraine agents, anti-asthmatic agents, antiinflammatory agents, anxiolytics, anti-Parkinson's agents, anti-Huntington's agents, anti-epileptics, anorectic agents, serotonin reuptake inhibitors, other anti-obesity agents, as well as antidiabetic agents, lipid lowering agents, and antihypertensive agents which may be administered separately or in the same pharmaceutical compositions.

The present invention also provides a method for the treatment or prevention of a CB1 receptor modulator mediated disease, which method comprises administration to a patient in need of such treatment or at risk of developing a CB1 receptor modulator mediated disease of an amount of a CB1 receptor modulator and an amount of one or more active ingredients, such that together they give effective relief.

In a further aspect of the present invention, there is provided a pharmaceutical composition comprising a CB1 receptor modulator and one or more active ingredients, together with at least one pharmaceutically acceptable carrier or excipient.

Thus, according to a further aspect of the present invention there is provided the use of a CB1 receptor modulator and one or more active ingredients for the manufacture of a medicament for the treatment or prevention of a CB1 receptor modulator mediated disease. In a further or alternative aspect of the present invention, there is therefore provided a product comprising a CB1 receptor modulator and one or more active ingredients as a combined preparation for simultaneous, separate or sequential use in the treatment or prevention of CB1 receptor modulator mediated disease. Such a combined preparation may be, for example, in the form of a twin pack.

It will be appreciated that for the treatment or prevention of eating disorders, including obesity, bulimia nervosa and compulsive eating disorders, a compound of the present invention may be used in conjunction with other anorectic agents.

The present invention also provides a method for the treatment or prevention of eating disorders, which method comprises administration to a patient in need of such treatment an amount of a compound of the present invention and an amount of an anorectic agent, such that together they give effective relief.

Suitable anorectic agents of use in combination with a compound of the present invention include, but are not limited to, a minorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; and pharmaceutically acceptable salts thereof. A particularly suitable class of anorectic agent are the halogenated amphetamine derivatives, including chlorphentermine, cloforex, clortermine, dexfenfluramine, fenfluramine, picilorex and sibutramine; and pharmaceutically acceptable salts thereof. Particular halogenated amphetamine derivatives of use in combination with a compound of the present invention include: fenfluramine and dexfenfluramine, and pharmaceutically acceptable salts thereof.

The present invention also provides a method for the treatment or prevention of obesity, which method comprises administration to a patient in need of such treatment an amount of a compound of the present invention and an amount of another agent useful in treating obesity and obesity-related conditions, such that together they give effective relief.

Suitable agents of use in combination with a compound of the present invention, include, but are not limited to:

(a) anti-diabetic agents such as (1) PPARγ agonists such as glitazones (e.g. ciglitazone; darglitazone; englitazone; isaglitazone (MCC-555); pioglitazone (ACTOS); rosiglitazone (AVANDIA); troglitazone; rivoglitazone, BRL49653; CLX-0921; 5-BTZD, GW-0207, LG-100641, R483, and LY-300512, and the like and compounds disclosed in WO97/10813, 97/27857, 97/28115, 97/28137, 97/27847, 03/000685, and 03/027112 and SPPARMS (selective PPAR gamma modulators) such as T131 (Amgen), FK614 (Fujisawa), netoglitazone, and metaglidasen; (2) biguanides such as buformin; metformin; and phenformin, and the like; (3) protein tyrosine phosphatase-1B (PTP-1B) inhibitors such as ISIS 113715, A-401674, A-364504, IDD-3, IDD 2846, KP-40046, KR61639, MC52445, MC52453, C7, OC-060062, OC-86839, OC29796, TTP-277BC1, and those agents disclosed in WO 04/041799, 04/050646, 02/26707, 02/26743, 04/092146, 03/048140, 04/089918, 03/002569, 04/065387, 04/127570, and US 2004/167183; (4) sulfonylureas such as acetohexamide; chlorpropamide; diabinese; glibenclamide; glipizide; glyburide; glimepiride; gliclazide; glipentide; gliquidone; glisolamide; tolazamide; and tolbutamide, and the like; (5) meglitinides such as repaglinide, metiglinide (GLUFAST) and nateglinide, and the like; (6) alpha glucoside hydrolase inhibitors such as acarbose; adiposine; camiglibose; emiglitate; miglitol; voglibose; pradimicin-Q; salbostatin; CKD-711; MDL-25,637; MDL-73,945; and MOR 14, and the like; (7) alpha-amylase inhibitors such as tendamistat, trestatin, and A1-3688, and the like; (8) insulin secreatagogues such as linogliride nateglinide, mitiglinide (GLUFAST), ID1101 A-4166, and the like; (9) fatty acid oxidation inhibitors, such as clomoxir, and etomoxir, and the like; (10) A2 antagonists, such as midaglizole; isaglidole; deriglidole; idazoxan; earoxan; and fluparoxan, and the like; (11) insulin or insulin mimetics, such as biota, LP-100, novarapid, insulin detemir, insulin lispro, insulin glargine, insulin zinc suspension (lente and ultralente); Lys-Pro insulin, GLP-1 (17-36), GLP-1 (73-7) (insulintropin); GLP-1 (7-36)-$NH_2$) exenatide/Exendin-4, Exenatide LAR, Linaglutide, AVE0010, CJC 1131, BIM51077, CS 872, TH0318, BAY-694326, GP010, ALBUGON (GLP-1 fused to albumin), HGX-007 (Epac agonist), S-23521, and compounds disclosed in WO 04/022004, WO 04/37859, and the like; (12) non-thiazolidinediones such as JT-501, and farglitazar (GW-2570/GI-262579), and the like; (13) PPARα/γ dual agonists such as AVE 0847, CLX-0940, GW-1536, GW1929, GW-2433, KRP-297, L-796449, LBM 642, LR-90, LY510919, MK-0767, ONO 5129, SB 219994, TAK-559, TAK-654, 677954 (GlaxoSmithkline), E-3030 (Eisai), LY510929 (Lilly), AK109 (Asahi), DRF2655 (Dr. Reddy), DRF8351 (Dr. Reddy), MC3002 (Maxocore), TY51501 (ToaEiyo), naveglitazar, muraglitizar, peliglitazar, tesaglitazar (GALIDA), reglitazar (JTT-501), chiglitazar, and those disclosed in WO 99/16758, WO 99/19313, WO 99/20614, WO 99/38850, WO 00/23415, WO 00/23417, WO 00/23445, WO 00/50414, WO 01/00579, WO 01/79150, WO 02/062799, WO 03/033481, WO 03/033450, WO 03/033453; and (14) other insulin sensitizing drugs; (15) VPAC2 receptor agonists; (16) GLK modulators, such as PSN105, RO 281675, RO 274375 and those disclosed in WO 03/015774, WO 03/000262, WO 03/055482, WO 04/046139, WO 04/045614, WO 04/063179, WO 04/063194, WO 04/050645, and the like; (17) retinoid modulators such as those disclosed in WO 03/000249; (18) GSK 3beta/GSK 3 inhibitors such as 4-[2-(2-bromophenyl)-4-(4-fluorophenyl-1H-imidazol-5-yl] pyridine, CT21022, CT20026, CT-98023, SB-216763, SB410111, SB-675236, CP-70949, XD4241 and those compounds disclosed in WO 03/037869, 03/03877, 03/037891, 03/024447, 05/000192, 05/019218 and the like; (19) glycogen phosphorylase (HGLPa) inhibitors, such as AVE 5688, PSN 357, GPi-879, those disclosed in WO 03/037864, WO 03/091213, WO 04/092158, WO 05/013975, WO 05/013981, US 2004/0220229, and JP 2004-196702, and the like; (20) ATP consumption promotors such as those disclosed in WO 03/007990; (21) fixed combinations of PPAR γ agonists and metformin such as AVANDAMET; (22) PPAR pan agonists such as GSK 677954; (23) GPR40 (G-protein coupled receptor 40) also called SNORF 55 such as BG 700, and those disclosed in WO 04/041266, 04/022551, 03/099793; (24) GPR119 (also called RUP3; SNORF 25) such as RUP3, HGPRBMY26, PFI 007, SNORF 25; (25) adenosine receptor 2B antagonists such as ATL-618, AT1-802, E3080, and the like; (26) carnitine palmitoyl transferase inhibitors such as ST 1327, and ST 1326, and the like; (27) Fructose 1,6-bisphosphohatase inhibitors such as CS-917, MB7803, and the like; (28) glucagon antagonists such as AT77077, BAY 694326, GW 4123X, NN2501, and those disclosed in WO 03/064404, WO 05/00781, US 2004/0209928, US 2004/029943, and the like; (30) glucose-6-phosphase inhibitors; (31) phosphoenolpyruvate carboxykinase (PEPCK) inhibitors; (32) pyruvate dehydrogenase kinase (PDK) activators; (33) RXR agonists such as MC1036, CS00018, JNJ 10166806, and those disclosed in WO 04/089916, U.S. Pat. No. 6,759,546, and the like; (34) SGLT inhibitors such as AVE 2268, KGT 1251, T1095/RWJ 394718; (35) BLX-1002; (36) alpha glucosidase inhibitors; (37) glucagon receptor agonists; and (38) glucokinase activators;

(b) lipid lowering agents such as (1) bile acid sequestrants such as, cholestyramine, colesevelem, colestipol, dialkylaminoalkyl derivatives of a cross-linked dextran; Colestid®; LoCholest®; and Questran®, and the like; (2) HMG-CoA reductase inhibitors such as atorvastatin, itavastatin, pitavastatin, fluvastatin, lovastatin, pravastatin, rivastatin, rosuvastatin, simvastatin, rosuvastatin (ZD-4522), and the like, particularly simvastatin; (3) HMG-CoA synthase inhibitors; (4) cholesterol absorption inhibitors such as FMVP4 (Forbes Medi-Tech), KT6-971 (Kotobuki Pharmaceutical), FM-VA12 (Forbes Medi-Tech), FM-VP-24 (Forbes Medi-Tech), stanol esters, beta-sitosterol, sterol glycosides such as tiqueside; and azetidinones such as ezetimibe, and those disclosed in WO 04/005247 and the like; (5) acyl coenzyme A-cholesterol acyl transferase (ACAT) inhibitors such as avasimibe, eflucimibe, pactimibe (KY505), SMP 797 (Sumitomo), SM32504 (Sumitomo), and those disclosed in WO 03/091216, and the like; (6) CETP inhibitors such as JTT 705 (Japan Tobacco), torcetrapib, CP 532,632, BAY63-2149 (Bayer), SC 591, SC 795, and the like; (7) squalene synthetase inhibitors; (8) anti-oxidants such as probucol, and the like; (9) PPARα agonists such as beclofibrate, benzafibrate, ciprofibrate, clofibrate, etofibrate, fenofibrate, gemcabene, and gemfibrozil, GW 7647, BM 170744 (Kowa), LY518674 (Lilly), GW590735 (GlaxoSmithkline), KRP-101 (Kyorin), DRF10945 (Dr. Reddy), NS-220/R1593 (Nippon Shinyaku/Roche, ST1929 (Sigma Tau) MC3001/MC3004 (MaxoCore Pharmaceuticals, gemcabene calcium, other fibric acid derivatives, such as Atromid®, Lopid® and Tricor®, and those disclosed in U.S. Pat. No. 6,548,538, and the like; (10) FXR receptor modulators such as GW 4064 (GlaxoSmithkline), SR 103912, QRX401, LN-6691 (Lion Bioscience), and those disclosed in WO 02/064125, WO 04/045511, and the like; (11) LXR receptor modulators such as GW 3965 (GlaxoSmithkline), T9013137, and XTC0179628 (X-Ceptor Therapeutics/Sanyo), and those disclosed in WO 03/031408, WO 03/063796, WO 04/072041, and the like; (12) lipoprotein synthesis inhibitors such as niacin; (13) renin angiotensin system inhibitors; (14) PPAR δ partial agonists, such as those disclosed in WO 03/024395; (15) bile acid reabsorption inhibitors, such as BARI 1453, SC435, PHA384640, S8921, AZD7706, and the like; and bile acid sequesterants such as colesevelam (WELCHOL/CHOLESTAGEL), (16) PPARδ agonists such as GW 501516 (Ligand, GSK), GW 590735, GW-0742 (GlaxoSmithkline), T659 (Amgen/Tularik), LY934 (Lilly), NNC610050 (Novo Nordisk) and those disclosed in WO97/28149, WO 01/79197, WO 02/14291, WO 02/46154, WO 02/46176, WO 02/076957, WO 03/016291, WO 03/033493, WO 03/035603, WO 03/072100, WO 03/097607, WO 04/005253, WO 04/007439, and JP10237049, and the like; (17) triglyceride synthesis inhibitors; (18) microsomal triglyceride transport (MTTP) inhibitors, such as implitapide, LAB687, JTT130 (Japan Tobacco), CP346086, and those disclosed in WO 03/072532, and the like; (19) transcription modulators; (20) squalene epoxidase inhibitors; (21) low density lipoprotein (LDL) receptor inducers; (22) platelet aggregation inhibitors; (23) 5-LO or FLAP inhibitors; and (24) niacin receptor agonists including HM74A receptor agonists; (25) PPAR modulators such as those disclosed in WO 01/25181, WO 01/79150, WO 02/79162, WO 02/081428, WO 03/016265, WO 03/033453; (26) niacin-bound chromium, as disclosed in WO 03/039535; (27) substituted acid derivatives disclosed in WO 03/040114; (28) infused HDL such as LUV/ETC-588 (Pfizer), APO-A1 Milano/ETC216 (Pfizer), ETC-642 (Pfizer), ISIS301012, D4F (Bruin Pharma), synthetic trimeric ApoA1, Bioral Apo A1 targeted to foam cells, and the like; (29) IBAT inhibitors such as BARI143/HMR145A/HMR1453 (Sanofi-Aventis, PHA384640E (Pfizer), S8921 (Shionogi) AZD7806 (AstrZeneca), AK105 (Asah Kasei), and the like; (30) Lp-PLA2 inhibitors such as SB480848 (GlaxoSmithkline), 659032 (GlaxoSmithkline), 677116 (GlaxoSmithkline), and the like;

(31) other agents which affect lipic composition including ETC1001/ESP31015 (Pfizer), ESP-55016 (Pfizer), AGI1067 (AtheroGenics), AC3056 (Amylin), AZD4619 (AstrZeneca); and (c) anti-hypertensive agents such as (1) diuretics, such as thiazides, including chlorthalidone, chlorthiazide, dichlorophenamide, hydroflumethiazide, indapamide, and hydrochlorothiazide; loop diuretics, such as bumetanide, ethacrynic acid, furosemide, and torsemide; potassium sparing agents, such as amiloride, and triamnterene; and aldosterone antagonists, such as spironolactone, epirenone, and the like; (2) beta-adrenergic blockers such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, propanolol, sotalol, tertatolol, tilisolol, and timolol, and the like; (3) calcium channel blockers such as amlodipine, aranidipine, azelnidipine, barnidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodepine, nisoldipine, nitrendipine, manidipine, pranidipine, and verapamil, and the like; (4) angiotensin converting enzyme (ACE) inhibitors such as benazepril; captopril; cilazapril; delapril; enalapril; fosinopril; imidapril; losinopril; moexipril; quinapril; quinaprilat; ramipril; perindopril; perindropril; quanipril; spirapril; tenocapril; trandolapril, and zofenopril, and the like; (5) neutral endopeptidase inhibitors such as omapatrilat, cadoxatril and ecadotril, fosidotril, sampatrilat, AVE7688, ER4030, and the like; (6) endothelin antagonists such as tezosentan, A308165, and YM62899, and the like; (7) vasodilators such as hydralazine, clonidine, minoxidil, and nicotinyl alcohol, and the like; (8) angiotensin II receptor antagonists such as candesartan, eprosartan, irbesartan, losartan, pratosartan, tasosartan, tehnisartan, valsartan, and EXP-3137, FI6828K, and RNH6270, and the like; (9) α/β adrenergic blockers as nipradilol, arotinolol and amosulalol, and the like; (10) alpha 1 blockers, such as terazosin, urapidil, prazosin, bunazosin, trimazosin, doxazosin, naftopidil, indoramin, WHIP 164, and XEN010, and the like; (11) alpha 2 agonists such as lofexidine, tiamenidine, moxonidine, rilmenidine and guanobenz, and the like; (12) aldosterone inhibitors, and the like; (13) angiopoietin-2-binding agents such as those disclosed in WO 03/030833; and (d) anti-obesity agents, such as (1) 5HT (serotonin) transporter inhibitors, such as paroxetine, fluoxetine, fenfluramine, fluvoxamine, sertraline, and imipramine, and those disclosed in WO 03/00663, as well as serotonin/noradrenaline re uptake inhibitors such as sibutramine (MERIDIA/REDUCTIL) and dopamine uptake inhibitor/Norepenephrine uptake inhibitors such as radafaxine hydrochloride, 353162 (GlaxoSmithkline), and the like; (2) NE (norepinephrine) transporter inhibitors, such as GW 320659, despiramine, talsupram, and nomifensine; (3) CB1 (cannabinoid-1 receptor) antagonist/inverse agonists, such as rimonabant (ACCOMPLIA Sanofi Synthelabo), SR-147778 (Sanofi Synthelabo), AVE1625 (Sanofi-Aventis), BAY 65-2520 (Bayer), SLV 319 (Solvay), SLV326 (Solvay), CP945598 (Pfizer), E-6776 (Esteve), O1691 (Organix), ORG14481 (Organon), VER24343 (Vernalis), NESS0327 (Univ of Sassari/Univ of Cagliari), and those disclosed in U.S. Pat. Nos. 4,973,587, 5,013,837, 5,081,122, 5,112,820, 5,292,736, 5,532,237, 5,624,941, 6,028,084, and 6,509,367; and WO 96/33159, WO97/29079, WO98/31227, WO 98/33765, WO98/37061, WO98/41519, WO98/43635, WO98/43636, WO99/02499, WO00/10967, WO00/10968, WO 01/09120, WO 01/58869, WO 01/64632, WO 01/64633, WO 01/64634, WO 01/70700, WO 01/96330, WO 02/076949, WO 03/006007, WO 03/007887, WO 03/020217, WO 03/026647, WO 03/026648, WO 03/027069, WO 03/027076, WO 03/027114, WO 03/037332, WO 03/040107, WO 04/096763, WO 04/111039, WO 04/111033, WO 04/111034, WO 04/111038, WO 04/013120, WO 05/000301, WO 05/016286, WO 05/066126 and EP-658546 and the like; (4) ghrelin agonists/antagonists, such as BVT81-97 (BioVitrum), RC1291 (Rejuvenon), SRD-04677 (Sumitomo), unacylated ghrelin (TheraTechnologies), and those disclosed in WO 01/87335, WO 02/08250, WO 05/012331, and the like; (5) H3 (histamine H3) antagonist/inverse agonists, such as thioperamide, 3-(1H-imidazol-4-yl) propyl N-(4-pentenyl)carbamate), clobenpropit, iodophenpropit, imoproxifan, GT2394 (Gliatech), and A331440, and those disclosed in WO 02/15905; and O-[3-(1H-imidazol-4-yl)propanol]carbamates (Kiec-Kononowicz, K. et al., Pharmazie, 55:349-55 (2000)), piperidine-containing histamine H3-receptor antagonists (Lazewska, D. et al., Pharmazie, 56:927-32 (2001), benzophenone derivatives and related compounds (Sasse, A. et al., Arch. Pharm. (Weinheim) 334: 45-52 (2001)), substituted N-phenylcarbamates (Reidemeister, S. et al., Pharmazie, 55:83-6 (2000)), and proxifan derivatives (Sasse, A. et al., J. Med. Chem. 43:3335-43 (2000)) and histamine H3 receptor modulators such as those disclosed in WO 03/024928 and WO 03/024929; (6) melanin-concentrating hormone 1 receptor (MCH1R) antagonists, such as T-226296 (Takeda), T71 (Takeda/Amgen), AMGN-608450, AMGN-503796 (Amgen), 856464 (GlaxoSmithkline), A224940 (Abbott), A798 (Abbott), ATC0175/AR224349 (Arena Pharmaceuticals), GW803430 (GlaxoSmithkine), NBI-1A (Neurocrine Biosciences), NGX-1 (Neurogen), SNP-7941 (Synaptic), SNAP9847 (Synaptic), T-226293 (Schering Plough), TPI-1361-17 (Saitama Medical School/University of California Irvine), and those disclosed WO 01/21169, WO 01/82925, WO 01/87834, WO 02/051809, WO 02/06245, WO 02/076929, WO 02/076947, WO 02/04433, WO 02/51809, WO 02/083134, WO 02/094799, WO 03/004027, WO 03/13574, WO 03/15769, WO 03/028641, WO 03/035624, WO 03/033476, WO 03/033480, WO 04/004611, WO 04/004726, WO 04/011438, WO 04/028459, WO 04/034702, WO 04/039764, WO 04/052848, WO 04/087680; and Japanese Patent Application Nos. JP 13226269, JP 1437059, JP2004315511, and the like; (7) MCH2R (melanin concentrating hormone 2R) agonist/antagonists; (8) NPY1 (neuropeptide Y Y1) antagonists, such as BMS205749, BIBP3226, J-115814, BIBO 3304, LY-357897, CP-671906, and GI-264879A; and those disclosed in U.S. Pat. No. 6,001,836; and WO 96/14307, WO 01/23387, WO 99/51600, WO 01/85690, WO 01/85098, WO 01/85173, and WO 01/89528; (9) NPY5 (neuropeptide Y Y5) antagonists, such as 152,804, S2367 (Shionogi), E-6999 (Esteve), GW-569180A, GW-594884A (GlaxoSmithkline), GW-587081X, GW-548118X; FR 235,208; FR226928, FR 240662, FR252384; 1229U91, GI-264879A, CGP71683A, C-75 (Fasgen) LY-377897, LY366377, PD-160170, SR-120562A, SR-120819A,S2367 (Shionogi), JCF-104, and H409/22; and those compounds disclosed in U.S. Pat. Nos. 6,140,354, 6,191,160, 6,258,837, 6,313,298, 6,326,375, 6,329,395, 6,335,345, 6,337,332, 6,329,395, and 6,340,683; and EP-01010691, EP-01044970, and FR252384; and PCT Publication Nos. WO 97/19682, WO 97/20820, WO 97/20821, WO 97/20822, WO 97/20823, WO 98/27063, WO 00/107409, WO 00/185714, WO 00/185730, WO 00/64880, WO 00/68197, WO 00/69849, WO 01/09120, WO 01/14376, WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/20488, WO 02/22592, WO 02/48152, WO 02/49648, WO 02/051806, WO 02/094789, WO 03/009845, WO 03/014083, WO 03/022849, WO 03/028726, WO 05/014592, WO 05/01493; and Norman et al., J. Med. Chem. 43:4288-4312 (2000); (10) leptin, such as recombinant human leptin (PEG-OB, Hoffman La Roche) and recombinant methionyl human leptin (Amgen); (11) leptin derivatives, such as those disclosed in U.S. Pat. Nos. 5,552,524; 5,552,523; 5,552,522; 5,521,283; and WO 96/23513; WO 96/23514; WO 96/23515; WO 96/23516; WO 96/23517; WO 96/23518; WO 96/23519; and WO 96/23520; (12) opioid antagonists, such as nalmefene (Revex®), 3-methoxynaltrexone, naloxone, and naltrexone; and those disclosed in WO 00/21509; (13) orexin antagonists, such as SB-334867-A (GlaxoSmithkline); and those disclosed in WO 01/96302, 01/68609, 02/44172, 02/51232, 02/51838, 02/089800, 02/090355, 03/023561, 03/032991, 03/037847, 04/004733, 04/026866, 04/041791, 04/085403, and the like; (14) BRS3 (bombesin receptor subtype 3) agonists; (15) CCK-A (cholecystokinin-A) agonists, such as AR-R 15849, GI 181771, JMV-180, A-71378, A-71623, PD170292, PD 149164, SR146131, SR125180, butabindide, and those disclosed in U.S. Pat. No. 5,739,106; (16) CNTF (ciliary neurotrophic factors), such as GI-181771 (Glaxo-SmithKline); SR146131 (Sanofi Synthelabo); butabindide; and PD170,292, PD 149164 (Pfizer); (17) CNTF derivatives, such as axokine (Regeneron); and those disclosed in WO 94/09134, WO 98/22128, and WO 99/43813; (18) GHS (growth hormone secretagogue receptor) agonists, such as NN703, hexarelin, MK-0677, SM-130686, CP-424,391, L-692,429 and L-163,255, and those disclosed in U.S. Pat. No. 6,358,951, U.S. Patent Application Nos. 2002/049196 and 2002/022637; and WO 01/56592, and WO 02/32888; (19) 5HT2c (serotonin receptor 2c) agonists, such as APD3546/AR10A (Arena Pharmaceuticals), ATH88651 (Athersys), ATH88740 (Athersys), BVT933 (Biovitrum/GSK), DPCA37215 (BMS), IK264; LY448100 (Lilly), PNU 22394; WAY 470 (Wyeth), WAY629 (Wyeth), WAY161503 (Biovitrum), R-1065, VR1065 (Vernalis/Roche) YM 348; and those disclosed in U.S. Pat. No. 3,914,250; and PCT Publications 01/66548, 02/36596, 02/48124, 02/10169, 02/44152; 02/51844, 02/40456, 02/40457, 03/057698, 05/000849, and the like; (20) Mc3r (melanocortin 3 receptor) agonists; (21) Mc4r (melanocortin 4 receptor) agonists, such as CHIR86036 (Chiron), CHIR915 (Chiron); ME-10142 (Melacure), ME-10145 (Melacure), HS-131 (Melacure), NBI72432 (Neurocrine Biosciences), NNC 70-619 (Novo Nordisk), TTP2435 (Transtech) and those disclosed in PCT Publications WO 99/64002, 00/74679, 01/991752, 01/0125192, 01/52880, 01/74844, 01/70708, 01/70337, 01/91752, 01/010842, 02/059095, 02/059107, 02/059108, 02/059117, 02/062766, 02/069095, 02/12166, 02/11715, 02/12178, 02/15909, 02/38544, 02/068387, 02/068388, 02/067869, 02/081430, 03/06604, 03/007949, 03/009847, 03/009850, 03/013509, 03/031410, 03/094918, 04/028453, 04/048345, 04/050610, 04/075823, 04/083208, 04/089951, 05/000339, and EP 1460069, and US 2005049269, and JP2005042839, and the like; (22) monoamine reuptake inhibitors, such as sibutratmine (Meridia®/Reductil®) and salts thereof, and those compounds disclosed in U.S. Pat. Nos. 4,746,680, 4,806,570, and 5,436,272, and U.S. Patent Publication No. 2002/0006964, and WO 01/27068, and WO 01/62341; (23) serotonin reuptake inhibitors, such as dexfenfluramine, fluoxetine, and those in U.S. Pat. No. 6,365,633, and WO 01/27060, and WO 01/162341; (24) GLP-1 (glucagon-like peptide 1) agonists; (25) Topiramate (Topimax®); (26) phytopharm compound 57 (CP 644,673); (27) ACC2 (acetyl-CoA carboxylase-2) inhibitors; (28) β3 (beta adrenergic receptor 3) agonists, such as rafebergron/AD9677/TAK677 (Dainippon/Takeda), CL-316,243, SB 418790, BRL-37344, L-796568, BMS-196085, BRL-35135A, CGP12177A, BTA-243, GRC1087 (Glenmark Pharmaceuticals) GW 427353 (solabegron hydrochloride), Trecadrine, Zeneca D7114, N-5984 (Nisshin Kyorin), LY-377604 (Lilly), KT07924 (Kissei), SR 59119A, and those disclosed in U.S. Pat. Nos. 5,705,515, 5,451,677; and WO94/18161, WO95/29159, WO97/46556, WO98/04526 WO98/32753, WO 01/74782, WO 02/32897, WO 03/014113, WO 03/016276, WO 03/016307, WO 03/024948, WO 03/024953, WO 03/037881, WO 04/108674, and the like; (29) DGAT1 (diacylglycerol acyltransferase 1) inhibitors; (30) DGAT2 (diacylglycerol acyltransferase 2) inhibitors; (31) FAS (fatty acid synthase) inhibitors, such as Cerulenin and C75; (32) PDE (phosphodiesterase) inhibitors, such as theophylline, pentoxifylline, zaprinast, sildenafil, anrinone, milrinone, cilostamide, rolipram, and cilomilast, as well as those described in WO 03/037432, WO 03/037899; (33) thyroid hormone, agonists, such as KB-2611 (KaroBioBMS), and those disclosed in WO 02/15845; and Japanese Patent Application No. JP 2000256190; (34) UCP-1 (uncoupling protein 1), 2, or 3 activators, such as phytanic acid, 4-[(E)-2-(5,6,7,8-tetrahydro-5,5,8,8-tetramethyl-2-napthalenyl)-1-propenyl]benzoic acid (TTNPB), and retinoic acid; and those disclosed in WO 99/00123; (35) acyl-estrogens, such as oleoyl-estrone, disclosed in del Mar-Grasa, M. et al., Obesity Research, 9:202-9 (2001); (36) glucocorticoid receptor antagonists, such as CP472555 (Pfizer), KB 3305, and those disclosed in WO 04/000869, WO 04/075864, and the like; (37) 11β HSD-1 (11-beta hydroxy steroid dehydrogenase type 1) inhibitors, such as BVT 3498 (AMG 331), BVT 2733, 3-(1-adamantyl)-4-ethyl-5-(ethylthio)-4H-1,2,4-triazole, 3-(1-adamantyl)-5-(3,4,5-trimethoxyphenyl)-4-methyl-4H-1,2,4-triazole, 3-adamantanyl-4,5,6,7,8,9,10,11,12,3a-decahydro-1,2,4-triazolo[4,3-a][11]annulene, and those compounds disclosed in WO 01/90091, 01/90090, 01/90092, 02/072084, 04/011410, 04/033427, 04/041264, 04/027047, 04/056744, 04/065351, 04/089415, 04/037251, and the like; (38) SCD-1 (stearoyl-CoA desaturase-1) inhibitors; (39) dipeptidyl peptidase IV (DPP-4) inhibitors, such as isoleucine thiazolidide, valine pyrrolidide, sitagliptin, saxagliptin, NVP-DPP728, LAF237 (vildagliptin), P93/01, TSL 225, TMC-2A/2B/2C, FE 999011, P9310/K364, VIP 0177, SDZ 274-444, GSK 823093, E 3024, SYR 322, TS021, SSR 162369, GRC 8200, K579, NN7201, CR 14023, PHX 1004, PHX 1149, PT-630, SK-0403; and the compounds disclosed in WO 02/083128, WO 02/062764, WO 02/14271, WO 03/000180, WO 03/000181, WO 03/000250, WO 03/002530, WO 03/002531, WO 03/002553, WO 03/002593, WO 03/004498, WO 03/004496, WO 03/005766, WO 03/017936, WO 03/024942, WO 03/024965, WO 03/033524, WO 03/055881, WO 03/057144, WO 03/037327, WO 04/041795, WO 04/071454, WO 04/0214870, WO 04/041273, WO 04/041820, WO 04/050658, WO 04/046106, WO 04/067509, WO 04/048532, WO 04/099185, WO 04/108730, WO 05/009956, WO 04/09806, WO 05/023762, US 2005/043292, and EP 1 258 476; (40) lipase inhibitors, such as tetrahydrolipstatin (orlistat/XENICAL), ATL962 (Alizyme/Takeda), GT389255 (Genzyme/Peptimmune) Triton WR1339, RHC80267, lipstatin, teasaponin, and diethylumbelliferyl phosphate, FL-386, WAY-121898, Bay-N-3176, valilactone, esteracin, ebelactone A, ebelactone B, and RHC 80267, and those disclosed in WO 01/77094, WO 04/111004, and U.S. Pat. Nos. 4,598,089, 4,452,813, 5,512,565, 5,391,571, 5,602,151, 4,405,644, 4,189,438, and 4,242,453, and the like; (41) fatty acid transporter inhibitors; (42) dicarboxylate transporter inhibitors; (43) glucose transporter inhibitors; and (44) phosphate transporter inhibitors; (45) anorectic bicyclic compounds such as 1426 (Aventis) and 1954 (Aventis), and the compounds disclosed in WO 00/18749, WO 01/32638, WO 01/62746, WO 01/62747, and WO 03/015769; (46) peptide YY and PYY agonists such as PYY336 (Nastech/Merck), AC162352 (IC Innovations/Curis/Amylin), TM30335/TM30338 (7™ Pharma), PYY336 (Emisphere Tehcnologies), pegylated peptide YY3-36, those disclosed in WO 03/026591, 04/089279, and the like; (47) lipid metabolism modulators such as maslinic acid, erythrodiol, ursolic acid uvaol, betulinic acid, betulin, and the like and compounds disclosed in WO 03/011267; (48) transcription factor modulators such as those disclosed in WO 03/026576; (49) Mc5r (melanocortin 5 receptor) modulators, such as those disclosed in WO 97/19952, WO 00/15826, WO 00/15790, US 20030092041, and the like; (50) Brain derived neutotropic factor (BDNF), (51) Mc1r (melanocortin 1 receptor modulators such as LK-184 (Proctor & Gamble), and the like; (52) 5HT6 antagonists such as BVT74316 (BioVitrum), BVT5182c (BioVitrum), E-6795 (Esteve), E-6814 (Esteve), SB399885 (GlaxoSmithkline), SB271046 (GlaxoSmithkline), RO-046790 (Roche), and the like; (53) fatty acid transport protein 4 (FATP4); (54) acetyl-CoA carboxylase (ACC) inhibitors such as CP640186, CP610431, CP640188 (Pfizer); (55) C-terminal growth hormone fragments such as AOD9604 (Monash Univ/Metabolic Pharmaceuticals), and the like; (56) oxyntomodulin; (57) neuropeptide FF receptor antagonists such as those disclosed in WO 04/083218, and the like; (58) amylin agonists such as Symlin/pramlintide/AC137 (Amylin); (59) Hoodia and trichocaulon extracts; (60) BVT74713 and other gut lipid appetite suppressants; (61) dopamine agonists such as bupropion (WELLBUTRIN/GlaxoSmithkline); (62) zonisamide (ZONEGRAN/Dainippon/Elan), and the like.

Specific compounds of use in combination with a compound of the present invention include: simvastatin, mevastatin, ezetimibe, atorvastatin, sitagliptin, metformin, sibutramine, orlistat, Qnexa, topiramate, naltrexone, bupriopion, phentermine, and losartan, losartan with hydrochlorothiazide. Specific CB1 antagonists/inverse agonists of use in combination with a compound of the present invention include: those described in WO03/077847, including: N-[3-(4-chlorophenyl)-2(S)-phenyl-1(S)-methylpropyl]-2-(4-trifluoromethyl-2-pyrimidyloxy)-2-methylpropanamide, N-[3-(4-chlorophenyl)-2-(3-cyanophenyl)-1-methylpropyl]-2-(5-trifluoromethyl-2-pyridyloxy)-2-methylpropanamide, N-[3-(4-chlorophenyl)-2-(5-chloro-3-pyridyl)-1-methylpropyl]-2-(5-trifluoromethyl-2-pyridyloxy)-2-methylpropanamide, and pharmaceutically acceptable salts thereof; as well as those in WO05/000809, which includes the following: 3-{1-[bis(4-chlorophenyl)methyl]azetidin-3-ylidene}-3-(3,5-difluorophenyl)-2,2-dimethylpropanenitrile, 1-{1-[1-(4-chlorophenyl)pentyl]azetidin-3-yl}-1-(3,5-difluorophenyl)-2-methylpropan-2-ol. 3-((S)-(4-chlorophenyl) {3-[(1S)-1-(3,5-difluorophenyl)-2-hydroxy-2-methylpropyl]azetidin-1-yl}methyl)benzonitrile, 3-((S)-(4-chlorophenyl) {3-[(1S)-1-(3,5-difluorophenyl)-2-fluoro-2-methylpropyl]azetidin-1-yl}methyl)benzonitrile, 3-((4-chlorophenyl) {3-[1-(3,5-difluorophenyl)-2,2-dimethylpropyl]azetidin-1-yl}methyl) benzonitrile, 3-((1S)-1-{1-[(S)-(3-cyanophenyl)(4-cyanophenyl)methyl]azetidin-3-yl}-2-fluoro-2-methylpropyl)-5-fluorobenzonitrile, 3-[(S)-(4-chlorophenyl)(3-{(1S)-2-fluoro-1-[3-fluoro-5-(4H-1,2,4-triazol-4-yl)phenyl]-2-methylpropyl}azetidin-1-yl)methyl]benzonitrile, and 5-((4-chlorophenyl) {3-[(1S)-1-(3,5-difluorophenyl)-2-fluoro-2-methylpropyl]azetidin-1-yl}methyl)thiophene-3-carbonitrile, and pharmaceutically acceptable salts thereof; as well as: 3-[(S)-(4-chlorophenyl)(3-{(1S)-2-fluoro-1-[3-fluoro-5-(5-oxo-4,5-dihydro-1,3,4-oxadiazol-2-yl)phenyl]-2-methylpropyl}azetidin-1-yl)methyl]benzonitrile, 3-[(S)-(4-chlorophenyl)(3-{(1S)-2-fluoro-1-[3-fluoro-5-(1,3,4-oxadiazol-2-yl)phenyl]-2-methylpropyl}azetidin-1-yl)methyl]benzonitrile, 3-[(S)-(3-{(1S)-1-[3-(5-amino-1,3,4-oxadiazol-2-yl)-5-fluorophenyl]-2-fluoro-2-methylpropyl}azetidin-1-yl)(4-chlorophenyl)methyl]benzonitrile, 3-[(S)-(4-cyanophenyl)(3-{(1S)-2-fluoro-1-[3-fluoro-5-(5-oxo-4,5-dihydro-1,3,4-oxadiazol-2-yl)phenyl]-2-methylpropyl}azetidin-1-yl)methyl]benzonitrile, 3-[(S)-(3-{(1S)-1-[3-(5-amino-1,3,4-oxadiazol-2-yl)-5-fluorophenyl]-2-fluoro-2-methylpropyl}azetidin-1-yl)(4-cyanophenyl)methyl]benzonitrile, 3-[(S)-(4-cyanophenyl)(3-{(1S)-2-fluoro-1-[3-fluoro-5-(1,3,4-oxadiazol-2-yl)phenyl]-2-methylpropyl}azetidin-1-yl)methyl]benzonitrile, 3-[(S)-(4-chlorophenyl)(3-{(1S)-2-fluoro-1-[3-fluoro-5-(1,2,4-oxadiazol-3-yl)phenyl]-2-methylpropyl}azetidin-1-yl)methyl]benzonitrile, 3-[(1S)-1-(1-{(S)-(4-cyanophenyl)[3-(1,2,4-oxadiazol-3-yl)phenyl]-methyl}azetidin-3-yl)-2-fluoro-2-methylpropyl]-5-fluorobenzonitrile, 5-(3-{1-[1-(diphenylmethyl)azetidin-3-yl]-2-fluoro-2-methylpropyl}-5-fluorophenyl)-1H-tetrazole, 5-(3-{1-[1-(diphenylmethyl)azetidin-3-yl]-2-fluoro-2-methylpropyl}-5-fluorophenyl)-1-methyl-1H-tetrazole, 5-(3-{1-[1-(diphenylmethyl)azetidin-3-yl]-2-fluoro-2-methylpropyl}-5-fluorophenyl)-2-methyl-2H-tetrazole, 3-[(4-chlorophenyl)(3-{2-fluoro-1-[3-fluoro-5-(2-methyl-2H-tetrazol-5-yl)phenyl]-2-methylpropyl}azetidin-1-yl)methyl]benzonitrile, 3-[(4-chlorophenyl)(3-{2-fluoro-1-[3-fluoro-5-(1-methyl-1H-tetrazol-5-yl)phenyl]-2-methylpropyl}azetidin-1-yl)methyl]benzonitrile, 3-[(4-cyanophenyl)(3-{2-fluoro-1-[3-fluoro-5-(1-methyl-1H-tetrazol-5-yl)phenyl]-2-methylpropyl}azetidin-1-yl)methyl]benzonitrile, 3-[(4-cyanophenyl)(3-{2-fluoro-1-[3-fluoro-5-(2-methyl-2H-tetrazol-5-yl)phenyl]-2-methylpropyl}azetidin-1-yl)methyl]benzonitrile, 5-{3-[(S)-{3-[(1S)-1-(3-bromo-5-fluorophenyl)-2-fluoro-2-methylpropyl]azetidin-1-yl}(4-chlorophenyl)methyl]phenyl}-1,3,4-oxadiazol-2(3H)-one, 3-[(1S)-1-(1-{(S)-(4-chlorophenyl)[3-(5-oxo-4,5-dihydro-1,3,4-oxadiazol-2-yl)phenyl]methyl}azetidin-3-yl)-2-fluoro-2-methylpropyl]-5-fluorobenzonitrile, 3-[(1S)-1-(1-{(S)-(4-cyanophenyl)[3-(5-oxo-4,5-dihydro-1,3,4-oxadiazol-2-yl)phenyl]methyl}azetidin-3-yl)-2-fluoro-2-methylpropyl]-5-fluorobenzonitrile, 3-[(1S)-1-(1-{(S)-(4-cyanophenyl)[3-(1,3,4-oxadiazol-2-yl)phenyl]methyl}azetidin-3-yl)-2-fluoro-2-methylpropyl]-5-fluorobenzonitrile, 3-[(is)-1-(1-{(S)-(4-chlorophenyl)[3-(1,3,4-oxadiazol-2-yl)phenyl]methyl}azetidin-3-yl)-2-fluoro-2-methylpropyl]-5-fluorobenzonitrile, 3-((1S)-1-{1-[(S)-[3-(5-amino-1,3,4-oxadiazol-2-yl)phenyl](4-chlorophenyl)methyl]azetidin-3-yl}-2-fluoro-2-methylpropyl)-5-fluorobenzonitrile, 3-((1S)-1-{1-[(S)-[3-(5-amino-1,3,4-oxadiazol-2-yl)phenyl](4-cyanophenyl)methyl]azetidin-3-yl}-2-fluoro-2-methylpropyl)-5-fluorobenzonitrile, 3-[(1S)-1-(1-{(S)-(4-cyanophenyl)[3-(1,2,4-oxadiazol-3-yl)phenyl]methyl}azetidin-3-yl)-2-fluoro-2-methylpropyl]-5-fluorobenzonitrile, 3-[(is)-1-(1-{(S)-(4-chlorophenyl)[3-(1,2,4-oxadiazol-3-yl)phenyl]methyl}azetidin-3-yl)-2-fluoro-2-methylpropyl]-5-fluorobenzonitrile, 5-[3-((S)-(4-chlorophenyl) {3-[(1S)-1-(3,5-difluorophenyl)-2-fluoro-2-methylpropyl]azetidin-1-yl}methyl)phenyl]-1,3,4-oxadiazol-2(3H)-one, 5-[3-((S)-(4-chlorophenyl) {3-[(is)-1-(3,5-difluorophenyl)-2-fluoro-2-methylpropyl]azetidin-1-yl}methyl)phenyl]-1,3,4-oxadiazol-2(3H)-one, 4-{(S)-{3-[(1S)-1-(3,5-difluorophenyl)-2-fluoro-2-methylpropyl]

azetidin-1-yl}[3-(5-oxo-4,5-dihydro-1,3,4-oxadiazol-2-yl) phenyl]methyl}-benzonitrile, and pharmaceutically acceptable salts thereof.

Specific NPY5 antagonists of use in combination with a compound of the present invention include: 3-oxo-N-(5-phenyl-2-pyrazinyl)-spiro[isobenzofuran-1(3H), 4'-piperidine]-1'-carboxamide, 3-oxo-N-(7-trifluoromethylpyrido[3,2-b] pyridin-2-yl)spiro-[isobenzofuran-1(3H), 4'-piperidine]-1'-carboxamide, N-[5-(3-fluorophenyl)-2-pyrimidinyl]-3-oxospiro-[isobenzofuran-1(3H), 4'-piperidine]-1'-carboxamide, trans-3'-oxo-N-(5-phenyl-2-pyrimidinyl)spiro [cyclohexane-1,1'(3'H)-isobenzofuran]-4-carboxamide, trans-3'-oxo-N-[1-(3-quinolyl)-4-imidazolyl]spiro[cyclohexane-1,1'(3'H)-isobenzofuran]-4-carboxamide, trans-3-oxo-N-(5-phenyl-2-pyrazinyl)spiro[4-azaiso-benzofuran-1 (3H), 1'-cyclohexane]-4'-carboxamide, trans-N-[5-(3-fluorophenyl)-2-pyrimidinyl]-3-oxospiro[5-azaisobenzofuran-1(3H), 1'-cyclohexane]-4'-carboxamide, trans-N-[5-(2-fluorophenyl)-2-pyrimidinyl]-3-oxospiro[5-azaisobenzofuran-1(3H), 1'-cyclohexane]-4'-carboxamide, trans-N-[1-(3,5-difluorophenyl)-4-imidazolyl]-3-oxospiro [7-azaisobenzofuran-1(3H), 1'-cyclohexane]-4'-carboxamide, trans-3-oxo-N-(1-phenyl-4-pyrazolyl)spiro[4-azaisobenzofuran-1(3H), 1'-cyclohexane]-4'-carboxamide, trans-N-[1-(2-fluorophenyl)-3-pyrazolyl]-3-oxospiro[6-azaisobenzofuran-1(3H), 1'-cyclohexane]-4'-carboxamide, trans-3-oxo-N-(1-phenyl-3-pyrazolyl)spiro[6-azaisobenzofuran-1(3H), 1'-cyclohexane]-4'-carboxamide, trans-3-oxo-N-(2-phenyl-1,2,3-triazol-4-yl)spiro[6-azaisobenzofuran-1 (3H),1'-cyclohexane]-4'-carboxamide, and pharmaceutically acceptable salts and esters thereof.

Specific ACC-1/2 inhibitors of use in combination with a compound of the present invention include: 1'-[(4,8-dimethoxyquinolin-2-yl)carbonyl]-6-(1H-tetrazol-5-yl) spiro[chroman-2,4'-piperidin]-4-one; (5-{1'-[(4,8-dimethoxyquinolin-2-yl)carbonyl]-4-oxospiro[chroman-2,4'-piperidin]-6-yl}-2H-tetrazol-2-yl)methyl pivalate; 5-{1'-[(8-cyclopropyl-4-methoxyquinolin-2-yl)carbonyl]-4-oxospiro [chroman-2,4'-piperidin]-6-yl}nicotinic acid; 1'-(8-methoxy-4-morpholin-4-yl-2-naphthoyl)-6-(1H-tetrazol-5-yl)spiro[chroman-2,4'-piperidin]-4-one; and 1'-[(4-ethoxy-8-ethylquinolin-2-yl)carbonyl]-6-(1H-tetrazol-5-yl)spiro [chroman-2,4'-piperidin]-4-one; and pharmaceutically acceptable salts and esters thereof.

Specific MCH1R antagonist compounds of use in combination with a compound of the present invention include: 1-{4-[(1-ethylazetidin-3-yl)oxy]phenyl}-4-[(4-fluorobenzyl)oxy]pyridin-2(1H)-one, 4-[(4-fluorobenzyl)oxy]-1-{4-[(1-isopropylazetidin-3-yl)oxy]phenyl}pyridin-2(1H)-one, 1-[4-(azetidin-3-yloxy)phenyl]-4-[(5-chloropyridin-2-yl) methoxy]pyridin-2(1H)-one, 4-[(5-chloropyridin-2-yl)methoxy]-1-{4-[(1-ethylazetidin-3-yl)oxy]phenyl}pyridin-2 (1H)-one, 4-[(5-chloropyridin-2-yl)methoxy]-1-{4-[(1-propylazetidin-3-yl)oxy]phenyl}pyridin-2(1H)-one, and 4-[(5-chloropyridin-2-yl)methoxy]-1-(4-{[(2S)-1-ethylazetidin-2-yl]methoxy}phenyl)pyridin-2(1H)-one, or a pharmaceutically acceptable salt thereof.

Specific DP-IV inhibitors of use in combination with a compound of the present invention are selected from 7-[(3R)-3-amino-4-(2,4,5-trifluorophenyl)butanoyl]-3-(trifluoromethyl)-5,6,7,8-tetrahydro-1,2,4-triazolo[4,3-a]pyrazine. In particular, the compound of formula I is favorably combined with 7-[(3R)-3-amino-4-(2,4,5-trifluorophenyl)butanoyl]-3-(trifluoromethyl)-5,6,7,8-tetrahydro-1,2,4-triazolo[4,3-a] pyrazine, and pharmaceutically acceptable salts thereof.

Specific H3 (histamine H3) antagonists/inverse agonists of use in combination with a compound of the present invention include: those described in WO05/077905, including: 3-{4-[(1-cyclobutyl-4-piperidinyl)oxy]phenyl}-2-ethylpyrido[2, 3-d]-pyrimidin-4(3H)-one, 3-{4-[(1-cyclobutyl-4-piperidinyl)oxy]phenyl}-2-methylpyrido[4,3-d]pyrimidin-4(3H)-one, 2-ethyl-3-(4-{3-[(3S)-3-methylpiperidin-1-yl] propoxy}phenyl)pyrido[2,3-d]pyrimidin-4(3H)-one 2-methyl-3-(4-{3-[(3S)-3-methylpiperidin-1-yl] propoxy}phenyl)pyrido[4,3-d]pyrimidin-4(3H)-one, 3-{4-[(1-cyclobutyl-4-piperidinyl)oxy]phenyl}-2,5-dimethyl-4 (3H)-quinazolinone, 3-{4-[(1-cyclobutyl-4-piperidinyl)oxy] phenyl}-2-methyl-5-trifluoromethyl-4(3H)-quinazolinone, 3-{4-[(1-cyclobutyl-4-piperidinyl)oxy]phenyl}-5-methoxy-2-methyl-4(3H)-quinazolinone, 3-{4-[(1-cyclobutylpiperidin-4-yl)oxy]phenyl}-5-fluoro-2-methyl-4(3H)-quinazolinone, 3-{4-[(1-cyclobutylpiperidin-4-yl)oxy]phenyl}-7-fluoro-2-methyl-4(3H)-quinazolinone, 3-{4-[(1-cyclobutylpiperidin-4-yl)oxy]phenyl}-6-methoxy-2-methyl-4(3H)-quinazolinone, 3-{4-[(1-cyclobutylpiperidin-4-yl)oxy]phenyl}-6-fluoro-2-methyl-4(3H)-quinazolinone, 3-{4-[(1-cyclobutylpiperidin-4-yl)oxy]phenyl}-8-fluoro-2-methyl-4(3H)-quinazolinone, 3-{4-[(1-cyclopentyl-4-piperidinyl)oxy]phenyl}-2-methylpyrido[4,3-d]pyrimidin-4 (3H)-one, 3-{4-[(1-cyclobutylpiperidin-4-yl)oxy]phenyl}-6-fluoro-2-methylpyrido[3,4-d]pyrimidin-4(3H)-one, 3-{4-[(1-cyclobutyl-4-piperidinyl)oxy]phenyl}-2-ethylpyrido[4, 3-d]pyrimidin-4(3H)-one, 6-methoxy-2-methyl-3-{4-[3-(1-piperidinyl)propoxy]phenyl}pyrido[3,4-d]pyrimidin-4(3H)-one, 6-methoxy-2-methyl-3-{4-[3-(1-pyrrolidinyl)propoxy] phenyl}pyrido[3,4-d]pyrimidin-4(3H)-one, 2,5-dimethyl-3-{4-[3-(1-pyrrolidinyl)propoxy]phenyl}-4(3H)-quinazolinone, 2-methyl-3-{4-[3-(1-pyrrolidinyl)propoxy] phenyl}-5-trifluoromethyl-4(3H)-quinazolinone, 5-fluoro-2-methyl-3-{4-[3-(1-piperidinyl)propoxy]phenyl}-4(3H)-quinazolinone, 6-methoxy-2-methyl-3-{4-[3-(1-piperidinyl) propoxy]phenyl}-4(3H)-quinazolinone, 5-methoxy-2-methyl-3-(4-{3-[(3S)-3-methylpiperidin-1-yl] propoxy}phenyl)-4(3H)-quinazolinone, 7-methoxy-2-methyl-3-(4-{3-[(3S)-3-methylpiperidin-1-yl] propoxy}phenyl)-4(3H)-quinazolinone, 2-methyl-3-(4-{3-[(3S)-3-methylpiperidin-1-yl]propoxy}phenyl)pyrido[2,3-d]pyrimidin-4(3H)-one, 5-fluoro-2-methyl-3-(4-{3-[(2R)-2-methylpyrrolidin-1-yl]propoxy}phenyl)-4(3H)-quinazolinone, 2-methyl-3-(4-{3-[(2R)-2-methylpyrrolidin-1-yl]propoxy}phenyl)pyrido[4,3-d]pyrimidin-4(3H)-one, 6-methoxy-2-methyl-3-(4-{3-[(2R)-2-methylpyrrolidin-1-yl]propoxy}phenyl)-4(3H)-quinazolinone, 6-methoxy-2-methyl-3-(4-{3-[(2S)-2-methylpyrrolidin-1-yl] propoxy}phenyl)-4(3H)-quinazolinone, and pharmaceutically acceptable salts thereof.

Specific CCK1R agonists of use in combination with a compound of the present invention include: 3-(4-{[1-(3-ethoxyphenyl)-2-(4-methylphenyl)-1H-imidazol-4-yl]carbonyl}-1-piperazinyl)-1-naphthoic acid; 3-(4-{[1-(3-ethoxyphenyl)-2-(2-fluoro-4-methylphenyl)-1H-imidazol-4-yl] carbonyl}-1-piperazinyl)-1-naphthoic acid; 3-(4-{[1-(3-ethoxyphenyl)-2-(4-fluorophenyl)-1H-imidazol-4-yl] carbonyl}-1-piperazinyl)-1-naphthoic acid; 3-(4-{[1-(3-ethoxyphenyl)-2-(2,4-difluorophenyl)-1H-imidazol-4-yl] carbonyl}-1-piperazinyl)-1-naphthoic acid; and 3-(4-{[1-(2, 3-dihydro-1,4-benzodioxin-6-yl)-2-(4-fluorophenyl)-1H-imidazol-4-yl]carbonyl}-1-piperazinyl)-1-naphthoic acid; and pharmaceutically acceptable salts thereof.

Specific MC4R agonists of use in combination with a compound of the present invention include: 1) (5S)-1'-{[(3R,4R)-1-tert-butyl-3-(2,3,4-trifluorophenyl)piperidin-4-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'- piperidine]; 2) (5R)-1'-{[(3R,4R)-1-tert-butyl-3-(2,3,4-trifluorophenyl)-piperidin-4-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 3) 2-(1'-{[(3S,4R)-1-tert-butyl-4-(2,4-difluorophenyl)pyrrolidin-3-yl]carbonyl}-3-chloro-2-methyl-5H-spiro[furo[3,4-b]pyridine-7,4'-piperidin]-5-yl)-2-methylpropanenitrile; 4) 1'-{[(3S,4R)-1-tert-butyl-4-(2,4-difluorophenyl)pyrrolidin-3-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 5) N-[(3R,4R)-3-({3-chloro-2-methyl-5-[1-methyl-1-(1-methyl-1H-1,2,4-triazol-5-yl)ethyl]-1'H,5H-spiro[furo-[3,4-b]pyridine-7,4'-piperidin]-1'-yl}carbonyl)-4-(2,4-difluorophenyl)-cyclopentyl]-N-methyltetrahydro-2H-pyran-4-amine; 6) 2-[3-chloro-1'-({(1R,2R)-2-(2,4-difluorophenyl)-4-[methyl(tetrahydro-2H-pyran-4-yl)amino]-cyclopentyl}-carbonyl)-2-methyl-5H-spiro[furo[3,4-b]pyridine-7,4'-piperidin]-5-yl]-2-methyl-propane-nitrile; and pharmaceutically acceptable salts thereof.

"Obesity" is a condition in which there is an excess of body fat. The operational definition of obesity is based on the Body Mass Index (BMI), calculated as body weight per height in meters squared (kg/$m^2$). "Obesity" refers to a condition whereby an otherwise healthy subject has a Body Mass Index (BMI) greater than or equal to 30 kg/$m^2$, or a condition whereby a subject with at least one co-morbidity has a BMI greater than or equal to 27 kg/$m^2$. An "obese subject" is an otherwise healthy subject with a Body Mass Index (BMI) greater than or equal to 30 kg/$m^2$ or a subject with at least one co-morbidity with a BMI greater than or equal to 27 kg/$m^2$. A "subject at risk for obesity" is an otherwise healthy subject with a BMI of 25 kg/$m^2$ to less than 30 kg/$m^2$ or a subject with at least one co-morbidity with a BMI of 25 kg/$m^2$ to less than 27 kg/$m^2$.

The increased risks associated with obesity occur at a lower Body Mass Index (BMI) in Asians. In Asian countries, including Japan, "obesity" refers to a condition whereby a subject with at least one obesity-induced or obesity-related co-morbidity that requires weight reduction or that would be improved by weight reduction, has a BMI greater than or equal to 25 kg/$m^2$. In Asian countries, including Japan, an "obese subject" refers to a subject with at least one obesity-induced or obesity-related co-morbidity that requires weight reduction or that would be improved by weight reduction, with a BMI greater than or equal to 25 kg/$m^2$. In Asian countries, a "subject at risk of obesity" is a subject with a BMI of greater than 23 kg/$m^2$ to less than 25 kg/$m^2$.

As used herein, the term "obesity" is meant to encompass all of the above definitions of obesity.

Obesity-induced or obesity-related co-morbidities include, but are not limited to, diabetes, non-insulin dependent diabetes mellitus—type 2, impaired glucose tolerance, impaired fasting glucose, insulin resistance syndrome, dyslipidemia, hypertension, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, diabetes mellitus, and other obesity-related conditions.

"Treatment" (of obesity and obesity-related disorders) refers to the administration of the compounds of the present invention to reduce or maintain the body weight of an obese subject. One outcome of treatment may be reducing the body weight of an obese subject relative to that subject's body weight immediately before the administration of the compounds of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in patients in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

"Prevention" (of obesity and obesity-related disorders) refers to the administration of the compounds of the present invention to reduce or maintain the body weight of a subject at risk of obesity. One outcome of prevention may be reducing the body weight of a subject at risk of obesity relative to that subject's body weight immediately before the administration of the compounds of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type II diabetes, polycystic ovarian disease, cardiovascular diseases, osteoarthritis, dermatological disorders, hypertension, insulin resistance, hypercholesterolemia, hypertriglyceridemia, and cholelithiasis.

The obesity-related disorders herein are associated with, caused by, or result from obesity. Examples of obesity-related disorders include overeating and bulimia, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovarian disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia. Further examples of obesity-related disorders are metabolic syndrome, also known as syndrome X, insulin resistance syndrome, sexual and reproductive dysfunction, such as infertility, hypogonadism in males and hirsutism in females, gastrointestinal motility disorders, such as obesity-related gastro-esophageal reflux, respiratory disorders, such as obesity-hypoventilation syndrome (Pickwickian syndrome), cardiovascular disorders, inflammation, such as systemic inflammation of the vasculature, arteriosclerosis, hypercholesterolemia, hyperuricaemia, lower back pain, gallbladder disease, gout, and kidney cancer. The compounds of the present invention are also useful for reducing the risk of secondary outcomes of obesity, such as reducing the risk of left ventricular hypertrophy.

The compounds of formula I are also useful for treating or preventing obesity and obesity-related disorders in cats and dogs. As such, the term "mammal" includes companion animals such as cats and dogs.

The term "diabetes," as used herein, includes both insulin-dependent diabetes mellitus (IDDM, also known as type I diabetes) and non-insulin-dependent diabetes mellitus (NIDDM, also known as Type II diabetes). Type I diabetes, or insulin-dependent diabetes, is the result of an absolute deficiency of insulin, the hormone which regulates glucose utilization. Type II diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type II diabetics are also obese. The compounds of the present invention are useful for treating both Type I and Type II diabetes. The compounds are especially effective for treating Type II diabetes. The compounds of the present invention are also useful for treating and/or preventing gestational diabetes mellitus.

It will be appreciated that for the treatment or prevention of migraine, a compound of the present invention may be used in conjunction with other anti-migraine agents, such as ergotamines or 5-$HT_1$ agonists, especially sumatriptan, naratriptan, zolmatriptan or rizatriptan.

It will be appreciated that for the treatment of depression or anxiety, a compound of the present invention may be used in conjunction with other anti-depressant or anti-anxiety agents.

Suitable classes of anti-depressant agents include norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists and atypical anti-depressants.

Suitable norepinephrine reuptake inhibitors include tertiary amine tricyclics and secondary amine tricyclics. Suitable examples of tertiary amine tricyclics include: amitriptyline, clomipramine, doxepin, imipramine and trimipramine, and pharmaceutically acceptable salts thereof. Suitable examples of secondary amine tricyclics include: amoxapine, desipramine, maprotiline, nortriptyline and protriptyline, and pharmaceutically acceptable salts thereof.

Suitable selective serotonin reuptake inhibitors include: fluoxetine, fluvoxamine, paroxetine, imipramine and sertraline, and pharmaceutically acceptable salts thereof.

Suitable monoamine oxidase inhibitors include: isocarboxazid, phenelzine, tranylcypromine and selegiline, and pharmaceutically acceptable salts thereof.

Suitable reversible inhibitors of monoamine oxidase include: moclobemide, and pharmaceutically acceptable salts thereof.

Suitable serotonin and noradrenaline reuptake inhibitors of use in the present invention include: venlafaxine, and pharmaceutically acceptable salts thereof.

Suitable CRF antagonists include those compounds described in International Patent Specification Nos. WO 94/13643, 94/13644, 94/13661, 94/13676 and 94/13677. Still further, neurokinin-1 (NK-1) receptor antagonists may be favorably employed with the CB1 receptor modulators of the present invention. NK-1 receptor antagonists of use in the present invention are fully described in the art. Specific neurokinin-1 receptor antagonists of use in the present invention include: (±)-(2R3R,2S3S)-N-{[2-cyclopropoxy-5-(trifluoromethoxy)-phenyl]methyl}-2-phenylpiperidin-3-amine; 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl) morpholine; aperpitant; CJ17493; GW597599; GW679769; R673; RO67319; R1124; R1204; SSR146977; SSR240600; T-2328; and T2763; or a pharmaceutically acceptable salts thereof.

Suitable atypical anti-depressants include: bupropion, lithium, nefazodone, trazodone and viloxazine, and pharmaceutically acceptable salts thereof.

Suitable classes of anti-anxiety agents include benzodiazepines and 5-$HT_{1A}$ agonists or antagonists, especially 5-$HT_{1A}$ partial agonists, and corticotropin releasing factor (CRF) antagonists. Suitable benzodiazepines include: alprazolam, chlordiazepoxide, clonazepam, chlorazepate, diazepam, halazepam, lorazepam, oxazepam and prazepam, and pharmaceutically acceptable salts thereof. Suitable 5-$HT_{1A}$ receptor agonists or antagonists include, in particular, the 5-$HT_{1A}$ receptor partial agonists buspirone, flesinoxan, gepirone and ipsapirone, and pharmaceutically acceptable salts thereof. Suitable corticotropin releasing factor (CRF) antagonists include those previously discussed herein.

As used herein, the term "substance abuse disorders" includes substance dependence or abuse with or without physiological dependence. The substances associated with these disorders are: alcohol, amphetamines (or amphetamine-like substances), caffeine, cannabis, cocaine, hallucinogens, inhalants, marijuana, nicotine, opioids, phencyclidine (or phencyclidine-like compounds), sedative-hypnotics or benzodiazepines, and other (or unknown) substances and combinations of all of the above.

In particular, the term "substance abuse disorders" includes drug withdrawal disorders such as alcohol withdrawal with or without perceptual disturbances; alcohol withdrawal delirium; amphetamine withdrawal; cocaine withdrawal; nicotine withdrawal; opioid withdrawal; sedative, hypnotic or anxiolytic withdrawal with or without perceptual disturbances; sedative, hypnotic or anxiolytic withdrawal delirium; and withdrawal symptoms due to other substances. It will be appreciated that reference to treatment of nicotine withdrawal includes the treatment of symptoms associated with smoking cessation.

Other "substance abuse disorders" include substance-induced anxiety disorder with onset during withdrawal; substance-induced mood disorder with onset during withdrawal; and substance-induced sleep disorder with onset during withdrawal.

In particular, compounds of structural formula I are useful for aiding in stopping consumption of tobacco and are useful in treating nicotine dependence and nicotine withdrawal. The compounds of formula I produce in consumers of nicotine, such as tobacco smokers, a total or partial abstinence from smoking. Further, withdrawal symptoms are lessened and the weight gain that generally accompanies quitting tobacco consumption is reduced or nonexistent. For smoking cessation, the compound of form I may be used in combination with a nicotine agonist or a partial nicotine agonist, including varenicline and selective alpha-4 beta 2 nicotinic partial agonists such as SSR 591813, or a monoamine oxidase inhibitor (MAOI), or another active ingredient demonstrating efficacy in aiding cessation of tobacco consumption; for example, an antidepressant such as bupropion, doxepine, ornortriptyline; or an anxiolytic such as buspirone or clonidine.

It will be appreciated that a combination of a conventional antipsychotic drug with a CB1 receptor modulator may provide an enhanced effect in the treatment of mania. Such a combination would be expected to provide for a rapid onset of action to treat a manic episode thereby enabling prescription on an "as needed basis". Furthermore, such a combination may enable a lower dose of the antipsychotic agent to be used without compromising the efficacy of the antipsychotic agent, thereby minimizing the risk of adverse side-effects. A yet further advantage of such a combination is that, due to the action of the CB1 receptor modulator, adverse side-effects caused by the antipsychotic agent such as acute dystonias, dyskinesias, akathesia and tremor may be reduced or prevented.

Thus, according to a further aspect of the present invention there is provided the use of a CB1 receptor modulator and an antipsychotic agent for the manufacture of a medicament for the treatment or prevention of mania.

The present invention also provides a method for the treatment or prevention of mania, which method comprises administration to a patient in need of such treatment or at risk of developing mania of an amount of a CB1 receptor modulator and an amount of an antipsychotic agent, such that together they give effective relief.

In a further aspect of the present invention, there is provided a pharmaceutical composition comprising a CB1 receptor modulator and an antipsychotic agent, together with at least one pharmaceutically acceptable carrier or excipient, wherein the CB1 receptor modulator and the antipsychotic agent may be present as a combined preparation for simultaneous, separate or sequential use for the treatment or prevention of mania. Such combined preparations may be, for example, in the form of a twin pack.

In a further or alternative aspect of the present invention, there is therefore provided a product comprising a CB1 receptor modulator and an antipsychotic agent as a combined preparation for simultaneous, separate or sequential use in the treatment or prevention of mania.

It will be appreciated that when using a combination of the present invention, the CB1 receptor modulator and the antipsychotic agent may be in the same pharmaceutically acceptable carrier and therefore administered simultaneously. They may be in separate pharmaceutical carriers such as conventional oral dosage forms which are taken simultaneously. The term "combination" also refers to the case where the compounds are provided in separate dosage forms and are administered sequentially. Therefore, by way of example, the antipsychotic agent may be administered as a tablet and then, within a reasonable period of time, the CB1 receptor modulator may be administered either as an oral dosage form such as a tablet or a fast-dissolving oral dosage form. By a "fast-dissolving oral formulation" is meant, an oral delivery form which when placed on the tongue of a patient, dissolves within about 10 seconds.

Included within the scope of the present invention is the use of CB1 receptor modulators in combination with an antipsychotic agent in the treatment or prevention of hypomania.

It will be appreciated that a combination of a conventional antipsychotic drug with a CB1 receptor modulator may provide an enhanced effect in the treatment of schizophrenic disorders. Such a combination would be expected to provide for a rapid onset of action to treat schizophrenic symptoms thereby enabling prescription on an "as needed basis". Furthermore, such a combination may enable a lower dose of the CNS agent to be used without compromising the efficacy of the antipsychotic agent, thereby minimizing the risk of adverse side-effects. A yet further advantage of such a combination is that, due to the action of the CB1 receptor modulator, adverse side-effects caused by the antipsychotic agent such as acute dystonias, dyskinesias, akathesia and tremor may be reduced or prevented.

As used herein, the term "schizophrenic disorders" includes paranoid, disorganized, catatonic, undifferentiated and residual schizophrenia; schizophreniform disorder; schizoaffective disorder; delusional disorder; brief psychotic disorder; shared psychotic disorder; substance-induced psychotic disorder; and psychotic disorder not otherwise specified.

Other conditions commonly associated with schizophrenic disorders include self-injurious behavior (e.g. Lesch-Nyhan syndrome) and suicidal gestures.

Suitable antipsychotic agents of use in combination with a CB1 receptor modulator include the phenothiazine, thioxanthene, heterocyclic dibenzazepine, butyrophenone, diphenylbutylpiperidine and indolone classes of antipsychotic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. Suitable examples of dibenzazepines include clozapine and olanzapine. An example of a butyrophenone is haloperidol. An example of a diphenylbutylpiperidine is pimozide. An example of an indolone is molindolone. Other antipsychotic agents include loxapine, sulpiride and risperidone. It will be appreciated that the antipsychotic agents when used in combination with a CB1 receptor modulator may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, olanzapine, haloperidol, pimozide and risperidone are commonly used in a non-salt form.

Other classes of antipsychotic agent of use in combination with a CB1 receptor modulator include dopamine receptor antagonists, especially D2, D3 and D4 dopamine receptor antagonists, and muscarinic ml receptor agonists. An example of a D3 dopamine receptor antagonist is the compound PNU-99194A. An example of a D4 dopamine receptor antagonist is PNU-101387. An example of a muscarinic ml receptor agonist is xanomeline.

Another class of antipsychotic agent of use in combination with a CB1 receptor modulator is the 5-$HT_{2A}$ receptor antagonists, examples of which include MDL100907 and fananserin. Also of use in combination with a CB1 receptor modulator are the serotonin dopamine antagonists (SDAs) which are believed to combine 5-$HT_{2A}$ and dopamine receptor antagonist activity, examples of which include olanzapine and ziperasidone.

Still further, NK-1 receptor antagonists may be favorably employed with the CB1 receptor modulators of the present invention. Preferred NK-1 receptor antagonists for use in the present invention are selected from the classes of compounds described previously.

It will be appreciated that a combination of a conventional anti-asthmatic drug with a CB1 receptor modulator may provide an enhanced effect in the treatment of asthma, and may be used for the treatment or prevention of asthma, which method comprises administration to a patient in need of such treatment an amount of a compound of the present invention and an amount of an anti-asthmatic agent, such that together they give effective relief.

Suitable anti-asthmatic agents of use in combination with a compound of the present invention include, but are not limited to: (a) VLA-4 antagonists such as natalizumab and the compounds described in U.S. Pat. No. 5,510,332, WO97/03094, WO97/02289, WO96/40781, WO96/22966, WO96/20216, WO96/01644, WO96/06108, WO95/15973 and WO96/31206; (b) steroids and corticosteroids such as beclomethasone, methylprednisolone, betamethasone, prednisone, dexamethasone, and hydrocortisone; (c) antihistamines (Hi-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, desloratadine, cetirizine, fexofenadine, descarboethoxyloratadine, and the like; (d) non-steroidal anti-asthmatics including β2-agonists (such as terbutaline, metaproterenol, fenoterol, isoetharine, albuterol, bitolterol, salmeterol, epinephrine, and pirbuterol), theophylline, cromolyn sodium, atropine, ipratropium bromide, leukotriene antagonists (such as zafirlukast, montelukast, pranlukast, iralukast, pobilukast, and SKB-106,203), and leukotriene biosynthesis inhibitors (such as zileuton and BAY-1005); (e) anti-cholinergic agents including muscarinic antagonists (such as ipratropium bromide and atropine); and (f) antagonists of the chemokine receptors, especially CCR-3; and pharmaceutically acceptable salts thereof.

It will be appreciated that a combination of a conventional anti-constipation drug with a CB1 receptor modulator may provide an enhanced effect in the treatment of constipation or chronic intestinal pseudo-obstruction, and for use for the manufacture of a medicament for the treatment or prevention of constipation or chronic intestinal pseudo-obstruction.

The present invention also provides a method for the treatment or prevention of constipation, which method comprises administration to a patient in need of such treatment an amount of a compound of the present invention and an amount of an anti-constipation agent, such that together they give effective relief.

Suitable anti-constipation agents of use in combination with a compound of the present invention include, but are not limited to, osmotic agents, laxatives and detergent laxatives (or wetting agents), bulking agents, and stimulants; and pharmaceutically acceptable salts thereof. A particularly suitable class of osmotic agents include, but are not limited to sorbitol, lactulose, polyethylene glycol, magnesium, phosphate, and sulfate; and pharmaceutically acceptable salts thereof. A particularly suitable class of laxatives and detergent laxatives, include, but are not limited to, magnesium, and docusate sodium; and pharmaceutically acceptable salts thereof. A particularly suitable class of bulking agents include, but are not limited to, psyllium, methylcellulose, and calcium polycarbophil; and pharmaceutically acceptable salts thereof. A particularly suitable class of stimulants include, but are not limited to, anthroquinones, and phenolphthalein; and pharmaceutically acceptable salts thereof.

It will be appreciated that a combination of a conventional anti-cirrhosis drug with a CB1 receptor modulator may provide an enhanced effect in the treatment or prevention of cirrhosis of the liver, and for use for the manufacture of a medicament for the treatment or prevention of cirrhosis of the liver, as well as non-alcoholic fatty liver disease (NAFLD) and non-alcoholic steatohepatitis (NASH).

The present invention also provides a method for the treatment or prevention of cirrhosis of the liver, which method comprises administration to a patient in need of such treatment an amount of a compound of the present invention and an anti-cirrhosis agent, such that together they give effective relief.

Suitable anti-cirrhosis agents of use in combination with a compound of the present invention include, but are not limited to, corticosteroids, penicillamine, colchicine, interferon-γ, 2-oxoglutarate analogs, prostaglandin analogs, and other anti-inflammatory drugs and antimetabolites such as azathioprine, methotrexate, leflunamide, indomethacin, naproxen, and 6-mercaptopurine; and pharmaceutically acceptable salts thereof.

The method of treatment of this invention comprises a method of modulating the CB1 receptor and treating CB1 receptor mediated diseases by administering to a patient in need of such treatment a non-toxic therapeutically effective amount of a compound of this invention that selectively antagonizes the CB1 receptor in preference to the other CB or G-protein coupled receptors.

The term "therapeutically effective amount" means the amount the compound of structural formula I that will elicit the biological or medical response of a tissue, system, animal or human that is being sought by the researcher, veterinarian, medical doctor or other clinician, which includes alleviation of the symptoms of the disorder being treated. The novel methods of treatment of this invention are for disorders known to those skilled in the art. The term "mammal" includes humans, and companion animals such as dogs and cats.

The weight ratio of the compound of the Formula I to the second active ingredient may be varied and will depend upon the effective dose of each ingredient. Generally, an effective dose of each will be used. Thus, for example, when a compound of the Formula I is combined with a β-3 agonist the weight ratio of the compound of the Formula I to the β-3 agonist will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

The following reaction schemes illustrate methods which may be employed for the synthesis of the novel pyrano[2,3-b]pyridines of structural formula I described in this invention. All substituents are as defined above unless indicated otherwise. Several strategies based upon synthetic transformations known in the literature of organic synthesis may be employed for the preparation of the title compounds of general formula I. A preferred synthetic process which is shown in the retrosynthetic sense in reaction Scheme 1 proceeds through a suitably substituted 3-cyano-2-pyridone of general formula 2. The 3-cyano-2-pyridone of general formula 2 is in turn derived from a 1,2-diarylethanone of general formula 1. Reaction Schemes 2-7 illustrate the preferred methods for the synthesis of the novel compounds of general formula I in the forward sense. In these schemes, group $Ar^1$ refers to the aryl/heteroaryl group optionally substituted by the substituents $R^4$ and $R^5$ at position 6 of the pyrano[2,3-b]pyridine of general formula I, and $Ar^2$ refers to the aryl/heteroaryl group optionally substituted by the substituents $R^6$ and $R^7$ at position 7 of the pyrano[2,3-b]pyridine of general formula I.

Scheme 1

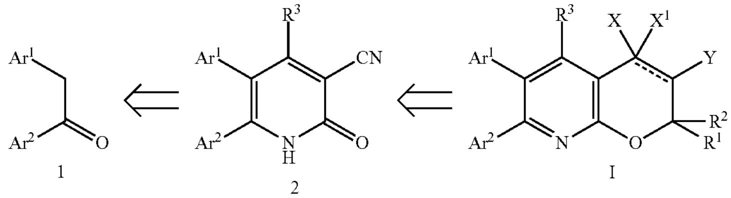

1 2 I 1,2-Diarylethanones of general formula 1 may be available commercially or they can be synthesized using one of several methods known in the art of organic synthesis. Scheme 2 illustrates three methods for the synthesis of the 1,2-diarylethanones of general formula 1. In the first example (equation 1), a substituted arylmethyl bromide of general formula 3 is converted to a Grignard reagent with magnesium metal in a solvent such as THF at a temperature between room temperature and the refluxing temperature of the solvent. The resulting Grignard reagent is then added to a substituted arylnitrile of general formula 4. Acidic hydrolysis of the reaction mixture followed by extraction of the organic product affords a 1,2-diarylethanone of general formula 1 as shown. An alternative synthesis of 1,2-diarylethanones 1 which is preferred when either of the aryl groups $Ar^1$ or $Ar^2$ are optionally substituted with functional groups that are reactive with Grignard reagents is shown in equation 2 of reaction Scheme 2. Here a substituted arylacetic acid of general formula 5 is reacted at low temperature (−78° to −50° C.) with two equivalents of a strong base such as lithium bis(trimethylsilylamide) in an aprotic solvent such as THF. This deprotonates the arylacetic acid 5, and generates a dianion which undergoes a Dieckmann reaction when the substituted arylcarboxylate ester of general formula 6 is added. In this modification of the Dieckmann reaction, the intermediate β-keto acid smoothly decarboxylates and a 1,2-diarylethanone of general formula 1 is produced. A third method for the preparation of the 1,2-diarylethanones of general formula 1 involves the palladium-catalyzed α-arylation of an acetophenone derivative of general formula 8 with an aryl halide, such as the aryl bromide of general formula 7, as illustrated in equation 3 (Fox, J. M.; Huang, X.; Chieffi, A.; Buchwald, S. L. *J. Am. Chem. Soc.* 2000, 122, 1360-70).

Scheme 2

(1)

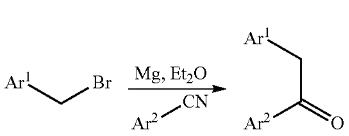

3 4 1

(2)

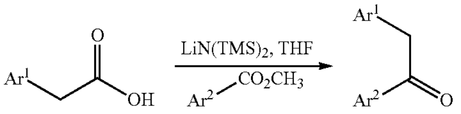

5 6 1

-continued (3)

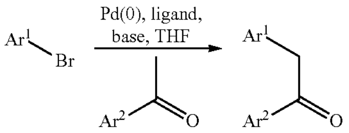

7 8 1

Reaction Scheme 3 illustrates two methods for the conversion of the 1,2-diarylethanone of general formula 1 into the 3-cyano-2-pyridones of general formula 2. This transformation is conducted using one of the two methods illustrated in reaction Scheme 3, and the preferred method depends upon the selection of the substituent $R^3$ in the resulting 2-pyridone (2). When it is desired that the $R^3$ substituent be a hydrogen atom, then the 1,2-diarylethanone of general formula 1 is first converted to a vinylogous amide of general formula 9 by reaction with an N,N-dimethylformamide dimethylacetal as shown in equation 1. The condensation reaction may be conducted using a solvent such as acetonitrile or simply by using the DMF acetal as the reaction solvent at an elevated temperature, typically between room temperature and 150° C., and the vinylogous amide 9 is produced as a mixture of E and Z diastereoisomers. In the second step of this sequence, the vinylogous amide 9 is condensed with cyanoacetamide to afford the 3-cyano-2-pyridone of general formula 2. The reaction is usually conducted in a polar aprotic solvent such as DMF in the presence of a strong base such as an alkali metal hydride or alkoxide.

Equation 2 at the bottom of reaction Scheme 3 illustrates an alternative procedure for the preparation of 3-cyano-2-pyridones of general formula 2 which may afford a superior overall yield in cases where the $R^3$ substituent is chosen to be a group other than a hydrogen atom. In this sequence, the 1,2-diarylethanone 1 is first condensed with an ortho-ester of general formula 10 to afford vinylogous esters of general formula 11 as a mixture of E and Z diastereoisomers. The vinylogous esters of general formula 11 may then be condensed with cyanoacetamide as described above to afford 3-cyano-2-pyridones of general formula 2.

Scheme 3

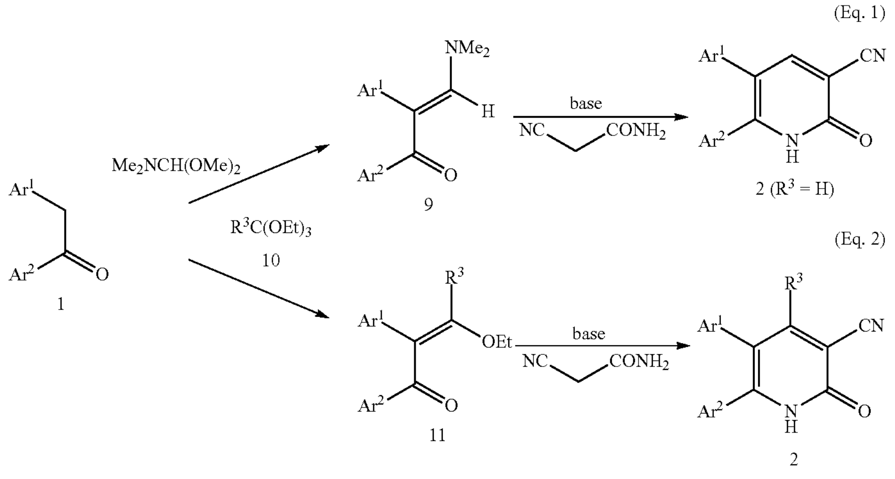

1, 9, 10, 11, 2 ($R^3$ = H), 2

A preferred method for the next stage of the synthesis of the novel compounds of general formula I is illustrated in reaction Schemes 4. In this Scheme, a 3-cyano-2-pyridone of general formula 2 is converted to an α,β-unsaturated ketone of general formula 13, which can undergo a spontaneous intramolecular Michael addition with the adjacent nucleophilic pyridone oxygen atom. The resulting product is the substituted 2,3-dihydro-4H-pyrano[2,3-b]pyridin-4-one 17, which corresponds to the title compounds of general formula I wherein the X and $X^1$ substituents together form a carbonyl group, and there is a single bond between the carbon atoms at positions 3 and 4 of the pyran ring. The 3-cyano-2-pyridone of general formula 2 may be converted to the intermediate α,β-unsaturated ketone of general formula 13, using one of several synthetic methods. For instance, reaction of 2 with a vinyl Grignard reagent of general formula 12 followed by acidic hydrolysis of the reaction mixture affords the α,β-unsaturated ketones of general formula 13 which in turn undergo the intramolecular cyclization that leads to compounds of general formula 17. Alternatively, the 3-cyano-2-pyridones (2) may be first converted to a ketone general formula 15, typically by reaction with an organometallic species, such as the Grignard reagent of general formula 14, followed by acidic hydrolysis. Reaction of the resulting ketone 15 under basic conditions with a carbonyl compound of general formula 16 effects an aldol condensation. A preferred method for conducting the aldol condensation involves using a secondary or tertiary amine as the base and conducting the reaction at an elevated temperature, for instance at temperatures between room temperature and 150° C. Under these conditions, the aldol condensation results in concomitant loss of water to initially afford an α,β-unsaturated ketone of general formula 13, which in turn may undergo the intramolecular cyclization that leads to compounds of general formula 17 as described above.

Scheme 4

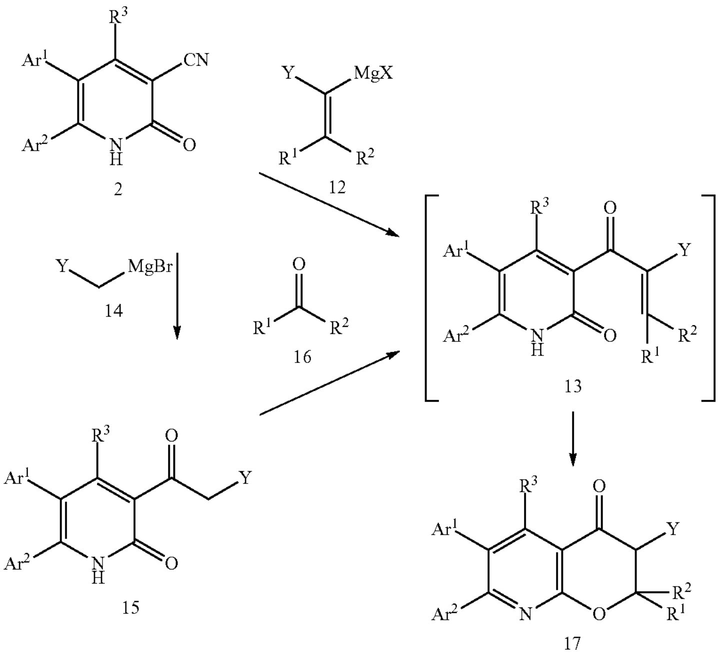

2, 12, 14, 16, 13, 15, 17

The substituted 2,3-dihydro-4H-pyrano[2,3-b]pyridin-4-ones of general formula 17 are versatile intermediates, and reaction Schemes 5-7 illustrate some of the preferred synthetic methods for the conversion of compounds (17) to the novel compounds of general formula I described in this invention. For instance, in reaction Scheme 5, reduction of the carbonyl group at the 4-position of the pyran ring in compounds of general formula 17 results in a secondary alcohol of general formula 18. The reduction of 17 can be accomplished using a variety of metal hydride reducing agents such as sodium borohydride in suitable solvent systems such as THF/methanol. The resulting secondary alcohols of general formula 18 contain a new stereogenic center and are formed as either a racemic mixture or as a mixture of diastereoisomers when an additional stereogenic center is present in the compound. Racemic mixtures of general formula 18 may be separated into their component enantiomerically pure alcohols by classical resolution methods, or by separation using chiral stationary phase HPLC columns. The reduction of the carbonyl group in compounds of general formula 17 may also be accomplished using asymmetric reduction methods such as hydrogenation in the presence of a chiral organometallic catalyst (Haack, K. J.; Hashiguchi, S.; Fujii, A.; Ikariya, T.; Noyori, R. *Angew. Chem. Int. Ed. Engl.* 1997, 36, 285-8). The secondary alcohols of general formula 18 may be further modified as shown in Scheme 5, for instance by conversion to ethers (R=alkyl), esters (R=acyl), and carbamates ($R{=}CONR_2$) of general formula 19. The hydroxyl group of compounds of general formula 18 may also be displaced by a new functional group. One preferred method for the hydroxyl displacement is the Mitsunobu reaction with a zinc azide complex (Viaud, M. C.; Rollin, P. *Synthesis* 1990, 130-2) which affords the azido compound of general formula 20. Reduction of the azido group in the compounds of general formula 20, for instance using Staudinger's conditions ($PPh_3$, $H_2O$), then affords amino derivatives of general formula 21 ($R_2{=}H$). The primary amino compounds of general formula 21 may in turn be further modified to incorporate additional substituents on the nitrogen atom that are within the scope of this invention using a variety of synthetic methods. For instance, the amino group may be reacted with acid chlorides or sulfonyl chlorides to afford the corresponding amides or sulfonamides respectively. The amino group may also be N-alkylated using reductive amination reactions or N-arylated using palladium catalyzed coupling reactions with suitable aryl or heteroaryl halides (Muci, A. R.; Buchwald, S. L. Topics in Current Chemistry 2002, 219 Cross-Coupling Reactions, 131-209. Hartwig, J. F. Handbook of Organopalladium Chemistry for Organic Synthesis 2002, 1, 1051-96). Finally the amino group of compounds of general formula 21 may also be incorporated into various nitrogen heterocyclic systems when it is desired that either the X or $X^1$ substituent in the compounds of general formula I be such a heterocyclic element. The resulting compounds of general formula 21 correspond to the title compounds of general formula I wherein the $X{=}NR_2$, $X^1{=}H$ and there is a single bond between the carbon atoms at positions 3 and 4 of the pyran ring.

Scheme 5

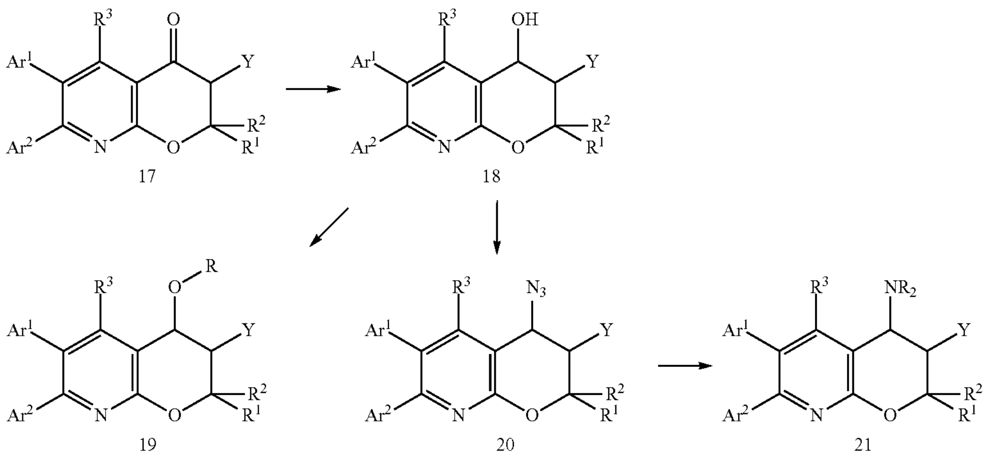

Reaction Scheme 6 illustrates two additional methods for the synthetic modification of the substituted 2,3-dihydro-4H-pyrano[2,3-b]pyridin-4-ones of general formula 17 when it is desired that either the X or $X^1$ substituent be an amino or optionally substituted amino group. The carbonyl group of compounds of general formula 17 may be subjected to reductive amination reactions with primary or secondary amino compounds 22, for instance using either sodium cyanoborohydride, sodium triacetoxy borohydride, or sodium borohydride in combination with titanium tetraisopropoxide as the reducing agent, and the substituted 4-aminopyrano[2,3-b]pyridine derivatives of general formula 21 are again produced. The substituted amino compounds of general formula 21 may be further modified into the title compounds of general formula I using the methods described above. The carbonyl group of compounds of general formula 17 may also be converted to the corresponding oximes 23 using hydroxylamine hydrochloride. These oximes may in turn be reduced to afford primary amine 21 ($R_2{=}H$), or be employed in a reductive amidation reaction (Burk, M. J.; Casy, G.; Johnson, N. B. *J. Org. Chem.* 1998, 63, 6084) which produces the enamides of general formula 24. Compounds of general formula 24 correspond to the title compounds of general formula I wherein the $X{=}NHR_2$, $X^1$ is absent and there is a double bond between the carbon atoms at positions 3 and 4 of the pyran ring.

Scheme 6

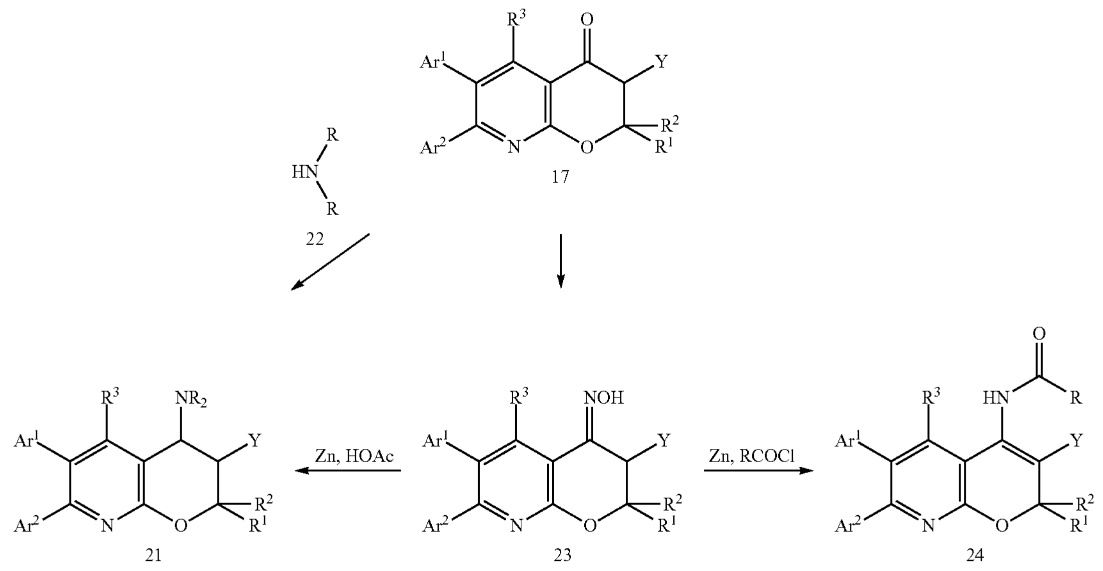

17, 22, 21, 23, 24

Reaction Scheme 7 illustrates methods for the synthetic modification of the substituted 2,3-dihydro-4H-pyrano[2,3-b]pyridin-4-ones of general formula 17 when it is desired that either the X or $X^1$ be a carbon substituent. The carbonyl group of compounds of general formula 17 undergo carbon-carbon bond forming reactions with nucleophilic carbon reagents that are commonly employed in organic synthesis. For instance, the compounds of general formula 17 may react in Wittig or Horner-Emmons olefination reactions, with organometallic reagents such as Grignard reagents or with a variety of stabilized carbanionic species such as enolates, and the like. Scheme 7 illustrates the reaction of a compound of general formula 17 with a Reformatsky reagent (25) which produces the tertiary alcohol of general formula 26. The alcohols of general formula 26 may be further synthetically modified, for instance they may be dehydrated to afford derivatives containing a new double bond, which is generally produced as a separable mixture of the endocyclic and exocyclic isomers. The carbonyl group of compounds of general formula 17 may also be converted to vinyl triflates of general formula 27 by treatment with a reagent such as trifluoromethansulfonic anhydride or N-phenyl-bis(trifluoromethanesulfonimide) in the presence of a suitable base. Vinyl triflates of general formula 27 may then be employed in a variety of palladium-catalyzed cross coupling reactions to afford compounds of general formula 28. For instance, when triflates of general formula 27 are reacted with aryl, heteroaryl, or vinylboronic acids in the presence of a palladium catalyst, the compounds of general formula 28 are produced wherein the X group is an aryl, heteroaryl or vinyl substituent. Additionally, the triflates of general formula 27 may be converted to carboxylic acid derivatives. Hydroxycarboxylation of compounds of general formula 27 using potassium acetate, carbon monoxide and a palladium catalyst in DMSO (Cacchi, S.; Lupi, A. *Tetrahedron Lett.* 1992, 33, 3939-42) afford the corresponding carboxylic acids (28, $X{=}CO_2H$). Similarly, compounds of general formula 27 may be converted directly to esters (28, $X{=}CO_2R$) or amides (28, $X{=}CONR_2$) by reaction with either an alcohol or a primary or secondary amine with a palladium catalyst in the presence of carbon monoxide. Compounds of general formula 28 correspond to the title compounds of general formula I wherein the X group is a directly bonded carbon substituent as described above, $X^1$ is absent and there is a double bond between the carbon atoms at positions 3 and 4 of the pyran ring.

Scheme 7

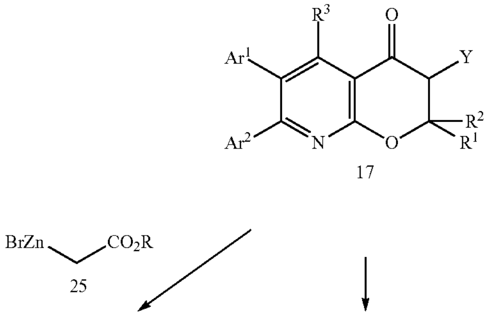

17, 25

-continued

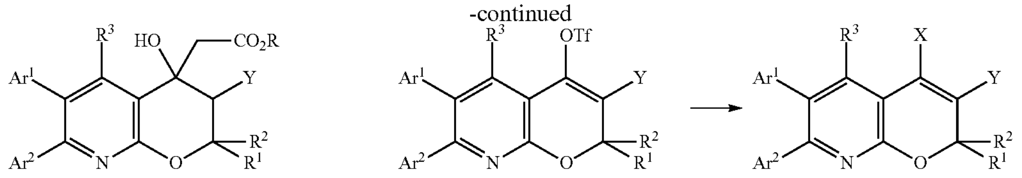

26 27 28

Reaction Scheme 8 illustrates a preferred method for the synthesis of the novel compounds of general formula I described in this invention when it is desired that the $R^1$ and $R^2$ substituents together form a carbonyl group. In this synthetic process, the cyano group of the substituted 3-cyano-2-pyridone of general formula 2 is first reduced to an aldehyde using a reagent such as diisobutylaluminum hydride in a solvent such as toluene. The resulting substituted 2-pyridone-3-carboxaldehydes of general formula 29 may then be condensed with a variety of substituted acetic ester derivatives of general formula 30 under basic reaction conditions. In these reactions the group Y is typically an electron-withdrawing group such as a carbonyl, cyano group or the like, which is capable of further stabilizing the enolate of the ester of general formula 30. The deprotonated form of the ester 30 condenses with the formyl group of the 2-pyridone-3-carboxaldehydes of general formula 29. This condensation reaction is typically conducted at an elevated temperature, such as the boiling point of the solvent used, and under these conditions the resulting intermediate from this condensation (eg. 31) may then further cyclize to form the pyrone ring of the 2H-pyrano[2,3-b]pyridin-2-one of general formula 32. Compounds of general formula 32 correspond to the title compounds of general formula I wherein the $R^1$ and $R^2$ taken together form a carbonyl group, the X group is a hydrogen atom, $X^1$ is absent, and there is a double bond between the carbon atoms at positions 3 and 4 of the pyran ring. The compounds of general formula 32 described in Scheme 8 may be further modified into the novel compounds of general formula I using the methods described in the preceding reaction Schemes for the compounds of general formula 17, or by using other synthetic reactions known in organic chemistry.

Scheme 8

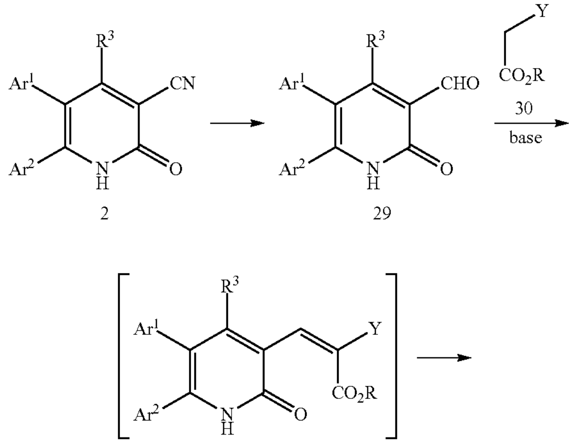

2 29

31

-continued

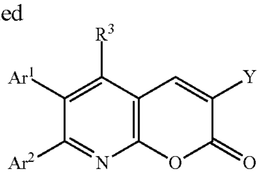

32

In order to illustrate the invention, the following examples are included. These examples do not limit the invention. They are only meant to suggest a method of reducing the invention to practice. Those skilled in the art may find other methods of practicing the invention which are readily apparent to them. However, those methods are also deemed to be within the scope of this invention.

General Procedures.

Reactions sensitive to moisture or air were performed under nitrogen or argon using anhydrous solvents and reagents. The progress of reactions was determined by either analytical thin layer chromatography (TLC) performed with E. Merck precoated TLC plates, silica gel. 60F-254, layer thickness 0.25 mm or liquid chromatography-mass spectrum (LC-MS). Mass analysis was performed on a Waters Micromass® ZQ™ with electrospray ionization in positive ion detection mode. High performance liquid chromatography (HPLC) was conducted on an Agilent 1100 series HPLC on Waters C18 XTerra 3.5 μm 2.1×20 mm column with gradient 10:90-98:2 v/v $CH_3CN/H_2O$+v 0.05% TFA over 3.25 min then hold at 98:2 v/v $CH_3CN/H_2O$+v 0.05% TFA for 0.75 min; flow rate 1.5 mL/min, UV wavelength 254 nm. Two other HPLC conditions applied were noted as LC-1 (Waters C18 XTerra 3.5 μm 2.1×20 mm column with gradient 10:90-98:2 v/v $CH_3CN/H_2O$+v 0.05% TFA over 1.25 min then hold at 98:2 v/v $CH_3CN/H_2O$+v 0.05% TFA for 0.75 min; flow rate 1.5 mL/min, UV wavelength 254 nm) and LC-2 (Waters C18 XTerra 3.5 μm 3.0×50 mm column with gradient 10:90-98:2 v/v $CH_3CN/H_2O$+v 0.05% TFA over 3.75 min then hold at 98:2 v/v $CH_3CN/H_2O$+v 0.05% TFA for 1.75 min; flow rate 1.0 mL/min, UV wavelength 254 nm). Concentration of solutions was carried out on a rotary evaporator under reduced pressure. Flash chromatography was performed using a Biotage Flash Chromatography apparatus (Dyax Corp.) on silica gel (32-63 mM, 60 Å pore size) in pre-packed cartridges of the size noted. $^1H$ NMR spectra were acquired at 500 MHz spectrometers in $CDCl_3$ solutions unless otherwise noted. Chemical shifts were reported in parts per million (ppm). Tetramethylsilane (TMS) was used as internal reference in $CD_3Cl$ solutions, and residual $CH_3OH$ peak or TMS was used as internal reference in $CD_3OD$ solutions. Coupling constants (J) were reported in hertz (Hz). Chiral analytical chromatography was performed on one of Chiralpak AS, Chiralpak AD, Chiralcel OD, or Chiralcel OJ columns (250×4.6 mm) (Daicel Chemical Industries, Ltd.) with noted percentage of either ethanol in hexane (% Et/Hex) or isopropanol in heptane (% IPA/Hep) as isocratic solvent systems. Chiral preparative chromatography was conducted on one of Chiralpak AS, Chiralpak AD, Chiralcel OD, or Chiralcel OJ columns (20× 250 mm) (Daicel Chemical Industries, Ltd.) with desired isocratic solvent systems identified on chiral analytical chromatography.

Abbreviations: acetic acid (AcOH), aqueous (aq), (benzotriazol-1-yloxy)tripyrrolidino-phosphonium hexafluorophosphate (PyBOP), 2,2'-bis(diphenylphosphino)-1,1'-binaphthalene (BINAP), 1,1'-bis(diphenylphosphino) ferrocene (dppf), 4-N,N-dimethylaminopyridine (DMAP), ethyl acetate (EtOAc), diethyl ether (ether or $Et_2O$), N,N-diisopropylethylamine (DIEA), N,N-dimethylformamide (DMF), gram(s) (g), hour(s) (h or hr), microliter(s) (μL), milligram(s) (mg), milliliter(s) (mL), millimole (mmol), mass spectrum (ms or MS), 2-propanol (IPA), retention time ($R_t$), room temperature (rt), saturated aq sodium chloride solution (brine), trifluoroacetic acid (TFA), tetrahydrofuran (THF), and minute(s) (min).

EXAMPLE 1

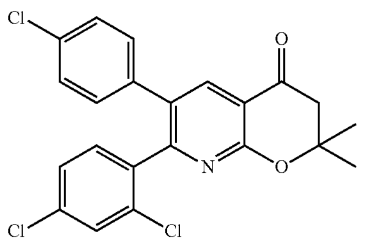

6-(4-Chlorophenyl)-7-(2,4-dichlorophenyl)-2,2-dimethyl-2,3-dihydro-4H-pyrano[2,3-b]pyridin-4-one Step A: 3-Dimethylamino-1-(2,4-dichlorophenyl)-2-(4-chlorophenyl)prop-2-en-1-one A solution of 4-chlorobenzyl 2,4-dichlorophenyl ketone (4.5 g, 14.4 mmol) and dimethylformamide dimethyl acetal (7.7 mL, 58 mmol) in DMF (60 mL) was heated at 75° C. for 20 h. The volatiles were removed in vacuo to provide the product which was used directly in the next step. (LC-2) HPLC/MS: 354 (M+1), 356 (M+3); $R_t$=3.47 min.

Step B: 6-(2,4-Dichlorophenyl)-5-(4-chlorophenyl)-2-oxo-1,2-dihydropyridine-3-carbonitrile To a solution of the product of Step A, cyanoacetamide (1.33 g, 15.8 mmol), and MeOH (1.3 mL, 32 mmol) in DMF (35 mL) was added dropwise to a suspension of NaH (60% in mineral oil) (1.45 g, 36 mmol) in DMF (16 mL) at rt. After the slow addition was complete, the reaction was heated to 95° C. for 2.5 h. Most of the DMF was then removed in vacuo before the reaction was diluted with aq 18% citric acid solution. The mixture was extracted twice with $CH_2Cl_2$ and the organic layers were washed with brine. The combined organic layers were dried ($Na_2SO_4$) and concentrated. The solid residue was triturated with ether, filtered, and air dried to afford the product. (LC-2) HPLC/MS: 375 (M+1), 377 (M+3); $R_t$=3.47 min.

Step C: 6-(4-Chlorophenyl)-7-(2,4-dichlorophenyl)-2,2-dimethyl-2,3-dihydro-4H-pyrano[2,3-b]pyridin-4-one. To the product of Step B (13.15 g, 35 mmol) in THF (160 mL) was added MeMgBr (1.4 M in toluene/THF, 26.25 mL, 36.75 mmol). After stirring 3 min, 2-methylprop-1-enylmagnesium bromide (0.5 M in THF, 100 mL, 50 mmol) was added and the temperature was increased to 50° C. After 20 min the reaction was cooled, quenched with 2 M HCl and diluted with EtOAc. The reaction was stirred for 3 days before work up. The solution was washed twice with brine, followed by twice with saturated aq $NaHCO_3$. The concentrated residue was purified by flash chromatography on silica gel gradient eluted with 0-25% EtOAc in hexane to afford the title compound. (LC-2) HPLC/MS: 432.2 (M+1), 434.2 (M+3); $R_t$=4.15 mm.

EXAMPLE 2

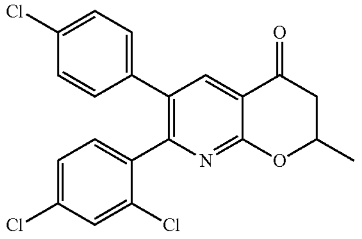

6-(4-Chlorophenyl)-7-(2,4-dichlorophenyl)-2-methyl-2,3-dihydro-4H-pyrano[2,3-b]pyridin-4-one To the product of Example 1 Step B (7.0 g, 18.6 mmol in THF (90 mL) was added MeMgBr (1.4 M in toluene/THF, 14 mL, 19.6 mmol). After stirring for 3 min, prop-1-enylmagnesium bromide (0.5 M in THF, 55.9 mL, 28 mmol) was added and the temperature was increased to 50° C. The reaction was quenched with 2 M HCl after 30 min and diluted with EtOAc. The solution was washed with brine, and concentrated The residue was purified by flash chromatography on silica gel gradient eluted with 0-35% EtOAc in hexane to afford the title compound. (LC-2) HPLC/MS: 418.2 (M+1), 420.2 (M+3); $R_t$=4.08 min.

EXAMPLE 3

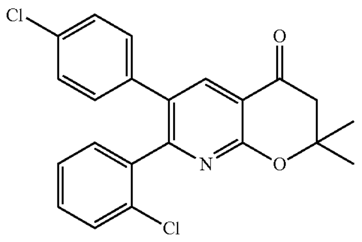

7-(2-Chlorophenyl)-6-(4-chlorophenyl)-2,2-dimethyl-2,3-dihydro-4H-pyrano[2,3-b]pyridin-4-one Starting with 6-(2-chlorophenyl)-5-(4-chlorophenyl)-2-oxo-1,2-dihydropyridine-3-carbonitrile prepared in similar fashion to Step B Example 1 and following a similar procedure as described in Example 1 step C the title compound was prepared. (LC-2) HPLC/MS: 398.1 (M+1), 400.1 (M+3); $R_t$=4.09 min.

EXAMPLE 4

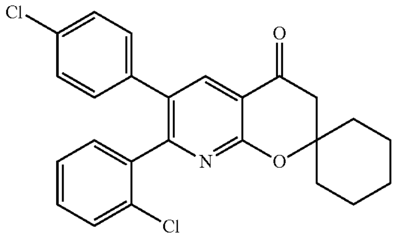

7'-(2-Chlorophenyl)-6'-(4-chlorophenyl)spiro[cyclohexane-1,2'-pyrano[2,3-b]pyridin]-4'(3'H)-one Step A: 3-Acetyl-6-(2-chlorophenyl)-5-(4-chlorophenyl)pyridin-2(1H)-one. To 6-(2-chlorophenyl)-5-(4-chlorophenyl)-2-oxo-1,2-dihydropyridine-3-carbonitrile (15.02 g, 44.0 mmol) prepared in similar fashion to Step B Example 1 was added THF (100 mL). The mixture was reacted with MeMgBr (70 mL, 1.4 M in toluene/THF) slowly over 30 min. The reaction mixture warmed, becoming homogenous yellow-orange, and the addition was maintained at a rate to keep the temperature below the boiling point of THF. After the addition was complete, the reaction stirred an additional 1 h at rt. The reaction mixture was quenched with 1.0 N HCl and the organic layer was separated and concentrated. The residue was dissolved in hot EtOAc and washed with water, brine, dried ($MgSO_4$), filtered and concentrated to afford the title compound which was used in the next step without further purification. (LC-2) HPLC/MS: 358.1 (M+1), 360.1 (M+3); $R_t$=3.62 min.

Step B: 7'-(2-Chlorophenyl)-6'-(4-chlorophenyl)spiro[cyclohexane-1,2'-pyrano[2,3-b]pyridin]-4'(3'H)-one To the product of Example 4 Step A (6.25 g, 17.5 mmol), was added cyclohexanone (20 mL) and pyrrolidine (1.44 mL, 17.4 mmol). The reaction was heated to 155° C. for 30 min in a sealed 80 mL tube in a CEM Corporation Discover microwave system. The reaction was then concentrated and the residue was purified directly by flash chromatography on silica gel gradient eluted with 0-25% EtOAc in hexane to afford the title compound. (LC-2) HPLC/MS: 438.3 (M+1), 440.3 (M+3); $R_t$=4.39 min.

Starting with the product of Example 4 Step A and using procedures similar to that of Example 4 Step B the following additional compounds were prepared using the appropriate ketones.

| | Name | HPLC/MS m/z (M + 1) m/z (M + 3) $R_t$ (min) (LC-2) | |
|---|---|---|---|
| Example 5 | 7'-(2-chlorophenyl)-6'-(4-chlorophenyl)spiro[cyclopentane-1,2'-pyrano[2,3-b]pyridin]-4'(3'H)-one | 478.1<br>480.1<br>4.54 | 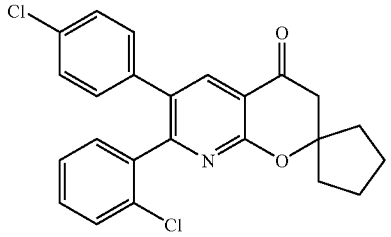 |
| Example 6 | 7-(2-chlorophenyl)-6-(4-chlorophenyl)-2',3',5',6'-tetrahydrospiro[pyrano[2,3-b]pyridine-2,4'-thiopyran]-4(3H)-one | 456.1<br>458.1<br>4.18 | 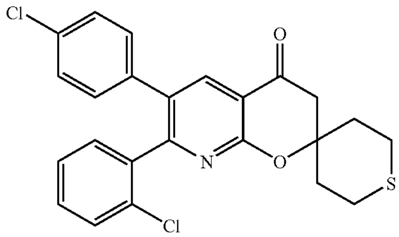 |
| Example 7 | 7'-(2-chlorophenyl)-6'-(4-chlorophenyl)-2,3,5,6-tetrahydrospiro[pyran-4,2'-pyrano[2,3-b]pyridin]-4'(3'H)-one | 440.1<br>442.1<br>3.88 | 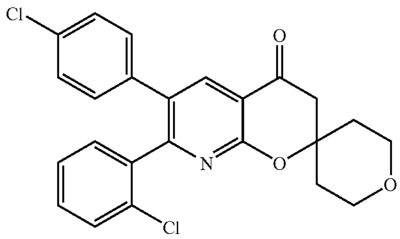 |

-continued

| | Name | HPLC/MS m/z (M + 1) m/z (M + 3) $R_t$ (min) (LC-2) | |
|---|---|---|---|
| Example 8 | 7"-(2-chlorophenyl)-6"-(4-chlorophenyl)dispiro[1,3-dioxolane-2,1'-cyclohexane-4',2"-pyrano[2,3-b]pyridin]-4"(3"H)-one | 496.1<br>498.1<br>4.11 | 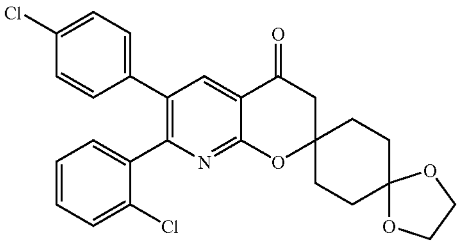 |
| Example 9 | 7-(2-chlorophenyl)-6-(4-chlorophenyl)-2,2-diethyl-2,3-dihydro-4H-pyrano[2,3-b]pyridin-4-one | 426.3<br>428.3<br>4.18 | 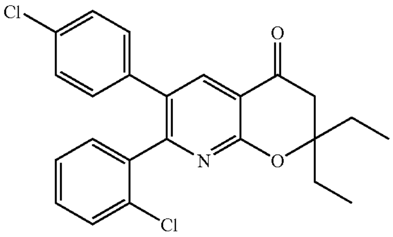 |
| Example 10 | 7-(2-Chlorophenyl)-6-(4-chlorophenyl)-2-isopropyl-2-methyl-2,3-dihydro-4H-pyrano[2,3-b]pyridin-4-one | 426.3<br>428.3<br>4.19 | 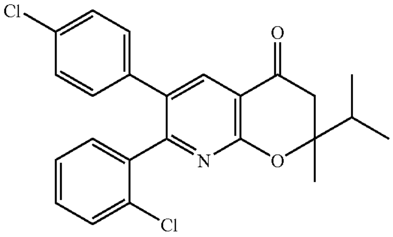 |
| Example 11 | 7-(2-Chlorophenyl)-6-(4-chlorophenyl)-2-ethyl-2-methyl-2,3-dihydro-4H-pyrano[2,3-b]pyridin-4-one | 412.1<br>414.1<br>4.03 | 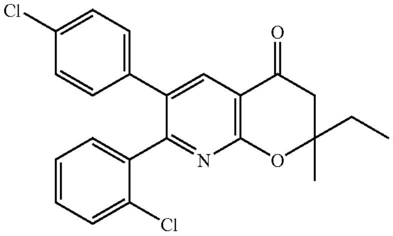 |

EXAMPLE 12

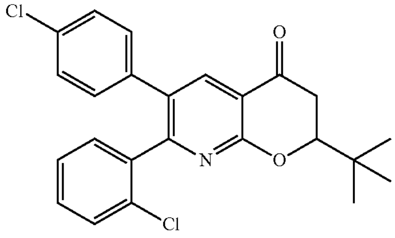

2-tert-Butyl-7-(2-chlorophenyl)-6-(4-chlorophenyl)-2,3-dihydro-4H-pyrano[2,3-b]pyridin-4-one To the product of Example 4 Step A (0.75 g, 2.09 mmol) was added pivalaldehyde (2. mL, 20.9 mmol), pyrrolidine (0.26 mL, 3.14 mmol) and acetonitrile (15 mL). The reaction was heated to 70° C. for 19 h. The reaction was then concentrated and the residue was purified directly by flash chromatography on silica gel gradient eluted with 0-35% EtOAc in hexane to afford the title compound. (LC-2) HPLC/MS: 426.3 (M+1), 428.3 (M+3); $R_t$=4.32 min.

Starting with the product of Example 4 Step A or 3-acetyl-6-(4-bromo-2-chlorophenyl)-5-(4-chlorophenyl)pyridin-2(1H)-one and using procedures similar to that of Example 12 the following compounds were prepared using the appropriate aldehydes.

| | Name | HPLC/MS m/z (M + 1) m/z (M + 3) $R_t$ (min) (LC-2) | |
|---|---|---|---|
| Example 13 | 7-(2-chlorophenyl)-6-(4-chlorophenyl)-2-isopropyl-2,3-dihydro-4H-pyrano[2,3-b] pyridin-4-one | 412.3 414.3 4.20 | 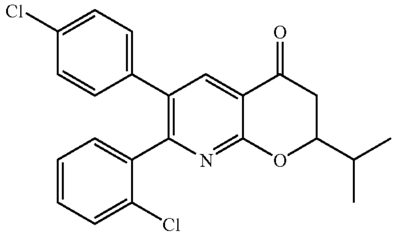 |
| Example 14 | 2-bicyclo[2.2.1]hept-5-en-2-yl-7-(2-chlorophenyl)-6-(4-chlorophenyl)-2,3-dihydro-4H-pyrano[2,3-b]pyridin-4-one | 462.2 464.2 4.23 | 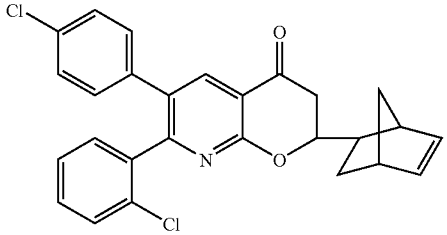 |
| Example 15 | 7-(4-Bromo-2-chlorophenyl)-2-tert-butyl-6-(4-chlorophenyl)-2,3-dihydro-4H-pyrano[2,3-b]pyridin-4-one | 503.9 505.9 4.64 | 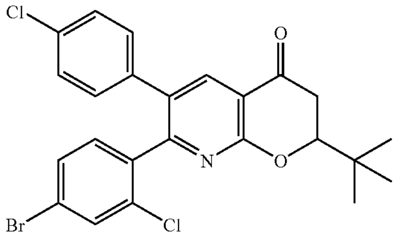 |

EXAMPLE 16

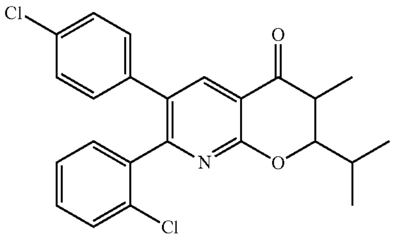

7-(2-Chlorophenyl)-6-(4-chlorophenyl)-2-isopropyl-3-methyl-2,3-dihydro-4H-pyrano[2,3-b]pyridin-4-one.

To 6-(2-chlorophenyl)-5-(4-chlorophenyl)-3-propionylpyridin-2(1H)-one (350 mg, 0.940 mmol), was added isobutyraldehyde (0.384. mL, 4.23 mmol), pyrrolidine (0.117 mL, 1.41 mmol) and acetonitrile (1.5 mL) The reaction was heated in a CEM Discover microwave system to 90° C. in a sealed microwave tube for 50 min. An additional charge of isobutyraldehyde (0.4 mL, 4.4 mmol) was added and the reaction was heated by microwave to 100° C. for 25 min and then 110° C. for 25 min. The reaction was diluted with EtOAc and washed with brine. The reaction was concentrated and the residue was purified by flash chromatography on silica gel gradient eluted with 0-60% EtOAc in hexane to afford the title compound. (LC-2) HPLC/MS: 426.1 (M+1), 428.1 (M+3); $R_t$=4.45 min.

EXAMPLE 17

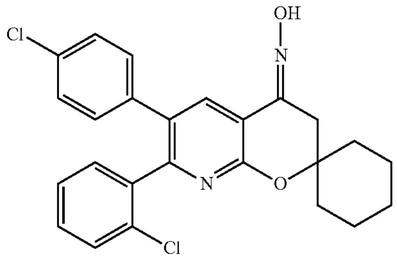

7'-(2-Chlorophenyl)-6'-(4-chlorophenyl)spiro[cyclohexane-1,2'-pyrano[2,3-b]pyridin]-4'(3'H)-one oxime (E/Z mixture).

To the product of Example 4 Step B (414 mg, 0.945 mmol), was added hydroxylamine hydrochloride (262 mg, 3.78 mmol), $NEt_3$ (0.527 mL, 3.78 mmol), potassium acetate (370 mg, 3.77 mmol) and methanol (23 mL). The reaction was heated to 65° C. for 90 min. The reaction was then concentrated and the residue was diluted with EtOAc and washed with brine, dried ($Na_2SO_4$), filtered and concentrated to afford the title compound which used without further purification. (LC-2) HPLC/MS: 453.1 (M+1), 455.1 (M+3); $R_t$=4.09 and 4.12 min.

The following examples were prepared using conditions similar to that of Example 17 and the appropriate ketone.

| | Name | HPLC/MS m/z (M + 1) m/z (M + 3) $R_t$ (min) (LC-2) | |
|---|---|---|---|
| Example 18 | 6-(4-chlorophenyl)-7-(2,4-dichlorophenyl)-2,2-dimethyl-2,3-dihydro-4H-pyrano[2,3-b]pyridin-4-one oxime | 447.1<br>449.1<br>4.16 | 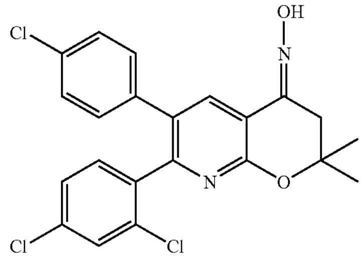 |
| Example 19 | 7-(2-chlorophenyl)-6-(4-chlorophenyl)-2',3',5',6'-tetrahydrospiro[pyrano[2,3-b] pyridine-2,4'-thiopyran]-4(3H)-one oxime | 471.1<br>473.1<br>3.99 & 4.04 | 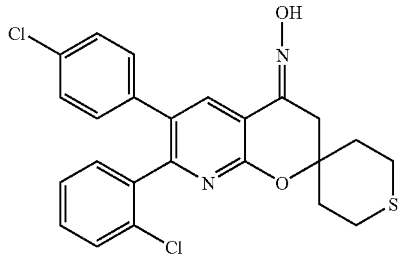 |
| Example 20 | 7'-(2-chlorophenyl)-6'-(4-chlorophenyl)spiro[cyclopentane-1,2'-pyrano[2,3-b]pyridin]-4'(3'H)-one oxime | 439.2<br>441.1<br>4.02 & 4.09 | 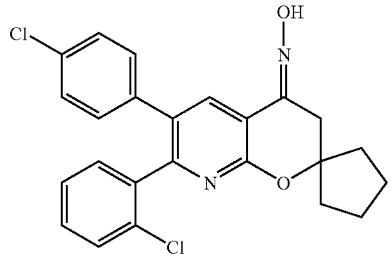 |
| Example 21 | 2-tert-butyl-7-(2-chlorophenyl)-6-(4-chlorophenyl)-2,3-dihydro-4H-pyrano[2,3-b]pyridin-4-one oxime | 441.3<br>443.3<br>4.13 | 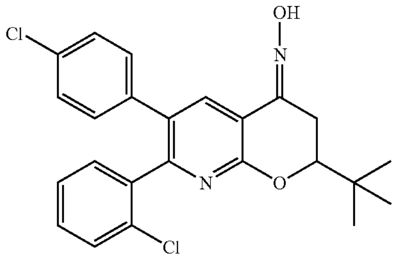 |
| Example 22 | 6-(4-chlorophenyl)-7-(2,4-dichlorophenyl)-2-methyl-2,3-dihydro-4H-pyrano[2,3-b]pyridin-4-one oxime | 433.3<br>435.3<br>3.93 | 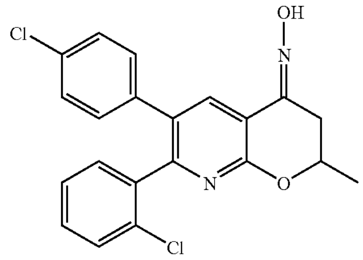 |

EXAMPLE 23

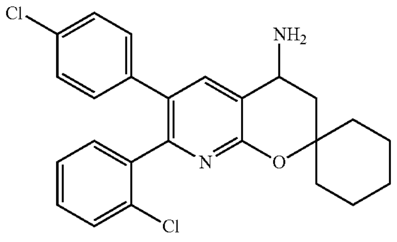

7'-(2-Chlorophenyl)-6'-(4-chlorophenyl)-3',4'-dihydrospiro[cyclohexane-1,2'-pyrano[2,3-b]pyridin]-4'-amine.

To the product of Example 17 (453 mg) was added Zn powder (196 mg, 3.0 mmol) and AcOH (10 mL). The reaction was heated to 95° C. for 15 min and then concentrated. The residue was diluted with EtOAc and washed with saturated aq $NaHCO_3$, dried ($Na_2SO_4$), filtered and concentrated to afford the title compound. (LC-2) HPLC/MS: 439.2 (M+1), 441.2 (M+3); $R_t$=3.26 min.

The following examples were prepared from the appropriate oximes utilizing similar procedures to that of Example 23

EXAMPLE 26

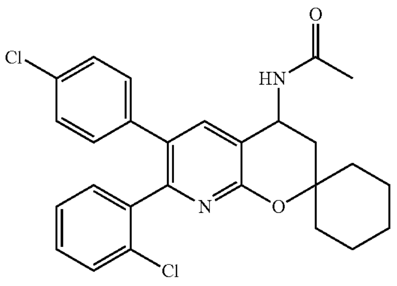

N-[7'-(2-Chlorophenyl)-6'-(4-chlorophenyl)-3',4'-dihydrospiro[cyclohexane-1,2'-pyrano[2,3-b]pyridin]-4'-yl]acetamide.

To the product of Example 23 (50 mg, 0.114 mmol) in $CH_2Cl_2$ (1 mL) was added acetyl chloride (9 µL, 0.127 mmol) and $NEt_3$ (40 µL, 0.286 mmol). The reaction was stirred 30 min and was purified directly by flash chromatography on silica gel gradient eluted with 0-100% EtOAc in hexane to afford the title compound. (LC-2) HPLC/MS: 481.2 (M+1), 483.2 (M+3); $R_t$=3.79 min.

| | Name | HPLC/MS m/z (M + 1) m/z (M + 3) $R_t$ (min) (LC-2) | Structure |
|---|---|---|---|
| Example 24 | 6-(4-chlorophenyl)-7-(2,4-dichlorophenyl)-2,2-dimethyl-3,4-dihydro-2H-pyrano[2,3-b]pyridin-4-amine | 433.1 435.2 3.37 | 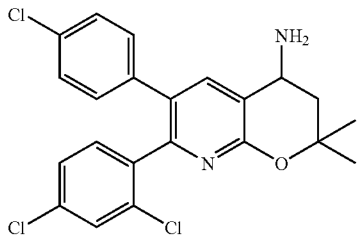 |
| Example 25 | 2-tert-butyl-7-(2-chlorophenyl)-6-(4-chlorophenyl)-3,4-dihydro-2H-pyrano[2,3-b]pyridin-4-amine | 427.0 429.0 3.21 | 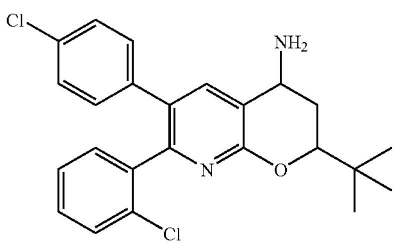 |

EXAMPLE 27

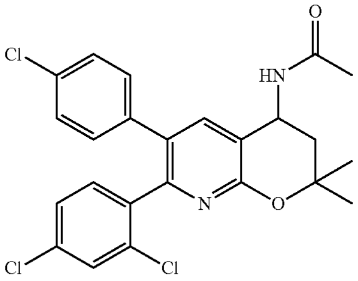

N-[6-(4-Chlorophenyl)-7-(2,4-dichlorophenyl)-2,2-dimethyl-3,4-dihydro-2H-pyrano[2,3-b]pyridin-4-yl] acetamide.

To the product of Example 18 (102 mg, 0.228 mmol) in AcOH (2 mL) was added Zn powder (75 mg, 1.15 mmol). The reaction was heated to 95° C. for 10 min before adding acetic anhydride (0.5 mL). After 15 min the reaction was concentrated. The residue was diluted with EtOAc and washed with 1M aq $Na_2CO_3$. The concentrated residue was purified by flash chromatography on silica gel gradient eluted with 0-100% EtOAc in hexane to afford the title compound. (LC-2) HPLC/MS: 475.2 (M+1), 477.1 (M+3); $R_t$=3.83 min.

EXAMPLE 28

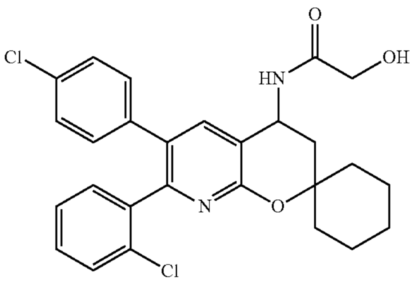

N-[7'-(2-Chlorophenyl)-6'-(4-chlorophenyl)-3',4'-dihydrospiro[cyclohexane-1,2'-pyrano[2,3-b]pyridin]-4'-yl]-2-hydroxyacetamide.

To the product of Example 23 (50 mg, 0.114 mmol) in $CH_2Cl_2$ (1 mL) was added acetoxyacetyl chloride (14.7 μL, 0.137 mmol) and $NEt_3$ (15.9 μL, 0.114 mmol). The reaction was stirred 20 min and was treated with sodium methoxide solution (0.3 mL, 30 wt %) and MeOH (1 mL). The reaction was stirred 90 min and was concentrated. The residue was diluted with $CH_2Cl_2$ and washed with aq $NaHSO_4$ (1 M). The concentrated residue was purified by flash chromatography on silica gel gradient eluted with 0-100% EtOAc in hexane to afford the title compound. (LC-2) HPLC/MS: 497.2 (M+1), 499.1 (M+3); $R_t$=3.61 min.

The following examples were prepared utilizing the appropriate amine and carboxylic acid or acid chloride in procedures similar to those of Example 26 and Example 88. Preparation of hydroxy acetamide compounds were carried out as per Example 28. Where noted the enantiomers, or the diastereomers, were separated either by chiral chromatography or via silica gel purification with the conditions as indicated:

| | Name | HPLC/MS m/z (M + 1) m/z (M + 3) $R_t$ (min) (LC-2) | |
|---|---|---|---|
| Example 29 | N-[7'-(2-chlorophenyl)-6'-(4-chlorophenyl)-3',4'-dihydrospiro[cyclohexane-1,2'-pyrano[2,3-b]pyridin]-4'-yl]isoxazole-5-carboxamide | 534.1<br>536.1<br>4.02 | 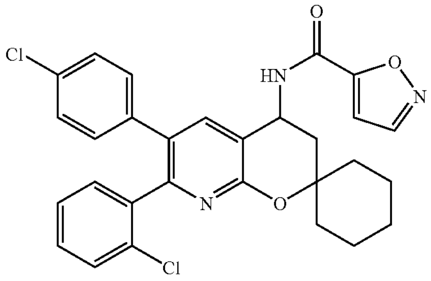 |
| Example 30 | N-[7-(2-chlorophenyl)-6-(4-chlorophenyl)-2',3,3',4,5',6'-hexahydrospiro[pyrano[2,3-b]pyridine-2,4'-thiopyran]-4-yl]-2-hydroxyacetamide (Racemic) | 515.2<br>517.1<br>3.51 | 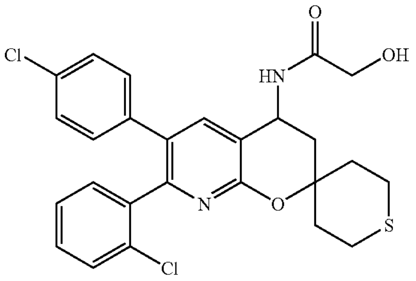 |

-continued

| | Name | HPLC/MS m/z (M + 1) m/z (M + 3) $R_t$ (min) (LC-2) | |
|---|---|---|---|
| Example 31 | N-[7-(2-chlorophenyl)-6-(4-chlorophenyl)-2',3,3',4,5',6'-hexahydrospiro[pyrano[2,3-b]pyridine-2,4'-thiopyran]-4-yl]-2-hydroxyacetamide<br>Faster isomer on AD column (8.09 min, 12% EtOH/Heptane) | 515.2<br>517.1<br>3.51 | 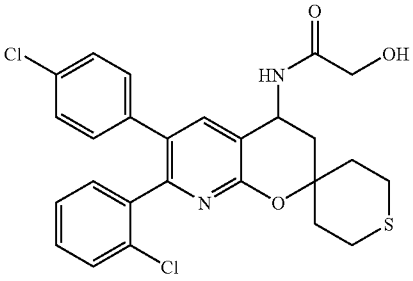 |
| Example 32 | N-[7-(2-chlorophenyl)-6-(4-chlorophenyl)-2',3,3',4,5',6'-hexahydrospiro[pyrano[2,3-b]pyridine-2,4'-thiopyran]-4-yl]-2-hydroxyacetamide<br>Slower isomer on AD column (16.81 min, 12% EtOH/Heptane) | 515.2<br>517.1<br>3.51 | 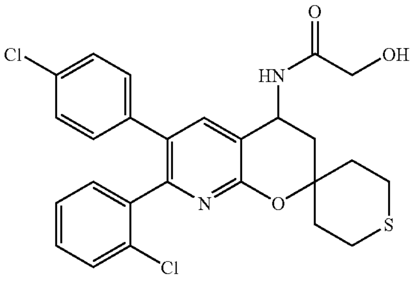 |
| Example 33 | N-[7'-(2-chlorophenyl)-6'-(4-chlorophenyl)-3',4'-dihydrospiro[cyclopentane-1,2'-pyrano[2,3-b]pyridin]-4'-yl]-2-hydroxyacetamide (Racemic) | 483.2<br>485.2<br>3.50 | 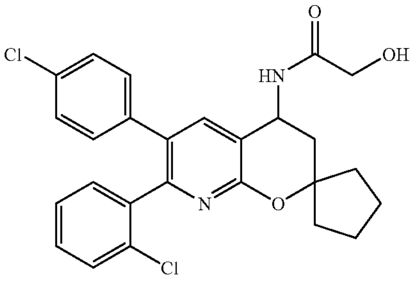 |
| Example 34 | N-[7'-(2-chlorophenyl)-6'-(4-chlorophenyl)-3',4'-dihydrospiro[cyclopentane-1,2'-pyrano[2,3-b]pyridin]-4'-yl]-2-hydroxyacetamide<br>Faster isomer on AD column (12.39 min, 12% EtOH/Heptane) | 483.2<br>485.2<br>3.50 | 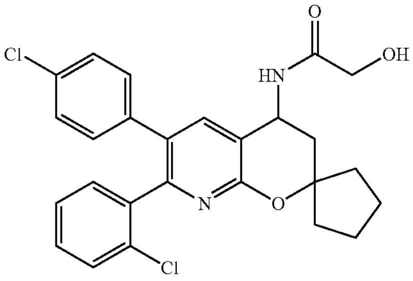 |
| Example 35 | N-[7'-(2-chlorophenyl)-6'-(4-chlorophenyl)-3',4'-dihydrospiro[cyclopentane-1,2'-pyrano[2,3-b]pyridin]-4'-yl]-2-hydroxyacetamide<br>Slower isomer on AD column (28.07 min, 12% EtOH/Heptane) | 483.2<br>485.2<br>3.50 | 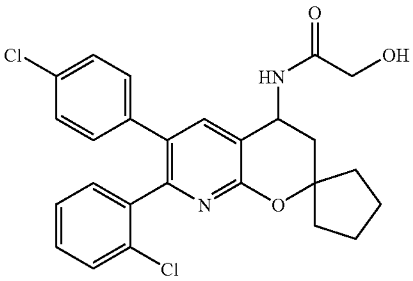 |

-continued

| | Name | HPLC/MS m/z (M + 1) m/z (M + 3) $R_t$ (min) (LC-2) | |
|---|---|---|---|
| Example 36 | ethyl[7'-(2-chlorophenyl)-6'-(4-chlorophenyl)-3',4'-dihydrospiro[cyclohexane-1,2'-pyrano[2,3-b]pyridin]-4'-yl]carbamate | 511.3 513.2 4.17 | 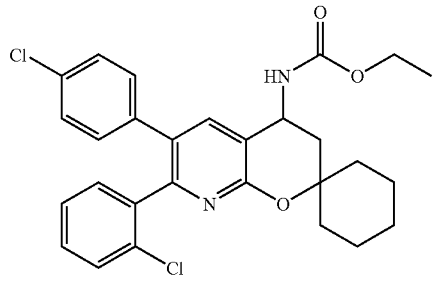 |
| Example 37 | 3-chloro-N-[7'-(2-chlorophenyl)-6'-(4-chlorophenyl)-3',4'-dihydrospiro[cyclohexane-1,2'-pyrano[2,3-b]pyridin]-4'-yl]-2,2-dimethylpropanamide | 557.2 559.2 4.23 | 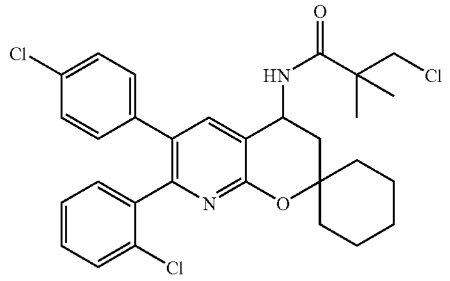 |
| Example 38 | N-[7'-(2-chlorophenyl)-6'-(4-chlorophenyl)-3',4'-dihydrospiro[cyclohexane-1,2'-pyrano[2,3-b]pyridin]-4'-yl] cyclopropanecarboxamide | 507.3 509.2 3.99 | 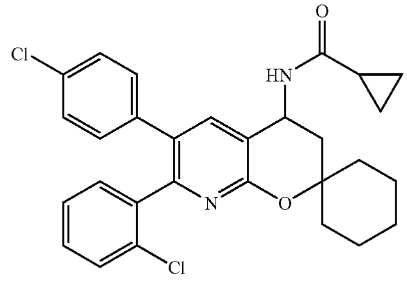 |
| Example 39 | 4-bromo-N-[7'-(2-chlorophenyl)-6'-(4-chlorophenyl)-3',4'-dihydrospiro[cyclohexane-1,2'-pyrano[2,3-b]pyridin]-4'-yl]butanamide | 587.2 589.2 4.12 | 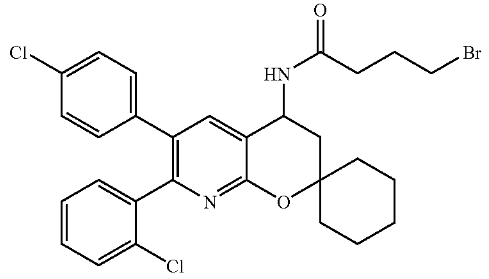 |
| Example 40 | N-[6-(4-chlorophenyl)-7-(2,4-dichlorophenyl)-2,2-dimethyl-3,4-dihydro-2H-pyrano[2,3-b]pyridin-4-yl]-2-hydroxyacetamide (Racemic) | 491.3 493.2 3.62 | 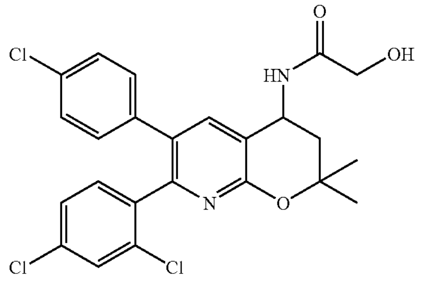 |

-continued

| | Name | HPLC/MS<br>m/z (M + 1)<br>m/z (M + 3)<br>$R_t$ (min)<br>(LC-2) | |
|---|---|---|---|
| Example 41 | N-[6-(4-chlorophenyl)-7-(2,4-dichlorophenyl)-2,2-dimethyl-3,4-dihydro-2H-pyrano[2,3-b]pyridin-4-yl]-2-hydroxyacetamide<br>Faster isomer on AD column (17.07 min, 5% EtOH/Hexane) | 491.3<br>493.2<br>3.62 | 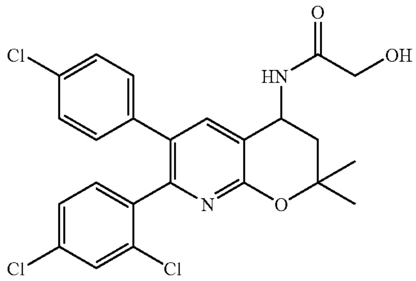 |
| Example 42 | N-[6-(4-chlorophenyl)-7-(2,4-dichlorophenyl)-2,2-dimethyl-3,4-dihydro-2H-pyrano[2,3-b]pyridin-4-yl]-2-hydroxyacetamide<br>Slower isomer on AD column (25.92 min, 5% EtOH/Hexane) | 491.3<br>493.2<br>3.62 | 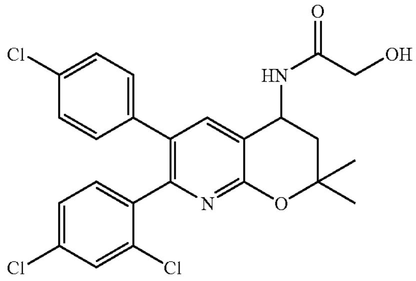 |
| Example 43 | N-[7-(2-chlorophenyl)-6-(4-chlorophenyl)-2,2-dimethyl-3,4-dihydro-2H-pyrano[2,3-b]pyridin-4-yl]-2-hydroxyacetamide<br>(Racemic) | 457.2<br>459.2<br>3.36 | 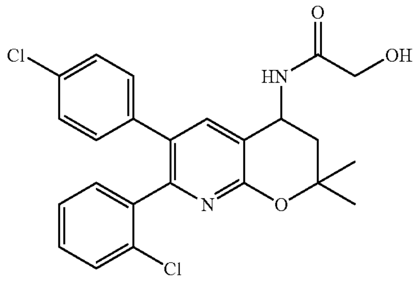 |
| Example 44 | N-[7-(2-chlorophenyl)-6-(4-chlorophenyl)-2,2-dimethyl-3,4-dihydro-2H-pyrano[2,3-b]pyridin-4-yl]-2-hydroxyacetamide<br>Faster isomer on AD column (10.38 min, 7% EtOH/Hexane) | 457.2<br>459.2<br>3.36 | 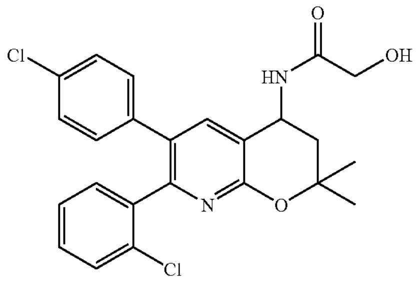 |
| Example 45 | N-[7-(2-chlorophenyl)-6-(4-chlorophenyl)-2,2-dimethyl-3,4-dihydro-2H-pyrano[2,3-b]pyridin-4-yl]-2-hydroxyacetamide<br>Slower isomer on AD column (14.17 min, 7% EtOH/Hexane) | 457.2<br>459.2<br>3.36 | 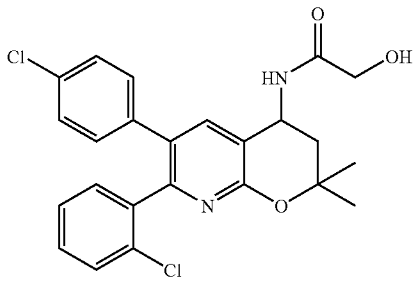 |

-continued

| | Name | HPLC/MS m/z (M + 1) m/z (M + 3) $R_t$ (min) (LC-2) | |
|---|---|---|---|
| Example 46 | (2R)-N-[2-tert-butyl-7-(2-chlorophenyl)-6-(4-chlorophenyl)-3,4-dihydro-2H-pyrano[2,3-b]pyridin-4-yl]-2-hydroxypropanamide | 499.3 501.4 3.70 | 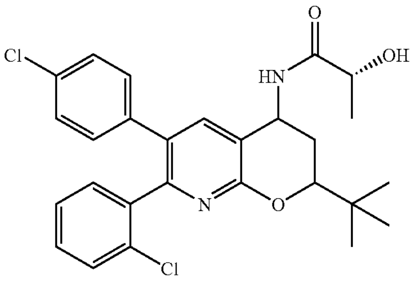 |
| Example 47 | (2R)-N-[2-tert-butyl-7-(2-chlorophenyl)-6-(4-chlorophenyl)-3,4-dihydro-2H-pyrano[2,3-b]pyridin-4-yl]-2-hydroxypropanamide 1st eluting isomer on AD column (15.12 min, 3% EtOH/Hexane) | | 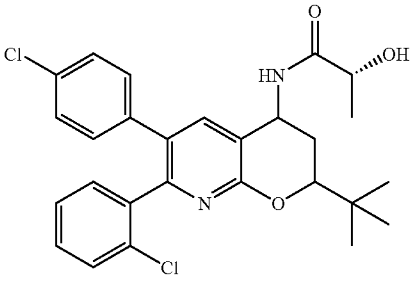 |
| Example 48 | (2R)-N-[2-tert-butyl-7-(2-chlorophenyl)-6-(4-chlorophenyl)-3,4-dihydro-2H-pyrano[2,3-b]pyridin-4-yl]-2-hydroxypropanamide 2nd eluting isomer on AD column (19.66 min, 3% EtOH/Hexane) | | 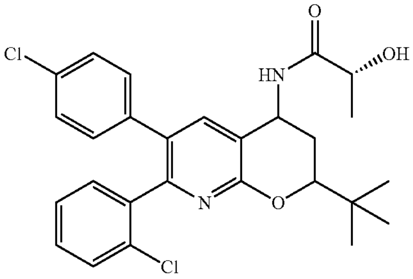 |
| Example 49 | (2R)-N-[2-tert-butyl-7-(2-chlorophenyl)-6-(4-chlorophenyl)-3,4-dihydro-2H-pyrano[2,3-b]pyridin-4-yl]-2-hydroxypropanamide 3rd eluting isomer on AD column (23.83 min, 3% EtOH/Hexane) | | 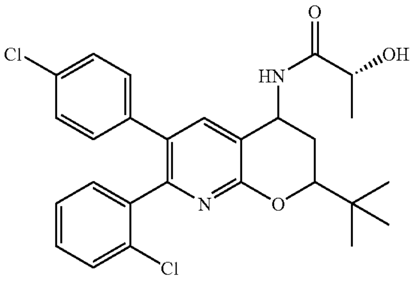 |
| Example 50 | N-[6-(4-chlorophenyl)-7-(2,4-dichlorophenyl)-2,2-dimethyl-3,4-dihydro-2H-pyrano[2,3-b]pyridin-4-yl]-4,4,4-trifluoro-3-hydroxybutanamide (Racemic) Faster diastereomer on silica gel | 573.0 575.0 3.67 | 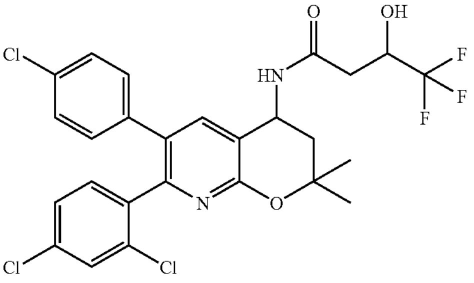 |

-continued

| | Name | HPLC/MS m/z (M + 1) m/z (M + 3) $R_t$ (min) (LC-2) | |
|---|---|---|---|
| Example 51 | N-[6-(4-chlorophenyl)-7-(2,4-dichlorophenyl)-2,2-dimethyl-3,4-dihydro-2H-pyrano[2,3-b]pyridin-4-yl]-4,4,4-trifluoro-3-hydroxybutanamide (Racemic) Slower diastereomer on silica gel | 573.0 575.0 3.71 | 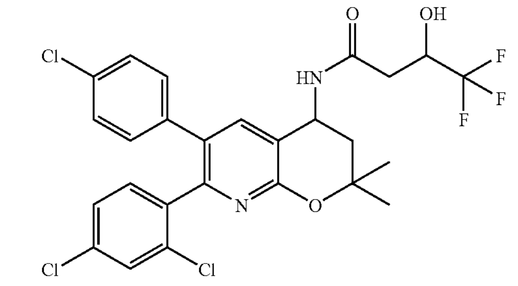 |
| Example 52 | 3-(benzyloxy)-N-[6-(4-chlorophenyl)-7-(2,4-dichlorophenyl)-2,2-dimethyl-3,4-dihydro-2H-pyrano[2,3-b]pyridin-4-yl]-2,2-dimethylpropanamide | 623.5 625.5 4.53 | 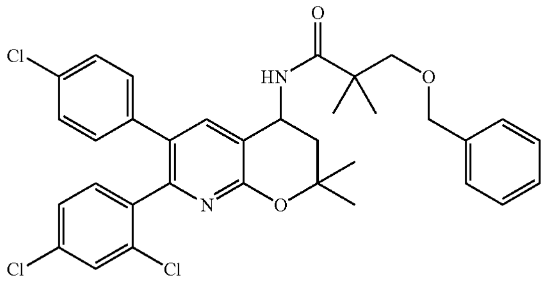 |

EXAMPLE 53

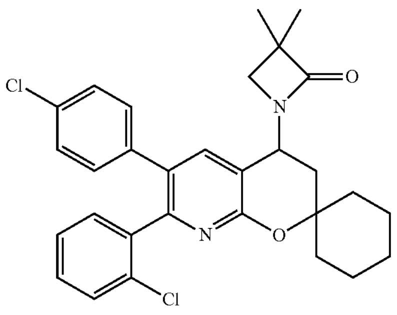

1-[7'-(2-Chlorophenyl)-6'-(4-chlorophenyl)-3',4'-dihydrospiro[cyclohexane-1,2'-pyrano[2,3-b]pyridin]-4'-yl]-3,3-dimethylazetidin-2-one.

To the product of Example 37 (34 mg, 0.0652 mmol) in DMF (1 mL) was added $Cs_2CO_3$ (20 mg, 0.061 mmol). The reaction was heated to 80° C. for 1 h. The reaction was diluted with EtOAc and washed with brine. The concentrated residue was purified by flash chromatography on silica gel gradient eluted with 0-100% EtOAc in hexane to afford the title compound. (LC-2) HPLC/MS: 521.3 (M+1), 523.2 (M+3); $R_t$=4.20 min.

EXAMPLE 54

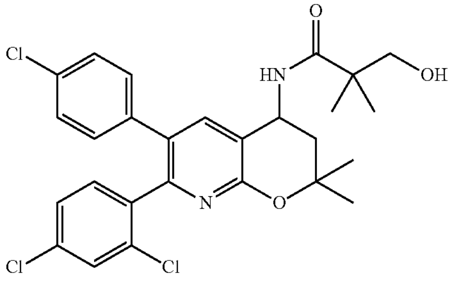

N-[6-(4-Chlorophenyl)-7-(2,4-dichlorophenyl)-2,2-dimethyl-3,4-dihydro-2H-pyrano[2,3-b]pyridin-4-yl]-3-hydroxy-2,2-dimethylpropanamide.

To the product of Example 52 (168 mg, 0.269 mmol) was added $FeCl_3$ (235 mg, 1.45 mmol) in $CH_2Cl_2$ (3.5 mL). The reaction was stirred 130 min at 30° C. and was then diluted with EtOAc. The reaction was washed with brine. The concentrated residue was purified by flash chromatography on silica gel gradient eluted with 0-100% EtOAc in hexane to afford the title compound. (LC-2) HPLC/MS: 533.3 (M+1), 535.3 (M+3); $R_t$=3.86 min.

The product of Example 54 was resolved on an AD column using the conditions indicated below.

| | Name | HPLC/MS m/z (M + 1) m/z (M + 3) $R_t$ (min) (LC-2) | |
|---|---|---|---|
| Example 55 | N-[6-(4-chlorophenyl)-7-(2,4-dichlorophenyl)-2,2-dimethyl-3,4-dihydro-2H-pyrano[2,3-b]pyridin-4-yl]-3-hydroxy-2,2-dimethylpropanamide Faster isomer on AD column (18.98 min, 4% EtOH/Hexane) | 533.3 535.3 3.86 | 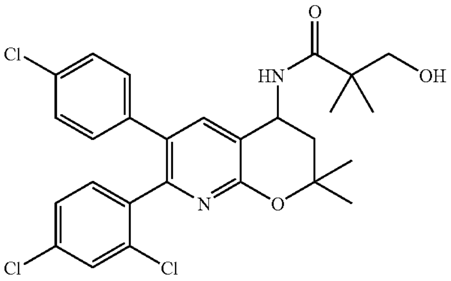 |
| Example 56 | N-[6-(4-chlorophenyl)-7-(2,4-dichlorophenyl)-2,2-dimethyl-3,4-dihydro-2H-pyrano[2,3-b]pyridin-4-yl]-3-hydroxy-2,2-dimethylpropanamide Slower isomer on AD column (23.13 min, 4% EtOH/Hexane) | 533.3 535.3 3.86 | 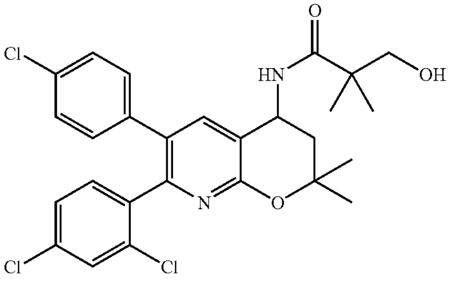 |

EXAMPLE 57

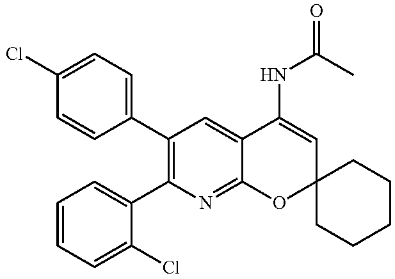

N-[7'-(2-Chlorophenyl)-6'-(4-chlorophenyl)spiro[cyclohexane-1,2'-pyrano[2,3-b]pyridin]-4'-yl]acetamide To the product of Example 17 (100 mg, 0.221 mmol), acetic anhydride (61 μL, 0.662 mmol) and AcOH (38 μL, 0.662 mmol) in toluene (3 mL) was added iron powder (25 mg, 0.448 mmol) at 67° C. After 15 min chlorotrimethylsilane (50 μL) was added. The reaction was concentrated, and the residue was diluted with EtOAc and filtered. The solution was washed with saturated aq $NaHCO_3$, concentrated and purified by flash chromatography on silica gel gradient eluted with 0-60% EtOAc in hexane affording the title compound. (LC-2) HPLC/MS: 479.2 (M+1), 481.2 (M+3); $R_t$=4.07 min.

The following examples were prepared in similar fashion to example Example 57 except that acetic anhydride was used as solvent instead of toluene. The resolution of Example 58 was carried out on an AD column eluting with 12% EtOH/Hexane.

| Name | | HPLC/MS m/z (M + 1) m/z (M + 3) $R_t$ (min) (LC-2) | |
|---|---|---|---|
| Example 58 | N-[2-tert-butyl-7-(2-chlorophenyl)-6-(4-chlorophenyl)-2H-pyrano[2,3-b]pyridin-4-yl]acetamide (Racemic) | 467.3 469.3 3.88 | 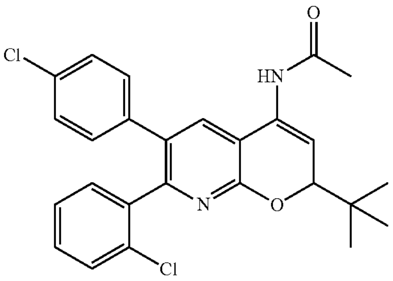 |
| Example 59 | N-[2-tert-butyl-7-(2-chlorophenyl)-6-(4-chlorophenyl)-2H-pyrano[2,3-b]pyridin-4-yl]acetamide Faster isomer on AD column (6.84 min, 14% EtOH/Hexane) | 467.3 469.3 3.88 | 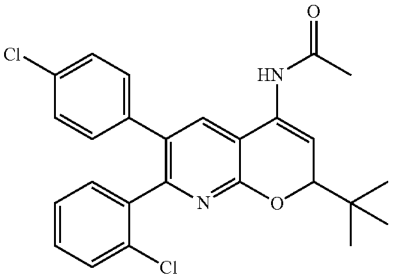 |
| Example 60 | N-[2-tert-butyl-7-(2-chlorophenyl)-6-(4-chlorophenyl)-2H-pyrano[2,3-b]pyridin-4-yl]acetamide Slower isomer on AD column (11.38 min, 14% EtOH/Hexane) | 467.3 469.3 3.88 | 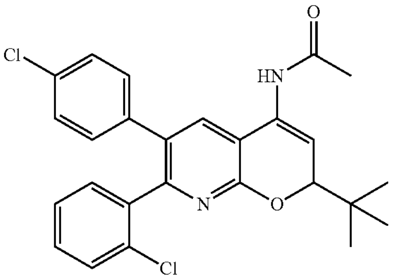 |

EXAMPLE 61

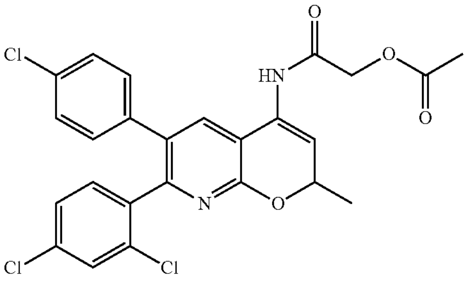

2-{[6-(4-Chlorophenyl)-7-(2,4-dichlorophenyl)-2-methyl-2H-pyrano[2,3-b]pyridin-4-yl]amino}-2-oxoethyl acetate.

To the product of Example 22 (150 mg, 0.346 mmol), acetoxyacetyl chloride (0.22 mL, 2.08 mmol) and AcOH (38 μL, 0.662 mmol) in toluene (2 mL) was added iron powder (116 mg, 2.08 mmol). The reaction was heated to 70° C. and was completed in 20 min. The reaction was diluted with EtOAc and washed with 1 M aq $Na_2CO_3$ followed by 1 M aq $NaHSO_4$. The concentrated residue was purified by flash chromatography on silica gel gradient eluted with 0-100% EtOAc in hexane affording the title compound. (LC-2) HPLC/MS: 517.3 (M+1), 519.3 (M+3); $R_t$=3.81 min.

EXAMPLE 62

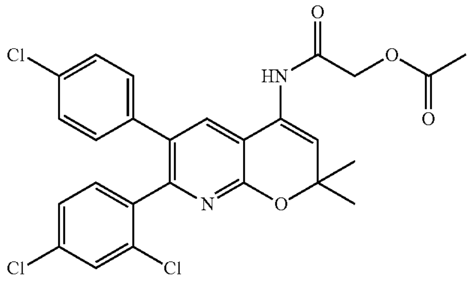

2-{[6-(4-Chlorophenyl)-7-(2,4-dichlorophenyl)-2,2-dimethyl-2H-pyrano[2,3-b]pyridin-4-yl]amino}-2-oxoethyl acetate.

The product of Example 18 was treated with conditions similar to that of Example 61 to afford the title compound. (LC-2) HPLC/MS: 531.1 (M+1), 533.1 (M+3); $R_t$=3.85 min.

The following examples were prepared by reacting the product of Example 61 (85 mg, 0.164 mmol) with $Cs_2CO_3$ (53 mg, 0.163 mmol) in MeOH (1.5 mL) and $CH_2Cl_2$ (0.5 mL). After 10 min the reaction was concentrated. The residue was diluted with EtOAc and washed with brine. The concentrated residue was purified by flash chromatography on silica gel gradient eluted with 0-100% EtOAc in hexane to afford the racemic product Example 63. The product was resolved on an AD column eluting 15% EtOH/Hexane

| | Name | HPLC/MS m/z (M + 1) m/z (M + 3) $R_t$ (min) (LC-2) | |
|---|---|---|---|
| Example 63 | N-[6-(4-chlorophenyl)-7-(2,4-dichlorophenyl)-2-methyl-2H-pyrano[2,3-b]pyridin-4-yl]-2-hydroxyacetamide (Racemic) | 475.2<br>477.2<br>3.60 | 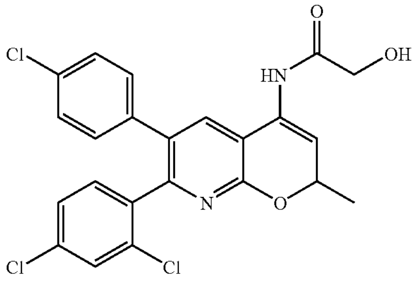 |
| Example 64 | N-[6-(4-chlorophenyl)-7-(2,4-dichlorophenyl)-2-methyl-2H-pyrano[2,3-b]pyridin-4-yl]-2-hydroxyacetamide Faster isomer on AD column (10.07 min, 15% EtOH/Hexane) | 475.2<br>477.2<br>3.60 | 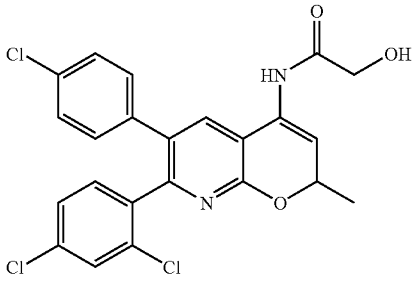 |
| Example 65 | N-[6-(4-chlorophenyl)-7-(2,4-dichlorophenyl)-2-methyl-2H-pyrano[2,3-b]pyridin-4-yl]-2-hydroxyacetamide Slower isomer on AD column (15.87 min, 15% EtOH/Hexane | 475.2<br>477.2<br>3.60 | 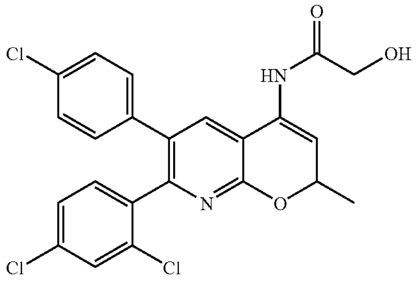 |

EXAMPLE 66

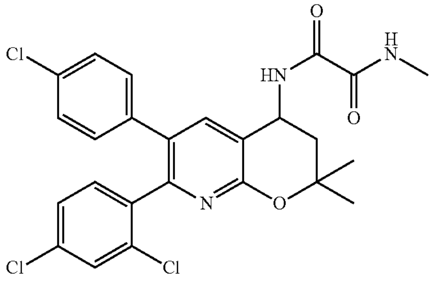

N-[6-(4-Chlorophenyl)-7-(2,4-dichlorophenyl)-2,2-dimethyl-3,4-dihydro-2H-pyrano[2,3-b]pyridin-4-yl]-N'-methylethanediamide.

To the product of Example 24 (110 mg, 0.254 mmol) in $CH_2Cl_2$ (2 mL) was added oxalyl chloride (0.5 mL, 5.71 mmol). After 10 min, the reaction was concentrated. The residue was diluted with 6 mL of 2 M methylamine in THF. After 30 min the reaction was concentrated The residue was diluted with EtOAc and washed with saturated aq $NaHCO_3$/brine (1:1). The concentrated residue was purified by flash chromatography on silica gel gradient eluted with 0-100% EtOAc in hexane affording the title compound. (LC-2) HPLC/MS: 518.0 (M+1), 520.0 (M+3); $R_t$=3.67 min.

EXAMPLE 67

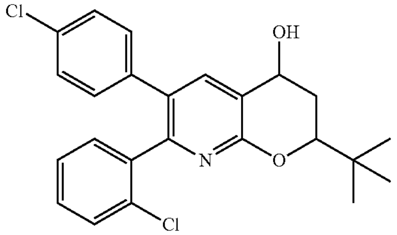

2-tert-Butyl-7-(2-chlorophenyl)-6-(4-chlorophenyl)-3,4-dihydro-2H-pyrano[2,3-b]pyridin-4-ol To the product of Example 12 (175 mg, 0.411 mmol) in THF (2.5 mL) and MeOH (0.5 mL) was added $NaBH_4$ (15.5 mg, 0.410 mmol). After 25 min the reaction was quenched 2 M aq HCl and diluted with EtOAc. The solution was washed with brine. The concentrated residue was purified by flash chromatography on silica gel gradient eluted with 0-50% EtOAc in hexane affording the title compound.

(LC-2) HPLC/MS: 428.3 (M+1), 430.3 (M+3); $R_t$=3.79 min.

EXAMPLE 68

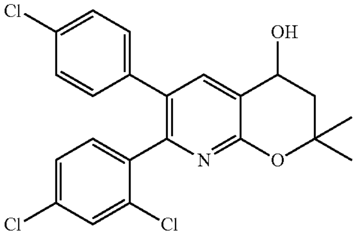

6-(4-Chlorophenyl)-7-(2,4-dichlorophenyl)-2,2-dimethyl-3,4-dihydro-2H-pyrano[2,3-b]pyridin-4-ol Starting with the product of Example 1 and utilizing conditions similar to that of Example 67 the title compound was prepared. (LC-2) HPLC/MS: 433.8 (M+1), 435.8 (M+3); $R_t$=3.63 min.

EXAMPLE 69

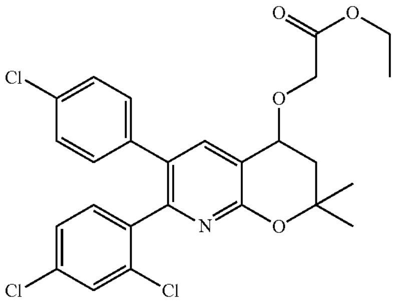

Ethyl {[6-(4-chlorophenyl)-7-(2,4-dichlorophenyl)-2,2-dimethyl-3,4-dihydro-2H-pyrano[2,3-b]pyridin-4-yl]oxy}acetate.

To the product of Example 68 (250 mg, 0.575 mmol) was added NaH (73.6 mg, 1.84 mmol, 60%) and ethyl 2-bromoacetate (0.23 mL 2.07 mmol) in DMF (3 mL). The reaction was stirred 3 h at 30° C. and 15 h at rt. The reaction was diluted with EtOAc and washed with 2 M aq HCl and brine. The concentrated residue was purified by flash chromatography on silica gel gradient eluted with 0-33% EtOAc in hexane affording the title compound. (LC-2) HPLC/MS: 520.1 (M+1), 522.0 (M+3); $R_t$=4.43 min.

EXAMPLE 70

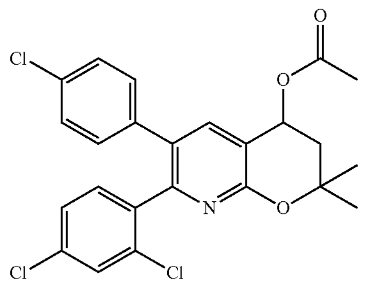

6-(4-Chlorophenyl)-7-(2,4-dichlorophenyl)-2,2-dimethyl-3,4-dihydro-2H-pyrano[2,3-b]pyridin-4-yl acetate.

To the product of Example 68 (25 mg, 0.0575 mmol) was added acetic anhydride (0.25 mL, 2.65 mmol) in pyridine (2 mL). The reaction was stirred 4 h and was concentrated. The residue was diluted with EtOAc and washed with 1 M aq HCl followed by saturated aq $NaHCO_3$/1 M aq NaOH (1:1). The solution was dried ($Na_2SO_4$). The concentrated residue was purified by flash chromatography on silica gel eluted with 50% EtOAc in hexane affording the title compound. (LC-2) HPLC/MS: 475.9 (M+1), 477.9 (M+3); $R_t$=4.29 min.

EXAMPLE 71

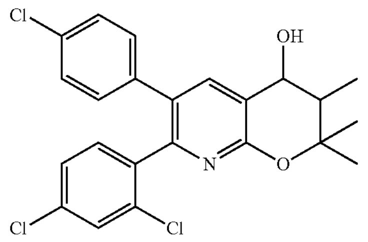

6-(4-Chlorophenyl)-7-(2,4-dichlorophenyl)-2,2,3-trimethyl-3,4-dihydro-2H-pyrano[2,3-b]pyridin-4-ol To the product of Example 1 (500 mg, 1.155 mmol) was added paraformaldehyde (347 mL, 11.6 mmol) and pyrrolidine (0.243 mL, 2.94 mmol) in EtOH (10 mL)/THF (3 mL). The reaction vessel was sealed and heated to 65° C. for 4.5 h. The reaction was cooled and diluted with EtOAc and washed with brine. The solution was dried ($Na_2SO_4$) and concentrated. The residue was dissolved in THF (8 mL) and MeOH (1 mL) and $NaBH_4$ (87 mg, 2.31 mmol) was added. After 25 min the reaction was diluted with EtOAc and washed with 2 M aq HCl and brine. The concentrated residue was purified by flash chromatography on silica gel gradient eluted with 0-60% EtOAc in hexane affording the title compound. (LC-2) HPLC/MS: 448.2 (M+1), 450.2 (M+3); $R_t$=4.23 min.

EXAMPLE 72

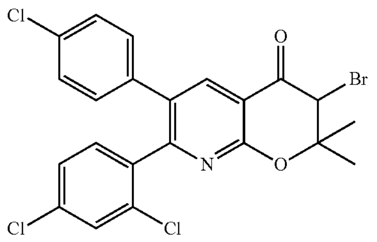

3-Bromo-6-(4-chlorophenyl)-7-(2,4-dichlorophenyl)-2,2-dimethyl-2,3-dihydro-4H-pyrano[2,3-b]pyridin-4-one.

To the product of Example 1 (150 mg, 0.347 mmol) was added AcOH (0.30 mL) and $Br_2$ (5 drops) in 1,4-dioxane (2 mL). The reaction was heated to 70° C. After 5 h the reaction was cooled. The reaction was diluted with EtOAc and washed with saturated aq $NaHCO_3$ and brine. The solution was dried ($Na_2SO_4$). The concentrated residue was purified by flash chromatography on silica gel gradient eluted with 0-40% EtOAc in hexane affording the title compound. (LC-2) HPLC/MS: 509.9 (M+1), 511.9 (M+3); $R_t$=4.34 min.

EXAMPLE 73

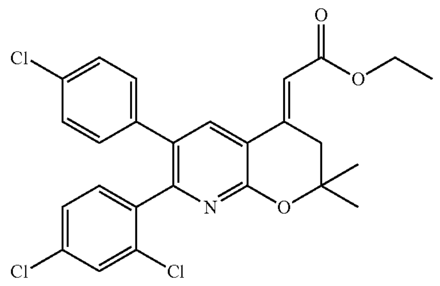

Ethyl 2-[6-(4-chlorophenyl)-7-(2,4-dichlorophenyl)-2,2-dimethyl-2,3-dihydro-4H-pyrano[2,3-b]pyridin-4-ylidene]acetate (E or Z).

Step A: ethyl 2-(6-(4-chlorophenyl)-7-(2,4-dichlorophenyl)-4-hydroxy-2,2-dimethyl-3,4-dihydro-2H-pyrano[2,3-b]pyridin-4-yl)acetate. A mixture of ethyl 2-bromoacetate (0.334 mL 3.01 mmol), 1,2-dibromoethane (0.02 mL, 0.23 mmol), Zn powder (0.227 g, 3.47 mmol) and THF (2.5 mL) was heated to 65° C. for 2 min before cooling to rt. Chlorotrimethylsilane (0.015 mL, 0.116 mmol) was added and the reaction was stirred for 5 min at which point the product of Example 1 (1 g, 2.315 mmol) in THF 10 mL was added. The reaction was heated to 70° C. After 1 h the reaction was cooled to rt. The reaction was diluted with EtOAc and washed with 2 M aq HCl and brine. The concentrated residue was purified by flash chromatography on silica gel gradient eluted with 0-10% EtOAc in $CH_2Cl_2$ affording the product (LC-2) HPLC/MS: 520.2 (M+1), 522.2 (M+3); $R_t$=3.97 min.

Step B: Ethyl 2-[6-(4-chlorophenyl)-7-(2,4-dichlorophenyl)-2,2-dimethyl-2,3-dihydro-4H-pyrano[2,3-b]pyridin-4- ylidene]acetate (E or Z). To the product of Step A this example (192 mg, 0.382 mmol) was added p-toluenesulfonic acid monohydrate (72.6 mg, 0.276 mmol) in toluene (3 mL). The reaction was heated to 104° C. After 80 min the reaction was cooled and diluted with EtOAc. The solution was washed with brine and saturated aq $NaHCO_3$. The concentrated residue was purified by flash chromatography on silica gel gradient eluted with 0-25% EtOAc in hexane affording the title compound as the faster eluting isomer on silica gel. (LC-2) HPLC/MS: 502.1 (M+1), 504.1 (M+3); $R_t$=4.52 min.

EXAMPLE 74

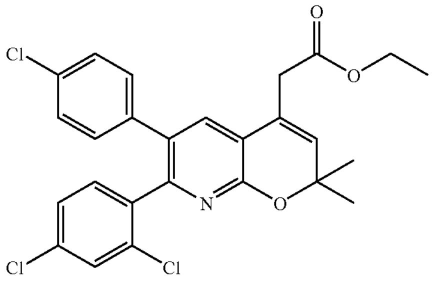

Ethyl [6-(4-chlorophenyl)-7-(2,4-dichlorophenyl)-2,2-dimethyl-2H-pyrano[2,3-b]pyridin-4-yl]acetate This example was isolated as a co-product from Example 73 step B as the slower moving isomer on silica gel. (LC-2) HPLC/MS: 502.1 (M+1), 504.1 (M+3); $R_t$=4.31 min.

EXAMPLE 75

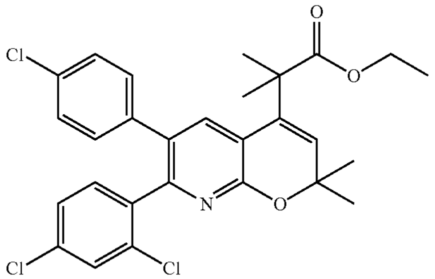

Ethyl 2-[6-(4-chlorophenyl)-7-(2,4-dichlorophenyl)-2,2-dimethyl-2H-pyrano[2,3-b]pyridin-4-yl]-2-methylpropanoate.

To the product of Example 74 (50 mg, 0.099 mmol) was added NaH (20 mg, 0.5 mmol, 60%) and iodomethane (0.125 mL, 2.0 mmol) in DMF (1 mL). The reaction stirred 19 h and diluted with EtOAc. The solution was washed with 2 M aq HCl and brine. The concentrated residue was purified by flash chromatography on silica gel gradient eluted with 0-33% EtOAc in hexane affording the title. (LC-2) HPLC/MS: 530.1 (M+1), 532.1 (M+3); $R_t$=4.60 min.

EXAMPLE 76

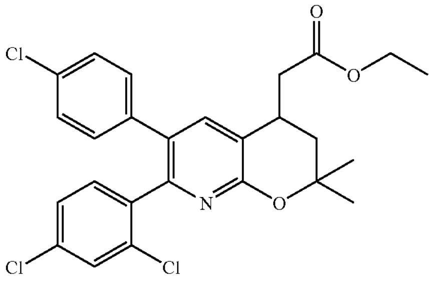

Ethyl 2-(6-(4-chlorophenyl)-7-(2,4-dichlorophenyl)-2,2-dimethyl-3,4-dihydro-2H-pyrano[2,3-b]pyridin-4-yl)acetate.

The product Example 73 (63.7 mg, 0.127 mmol) was added Zn powder (120 mg, 1.835 mmol) in AcOH (2 mL). The reaction was heated to 100° C. After 20 min the reaction was cooled and diluted with EtOAc. The solution was filtered and washed with 10% aq $Na_2CO_3$ and brine. The concentrated residue was purified by flash chromatography on silica gel gradient eluted with 0-40% EtOAc in hexane affording the title compound. (LC-2) HPLC/MS: 504.0 (M+1), 506.0 (M+3); $R_t$=4.38 min.

EXAMPLE 77

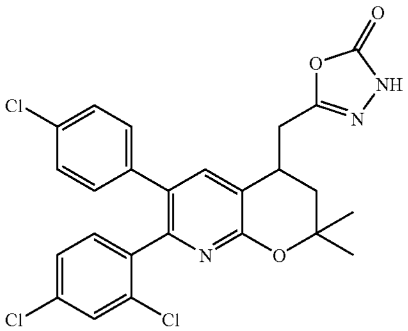

5-{[6-(4-Chlorophenyl)-7-(2,4-dichlorophenyl)-2,2-dimethyl-3,4-dihydro-2H-pyrano[2,3-b]pyridine-4-yl]methyl}-1,3,4-oxadiazol-2(3H)-one Step A: 2-(6-(4-Chlorophenyl)-7-(2,4-dichlorophenyl)-2,2-dimethyl-3,4-dihydro-2H-pyrano[2,3-b]pyridin-4-yl)acetic acid. To the product of Example 76 (46.5 mg, 0.127 mmol) was added KOH (10.3 mg, 0.184 mmol) in THF (1.5 mL), MeOH (0.2 mL) and water (0.075 mL). The reaction was heated to 50° C. After 27 min the reaction was cooled and diluted with EtOAc. The solution was washed with aq 2 M HCl and brine, dried ($Na_2SO_4$), filtered and concentrated to afford the product that was not purified further (LC-2) HPLC/MS: 476.0 (M+1), 478.0 (M+3); $R_t$=3.96 min.

Step B: 5-{[6-(4-Chlorophenyl)-7-(2,4-dichlorophenyl)-2,2-dimethyl-3,4-dihydro-2H-pyrano[2,3-b]yridine-4-yl] methyl}-1,3,4-oxadiazol-2(3H)-one. To the product of step A of this example (40.0 mg, 0.084 mmol) was added HOBt (1H-1,2,3-benzotriazol-1-ol hydrate) (15.4 mg, 0.101 mmol), EDAC (N'-((ethylimino)methylene)-$N^3$,$N^3$-dimethylpropane-1,3-diamine hydrochloride) (19.3 mg, 0.101 mmol) in $CH_2Cl_2$ (1.5 mL). The reaction was stirred 1 min before hydrazine hydrate (8.1 μL, 0.168 mmol) was added. After 10 min EDAC (19.3 mg) and hydrazine hydrate (16.3, μL, 0.336 mmol) were added. The reaction was stirred an additional 3.5 h and then diluted with EtOAc. The solution was washed with brine, dried ($Na_2SO_4$), and filtered. The concentrated residue was diluted with $CH_2Cl_2$ (1.5 mL) and reacted with trichloromethyl chloridocarbonate (0.02 mL, 0.167 mmol). After 20 min the reaction was diluted with EtOAc. The solution was washed with saturated aq $NaHCO_3$ and brine. The concentrated residue was purified by flash chromatography on silica gel gradient eluted with 0-100% EtOAc in hexane affording the title compound. (LC-2) HPLC/MS: 516.0.0 (M+1), 518.0 (M+3); $R_t$=4.04 min.

The following examples were prepared by the resolution of Example 77 on an AD column eluting with 23% IPA/Heptane:

EXAMPLE 80

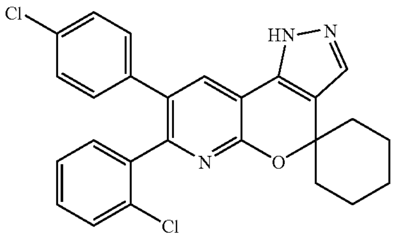

7'-(2-Chlorophenyl)-8'-(4-chlorophenyl)-1'H-spiro [cyclohexane-1,4'-pyrazolo[3',4',4,5]pyrano[2,3-b] pyridine].

The product of Example 4 (70 mg) reacted with N,N-dimethylformamide dimethyl acetal (1.5 mL) at 107° C. for 2 h. The reaction was concentrated, and the residue was diluted with EtOAc and washed with brine. The solution was concentrated and diluted with EtOH (2 mL) before hydrazine hydrate (200 μL) was added. The reaction was heated to 80° C. for 90 min. The reaction was concentrated, and the residue was diluted with EtOAc and washed with brine. The concentrated residue was purified by flash chromatography on silica

| | Name | HPLC/MS m/z (M + 1) m/z (M + 3) $R_t$ (min) (LC-2) | |
|---|---|---|---|
| Example 78 | 5-{[6-(4-chlorophenyl)-7-(2,4-dichlorophenyl)-2,2-dimethyl-3,4-dihydro-2H-pyrano[2,3-b] yridine-4-yl]methyl}-1,3,4-oxadiazol-2(3H)-one Faster isomer on AD column (13.01 min, 24% IPA/Heptane) | 516.0 518.0 4.04 | 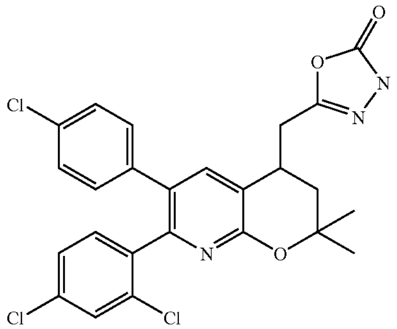 |
| Example 79 | 5-{[6-(4-chlorophenyl)-7-(2,4-dichlorophenyl)-2,2-dimethyl-3,4-dihydro-2H-pyrano[2,3-b] yridine-4-yl]methyl}-1,3,4-oxadiazol-2(3H)-one Slower isomer on AD column (17.58 min, 24% IPA/Heptane) | 516.0 518.0 4.04 | 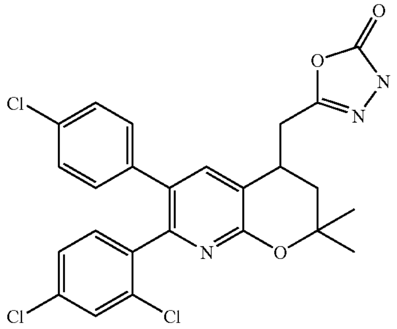 |

gel gradient eluted with 0-80% EtOAc in hexane affording the title compound. (LC-2) HPLC/MS: 462.1 (M+1), 464.1 (M+3); $R_t$=4.10 min.

EXAMPLE 81

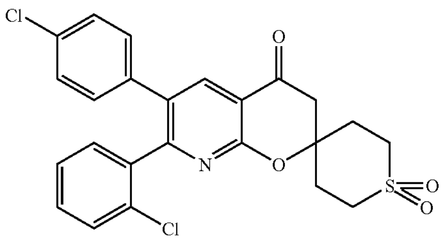

7-(2-Chlorophenyl)-6-(4-chlorophenyl)-2',3',5',6'-tetrahydrospiro[pyrano[2,3-b]pyridine-2,4'-thiopyran]-4(3H)-one 1',1'-dioxide.

The product of Example 6 (75 mg, 0.165 mmol) in $CH_2Cl_2$ (2 mL) and MeOH (3 mL) reacted with magnesium bis (monoperoxyphthalate) hexahydrate (254 mg, 0.41 mmol, 80%) at rt for 90 min. The reaction was concentrated, and the residue was diluted with EtOAc and washed with saturated aq $NaHCO_3$ and brine. The concentrated residue was purified by flash chromatography on silica gel gradient eluted with 0-100% EtOAc in hexane affording the title compound. (LC-2) HPLC/MS: 488.1 (M+1), 490.0 (M+3); $R_t$=3.74 min.

The following examples were prepared utilizing the product of Example 31 using a procedure similar to that of Example 81. Where noted the enantiomers were separated by chiral chromatography with conditions as indicated:

| | Name | HPLC/MS m/z (M + 1) m/z (M + 3) $R_t$ (min) (LC-2) | |
|---|---|---|---|
| Example 82 | N-[7-(2-chlorophenyl)-6-(4-chlorophenyl)-1',1'-dioxido-2',3,3',4,5',6'-hexahydrospiro[pyrano[2,3-b]pyridine-2,4'-thiopyran]-4-yl]-2-hydroxyacetamide (Racemic) | 547.2 549.1 3.17 | 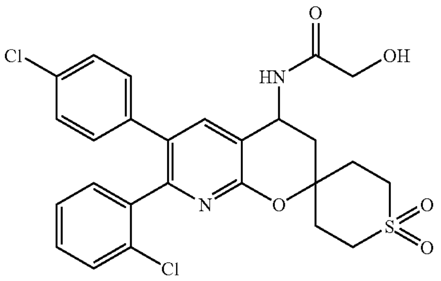 |
| Example 83 | N-[7-(2-chlorophenyl)-6-(4-chlorophenyl)-1',1'-dioxido-2',3,3',4,5',6'-hexahydrospiro[pyrano[2,3-b]pyridine-2,4'-thiopyran]-4-yl]-2-hydroxyacetamide Faster isomer on AD column (16.03 min, 15% EtOH/Heptane) | 547.2 549.1 3.17 | 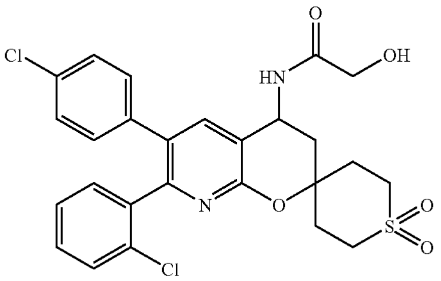 |
| Example 84 | N-[7-(2-chlorophenyl)-6-(4-chlorophenyl)-1',1'-dioxido-2',3,3',4,5',6'-hexahydrospiro[pyrano[2,3-b]pyridine-2,4'-thiopyran]-4-yl]-2-hydroxyacetamide Slower isomer on AD column (25.06 min, 15% EtOH/Heptane) | 547.2 549.1 3.17 | 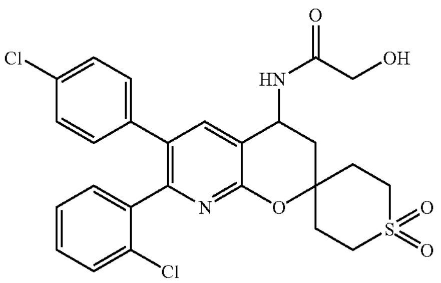 |

EXAMPLE 85

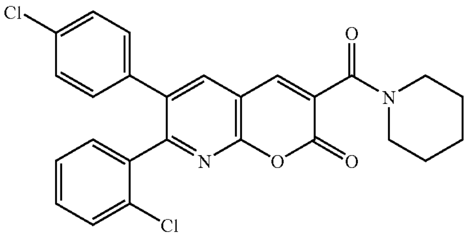

7-(2-Chlorophenyl)-6-(4-chlorophenyl)-3-(piperidin-1-ylcarbonyl)-2H-pyrano[2,3-b]-pyridin-2-one Step A: 6-(2-Chlorophenyl)-5-(4-chlorophenyl)-2-oxo-1,2-dihydropyridine-3-carbaldehyde. An oven dried three-necked 250 mL 14/20 standard taper round bottom flask was equipped with a magnetic stir bar and a rubber septum, a glass stopper, and a reflux condenser in each of the three necks. A piece of vacuum tubing from a Firestone valve was connected to a tubing adapter placed at the top of the condenser. The flask was then charged with a suspension of 10.473 g (30.7 mmol) of 6-(2-chlorophenyl)-5-(4-chlorophenyl)-2-oxo-1,2-dihydropyridine-3-carbonitrile (prepared in similar fashion to Step B Example 1) in 35 mL toluene, the atmosphere in the reaction vessel was replaced with nitrogen by cycling the Firestone valve, and finally hexamethyldisilazane (6.40 mL, 30.7 mmol) was added via syringe. The reaction mixture was stirred and gently refluxed for 2.5 h, then cooled and stirred at −40° C. using an external dry ice-acetone bath and diisobutylaluminum hydride (31.0 mL, 46.0 mmol) was then slowly added by syringe. The reaction mixture was stirred at −40° to −30° C. for 3 h at which point LC/MS analysis of an acid-quenched aliquot indicated that the reduction was complete. The cooling bath was removed and the reaction was quenched by dropwise addition of 40 mL of 2 N HCl. After gas evolution had ceased, the reaction mixture was transferred to a 1 L Erlenmeyer flask using 100 mL THF to rinse the solids. Additional 2 N HCl was added (200 mL), and the two phase mixture was stirred and heated for 30 min on a hot plate to ensure complete hydrolysis of the intermediate imine. EtOAc (200 mL) was added and the reaction mixture was stirred and heated until the solids had dissolved. The organic layer was separated, evaporated to dryness, then redissolved in EtOAc. The aq layer was adjusted to pH=7 with 6 N sodium hydroxide solution, then added back to organic layer. The layers were again heated and magnetically stirred to dissolve all the solids, then separated. The aq layer was washed with additional hot EtOAc, the organic layers were combined and then washed with water, brine, then dried ($MgSO_4$), filtered and slowly evaporated. The product was crystallized from the EtOAc solution during the evaporation process and collected by vacuum filtration. The yellow crystalline solid was dried in vacuo to afford the title compound. HPLC/MS: 344.1 (M+1), 346.1 (M+3); $R_t$=3.17 min.

Step B: 7-(2-chlorophenyl)-6-(4-chlorophenyl)-3-(piperidin-1-ylcarbonyl)-2H-pyrano[2,3-b]-pyridin-2-one. A 10 mL CEM microwave reactor vial was equipped with a magnetic stir bar and charged with 0.163 g (0.474 mmol) of the product of Step A and 1 mL of DMF, followed by dimethyl malonate (0.060 mL, 0.521 mmol), and finally piperidine (0.056 mL, 0.568 mmol).

The reaction mixture was stirred and heated in a CEM Discover Microwave reactor under PowerMax control at 150° C. for 20 min. At this point TLC (50% EtOAc-hexane) and LC/MS analysis indicated that the starting material was nearly consumed and that a new less-polar product had formed. The reaction mixture was partitioned between EtOAc and 10% aq $NaHSO_4$ solution. The organic phase was separated, washed with water and brine, then dried ($MgSO_4$), filtered and evaporated. The residue was purified on an ISCO 40 g silica gel cartridge using a Sequential 16 MPLC system eluted with a 0-50% EtOAc-hexane gradient to afford the title compound. HPLC/MS: 479.2 (M+1), 481.2 (M+3); $R_t$=3.58 min.

EXAMPLE 86

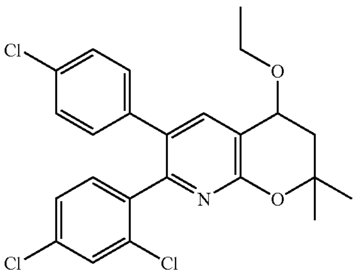

6-(4-Chlorophenyl)-7-(2,4-dichlorophenyl)-4-ethoxy-2,2-dimethyl-3,4-dihydro-2H-pyrano[2,3-b]pyridine To the product of Example 68 (60 mg, 0.14 mmol) in DMF (1 mL) was added bromoethane (152 mg, 1.4 mmol) and NaH (6 mg, 0.14 mmol) and the suspension was stirred for 1 h at rt. The reaction was quenched by adding 1N HCl and water. The reaction was diluted with EtOAc, washed with a saturated aq $NaHCO_3$ solution, brine, dried ($Na_2SO_4$), filtered and concentrated The residue was purified by flash chromatography on silica gel gradient eluted with 85% $CH_2Cl_2$ in hexane to afford the title compound. (LC-2) HPLC/MS: 462.2 (M+1), 464.2 (M+3); $R_t$=4.51 min Using the procedure described in Example 86 and bromomethane instead of bromoethane the following compound was obtained:

| | Name | HPLC/MS m/z (M + 1) m/z (M + 3) $R_t$ (min) (LC-2) | |
|---|---|---|---|
| Example 87 | 6-(4-Chlorophenyl)-7-(2,4-dichlorophenyl)-4-methoxy-2,2-dimethyl-3,4-dihydro-2H-pyrano[2,3-b]pyridine | 448.0 450.0 4.40 | 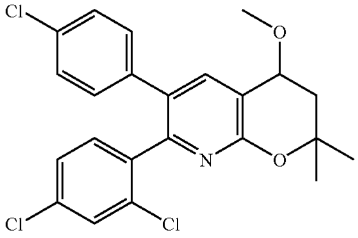 |

EXAMPLE 88

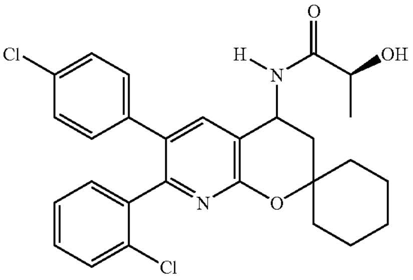

(2S)-N-[7'-(2-Chlorophenyl)-6'-(4-chlorophenyl)-3',4'-dihydrospiro[cyclohexane-1,2'-pyrano[2,3-b]pyridin]-4'-yl]-2-hydroxypropanamide To the product of Example 23 (70 mg, 0.16 mmol) in DMF (2 mL) was added L-lactic acid sodium salt (18 mg, 0.16 mmol), 1-hydroxybenzotriazole (HOBt) (32 mg, 0.24 mmol), PYBOP (125 mg, 0.24 mmol) and DIEA (80 μL, 0.48 mmol) and the reaction was stirred at rt for 30 min. EtOAc was added and the solution was washed with brine, dried ($Na_2SO_4$), filtered and concentrated. The residue was purified by flash chromatography on silica gel gradient eluted with 60% EtOAc in $CH_2Cl_2$. Evaporation of the purified fractions and drying in vacuo afforded the two diastereomers. (LC-2) HPLC/MS (less polar isomer on silica): 511.2 (M+1), 513.2 (M+3); $R_t$=3.73 min and (LC-2) HPLC/MS (more polar isomer on silica): 511.2 (M+1), 513.2 (M+3); $R_t$=3.73 min Using the procedure described in Example 88, and the appropriate amine and carboxylic acid, the following compounds were prepared. Where noted the enantiomers, or the diastereomers, were separated either on chiral chromatography or via silica gel purification with conditions as indicated:

| | Name | HPLC/MS m/z (M + 1) m/z (M + 3) $R_t$ (min) (LC-2) | |
|---|---|---|---|
| Example 89 | (2R)-N-[7'-(2-chlorophenyl)-6'-(4-chlorophenyl)-3',4'-dihydrospiro[cyclohexane-1,2'-pyrano[2,3-b]pyridin]-4'-yl]-2-hydroxypropanamide | 511.2 513.2 3.71 | 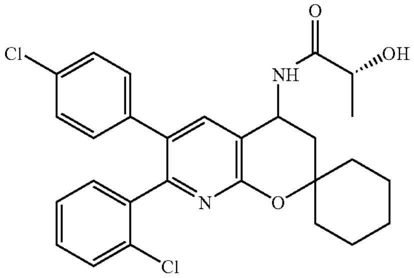 (less polar isomer on silica) |

-continued

| | Name | HPLC/MS m/z (M + 1) m/z (M + 3) $R_t$ (min) (LC-2) | |
|---|---|---|---|
| Example 90 | (2R)-N-[7'-(2-chlorophenyl)-6'-(4-chlorophenyl)-3',4'-dihydrospiro[cyclohexane-1,2'-pyrano[2,3-b]pyridin]-4'-yl]-2-hydroxypropanamide | 511.2<br>513.2<br>3.74 | 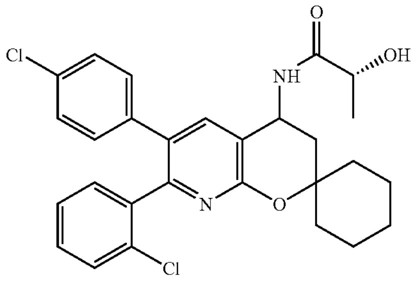<br>(more polar isomer on silica) |
| Example 91 | N-[7'-(2-chlorophenyl)-6'-(4-chlorophenyl)-3',4'-dihydrospiro[cyclohexane-1,2'-pyrano[2,3-b]pyridin]-4'-yl]-2-hydroxy-2-methylpropanamide | 525.3<br>527.3<br>3.83 | 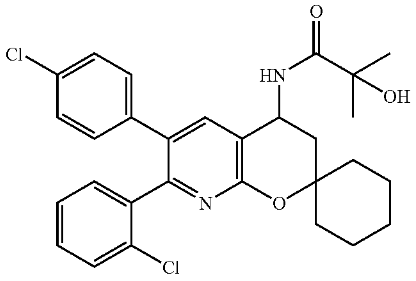<br>(fast isomer, AD 10% EtOH/heptane) |
| Example 92 | N-[7'-(2-chlorophenyl)-6'-(4-chlorophenyl)-3',4'-dihydrospiro[cyclohexane-1,2'-pyrano[2,3-b]pyridin]-4'-yl]-2-hydroxy-2-methylpropanamide | 525.3<br>527.3<br>3.80 | 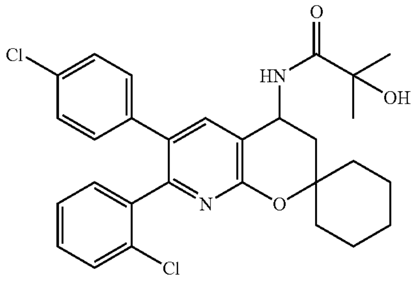<br>(slow isomer, AD 10% EtOH/heptane) |
| Example 93 | N-[6-(4-chlorophenyl)-7-(2,4-dichlorophenyl)-2,2-dimethyl-3,4-dihydro-2H-pyrano[2,3-b]pyridin-4-yl]-2-hydroxy-2-methylpropanamide | 519.3<br>521.3<br>3.83 | 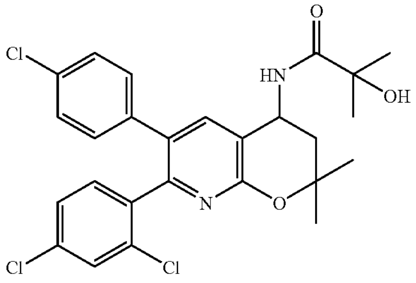<br>(fast isomer, AD 5% EtOH/heptane) |

-continued

| | Name | HPLC/MS m/z (M + 1) m/z (M + 3) $R_t$ (min) (LC-2) | |
|---|---|---|---|
| Example 94 | N-[6-(4-chlorophenyl)-7-(2,4-dichlorophenyl)-2,2-dimethyl-3,4-dihydro-2H-pyrano[2,3-b]pyridin-4-yl]-2-hydroxy-2-methylpropanamide | 519.3 521.3 3.83 | 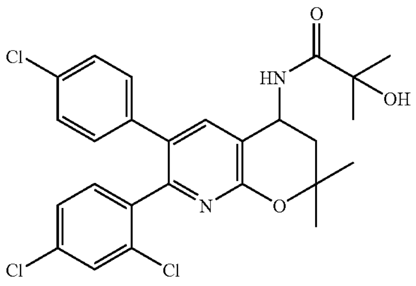 (slow isomer, AD 5% EtOH/heptane) |
| Example 95 | (2S)-N-[6-(4-chlorophenyl)-7-(2,4-dichlorophenyl)-2,2-dimethyl-3,4-dihydro-2H-pyrano[2,3-b]pyridin-4-yl]-2-hydroxypropanamide | 505.3 507.3 3.72 | 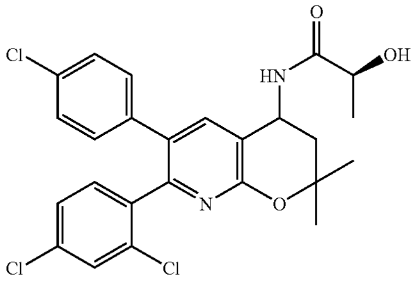 (fast isomer, AD 5% EtOH/Heptane) |
| Example 96 | (2R)-N-[6-(4-chlorophenyl)-7-(2,4-dichlorophenyl)-2,2-dimethyl-3,4-dihydro-2H-pyrano[2,3-b]pyridin-4-yl]-2-hydroxypropanamide | 505.3 507.3 3.72 | 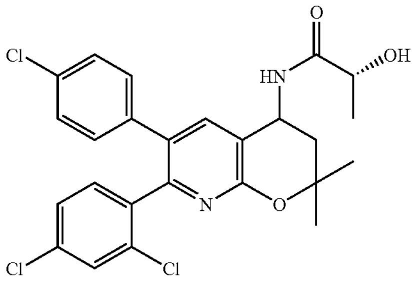 (fast isomer, AD 5% EtOH/heptane) |
| Example 97 | (2R)-N-[6-(4-chlorophenyl)-7-(2,4-dichlorophenyl)-2,2-dimethyl-3,4-dihydro-2H-pyrano[2,3-b]pyridin-4-yl]-2-hydroxypropanamide | 505.3 507.3 3.72 | 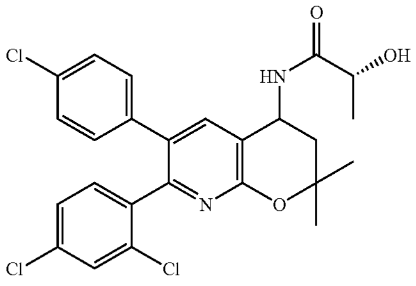 (slow isomer, AD 5% EtOH/heptane) |

-continued

| | Name | HPLC/MS m/z (M + 1) m/z (M + 3) $R_t$ (min) (LC-2) | |
|---|---|---|---|
| Example 98 | N-[6-(4-chlorophenyl)-7-(2,4-dichlorophenyl)-2,2-dimethyl-3,4-dihydro-2H-pyrano[2,3-b]pyridin-4-yl]-4,4,4-trifluoro-3-hydroxybutanamide | 573.0<br>575.0<br>3.71 | 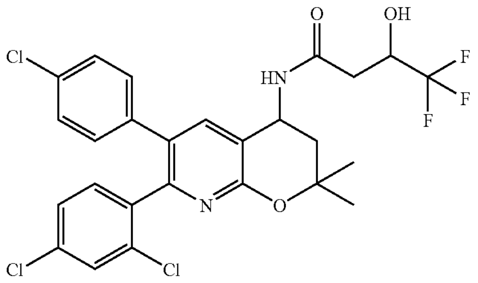<br>(fast isomer, AD 7% IPA/heptane) |
| Example 99 | N-[6-(4-chlorophenyl)-7-(2,4-dichlorophenyl)-2,2-dimethyl-3,4-dihydro-2H-pyrano[2,3-b]pyridin-4-yl]-4,4,4-trifluoro-3-hydroxybutanamide | 573.0<br>575.0<br>3.71 | 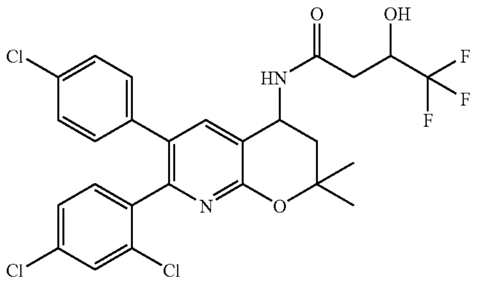<br>(slow isomer, AD 7% IPA/heptane)) |
| Example 100 | N-[6-(4-chlorophenyl)-7-(2,4-dichlorophenyl)-2,2-dimethyl-3,4-dihydro-2H-pyrano[2,3-b]pyridin-4-yl]-4,4,4-trifluoro-3-hydroxybutanamide | 573.0<br>575.0<br>3.75 | 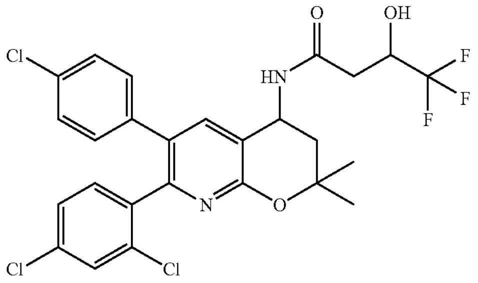<br>(fast isomer, AS 7% IPA/heptane) |
| Example 101 | N-[6-(4-chlorophenyl)-7-(2,4-dichlorophenyl)-2,2-dimethyl-3,4-dihydro-2H-pyrano[2,3-b]pyridin-4-yl]-4,4,4-trifluoro-3-hydroxybutanamide | 573.0<br>575.0<br>3.75 | 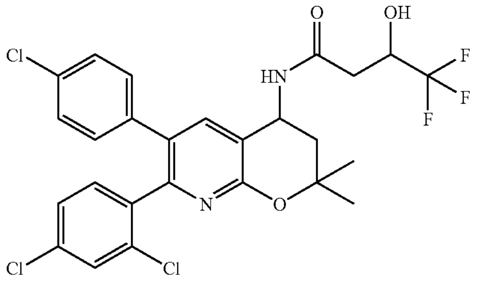<br>(slow isomer, AS 7% IPA/heptane)) |

The following Examples were prepared from the appropriate acid chloride or sulfonyl chloride:

| | Name | HPLC/MS m/z (M + 1) m/z (M + 3) $R_t$ (min) (LC-2) | |
|---|---|---|---|
| Example 102 | N-[7'-(2-chlorophenyl)-6'-(4-chlorophenyl)-3',4'-dihydrospiro[cyclohexane-1,2'-pyrano[2,3-b]pyridin]-4'-yl]-2-methylpropanamide | 509.3<br>511.2<br>4.04 | 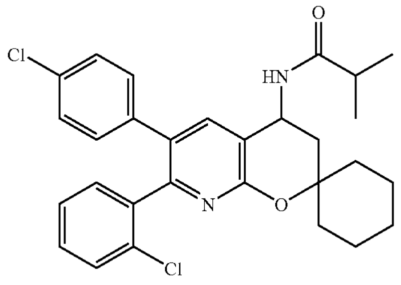<br>(fast isomer AD, 7% EtOH/heptane) |
| Example 103 | N-[7'-(2-chlorophenyl)-6'-(4-chlorophenyl)-3',4'-dihydrospiro[cyclohexane-1,2'-pyrano[2,3-b]pyridin]-4'-yl]-2-methylpropanamide | 509.3<br>511.2<br>4.04 | 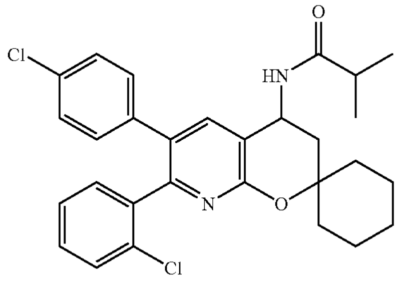<br>(slow isomer AD, 7% EtOH/heptane) |
| Example 104 | N-[7'-(2-chlorophenyl)-6'-(4-chlorophenyl)-3',4'-dihydrospiro[cyclohexane-1,2'-pyrano[2,3-b]pyridin]-4'-yl]propanamide | 495.3<br>497.2<br>3.90 | 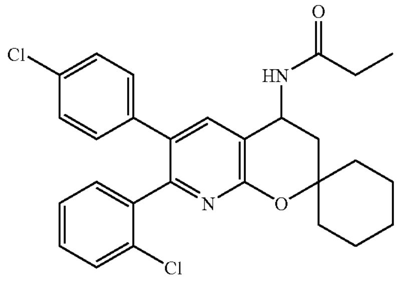<br>(fast isomer AD, 9% EtOH/heptane) |
| Example 105 | N-[7'-(2-chlorophenyl)-6'-(4-chlorophenyl)-3',4'-dihydrospiro[cyclohexane-1,2'-pyrano[2,3-b]pyridin]-4'-yl]propanamide | 495.3<br>497.2<br>3.90 | 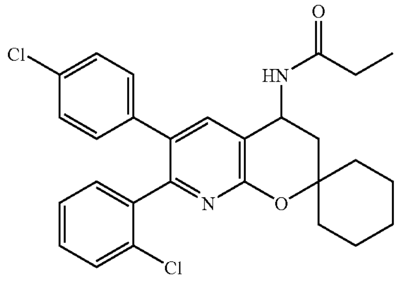<br>(slow isomer AD, 9% EtOH/heptane) |

-continued

| | Name | HPLC/MS m/z (M + 1) m/z (M + 3) $R_t$ (min) (LC-2) | |
|---|---|---|---|
| Example 106 | N-[7'-(2-chlorophenyl)-6'-(4-chlorophenyl)-3',4'-dihydrospiro[cyclohexane-1,2'-pyrano[2,3-b]pyridin]-4'-yl]propane-1-sulfonamide | 545.3<br>547.2<br>4.12 | 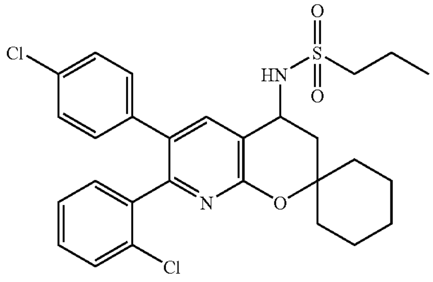<br>(fast isomer AD, 9% EtOH/heptane) |
| Example 107 | N-[7'-(2-chlorophenyl)-6'-(4-chlorophenyl)-3',4'-dihydrospiro[cyclohexane-1,2'-pyrano[2,3-b]pyridin]-4'-yl]propane-1-sulfonamide | 545.3<br>547.2<br>4.12 | 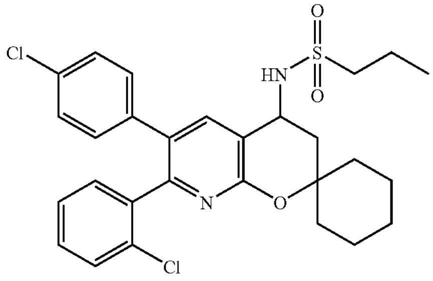<br>(slow isomer AD, 9% EtOH/heptane) |
| Example 108 | 3-Chloro-N-[7'-(2-chlorophenyl)-6'-(4-chlorophenyl)-3',4'-dihydrospiro[cyclohexane-1,2'-pyrano[2,3-b]pyridin]-4'-yl]propane-1-sulfonamide | 579.2<br>581.3<br>4.16 | 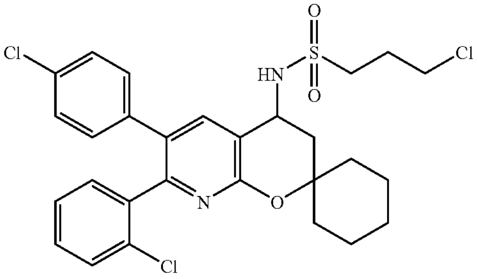<br>(racemic) |
| Example 109 | N-[6-(4-chlorophenyl)-7-(2,4-dichlorophenyl)-2,2-dimethyl-3,4-dihydro-2H-pyrano[2,3-b]pyridin-4-yl]methanesulfonamide | 511.2<br>513.2<br>3.92 | 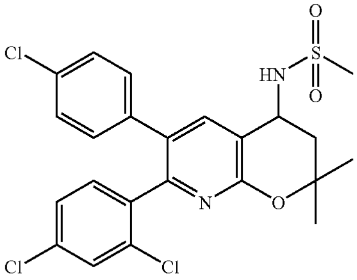<br>(racemic) |

-continued

| | Name | HPLC/MS m/z (M + 1) m/z (M + 3) $R_t$ (min) (LC-2) | |
|---|---|---|---|
| Example 110 | N'-[6-(4-chlorophenyl)-7-(2,4-dichlorophenyl)-2,2-dimethyl-3,4-dihydro-2H-pyrano[2,3-b]pyridin-4-yl]-N,N-dimethylsulfamide | 540.0<br>542.0<br>3.84 | 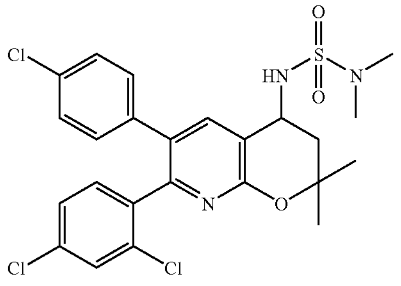<br>(racemic) |
| Example 111 | N'-[6-(4-chlorophenyl)-7-(2,4-dichlorophenyl)-2,2-dimethyl-3,4-dihydro-2H-pyrano[2,3-b]pyridin-4-yl]-N,N-dimethylurea | 504.0<br>506.0<br>3.67 | 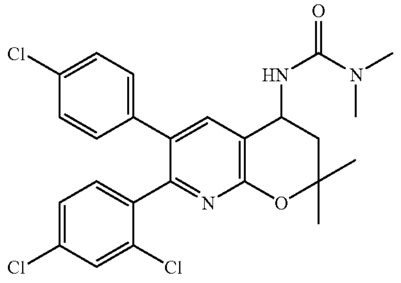<br>(racemic) |

EXAMPLE 112

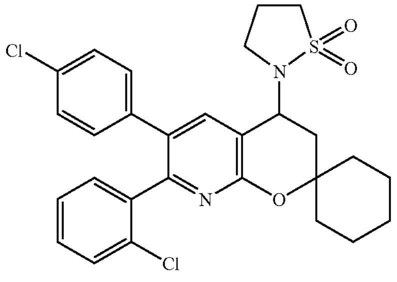

7'-(2-Chlorophenyl)-6'-(4-chlorophenyl)-4'-(1,1-dioxidoisothiazolidin-2-yl)-3',4'-dihydrospiro[cyclohexane-1,2'-pyrano[2,3-b]pyridine The product from Example 108 (48 mg, 0.08 mmol) was dissolved in DMF (1 mL) and $Cs_2CO_3$ (40 mg, 0.13 mmol) was added. The reaction was stirred for 1 h. The reaction was diluted with EtOAc and washed with a saturated $NaHCO_3$ solution, brine, dried ($Na_2SO_4$), filtered and concentrated. The residue was purified by flash chromatography on silica gel gradient eluted with 0 to 40% EtOAc in hexane to afford the title compound. (LC-2) HPLC/MS: 543.2 (M+1), 545.2 (M+3); $R_t$=4.05 min The following examples were prepared by the reaction sequence indicated below:

Step A: 2-Chloro-N-({[6-(4-chlorophenyl)-7-(2,4-dichlorophenyl)-2,2-dimethyl-3,4-dihydro-2H-pyrano[2,3-b]pyridin-4-yl]amino}carbonyl)acetamide. The product from Example 24 (100 mg, 0.23 mmol) was dissolved in THF (2 mL). Chloroacetyl isocyanate (40 mg, 0.34 mmol) was added and the reaction was stirred at rt for 30 min. The product was concentrated and used without further purification.

Step B: 1-[6-(4-Chlorophenyl)-7-(2,4-dichlorophenyl)-2,2-dimethyl-3,4-dihydro-2H-pyrano[2,3-b]pyridin-4-yl]imidazolidine-2,4-dione. The product obtained in Step A (127 mg, 0.23 mmol) was dissolved in DMSO (2 mL). NaH (20 mg, 0.51 mmol) was added and the reaction was stirred at rt for 1 h. The reaction was diluted with EtOAc and washed with a saturated $NaHCO_3$ solution, 10% $NaHSO_4$, brine, dried ($Na_2SO_4$), filtered and concentrated The residue was purified by flash chromatography on silica gel gradient eluted with 0-70% EtOAc in hexane to afford Example 113. Further purification on an AD column, eluting with 12% IPA/heptane provided the two pure enantiomers indicated below:

| | Name | HPLC/MS m/z (M + 1) m/z (M + 3) $R_t$ (min) (LC-2) | |
|---|---|---|---|
| Example 113 | 1-[6-(4-Chlorophenyl)-7-(2,4-dichlorophenyl)-2,2-dimethyl-3,4-dihydro-2H-pyrano[2,3-b]pyridin-4-yl]imidazolidine-2,4-dione. | 516.0 518.0 3.49 | 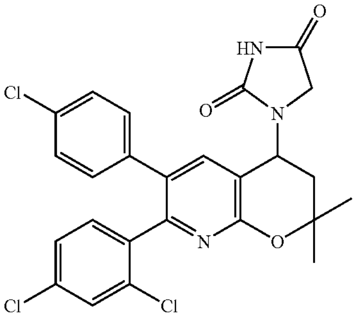 |
| Example 114 | 1-[6-(4-Chlorophenyl)-7-(2,4-dichlorophenyl)-2,2-dimethyl-3,4-dihydro-2H-pyrano[2,3-b]pyridin-4-yl]imidazolidine-2,4-dione. (fast isomer on the AD column) | 516.0 518.0 3.49 | 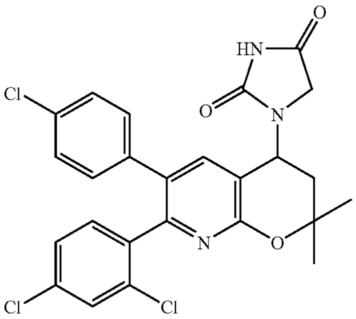 |
| Example 115 | 1-[6-(4-Chlorophenyl)-7-(2,4-dichlorophenyl)-2,2-dimethyl-3,4-dihydro-2H-pyrano[2,3-b]pyridin-4-yl]imidazolidine-2,4-dione. (slow isomer on the AD column) | 516.0 518.0 3.49 | 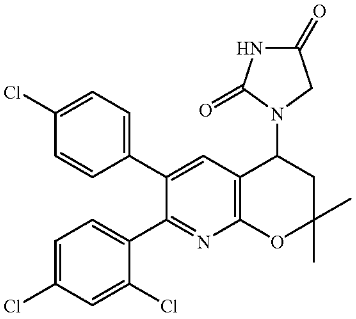 |

EXAMPLE 116

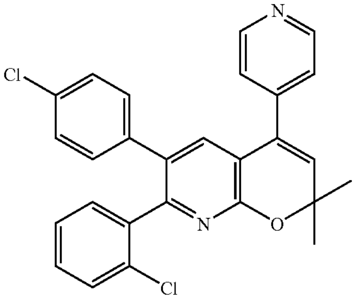

7-(2-Chlorophenyl)-6-(4-chlorophenyl)-2,2-dimethyl-4-pyridin-4-yl-2H-pyrano[2,3-b]pyridine Step A: 7-(2-Chlorophenyl)-6-(4-chlorophenyl)-2,2-dimethyl-2H-pyrano[2,3-b]pyridin-4-yl trifluoromethanesulfonate. To the product of Example 3 (0.47 g, 1.2 mmol) in DMF (9 mL) at −78° C., was added 1 M LiHMDS in THF (1.3 mL, 1.3 mmol) and the reaction was stirred for 5 min. N-phenyl trifluoromethanesulfonamide (0.47 g, 1.3 mmol) was added and the reaction was allowed to come to rt. The reaction was stirred an additional 15 min, concentrated and the residue was purified by flash chromatography on silica gel gradient eluted with 0-20% EtOAc in hexane to afford the title compound. Step B: 7-(2-Chlorophenyl)-6-(4-chlorophenyl)-2,2-dimethyl-4-pyridin-4-yl-2H-pyrano[2,3-b]pyridine The product of Step A (40 mg, 0.075 mmol) was dissolved in DME (0.9 mL), water (0.4 mL) and ethanol (0.2 mL) in a 10 mL reaction tube of a CEM Corporation Discover microwave reactor. A 2 M solution of $Na_2CO_3$ (0.11 mL), pyridinyl-4-yl boronic acid (10 mg, 0.08 mmol) and tetrakis(triphenylphosphine)palladium(0) (8 mg, 0.0075 mmol) were added and the tube was purged with nitrogen, capped and inserted into the microwave reactor and heated at 120° C., at 50 Watts, for 10 min. The reaction was diluted with EtOAc and washed with brine, dried ($Na_2SO_4$), filtered and evaporated. The residue was purified by flash chromatography on silica gel gradient eluted with 0-70% EtOAc in hexane to afford the title compound. (LC-2) HPLC/MS: 459.2 (M+1), 461.2 (M+3); $R_t$=3.45 min.

Using the procedure described in Example 116 Step B with the appropriate boronic acid and the product of Example 116 Step A, the following compounds were afforded:

| | Name | HPLC/MS m/z (M + 1) m/z (M + 3) $R_t$ (min) (LC-2) | |
|---|---|---|---|
| Example 117 | 7-(2-Chlorophenyl)-6-(4-chlorophenyl)-2,2-dimethyl-4-(1-methyl-1H-pyrazol-4-yl)-2H-pyrano[2,3-b]pyridine | 462.2<br>464.2<br>4.06 | 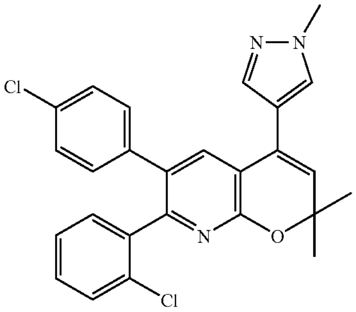 |
| Example 118 | 7-(2-Chlorophenyl)-6-(4-chlorophenyl)-4-(4-fluorophenyl)-2,2-dimethyl-2H-pyrano[2,3-b]pyridine | 476.2<br>478.2<br>4.68 | 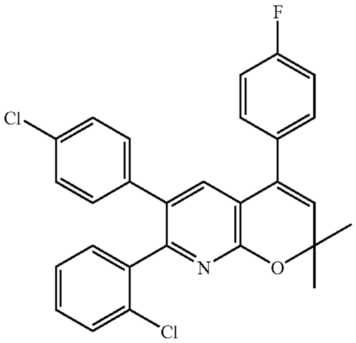 |
| Example 119 | 6-(4-Chlorophenyl)-7-(2,4-dichlorophenyl)-2,2-dimethyl-4-(1H-pyrazol-4-yl)-2H-pyrano[2,3-b]pyridine | 482.1<br>484.1<br>3.81 | 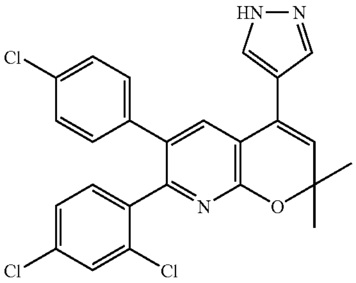 |
| Example 120 | 6-(4-Chlorophenyl)-7-(2,4-dichlorophenyl)-2,2-dimethyl-4-(1H-pyrazol-3-yl)-2H-pyrano[2,3-b]pyridine | 482.1<br>484.1<br>3.88 | 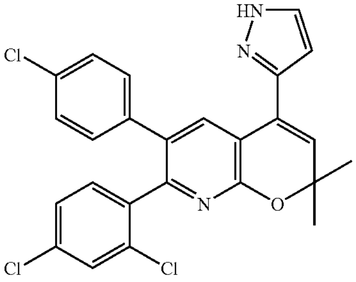 |

EXAMPLE 121

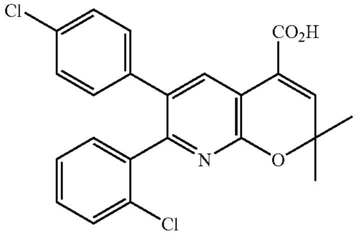

7-(2-Chlorophenyl)-6-(4-chlorophenyl)-2,2-dimethyl-2H-pyrano[2,3-b]pyridine-4-carboxylic acid The product of Step A, Example 116 (50 mg, 0.09 mmol) was dissolved in 1 mL dimethyl sulfoxide. Potassium acetate (47 mg, 0.47 mmol) and dichloro[1,1'-bis(diphenylphosphino)ferrocene]palladium (II) dichloromethane adduct (4 mg, 0.0045 mmol) was added and the flask was evacuated and backfilled with carbon monoxide 3 times. The mixture was stirred under a carbon monoxide atmosphere at 50° C. overnight. The reaction was cooled and 2 M HCl and EtOAc were added. The organic layer was separated, dried ($Na_2SO_4$), filtered and concentrated. The residue was purified by flash chromatography on silica gel gradient eluted with 0-70% EtOAc in hexane to afford the title compound. (LC-2) HPLC/MS: 426.0 (M+1), 428.0 (M+3); $R_t$=3.79 min.

EXAMPLE 122

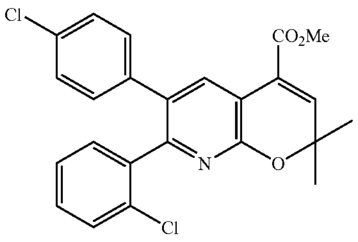

Methyl 7-(2-chlorophenyl)-6-(4-chlorophenyl)-2,2-dimethyl-2H-pyrano[2,3-b]pryidine-4-carboxylate To the product of Step A, Example 116 (1.9 g, 3.36 mmol) was added DMF (20 mL), MeOH (6 mL), $NEt_3$ (1.4 mL, 10 mmol) and dichloro[1,1'-bis(diphenylphosphino)ferrocene] palladium (II) dichloromethane adduct (275 mg, 0.336 mmol). The flask was evacuated and backfilled with carbon monoxide 3 times. The mixture was stirred under a carbon monoxide atmosphere at 70° C. overnight. The reaction was cooled and 2 M HCl and EtOAc were added. The organic layer was separated, dried ($Na_2SO_4$), filtered and concentrated. The residue was purified by flash chromatography on silica gel gradient eluted with 0-20% EtOAc in hexane to afford the title compound. (LC-2) HPLC/MS: 442.3 (M+1), 444.3 (M+3); $R_t$=3.87 min.

The triflate derived from the product of Example 1 using a procedure similar to Example 116 Step A was used in a procedure similar to that described in Example 122 to afford the following compound:

| | Name | HPLC/MS m/z (M + 1) m/z (M + 3) $R_t$ (min) (LC-2) | |
|---|---|---|---|
| Example 123 | Methyl 6-(4-chlorophenyl)-7-(2,4-dichlorophenyl)-2,2-dimethyl-2H-pyrano[2,3-b]pyridine-4-carboxylate | 474.2<br>476.2<br>4.34 | 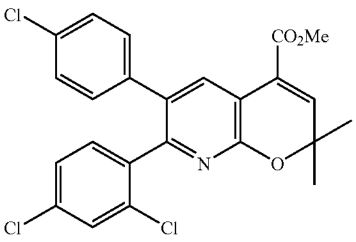 |

EXAMPLE 124

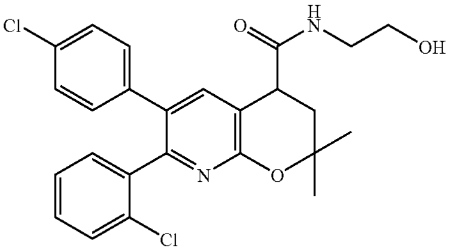

7-(2-Chlorophenyl)-6-(4-chlorophenyl)-N-(2-hydroxyethyl)-2,2-dimethyl-3,4-dihydro-2H-pyrano[2,3-b]pyridine-4-carboxamide Step A: Methyl 7-(2-chlorophenyl)-6-(4-chlorophenyl)-2,2-dimethyl-3,4-dihydro-2H-pyrano[2,3-b]pyridine-4-carboxylate. Powdered tellurium (70 mg, 0.57 mmol) was dissolved in EtOH (1.5 mL) at rt and $NaBH_4$ (50 mg, 1.4 mmol) was added. The reaction was heated to 70° C. for 20 min. The reaction was cooled to −20° C. and deoxygenated AcOH (0.07 mL, 1.21 mmol) was added. The mixture was stirred for 5 min and the product of Example 122 (150 mg, 0.34 mmol) was added. The reaction was allowed to come to rt and was stirred an additional 30 min. The reaction was filtered through Celite with $CH_2Cl_2$ and the filtrate was concentrated. The residue was purified by flash chromatography on silica gel gradient eluted with 0-20% EtOAc in hexane to afford the title compound.

Step B: 7-(2-Chlorophenyl)-6-(4-chlorophenyl)-2,2-dimethyl-3,4-dihydro-2H-pyrano[2,3-b]pyridine-4-carboxylic acid. Product from Step A (66 mg, 0.14 mmol) was dissolved in THF (1 mL) and 10% KOH (1 mL) was added. The reaction was heated to 70° C. for 1 hr. The reaction was diluted with EtOAc and washed with 10% $NaHSO_4$. The organic layer was separated, dried ($Na_2SO_4$), filtered and concentrated and used without any further purification Step C: 7-(2-Chlorophenyl)-6-(4-chlorophenyl)-N-(2-hydroxyethyl)-2,2-dimethyl-3,4-dihydro-2H-pyrano[2,3-b]pyridine-4-carboxamide. Using the product of Step B and ethanolamine, along with the procedure described in Example 88, the title compound was afforded. Further separation on an AS chiral column, eluting with 7% EtOH/heptane, afforded the enantiomers: (LC-2) HPLC/MS (fast isomer on AS): 471.3 (M+1), 473.3 (M+3); $R_t$=3.13 min. (LC-2) HPLC/MS (slow isomer on AS): 471.3 (M+1), 473.3 (M+3); $R_t$=3.13 min.

Using the product of Example 124 Step B and following a procedure similar to Example 124 Step C with the appropriate amine the following compounds were afforded. Where noted the enantiomers were separated on chiral chromatography with conditions as indicated.

| | Name | HPLC/MS m/z (M + 1) m/z (M + 3) $R_t$ (min) (LC-2) | |
|---|---|---|---|
| Example 125 | 6-(4-Chlorophenyl)-7-(2,4-dichlorophenyl)-N-(2-hydroxyethyl)-2,2-dimethyl-3,4-dihydro-2H-pyrano[2,3-b]pyridine-4-carboxamide | 505.3 507.3 3.44 | 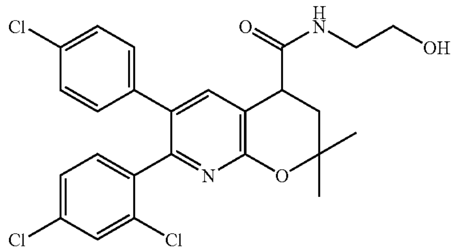 (fast isomer, AS 6% EtOH/heptane) |
| Example 126 | 6-(4-Chlorophenyl)-7-(2,4-dichlorophenyl)-N-(2-hydroxyethyl)-2,2-dimethyl-3,4-dihydro-2H-pyrano[2,3-b]pyridine-4-carboxamide | 505.3 507.3 3.44 | 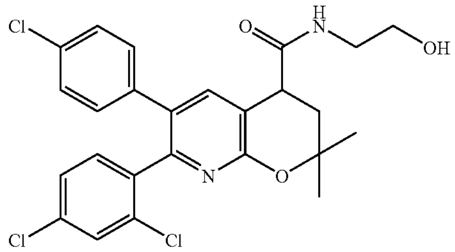 (slow isomer, AS 6% EtOH/heptane) |
| Example 127 | 6-(4-Chlorophenyl)-7-(2,4-dichlorophenyl)-N-(2-hydroxy-1,1-dimethylethyl)-2,2-dimethyl-3,4-dihydro-2H-pyrano[2,3-b]pyridine-4-carboxamide | 533.4 535.3 3.73 | 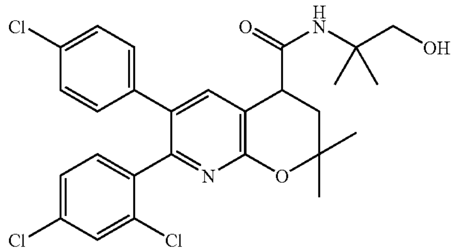 (fast isomer, AS 5% IPA/heptane) |

-continued

| | Name | HPLC/MS m/z (M + 1) m/z (M + 3) $R_t$ (min) (LC-2) | |
|---|---|---|---|
| Example 128 | 6-(4-Chlorophenyl)-7-(2,4-dichlorophenyl)-N-(2-hydroxy-1,1-dimethylethyl)-2,2-dimethyl-3,4-dihydro-2H-pyrano[2,3-b]pyridine-4-carboxamide | 533.4 535.3 3.73 | 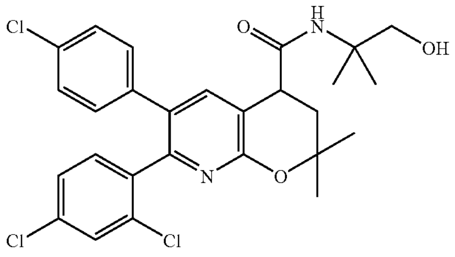 (slow isomer, AS 5% IPA/heptane) |
| Example 129 | 6-(4-Chlorophenyl)-7-(2,4-dichlorophenyl)-N-isopropyl-2,2-dimethyl-3,4-dihydro-2H-pyrano[2,3-b]pyridine-4-carboxamide | 503.4 505.3 3.90 | 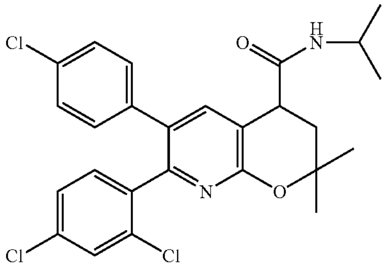 (racemic) |
| Example 130 | 6-(4-Chlorophenyl)-7-(2,4-dichlorophenyl)-2,2-dimethyl-N-(3,3,3-trifluoro-2-hydroxypropyl)-3,4-dihydro-2H-pyrano[2,3-b]pyridine-4-carboxamide | 573.0 575.1 3.70 | 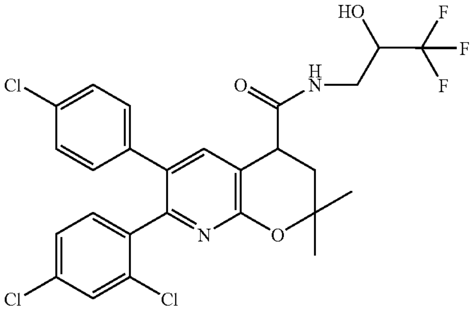 (first isomer, AD 7% IPA/heptane) |
| Example 131 | 6-(4-Chlorophenyl)-7-(2,4-dichlorophenyl)-2,2-dimethyl-N-(3,3,3-trifluoro-2-hydroxypropyl)-3,4-dihydro-2H-pyrano [2,3-b]pyridine-4-carboxamide | 573.0 575.1 3.69 | 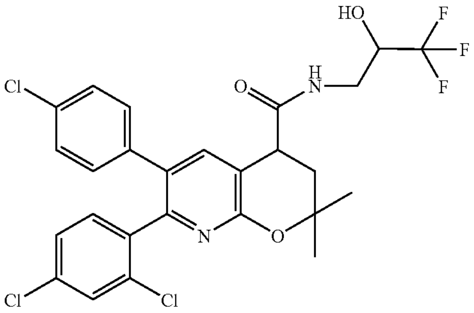 second isomer, AD 7% IPA/Heptane |

-continued

| Name | | HPLC/MS m/z (M + 1) m/z (M + 3) $R_t$ (min) (LC-2) | |
|---|---|---|---|
| Example 132 | 6-(4-Chlorophenyl)-7-(2,4-dichlorophenyl)-2,2-dimethyl-N-(3,3,3-trifluoro-2-hydroxypropyl)-3,4-dihydro-2H-pyrano[2,3-b]pyridine-4-carboxamide | 573.0<br>575.1<br>3.70 | 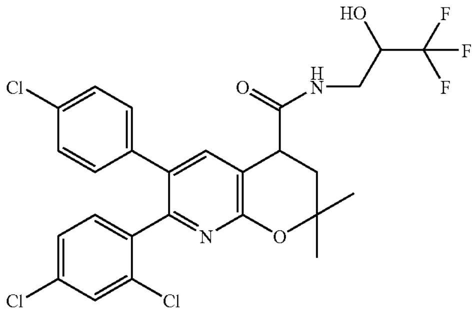<br>(third isomer, AD 7% IPA/heptane) |
| Example 133 | 6-(4-Chlorophenyl)-7-(2,4-dichlorophenyl)-2,2-dimethyl-N-(3,3,3-trifluoro-2-hydroxypropyl)-3,4-dihydro-2H-pyrano[2,3-b]pyridine-4-carboxamide | 573.0<br>575.1<br>3.69 | 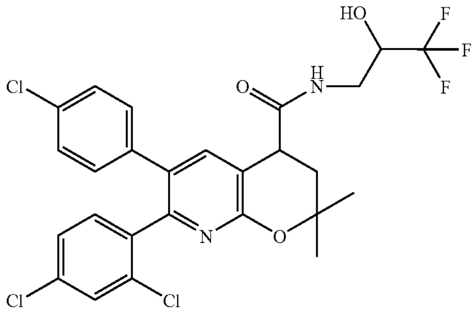<br>(fourth isomer, AD 7% IPA/heptane) |

EXAMPLE 134

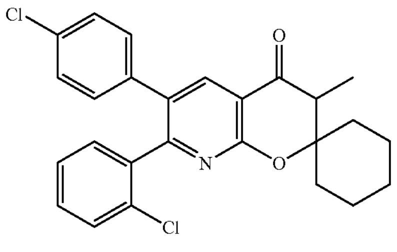

7'-(2-Chlorophenyl)-6'-(4-chlorophenyl)-3'-methylspiro[cyclohexane-1,2'-pyrano[2,3-b]pyridin]-4'(3'H)-one Step A: 3'-bromo-7'-(2-chlorophenyl)-6'-(4-chlorophenyl)spiro[cyclohexane-1,2'-pyrano[2,3-b]pyridin]-4'(3'H)-one. The product of Example 4 was dissolved in $CH_2Cl_2$ (0.5 mL) and thionyl bromide (0.5 mL) was added. The reaction was stirred at rt for 3 h and concentrated. The residue was purified by flash chromatography on silica gel gradient eluted with 0-50% EtOAc in hexane. (LC-2) HPLC/MS: 516.1 (M+1), 518.1 (M+3); $R_t$=4.51 min.

Step B: 3'-Bromo-7'-(2-chlorophenyl)-6'-(4-chlorophenyl)-3'-methylspiro[cyclohexane-1,2'-pyrano[2,3-b]pyridin]-4'(3'H)-one. To the product (0.08 g, 0.15 mmol) from Step A in DMF (1 mL) at −78° C., was added 1 M LiHMDS in THF (0.19 mL, 0.19 mmol) and the reaction was stirred for 10 min. Iodomethane (0.05 mL, 0.77 mmol) was added and the reaction was allowed to come to rt. The reaction was stirred an additional 20 min. The reaction was diluted with EtOAc and washed with brine, dried ($Na_2SO_4$), filtered and evaporated. The residue was purified by flash chromatography on silica gel gradient eluted with 0-20% EtOAc in hexane.

Step C: 7'-(2-Chlorophenyl)-6'-(4-chlorophenyl)-3'-methylspiro[cyclohexane-1,2'-pyrano[2,3-b]pyridin]-4'(3'H)-one. The product of Step B (20 mg, 0.037 mmol) was dissolved in EtOAc (1 mL) and AcOH (1 mL) and zinc (5 mg) were added. The reaction was stirred at rt for 10 min and concentrated. The residue was redissolved in $CH_2Cl_2$ and purified directly by silica gel flash chromatography gradient eluted with 0-15% EtOAc in hexane to afford the title compound. (LC-2) HPLC/MS: 452.4 (M+1), 545.4 (M+3); $R_t$=4.30 min.

EXAMPLE 135

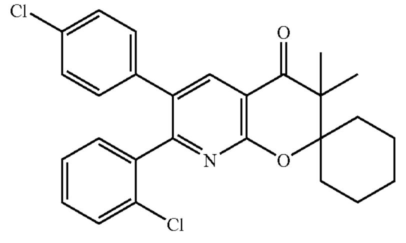

7'-(2-Chlorophenyl)-6'-(4-chlorophenyl)-3',3'-dimethylspiro[cyclohexane-1,2'-pyrano[2,3-b]pyridin]-4'(3'H)-one The above compound was isolated as a side-product in Step B, Example 134. (LC-2) HPLC/MS: 466.4 (M+1), 568.4 (M+3); $R_t$=4.43 min.

EXAMPLE 136

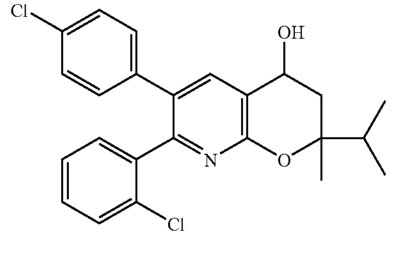

7-(2-Chlorophenyl)-6-(4-chlorophenyl)-2-isopropyl-2-methyl-3,4-dihydro-2H-pyrano[2,3-b]pyridin-4-ol To the product of Example 10 (0.13 g, 0.3 mmol) in MeOH (2 mL) and THF (1 mL) was added $NaBH_4$ (5 mg, 0.15 mmol)

and the suspension was stirred 10 min. The reaction was diluted with EtOAc and washed with a 10% aq. $NaHSO_4$ solution, brine, dried ($Na_2SO_4$), filtered and concentrated The residue was taken up in $CH_2Cl_2$ and filtered. Separation of the product isomers on an OJ chiral column, eluting with 6% EtOH/heptane afforded the last eluting diastereomer (fourth isomer): (LC-2) HPLC/MS 428.4 (M+1), 430.4 (M+3); $R_t$=3.70 min.

Using the procedure described in Example 136 and the product of Example 11 the following compound was afforded:

| | Name | HPLC/MS m/z (M + 1) m/z (M + 3) $R_t$ (min) (LC-2) | |
|---|---|---|---|
| Example 137 | 7-(2-Chlorophenyl)-6-(4-chlorophenyl)-2-ethyl-2-methyl-3,4-dihydro-2H-pyrano[2,3-b]pyridin-4-ol | 414.4<br>416.4<br>3.58 | 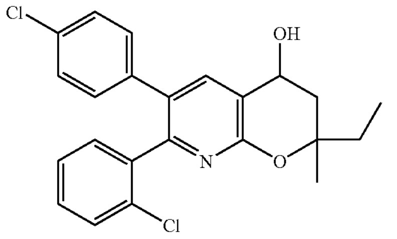<br>(fourth eluting isomer, OJ 6% IPA/heptane) |

EXAMPLE 138

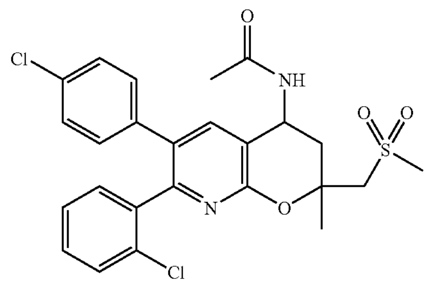

N-{7-(2-chlorophenyl)-6-(4-chlorophenyl)-2-methyl-2-[(methylsulfonyl)methyl]-3,4-dihydro-2H-pyrano[2,3-b]pyridin-4-yl}acetamide Step A: 7-(2-Chlorophenyl)-6-(4-chlorophenyl)-2-methyl-2-[(methylthio)methyl]-2,3-dihydro-4H-pyrano[2,3-b]pyridin-4-one. Using the product of Step A in Example 4 and a procedure similar to that of Example 4 Step B and 1-methylthio-2-propanone the title compound was obtained.

Step B: 7-(2-Chlorophenyl)-6-(4-chlorophenyl)-2-methyl-2-[(methylsulfonyl)methyl]-2,3-dihydro-4H-pyrano[2,3-b]pyridin-4-one. To the product from Step A this example (0.03 g, 0.07 mmol) in $CH_2Cl_2$ (1 mL) and MeCN (2 mL) was added 3-chloroperbenzoic acid (MCPBA) (30 mg, 0.14 mmol, ~77%) and the reaction was stirred at rt for 1 h. The reaction was diluted with EtOAc and washed with a saturated solution of $NaHCO_3$, brine, dried ($Na_2SO_4$), filtered and concentrated. The residue was purified by flash chromatography on silica gel gradient eluted with 0-50% EtOAc in hexane.

Step C: N-{7-(2-Chlorophenyl)-6-(4-chlorophenyl)-2-methyl-2-[(methylsulfonyl)methyl]-3,4-dihydro-2H-pyrano[2,3-b]pyridin-4-yl}acetamide. To the product of Step B this example was applied a procedure similar to that of Example 17 to generate the corresponding oxime. This material was then converted to the title compound using a procedure similar to that of Example 27. (LC-2) HPLC/MS: 519.3 (M+1), 521.3 (M+3); $R_t$=2.88 min.

EXAMPLE 139

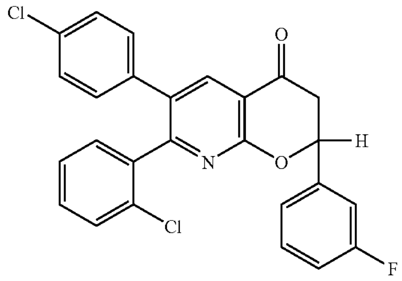

7-(2-Chlorophenyl)-6-(4-chlorophenyl)-2-(3-fluorophenyl)-2,3-dihydro-4H-pyrano[2,3-b]pyridin-4-one Step A: 6-(2-Chlorophenyl)-5-(4-chlorophenyl)-3-[3-(3-fluorophenyl)-3-hydroxypropanoyl]pyridin-2(3H)-one. To the product of Example 4, Step A (0.5 g, 1.4 mmol) in THF (3 mL) and MeOH (1.5 mL) was added 3-fluorobenzaldehyde (0.6 mL, 2.8 mmol) and NaOMe (0.2 g, 0.56 mmol). The reaction was stirred at rt overnight, followed by heating at 50° C. for an additional day. The reaction was diluted with EtOAc and washed with saturated aq $NaHCO_3$, brine, dried ($Na_2SO_4$), filtered and concentrated The residue was purified by flash chromatography on silica gel gradient eluted with 0-30% EtOAc in hexane to afford the product.

Step B: 7-(2-Chlorophenyl)-6-(4-chlorophenyl)-2-(3-fluorophenyl)-2,3-dihydro-4H-pyrano[2,3-b]pyridin-4-one. The product of step A (200 mg, 0.42 mmol) was dissolved in toluene (2 mL) and p-toluenesulfonic acid (30 mg, 0.16 mmol) was added. The reaction was heated at 120° C. for 4 h and allowed to cool overnight. The reaction was diluted with EtOAc and washed with a saturated solution of $NaHCO_3$, brine, dried ($Na_2SO_4$), filtered and concentrated The residue was purified by flash chromatography on silica gel gradient eluted with 0-30% EtOAc in hexane to afford the title compound. (LC-2) HPLC/MS: 464.2 (M+1), 466.2 (M+3); $R_t$=2.61 min.

EXAMPLE 140

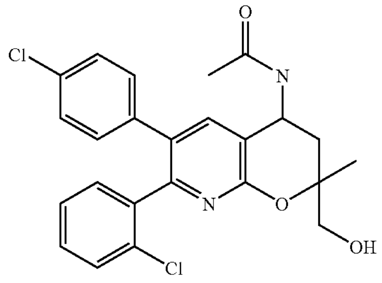

N-[7-(2-Chlorophenyl)-6-(4-chlorophenyl)-2-(hydroxymethyl)-2-methyl-3,4-dihydro-2H-pyrano[2,3-b]pyridin-4-yl]acetamide Step A: 2-(Benzyloxy)-7-(2-chlorophenyl)-6-(4-chlorophenyl)-2-methyl-2,3-dihydro-4H-pyrano[2,3-b]pyridin-4-one. The product of Example 4 Step A and 1-(benzyloxy) acetone were combined in a procedure similar to Example 4 Step B to obtain the title compound.

Step B: N-[2-[(Benzyloxy)methyl]-7-(2-chlorophenyl)-6-(4-chlorophenyl)-2-methyl-3,4-dihydro-2H-pyrano[2,3-b]pyridin-4-yl]acetamide. The product of Step A this example was converted to the corresponding oxime using a procedure similar to that of Example 17. The material was then converted to the title compound using a similar procedure to that of Example 27. (LC-2) HPLC/MS: 547.4 (M+1), 549.4 (M+3); $R_t$=3.78 min.

Step C: N-[7-(2-Chlorophenyl)-6-(4-chlorophenyl)-2-(hydroxymethyl)-2-methyl-3,4-dihydro-2H-pyrano[2,3-b]pyridin-4-yl]acetamide. The product of step B (20 mg, 0.037 mmol) was dissolved in $CH_2Cl_2$ (1 mL) and $FeCl_3$ (25 mg, 0.15 mmol) was added. The reaction was stirred at rt for 30 min and was concentrated. The residue was added to a silica gel flash chromatography column and eluted with 0-100% EtOAc in hexane. After concentration of the desired fractions the product was repurified by semi preparative reverse phase HPLC on a C18 column, eluting with 10 to 80% MeCN/$H_2O$ (each containing 0.5% TFA). The desired fractions were neutralized with a saturated solution of $NaHCO_3$ and extracted with EtOAc. Evaporation and drying in vacuo afforded the title compound. (LC-2) HPLC/MS: 457.3 (M+1), 459.3 (M+3); $R_t$=3.11 min.

EXAMPLE 141

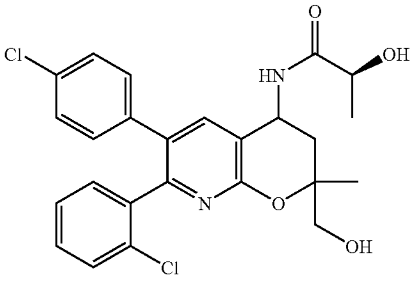

(2S)-N-[7-(2-Chlorophenyl)-6-(4-chlorophenyl)-2-(hydroxymethyl)-2-methyl-3,4-dihydro-2H-pyrano[2,3-b]pyridin-4-yl]-2-hydroxypropanamide Step A: 2-[(Benzyloxy)methyl]-7-(2-chlorophenyl)-6-(4-chlorophenyl)-2-methyl-3,4-dihydro-2H-pyrano[2,3-b]pyridin-4-amine. Using the product from Step A Example 140 and a similar procedure to that of Example 23 the titled compound was obtained.

Step B: (2S)-N-[2-[(Benzyloxy)methyl]-7-(2-chlorophenyl)-6-(4-chlorophenyl)-2-methyl-3,4-dihydro-2H-pyrano [2,3-b]pyridin-4-yl]-2-hydroxypropanamide. To the product of Step A was applied a procedure similar to that of Example 88 to afford the title compound. (LC-2) HPLC/MS: 611.3 (M+1), 613.3 (M+3); $R_t$=3.88 min. The residue was further purified using an AS chiral column, eluting with 6% EtOH/heptane, affording the first eluting isomer (A), the second eluting isomer (B) and a mixture of the third and fourth eluting isomers (C+D).

Step C: (2S)-N-[7-(2-Chlorophenyl)-6-(4-chlorophenyl)-2-(hydroxymethyl)-2-methyl-3,4-dihydro-2H-pyrano[2,3-b] pyridin-4-yl]-2-hydroxypropanamide. Using the isolated isomers (A) or (B) from Step C, along with the procedure for Step C, Example 140, two individual reactions were carried out to get pure diastereomers. (LC-2) HPLC/MS (product of deprotected isomer A): 521.2 (M+1), 523.2 (M+3); $R_t$=3.34 min and (LC-2) HPLC/MS (product of deprotected isomer B): 521.2 (M+1), 523.2 (M+3); $R_t$=3.36 min.

EXAMPLE 142

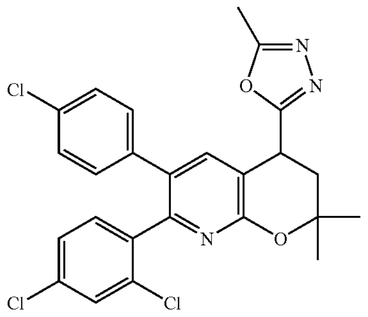

6-(4-Chlorophenyl)-7-(2,4-dichlorophenyl)-2,2-dimethyl-4-(5-methyl-1,3,4-oxadiazol-2-yl)-3,4-dihydro-2H-pyrano[2,3-b]pyridine To 6-(4-chlorophenyl)-7-(2,4-dichlorophenyl)-2,2-dimethyl-3,4-dihydro-2H-pyrano[2,3-b]pyridine-4-carboxylic acid prepared in similar fashion to the product of Example 124 Step B (20 mg, 0.05 mmol) in MeCN (1 mL) was added 1-hydroxybenzotriazole (HOBt) (7 mg, 0.005 mmol), N-(3-dimethylaminopropyl)-N'-ethylcarboddimide hydrochloride (EDAC) (10 mg, 0.05 mmol) and the reaction was stirred at rt for 30 min. The reaction was cooled to 0° C. and hydrazine hydrate (0.005 mL, 0.09 mmol) was added and the reaction was stirred for 5 min. EtOAc was added and the organic portion was washed with saturated aq $NaHCO_3$ and water, dried ($Na_2SO_4$), filtered and concentrated. The residue was dissolved in $CH_2Cl_2$ (2 mL). Acetyl chloride (0.025 mL, 0.35 mmol) was added and the reaction was stirred 10 min. EtOAc was added and the solution was washed with saturated aq $NaHCO_3$, dried ($Na_2SO_4$), filtered and concentrated. The residue was dissolved in toluene (0.5 mL) and $POCl_3$ (0.2 mL) was added. The reaction was refluxed overnight, diluted with $CH_2Cl_2$, washed with a saturated aq solution of $NaHCO_3$, dried ($Na_2SO_4$), filtered and concentrated. The residue was purified by flash chromatography on silica gel gradient eluted with 0-50% EtOAc in hexane to afford the title compound. (LC-2) HPLC/MS: 500.2 (M+1), 502.2 (M+3); $R_t$=3.91 min.

Using the procedure described in Example 142, and the appropriate acid chloride, the following compounds were afforded. The enantiomers were separated by chiral chromatography with conditions as indicated:

| | Name | HPLC/MS m/z (M + 1) m/z (M + 3) $R_t$ (min) (LC-2) | |
|---|---|---|---|
| Example 143 | 6-(4-Chlorophenyl)-7-(2,4-dichlorophenyl)-4-(5-isopropyl-1,3,4-oxadiazol-2-yl)-2,2-dimethyl-3,4-dihydro-2H-pyrano[2,3-b]pyridine | 528.2<br>530.2<br>4.15 | 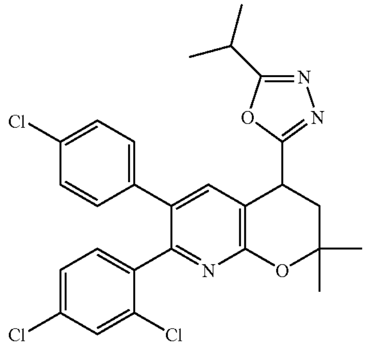<br>(fast isomer, AD 20% IPA/heptane) |

-continued

| | Name | HPLC/MS m/z (M + 1) m/z (M + 3) $R_t$ (min) (LC-2) | |
|---|---|---|---|
| Example 144 | 6-(4-Chlorophenyl)-7-(2,4-dichlorophenyl)-4-(5-isopropyl-1,3,4-oxadiazol-2-yl)-2,2-dimethyl-3,4-dihydro-2H-pyrano[2,3-b]pyridine | 528.2<br>530.2<br>4.154 | 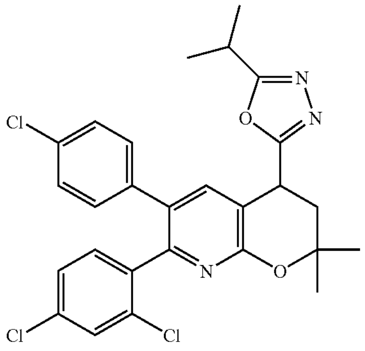<br>(slow isomer, AD 20% IPA/heptane) |

EXAMPLE 145

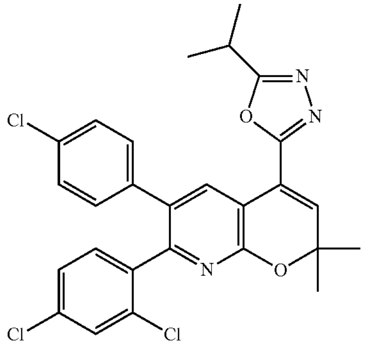

6-(4-Chlorophenyl)-7-(2,4-dichlorophenyl)-4-(5-isopropyl-1,3,4-oxadiazol-2-yl)-2,2-dimethyl-2H-pyrano[2,3-b]pyridine The title compound was isolated as an unanticipated side product from Example 144. (LC-2) HPLC/MS: 526.2 (M+1), 528.2 (M+3); $R_t$=4.42 min.

EXAMPLE 146

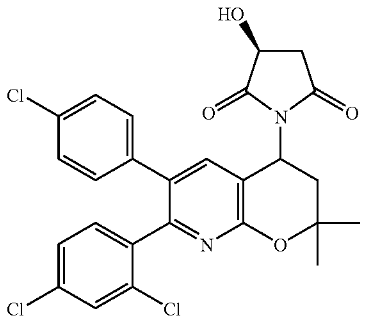

(3S)-1-[6-(4-Chlorophenyl)-7-(2,4-dichlorophenyl)-2,2-dimethyl-3,4-dihydro-2H-pyrano[2,3-b]pyridin-4-yl]-3-hydroxypyrrolidine-2,5-dione Step A: (3S)-1-[6-(4-Chlorophenyl)-7-(2,4-dichlorophenyl)-2,2-dimethyl-3,4-dihydro-2H-pyrano[2,3-b]pyridin-4-yl]-2,5-dioxopyrrolidin-3-yl acetate. To the product of Example 24 (50 mg, 0.12 mmol) was added (3S)-2,5-dioxotetrahydrofuran-3-yl acetate (0.5 g) and the reaction was heated to 85° C. for 1 hr. The reaction was cooled and AcOH was added (1 mL). Heating was continued at 85° C. an additional 2 h. The reaction was diluted with EtOAc, washed with saturated aq $NaHCO_3$, dried ($Na_2SO_4$), filtered and concentrated. The residue was purified by flash chromatography on silica gel gradient eluted with 0-30% EtOAc in hexane to afford the title compound. (LC-2) HPLC/MS: 573.0 (M+1), 575.0 (M+3); $R_t$=3.80.

Step B: (3S)-1-[6-(4-Chlorophenyl)-7-(2,4-dichlorophenyl)-2,2-dimethyl-3,4-dihydro-2H-pyrano[2,3-b]pyridin-4-yl]-3-hydroxypyrrolidine-2,5-dione. The product of Step A (38 mg, 0.7 mmol) was dissolved in MeOH (2 mL) and p-toluenesulfonic acid (6 mg, 0.03 mmol) was added. The reaction was heated at 85° C. for 2 h and concentrated. The residue was dissolved in EtOAc and the solution was washed with saturated aq $NaHCO_3$, dried ($Na_2SO_4$), filtered and concentrated. The residue was purified by flash chromatography on silica gel gradient eluted with 0-60% EtOAc in hexane to afford the title compound. Further separation on an AD chiral column, eluting with 50% IPA/heptane, afforded the diastereomers: (LC-2) HPLC/MS (fast isomer on AD): 531.0 (M+1), 533.0 (M+3); $R_t$=3.58 min. (LC-2) HPLC/MS (slow isomer): 531.0 (M+1), 533.0 (M+3); $R_t$=3.59 min.

The following examples were prepared utilizing the appropriate amine and carboxylic acid or acid chloride in procedures similar to that described for Example 26 and Example 88.

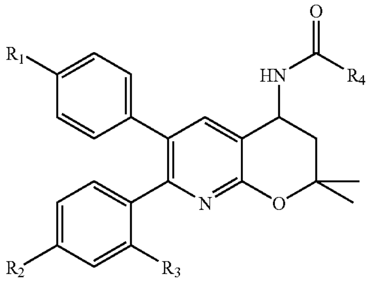
| Example | $R_1$, $R_2$, $R_3$ | $R_4$ | HPLC $R_t$ (min) | MS (M + H/M + 3H) |
|---|---|---|---|---|
| 147 | Cl, Cl, Cl | 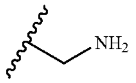 | 3.11 (LC-2) | 490.2/492.2 |
| 148 (Enantiomer 1) | Cl, Cl, Cl | 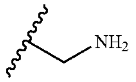 | 3.10 (LC-2) | 490.2/492.2 |
| 149 (Enantiomer 2) | Cl, Cl, Cl | 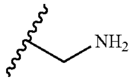 | 3.12 (LC-2) | 490.2/492.2 |
| 150 | Cl, Cl, Cl | 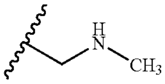 | 3.15 (LC-2) | 504.2/506.2 |
| 151 | Cl, Cl, Cl | 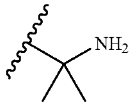 | 3.18 (LC-2) | 518.2/520.2 |
| 152 (Enantiomer 1) | Cl, Cl, Cl | 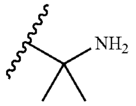 | 3.19 (LC-2) | 518.2/520.2 |
| 153 (Enantiomer 2) | Cl, Cl, Cl | 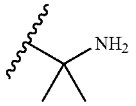 | 3.18 (LC-2) | 518.2/520.2 |
| 154 | Cl, Cl, Cl | 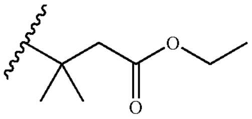 | 4.09 (LC-2) | 589.3/591.3 |
| 155 | Cl, Cl, Cl | 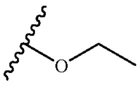 | 4.03 (LC-2) | 505.2/507.2 |
| 156 (Diastereomer 1) | Cl, Cl, Cl | 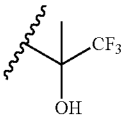 | 3.92 (LC-2) | 573.1/575.1 |
| 157 (Enantiomer 1) | Cl, Cl, Cl | 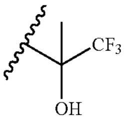 | 3.89 (LC-2) (8.42, AD, 5% Et/Hex) | 573.2/575.1 |

-continued
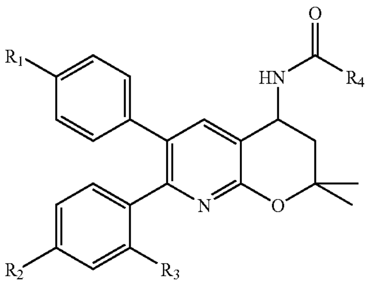
| Example | $R_1$, $R_2$, $R_3$ | $R_4$ | HPLC $R_t$ (min) | MS (M + H/M + 3H) |
|---|---|---|---|---|
| 158 (Enantiomer 2) | Cl, Cl, Cl | 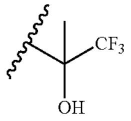 | 3.94 (LC-2) (11.82, AD 5% Et/Hex) | 573.0/575.0 |
| 159 (Diastereomer 2) | Cl, Cl, Cl | 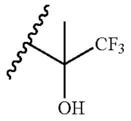 | 3.93 (LC-2) | 573.1/575.1 |
| 160 (Diastereomer 1) | Cl, Cl, Cl | 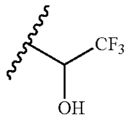 | 3.84 (LC-2) | 559.2/561.2 |
| 161 (Enantiomer 1) | Cl, Cl, Cl | 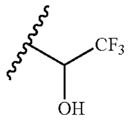 | 3.84 (LC-2) (7.53, AD 7% Et/Hex) | 559.2/561.2 |
| 162 (Enantiomer 2) | Cl, Cl, Cl | 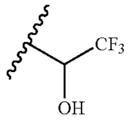 | 3.84 (LC-2) (11.72, AD 7% Et/Hex) | 559.2/561.2 |
| 163 (Diastereomer 2) | Cl, Cl, Cl | 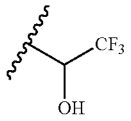 | 3.87 (LC-2) | 559.2/561.2 |
| 164 (Enantiomer 1) | Cl, Cl, Cl | 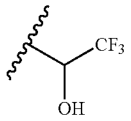 | 3.84 (LC-2) (11.30, AD 5% Et/Hex) | 559.0/561.0 |
| 165 (Enantiomer 2) | Cl, Cl, Cl | 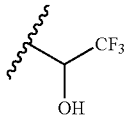 | 3.84 (LC-2) (17.27, AD 5% Et/Hex) | 559.0/561.0 |
| 166 (Diastereomer 1) | Cl, Cl, Cl | 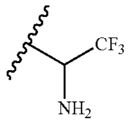 | 3.49 (LC-2) | 558.0/560.0 |

-continued
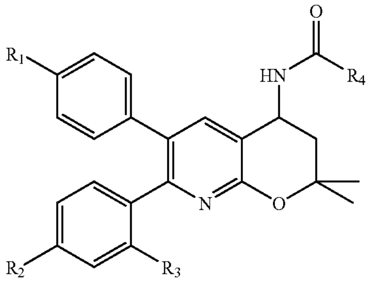
| Example | $R_1$, $R_2$, $R_3$ | $R_4$ | HPLC $R_t$ (min) | MS (M + H/M + 3H) |
|---|---|---|---|---|
| 167 (Enantiomer 1) | Cl, Cl, Cl | 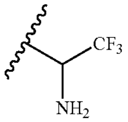 | 3.48 (LC-2) (4.10, AD 30% IPA/Hep) | 558.1/560.0 |
| 168 (Enantiomer 2) | Cl, Cl, Cl | 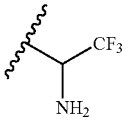 | 3.45 (LC-2) (5.43, AD 30% IPA/Hep) | 558.1/560.0 |
| 169 (Diastereomer 2) | Cl, Cl, Cl | 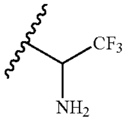 | 3.48 (LC-2) | 558.0/560.0 |
| 170 (Enantiomer 1) | Cl, Cl, Cl | 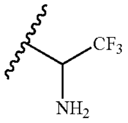 | 3.45 (LC-2) (4.02, OD 30% IPA/Hep) | 558.0/560.0 |
| 171 (Enantiomer 1) | Cl, Cl, Cl | 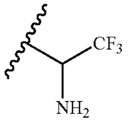 | 3.48 (LC-2) (5.42, OD 30% IPA/Hep) | 558.0/560.0 |
| 172 | Cl, Cl, Cl | 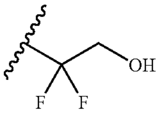 | 3.71 (LC-2) | 541.0/543.0 |
| 173 (Enantiomer 1) | Cl, Cl, Cl | 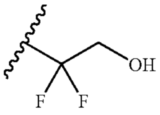 | 3.73 (LC-2) (10.01, OD 7% Et/Hex) | 541.0/543.0 |
| 174 (Enantiomer 1) | Cl, Cl, Cl | 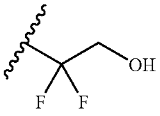 | 3.73 (LC-2) (13.45, OD 7% Et/Hex) | 541.0/543.0 |
| 175 | Cl, Cl, Cl | 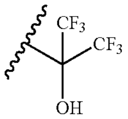 | 2.62 | 626.9/628.9 |

-continued
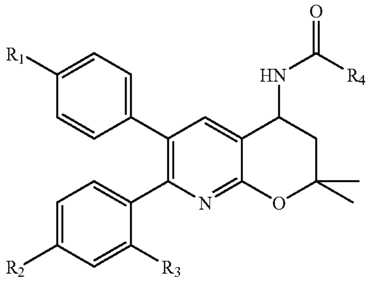
| Example | $R_1$, $R_2$, $R_3$ | $R_4$ | HPLC $R_t$ (min) | MS (M + H/M + 3H) |
|---|---|---|---|---|
| 176 | Cl, Cl, Cl | 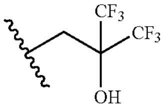 | 2.74 | 640.9/642.9 |
| 177 (Enantiomer 1) | Cl, Cl, Cl | 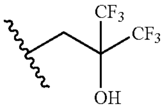 | 4.20 (LC-2) (9.33, AD 3% Et/Hex) | 641.0/643.0 |
| 178 (Enantiomer 2) | Cl, Cl, Cl | 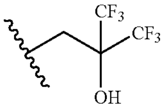 | 4.21 (LC-2) (13.29, OD 3% Et/Hex) | 641.0/643.1 |
| 179 | Cl, Cl, Cl | 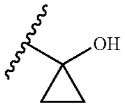 | 3.70 (LC-2) | 517.1/519.1 |
| 180 | Br, Cl, Cl | 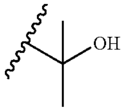 | 3.78 (LC-2) | 565.0/567.0 |
| 181 | CN, Cl, Cl | 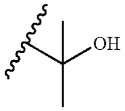 | 3.42 (LC-2) | 510.0/513.0 |
| 182 | $CH_3$, Cl, Cl | 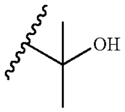 | 3.67 (LC-2) | 499.3/501.3 |
| 183 (Enantiomer 1) | $CH_3$, Cl, Cl | 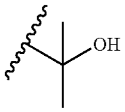 | 3.67 (LC-2) (11.65, AD 5% Et/Hex) | 499.3/501.3 |
| 184 (Enantiomer 2) | $CH_3$, Cl, Cl | 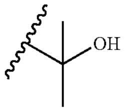 | 3.67 (LC-2) (14.13, AD 5% Et/Hex) | 499.3/501.3 |
| 185 | $CH_3$, Cl, Cl | 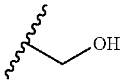 | 3.45 (LC-2) | 471.1/473.1 |

-continued
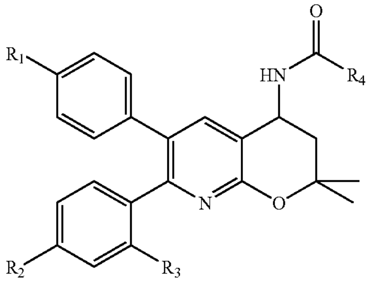
| Example | $R_1$, $R_2$, $R_3$ | $R_4$ | HPLC $R_t$ (min) | MS (M + H/M + 3H) |
|---|---|---|---|---|
| 186 | $CF_3$, Cl, Cl | 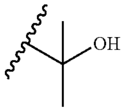 | 1.29 (LC-1) | 553.2/555.2 |
| 187 (Enantiomer 1) | $CF_3$, Cl, Cl | 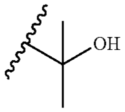 | 1.29 (LC-1) (8.70, AD 6% Et/Hex) | 553.2/555.2 |
| 188 (Enantiomer 2) | $CF_3$, Cl, Cl | 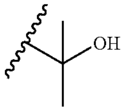 | 1.29 (LC-1) (12.87, AD 6% Et/Hex) | 553.2/555.2 |
| 189 (Diastereomer 1) | $CF_3$, Cl, Cl | 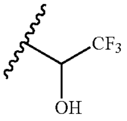 | 3.86 (LC-2) | 593.2/595.2 |
| 190 (Enantiomer 1) | $CF_3$, Cl, Cl | 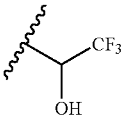 | 3.86 (LC-2) (7.39, AD 6% Et/Hex) | 593.2/595.2 |
| 191 (Enantiomer 2) | $CF_3$, Cl, Cl | 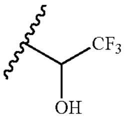 | 3.86 (LC-2) (12.41, AD 6% Et/Hex) | 593.2/595.2 |
| 192 (Diastereomer 2) | $CF_3$, Cl, Cl | 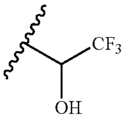 | 3.86 (LC-2) | 593.2/595.2 |
| 193 (Enantiomer 1) | $CF_3$, Cl, Cl | 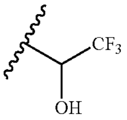 | 3.86 (LC-2) (8.42, AD 6% Et/Hex) | 593.2/595.2 |
| 194 (Enantiomer 2) | $CF_3$, Cl, Cl | 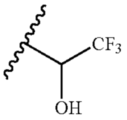 | 3.86 (LC-2) (11.82, AD 6% Et/Hex) | 593.2/595.2 |

-continued
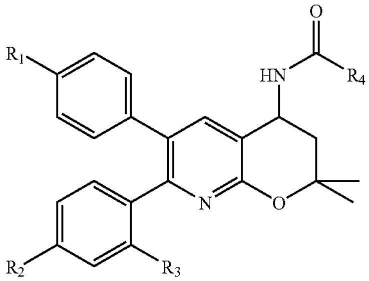
| Example | $R_1$, $R_2$, $R_3$ | $R_4$ | HPLC $R_t$ (min) | MS (M + H/M + 3H) |
|---|---|---|---|---|
| 195 | $CF_3$, Cl, Cl | 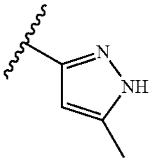 | 3.80 (LC-2) | 575.1/577.1 |
| 196 (Enantiomer 1) | $CF_3$, Cl, Cl | 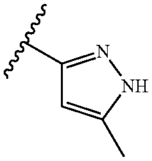 | 3.80 (LC-2) (4.20, AD 30% IPA/Hep) | 575.1/577.1 |
| 197 (Enantiomer 2) | $CF_3$, Cl, Cl | 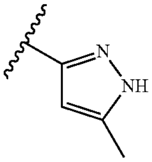 | 3.80 (LC-2) (10.98, AD 30% IPA/Hep) | 575.1/577.1 |
| 198 | $OCH_3$, Cl, Cl | 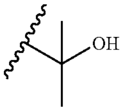 | 3.51 (LC-2) | 515.2/517.2 |
| 199 (Enantiomer 1) | $OCH_3$, Cl, Cl | 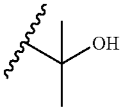 | 3.45 (LC-2) (9.01, AD 8% Et/Hex) | 515.3/517.3 |
| 200 (Enantiomer 2) | $OCH_3$, Cl, Cl | 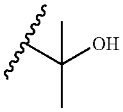 | 3.46 (LC-2) (11.87, AD 8% Et/Hex) | 515.3/517.3 |
| 201 | $OCH_3$, Cl, Cl | 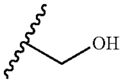 | 3.22 (LC-2) | 487.2/489.2 |
| 202 (Diastereomer 1) | $OCH_3$, Cl, Cl | 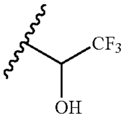 | 3.58 (LC-2) | 555.2/557.2 |
| 203 (Enantiomer 1) | $OCH_3$, Cl, Cl | 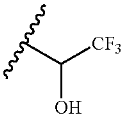 | 3.58 (LC-2) (9.13, AD 15% IPA/Hep) | 555.2/557.2 |

-continued
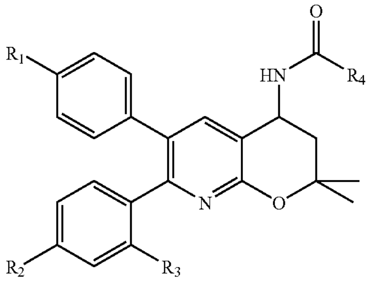
| Example | $R_1$, $R_2$, $R_3$ | $R_4$ | HPLC $R_t$ (min) | MS (M + H/M + 3H) |
|---|---|---|---|---|
| 204 (Enantiomer 2) | $OCH_3$, Cl, Cl | 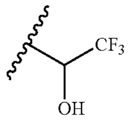 | 3.58 (LC-2) (13.22, AD 15% IPA/Hep) | 555.2/557.2 |
| 205 (Diastereomer 2) | $OCH_3$, Cl, Cl | 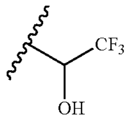 | 3.58 (LC-2) | 555.2/557.2 |
| 206 (Enantiomer 1) | $OCH_3$, Cl, Cl | 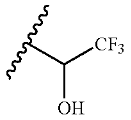 | 3.58 (LC-2) (11.29, AD 15% IPA/Hep) | 555.2/557.2 |
| 207 (Enantiomer 2) | $OCH_3$, Cl, Cl | 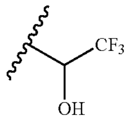 | 3.58 (LC-2) (14.00, AD 15% IPA/Hep) | 555.2/557.2 |
| 208 | Cl, Br, Cl | 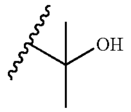 | 3.87 (LC-2) | 563.1/565.1 |
| 209 (Enantiomer 1) | Cl, Br, Cl | 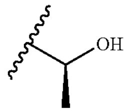 | 3.65 (LC-2) | 549.0/551.0 |
| 210 (Enantiomer 2) | Cl, Br, Cl | 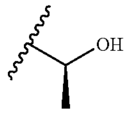 | 3.63 (LC-2) | 549.0/551.0 |
| 211 | Cl, Br, Cl | 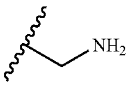 | 3.06 (LC-2) | 534.0/536.0 |
| 212 | Cl, Br, Cl | 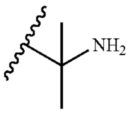 | 3.22 (LC-2) | 562.1/564.1 |
| 213 | Cl, CN, Cl | 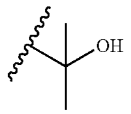 | 3.60 (LC-2) | 510.2/512.2 |

-continued
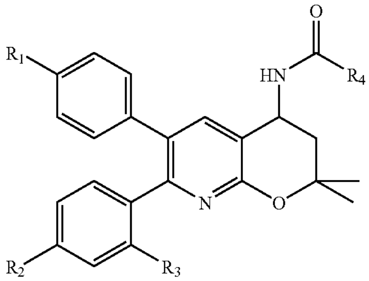
| Example | $R_1$, $R_2$, $R_3$ | $R_4$ | HPLC $R_t$ (min) | MS (M + H/M + 3H) |
|---|---|---|---|---|
| 214 (Enantiomer 1) | Cl, CN, Cl | 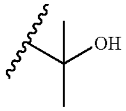 | 3.60 (LC-2) (11.01, AD 10% Et/Hex) | 510.2/512.2 |
| 215 (Enantiomer 2) | Cl, CN, Cl | 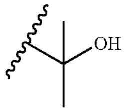 | 3.59 (LC-2) (16.23, AD 10% Et/Hex) | 510.2/512.2 |
| 216 | Cl, CN, Cl | 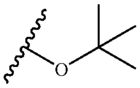 | 3.98 (LC-2) | 524.1/526.2 |
| 217 (Enantiomer 1) | Cl, CN, Cl | 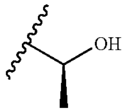 | 3.28 (LC-2) (11.26, AD 10% Et/Hex) | 496.1/498.1 |
| 218 (Enantiomer 2) | Cl, CN, Cl | 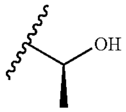 | 3.26 (LC-2) (22.48, AD 10% Et/Hex) | 496.1/498.1 |
| 219 (Diastereomer 1) | Cl, CN, Cl | 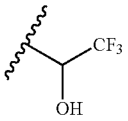 | 3.51 (LC-2) | 550.1/553.2 |
| 220 (Enantiomer 1) | Cl, CN, Cl | 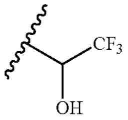 | 3.54 (LC-2) (6.63, AS 15% Et/Hex) | 550.1/553.2 |
| 221 (Enantiomer 2) | Cl, CN, Cl | 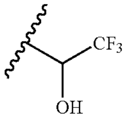 | 3.55 (LC-2) (15.14, AS 15% Et/Hex) | 550.1/553.1 |
| 222 (Diastereomer 2) | Cl, CN, Cl | 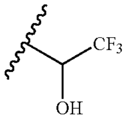 | 3.48 (LC-2) | 549.9/553.0 |
| 223 (Enantiomer 1) | Cl, CN, Cl | 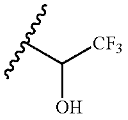 | 3.48 (LC-2) (13.66, OD 19% Et/Hex) | 549.9/553.0 |

-continued
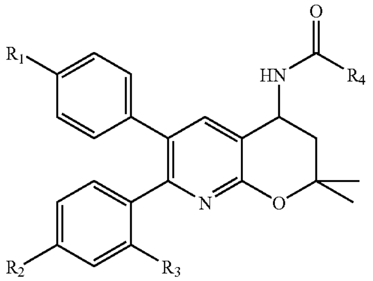
| Example | $R_1$, $R_2$, $R_3$ | $R_4$ | HPLC $R_t$ (min) | MS (M + H/M + 3H) |
|---|---|---|---|---|
| 224 (Enantiomer 2) | Cl, CN, Cl | 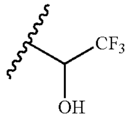 | 3.48 (LC-2) (16.16, OD 19% Et/Hex) | 549.9/553.0 |
| 225 | Cl, CN, Cl | 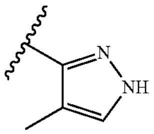 | 3.56 (LC-2) | 532.1/534.1 |
| 226 | Cl, $CH_3$, Cl | 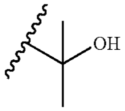 | 3.60 (LC-2) | 499.2/501.2 |
| 227 | Cl, $OCH_3$, Cl | 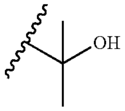 | 3.47 (LC-2) | 515.2/517.2 |
| 228 (Enantiomer 1) | Cl, $OCH_3$, Cl | 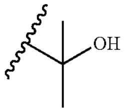 | 3.38 (LC-2) (10.53, AD 8% Et/Hex) | 515.1/517.1 |
| 229 (Enantiomer 2) | Cl, $OCH_3$, Cl | 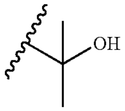 | 3.38 (LC-2) (16.10, AD 8% Et/Hex) | 515.1/517.1 |
| 230 (Diastereomer 1) | Cl, $OCH_3$, Cl | 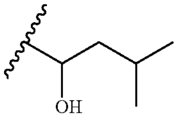 | 3.67 (LC-2) | 343.4/345.3 |
| 231 (Diastereomer 2) | Cl, $OCH_3$, Cl | 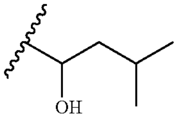 | 3.68 (LC-2) | 543.4/545.4 |
| 232 | Cl, OH, Cl | 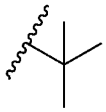 | 3.72 (LC-2) | 499.3/501.3 |
| 233 | Cl, Cl, Br | 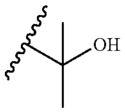 | 3.85 (LC-2) | 563.2/565.1 |

-continued
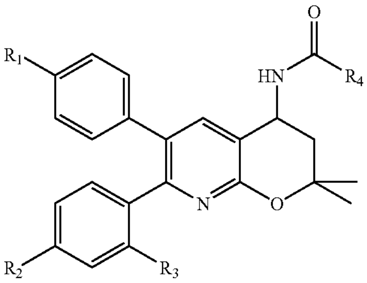
| Example | $R_1$, $R_2$, $R_3$ | $R_4$ | HPLC $R_t$ (min) | MS (M + H/M + 3H) |
|---|---|---|---|---|
| 234 (Enantiomer 1) | Cl, Cl, Br | 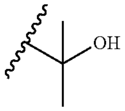 | 3.85 (LC-2) (11.19, AD 5% Et/Hex) | 563.2/565.1 |
| 235 (Enantiomer 2) | Cl, Cl, Br | 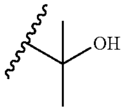 | 3.85 (LC-2) (19.04, AD 5% Et/Hex) | 563.2/565.1 |
| 236 | Cl, Cl, Br | 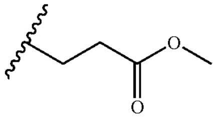 | 3.89 (LC-2) | 591.2/593.2 |
| 237 | Cl, Cl, CN | 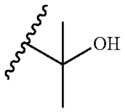 | 3.66 (LC-2) | 510.2/512.2 |
| 238 (Enantiomer 1) | Cl, Cl, CN | 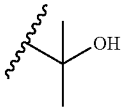 | 3.61 (LC-2) (20.08, AD 5% Et/Hex) | 510.2/512.2 |
| 239 (Enantiomer 2) | Cl, Cl, CN | 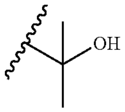 | 3.60 (LC-2) (30.54, AD 5% Et/Hex) | 510.2/512.2 |
| 240 | Cl, Cl, $CH_3$ | 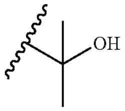 | 3.67 (LC-2) | 499.3/501.3 |
| 241 | Cl, $CF_3$, $CF_3$ | 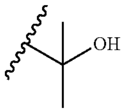 | 3.86 (LC-2) | 587.3/589.3 |
| 242 (Enantiomer 1) | Cl, $CF_3$, $CF_3$ | 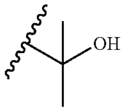 | 3.86 (LC-2) (6.89, AD 6% Et/Hex) | 587.3/589.3 |

-continued

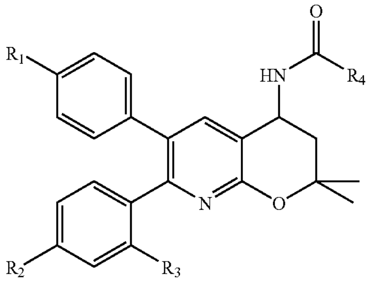

| Example | $R_1$, $R_2$, $R_3$ | $R_4$ | HPLC $R_t$ (min) | MS (M + H/M + 3H) |
|---|---|---|---|---|
| 243 (Enantiomer 2) | Cl, $CF_3$, $CF_3$ | 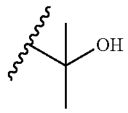 | 3.86 (LC-2) (9.37, AD 6% Et/Hex) | 587.3/589.3 |
| 244 | Cl, CN, CN | 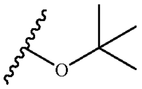 | 3.80 (LC-2) | 515.2/517.2 |

EXAMPLE 245

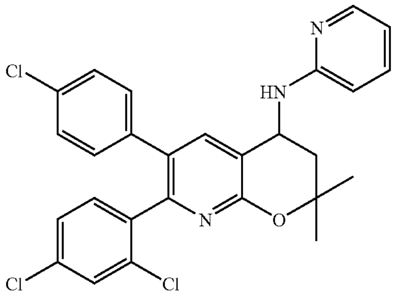

6-(4-Chlorophenyl)-7-(2,4-dichlorophenyl)-2,2-dimethyl-N-(pyridine-2-yl)-3,4-dihydro-2H-pyrano[2,3-b]pyridin-4-amine A mixture of the product of Example 24 (160 mg, 0.37 mmol), 2-bromopyridine (35 μL, 0.37 mmol), palladium(II) acetate (4.1 mg, 0.02 mmol), (±)-BINAP (11.5 mg, 0.02 mmol), and sodium tert-butoxide (39.0 mg, 0.41 mmol) in 10 mL of toluene was degassed and allowed to stir at 70° C. for 16 h. The reaction mixture was cooled to rt, diluted with EtOAc (50 mL) and filtered through a cake of Celite. The filtrate was concentrated and purified by chromatography on preparative TLC plates (Analtech TLC Uniplates™, silica gel, 20×20 cm, 1000 μm) using 9:11 v/v $Et_2O$/hexanes as the mobile phase afforded the title compound: $^1H$ NMR δ 1.52 (s, 3H), 1.56 (s, 3H), 1.86 (m, 1H), 2.38 (dd, J=6.1, 13.4, 1H), 4.58 (br. s, 1H), 5.54 (m, 1H), 6.47 (d, J=8.5, 1H), 6.65 (dd, J=5.4, 6.8, 1H), 6.97-6.99 (m, 2H), 7.13-7.26 (m, 4H), 7.42-7.46 (m, 1H), 7.79 (s, 1H), 8.13 (d, J=4.2, 1H).

EXAMPLE 246

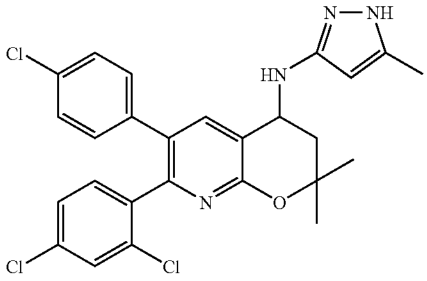

6-(4-Chlorophenyl)-7-(2,4-dichlorophenyl)-2,2-dimethyl-N-(5-methyl-1H-pyrazol-3-yl)-3,4-dihydro-2H-pyrano[2,3-b]pyridin-4-amine Step A: N-[6-(4-chlorophenyl)-7-(2,4-dichlorophenyl)-2,2-dimethyl-3,4-dihydro-2H-pyrano[2,3-b]pyridin-4-yl]-3-oxobutanamide. To a solution of the product of Example 24 (129.5 mg, 0.30 mmol) in 10 mL of $CH_2Cl_2$ at 0° C. was added diketene (50 μL, 0.66 mmol). The mixture was allowed to stir at rt for 1 h and then concentrated. Chromatography on a Biotage 40+S cartridge using 3:2 v/v EtOAc/hexanes as the eluant afforded the title compound: $^1H$ NMR δ 1.46 (s, 3H), 1.55 (s, 3H), 1.87 (m, 1H), 2.24-2.29 (m, 4H), 3.54 (s, 2H), 5.48 (m, 1H), 7.01 (d, J=8.4, 2H), 7.17-7.26 (m, 4H), 7.40 (br. s, 1H), 7.63 (s, 1H).

Step B: N-[6-(4-Chlorophenyl)-7-(2,4-dichlorophenyl)-2,2-dimethyl-3,4-dihydro-2H-pyrano[2,3-b]pyridin-4-yl]-3-oxobutanethioamide. A solution of the product of Step A (136 mg, 0.26 mmol) and Lawesson's reagent (106 mg, 0.26 mmol) in 5.0 mL of toluene was stirred at 120° C. for 3 h and then concentrated. Chromatography on a Biotage 40+S cartridge using 1:3 v/v EtOAc/hexanes as the eluant afforded the title compound.

Step C: 6-(4-Chlorophenyl)-7-(2,4-dichlorophenyl)-2,2-dimethyl-N-(5-methyl-1H-pyrazol-3-yl)-3,4-dihydro-2H-pyrano[2,3-b]pyridin-4-amine. A mixture of the product of Step B (56 mg, 0.11 mmol), hydrazine (6.6 μL, 0.21 mmol), and AcOH (12.0 μL, 0.21 mmol) in 5.0 mL of EtOH was refluxed for 16 h. The reaction mixture was then cooled to rt, diluted with $Et_2O$ (50 mL), and washed with saturated aq $NaHCO_3$ (2×50 mL) and brine (50 mL). After phase separation, the organic phase was dried over $MgSO_4$ and concentrated. Chromatography on a Biotage 40+S cartridge using 2:3 v/v acetone/hexanes as the eluant afforded the title compound: $^1$H NMR δ 1.48 (s, 3H), 1.54 (s, 3H), 1.82 (t, J=12.4, 1H), 2.26 (s, 3H), 2.41 (dd, J=5.9, 13.3, 1H), 3.86 (br. s, 1H), 4.92 (m, 1H), 5.45 (s, 1H), 7.00 (d, J=8.4, 2H), 7.15-7.26 (m, 5H), 7.97 (s, 1H).

The racemic mixture of Example 246 was resolved by chiral preparative chromatography with conditions indicated to afford the enantiomers listed in the following examples

| Example | HPLC $R_t$ (min) | MS (M + H/M + 3H) |
|---|---|---|
| 247 | 2.11 (17.72, OJ 7Et/hex) | 513.1/515.1 |
| 248 | 2.10 (25.05, OJ 7Et/hex) | 513.1/515.1 |

The following examples were prepared utilizing the appropriate amine and carboxylic acid or acid chloride in procedures similar to those described for Example 26 or Example 88.

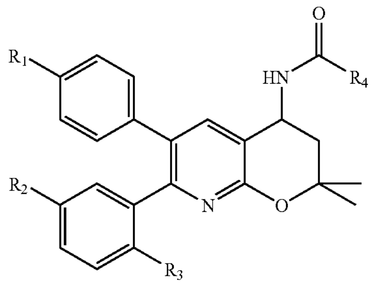

| Example | $R_1$, $R_2$, $R_3$ | $R_4$ | HPLC $R_t$ (min) | MS (M + H/M + 3H) |
|---|---|---|---|---|
| 249 | Cl, Cl, Cl | 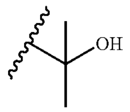 | 3.71 (LC-2) | 519.2/521.2 |
| 250 (Enantiomer 1) | Cl, Cl, Cl | 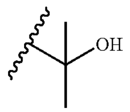 | 3.66 (LC-2) (8.11, AD 6% Et/Hex) | 519.2/521.2 |
| 251 (Enantiomer 2) | Cl, Cl, Cl | 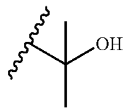 | 3.66 (LC-2) (11.57, AD 6% Et/Hex) | 519.2/521.2 |
| 252 | Cl, Cl, Cl | 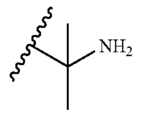 | 3.13 (LC-2) | 518.2/520.2 |
| 253 (Diastereomer 1) | Cl, Cl, Cl | 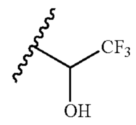 | 3.77 (LC-2) | 559.1/561.0 |
| 254 (Enantiomer 1) | Cl, Cl, Cl | 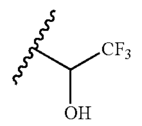 | 3.72 (LC-2) (3.40, AS 30% Et/Hex) | 558.9/560.9 |

-continued
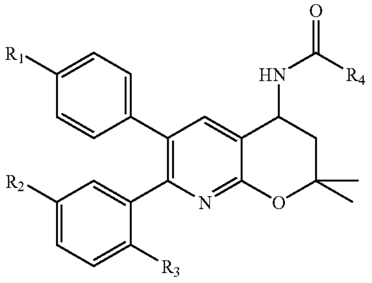
| Example | $R_1, R_2, R_3$ | $R_4$ | HPLC $R_t$ (min) | MS (M + H/M + 3H) |
|---|---|---|---|---|
| 255 (Enantiomer 2) | Cl, Cl, Cl | 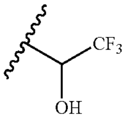 | 3.72 (LC-2) (4.60, AS 30% Et/Hex) | 558.9/560.9 |
| 256 (Diastereomer 2) | Cl, Cl, Cl | 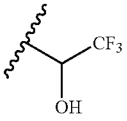 | 3.77 (LC-2) | 559.1/561.0 |
| 257 (Enantiomer 1) | Cl, Cl, Cl | 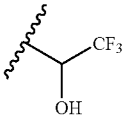 | 3.72 (LC-2) (8.63, AD 6% Et/Hex) | 558.9/560.9 |
| 258 (Enantiomer 2) | Cl, Cl, Cl | 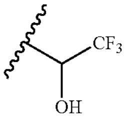 | 3.72 (LC-2) (10.59, AD 6% Et/Hex) | 558.9/560.9 |
| 259 | Cl, Cl, Cl | 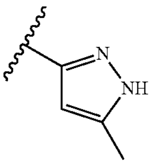 | 3.71 (LC-2) | 541.1/543.1 |
| 260 (Enantiomer 1) | Cl, Cl, Cl | 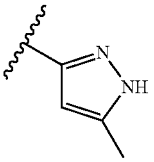 | 3.71 (LC-2) (3.65, AD 30% IPA/Hep) | 541.1/543.1 |
| 261 (Enantiomer 2) | Cl, Cl, Cl | 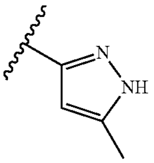 | 3.71 (LC-2) (5.45, AD 30% IPA/Hep) | 541.1/543.1 |
| 262 | Cl, Br, Cl | 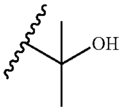 | 3.78 (LC-2) | 565.2/567.2 |

-continued
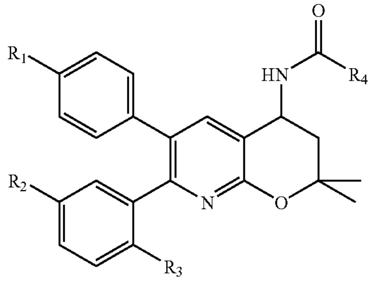
| Example | $R_1$, $R_2$, $R_3$ | $R_4$ | HPLC $R_t$ (min) | MS (M + H/M + 3H) |
|---|---|---|---|---|
| 263 (Enantiomer 1) | Cl, Br, Cl | 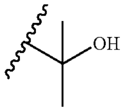 | 3.78 (LC-2) (8.29, AD 6% Et/Hex) | 565.2/567.2 |
| 264 (Enantiomer 2) | Cl, Br, Cl | 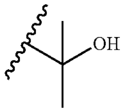 | 3.78 (LC-2) (12.40, AD 6% Et/Hex) | 565.2/567.2 |
| 265 (Diastereomer 1) | Cl, Br, Cl | 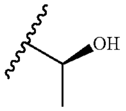 | 3.66 (LC-2) | 551.1/553.1 |
| 266 (Diastereomer 2) | Cl, Br, Cl | 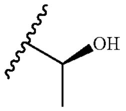 | 3.66 (LC-2) | 551.1/553.1 |
| 267 (Diastereomer 1) | Cl, Br, Cl | 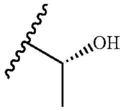 | 3.66 (LC-2) | 551.1/553.1 |
| 268 (Diastereomer 2) | Cl, Br, Cl | 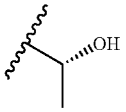 | 3.66 (LC-2) | 551.1/553.1 |
| 269 (Diastereomer 1) | Cl, Br, Cl | 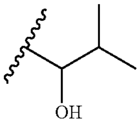 | 3.71 (LC-2) | 579.2/581.2 |
| 270 (Diastereomer 2) | Cl, Br, Cl | 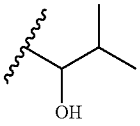 | 3.71 (LC-2) | 579.2/581.2 |
| 271 | Cl, Br, Cl | 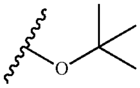 | 4.22 (LC-2) | 576.9/578.9 |
| 272 | Cl, Br, Cl | 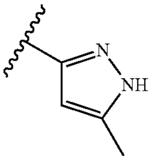 | 2.37 | 587.0/589.0 |

-continued
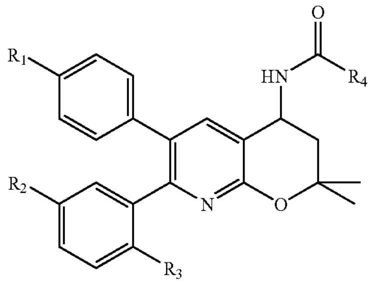
| Example | $R_1$, $R_2$, $R_3$ | $R_4$ | HPLC $R_t$ (min) | MS (M + H/M + 3H) |
|---|---|---|---|---|
| 273 | Cl, CN, Cl | 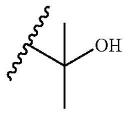 | 3.47 (LC-2) | 510.3/512.3 |
| 274 | Cl, $CH_3$, Cl | 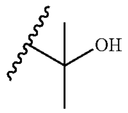 | 3.55 (LC-2) | 499.1/501.1 |
| 275 (Enantiomer 1) | Cl, $CH_3$, Cl | 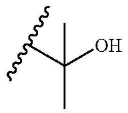 | 3.55 (LC-2) (7.64, AD 6% Et/Hex) | 499.1/501.1 |
| 276 (Enantiomer 2) | Cl, $CH_3$, Cl | 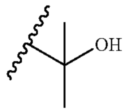 | 3.55 (LC-2) (12.30, AD 6% Et/Hex) | 499.1/501.1 |
| 277 | Cl, $CH_3$, Cl | 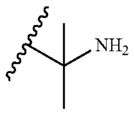 | 3.07 (LC-2) | 498.2/500.2 |
| 278 | Cl, $CF_3$, Cl | 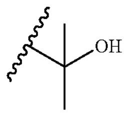 | 3.78 (LC-2) | 553.2/555.2 |
| 279 (Enantiomer 1) | Cl, $CF_3$, Cl | 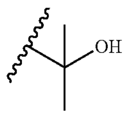 | 3.78 (LC-2) (6.44, AD 6% Et/Hex) | 553.3/555.3 |
| 280 (Enantiomer 2) | Cl, $CF_3$, Cl | 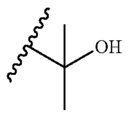 | 3.78 (LC-2) (8.61, AD 6% Et/Hex) | 553.3/555.3 |
| 281 (Diastereomer 1) | Cl, $CF_3$, Cl | 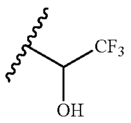 | 3.83 (LC-2) | 593.1/595.1 |

-continued
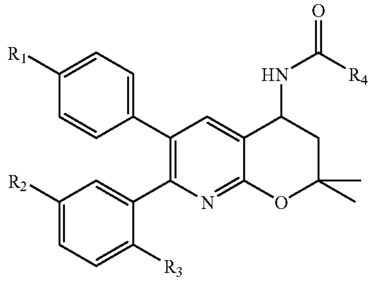
| Example | $R_1$, $R_2$, $R_3$ | $R_4$ | HPLC $R_t$ (min) | MS (M + H/M + 3H) |
|---|---|---|---|---|
| 282 (Enantiomer 1) | Cl, $CF_3$, Cl | 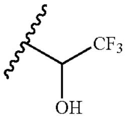 | 3.87 (LC-2) (7.63, AS 6% Et/Hex) | 593.1/595.1 |
| 283 (Enantiomer 2) | Cl, $CF_3$, Cl | 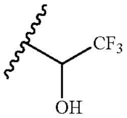 | 3.87 (LC-2) (12.74, AS 6% Et/Hex) | 593.1/595.1 |
| 284 (Diastereomer 2) | Cl, $CF_3$, Cl | 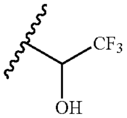 | 3.83 (LC-2) | 593.1/595.1 |
| 285 (Enantiomer 1) | Cl, $CF_3$, Cl | 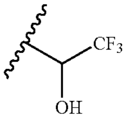 | 3.88 (LC-2) (7.86, AS 6% Et/Hex) | 593.1/595.1 |
| 286 (Enantiomer 2) | Cl, $CF_3$, Cl | 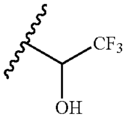 | 3.88 (LC-2) (10.67, AS 6% Et/Hex) | 593.1/595.1 |
| 287 | Cl, $CF_3$, Cl | 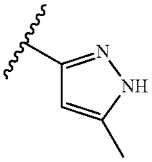 | 2.39 | 575.1/577.1 |
| 288 (Enantiomer 1) | Cl, $CF_3$, Cl | 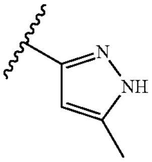 | 2.39 (8.94, AD 10% Et/Hex) | 575.1/577.1 |
| 289 (Enantiomer 2) | Cl, $CF_3$, Cl | 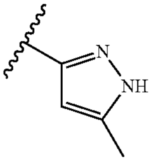 | 2.39 (17.53, AD 10% Et/Hex) | 575.1/577.1 |

-continued

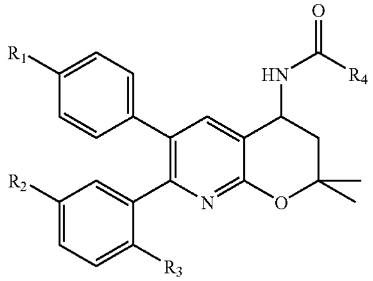

| Example | $R_1$, $R_2$, $R_3$ | $R_4$ | HPLC $R_t$ (min) | MS (M + H/M + 3H) |
|---|---|---|---|---|
| 290 (Diastereomer 1) | Cl, Cl, Br | 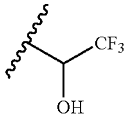 | 3.76 (LC-2) | 603.0/605.0 |
| 291 (Diastereomer 2) | Cl, Cl, Br | 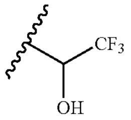 | 3.78 (LC-2) | 603.0/605.0 |
| 292 (Diastereomer 1) | Cl, Cl, CN | 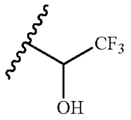 | 3.55 (LC-2) | 550.2/552.2 |
| 293 | Cl, Cl, $CF_3$ | 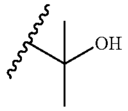 | 3.76 (LC-2) | 553.3/555.3 |

The following examples were prepared utilizing the appropriate amine and carboxylic acid or acid chloride in procedures similar to those described for Example 26 or Example 88.

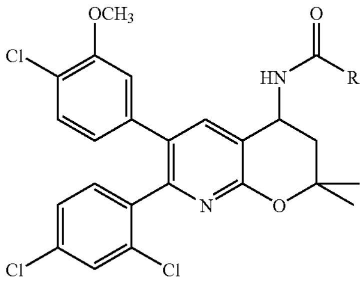

| Example | R | HPLC $R_t$ (min) | MS (M + H/M + 3H) |
|---|---|---|---|
| 294 | 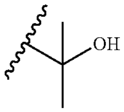 | 3.73 (LC-2) | 549.2/551.2 |

-continued

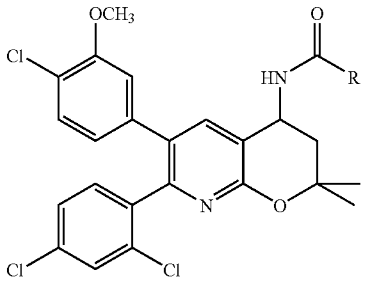

| Example | R | HPLC $R_t$ (min) | MS (M + H/M + 3H) |
|---|---|---|---|
| 295 (Enantiomer 1) | 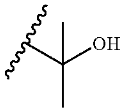 | 3.68 (LC-2) (9.54, AD 7% Et/Hex) | 549.1/551.1 |
| 296 (Enantiomer 2) | 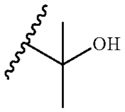 | 3.68 (LC-2) (15.52, AD 7% Et/Hex) | 549.1/551.1 |

-continued

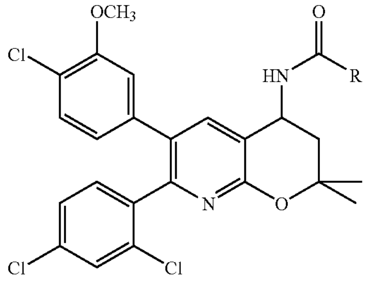

| Example | R | HPLC $R_t$ (min) | MS (M + H/M + 3H) |
|---|---|---|---|
| 297 (Enantiomer 1) | 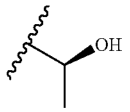 | 3.61 (LC-2) | 535.2/537.2 |
| 298 (Enantiomer 2) | 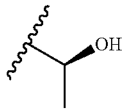 | 3.61 (LC-2) | 535.2/537.2 |
| 299 (Enantiomer 1) | 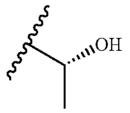 | 3.61 (LC-2) | 535.2/537.2 |
| 300 (Enantiomer 2) | 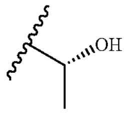 | 3.61 (LC-2) | 535.2/537.2 |
| 301 (Diastereomer 1) | 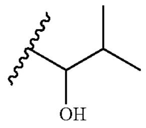 | 3.81 (LC-2) | 563.2/565.2 |
| 302 (Diastereomer 2) | 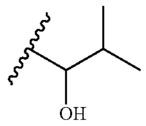 | 3.83 (LC-2) | 563.1/565.2 |
| 303 | 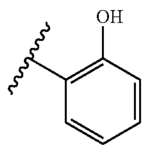 | 4.14 (LC-2) | 583.3/585.2 |
| 304 | 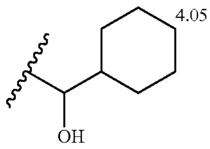 | 4.05 (LC-2) | 603.3/605.3 |

EXAMPLE 305

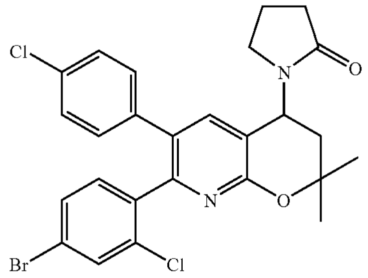

1-[7-(4-Bromo-2-chlorophenyl)-6-(4-chlorophenyl)-2,2-dimethyl-3,4-dihydro-2H-pyrano[2,3-b]pyridin-4-yl]pyrrolidin-2-one Step A: 4-Bromo-N-[7-(4-bromo-2-chlorophenyl)-6-(4-chlorophenyl)-2,2-dimethyl-3,4-dihydro-2H-pyrano[2,3-b]pyridin-4-yl]butanamide. To a mixture of 7-(4-bromo-2-chlorophenyl)-6-(4-chloro-phenyl)-2,2-dimethyl-3,4-dihydro-2H-pyrano[2,3-b]pyridin-4-amine (303 mg, 0.63 mmol) and $NEt_3$ (221 μL, 1.6 mmol) in 10 mL of $CH_2Cl_2$ was added 4-bromobutyryl chloride (110 μL, 0.95 mmol). After stirring at rt for 16 h, the reaction mixture was combined with saturated aq $NaHCO_3$ (20 mL). The aq layer was separated and extracted with $CH_2Cl_2$ (3×20 mL). The organic layers were combined, dried over $MgSO_4$, and concentrated to afford the product.

Step B: 1-[7-(4-Bromo-2-chlorophenyl)-6-(4-chlorophenyl)-2,2-dimethyl-3,4-dihydro-2H-pyrano[2,3-b]pyridin-4-yl]pyrrolidin-2-one. To a solution of the product of Step A (133 mg, 0.21 mmol) in 5.0 mL of THF was added 60% NaH (12.7 mg, 0.32 mmol) at rt. After stirring for 16 h, the reaction mixture was diluted with EtOAc (20 mL) and washed with brine (20 mL). The organic layer was separated, dried over $MgSO_4$ and concentrated. Chromatography on a Biotage 40+S cartridge using 4:1 v:v EtOAc/hexanes as the eluant afforded the product: $^1H$ NMR δ 1.48 (s, 3H), 1.58 (s, 3H), 1.96-2.10 (m, 4H), 2.50-2.54 (m, 2H), 3.13 (m, 1H), 3.30-3.33 (m, 1H), 5.65-5.69 (m, 1H), 6.98 (d, J=8.5, 2H), 7.19-7.42 (m, 6H).

EXAMPLE 306

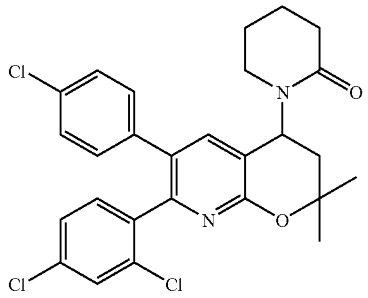

1-[6-(4-Chlorophenyl)-7-(2,4-dichlorophenyl)-2,2-dimethyl-3,4-dihydro-2H-pyrano[2,3-b]pyridin-4-yl]piperidin-2-one This example was prepared using procedures analogous to those described for Example 305 substituting 5-chlorovaleroyl chloride for 4-bromobutyryl chloride and 6-(4-chlorophenyl)-7-(2,4-dichlorophenyl)-2,2-dimethyl-3,4-dihydro-2H-pyrano[2,3-b]pyridin-4-amine for 7-(4-bromo-2-chlorophenyl)-6-(4-chlorophenyl)-2,2-dimethyl-3,4-dihydro-2H-pyrano[2,3-b]pyridin-4-amine, respectively, in Step A. HPLC/MS: 515.2 (M+1), 517.2 (M+3); $R_t$=3.95 min.

The following examples were prepared using procedures analogous to those described for Example 305 using either (2R)-4-bromo-2-hydroxybutanoic acid or (2S)-4-bromo-2-hydroxybutanoic acid (*Tetrahedron Lett.* 1997, 38,4935) for 4-bromobutyryl chloride and using PyBOP as the coupling reagent in Step A. All four enantiomers were separated by silica gel chromatography.

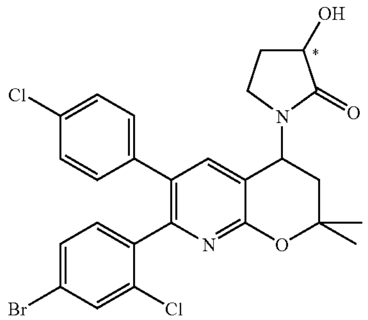

| Example | Stereo-chemistry of 2-hydroxyl | HPLC $R_t$ (min) | MS (M + H/M + 3H) |
|---|---|---|---|
| 307 (Enantiomer 1) | R | 3.60 (LC-2) (18.97, AD 8% Et/Hex) | 561.0/563.0 |
| 308 (Enantiomer 2) | R | 3.62 (LC-2) (24.86, AD 8% Et/Hex) | 561.0/563.0 |
| 309 (Enantiomer 1) | S | 3.68 (LC-2) (20.51, AD 8% Et/Hex) | 561.1/563.2 |
| 310 (Enantiomer 2) | S | 3.70 (LC-2) (18.01, AD 8% Et/Hex) | 561.2/563.2 |

EXAMPLE 311

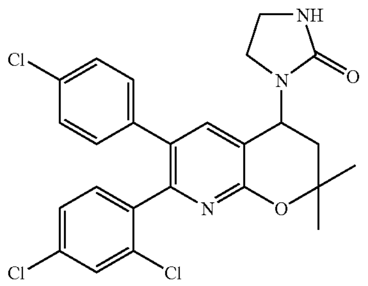

1-[6-(4-Chlorophenyl)-7-(2,4-dichlorophenyl)-2,2-dimethyl-3,4-dihydro-2H-pyrano[2,3-b]pyridin-4-yl]imidazolidin-2-one Step A: tert-Butyl (2-{[6-(4-chlorophenyl)-7-(2,4-dichlorophenyl)-2,2-dimethyl-3,4-dihydro-2H-pyrano[2,3-b]pyridin-4-yl]amino}ethyl)carbamate. To the product of Example 3 (407 mg, 0.94 mmol) in 10 mL of EtOH was added tert-butyl (2-aminoethyl)carbamate (223 μL, 1.41 mmol) and titanium(IV) isopropoxide (1.4 mL, 4.70 mmol). After refluxing for 16 h, the reaction mixture was cooled to rt and $NaBH_4$ (78.2 mg, 2.07 mmol) was added. After stirring at rt for 2 h, $NH_4OH$ (10 mL, ~28% $NH_3$ content) and $Et_2O$ (20 mL) were added sequentially. After stirring for 30 min, the solid was filtered off and washed with copious EtOAc. The filtrate was washed with brine (2×50 mL). The organic layer was separated, dried over $MgSO_4$, and concentrated. Chromatography on a Biotage 40+M cartridge using 11:9 v/v EtOAc/hexanes as the eluant afforded the product.

Step B: N-[6-(4-Chlorophenyl)-7-(2,4-dichlorophenyl)-2,2-dimethyl-3,4-dihydro-2H-pyrano[2,3-b]pyridin-4-yl]ethane-1,2-diamine. A solution of the product of Step A (42.9 mg, 0.07 mmol) in 2.5 mL of 20% TFA in $CH_2Cl_2$ was stirred at rt for 1 h. The reaction mixture was concentrated to give the product which was used without further purification.

Step C: 1-[6-(4-Chlorophenyl)-7-(2,4-dichlorophenyl)-2,2-dimethyl-3,4-dihydro-2H-pyrano[2,3-b]pyridin-4-yl]imidazolidin-2-one. To a solution of 1,1'-carbonyldiimidazole (18.1 mg, 0.11 mmol) in 5.0 mL of $CHCl_3$ was added the product of Step B (0.07 mmol) and $NEt_3$ (51.8 μL, 0.37 mmol) in 5.0 mL of $CHCl_3$. The mixture was allowed to stir at rt for 2 h and then refluxed for 16 h. After cooling to rt, the reaction mixture was diluted with EtOAc (50 mL) and washed with brine (2×50 mL). The organic layer was separated, dried over $MgSO_4$, and concentrated. Chromatography on a Biotage 40+S cartridge using EtOAc as the eluant afforded the title compound: $^1$H NMR δ 1.48 (s, 3H), 1.58 (s, 3H), 2.00-2.09 (m, 2H), 3.18-3.50 (m, 4H), 4.70 (br. s, 1H), 5.44 (m, 1H), 7.00 (d, J=8.5, 2H), 7.18-7.27 (m, 4H), 7.50 (s, 1H).

EXAMPLE 312

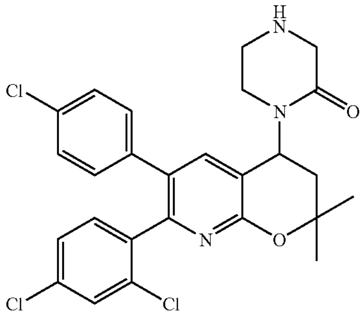

1-[6-(4-Chlorophenyl)-7-(2,4-dichlorophenyl)-2,2-dimethyl-3,4-dihydro-2H-pyrano[2,3-b]pyridin-4-yl]piperazin-2-one Step A: tert-Butyl (2-{(bromoacetyl)[6-(4-chlorophenyl)-7-(2,4-dichlorophenyl)-2,2-dimethyl-3,4-dihydro-2H-pyrano[2,3-b]pyridin-4-yl]amino}ethyl)carbamate. To a solution of the product of Example 311, Step A (90.5 mg, 0.16 mmol) in 5.0 mL of $CH_2Cl_2$ at 0° C. was added $NEt_3$ (54.7 μL, 0.39 mmol) and bromoacetyl bromide (15.0 μL, 0.17 mmol). The mixture was allowed to stir at rt for 1 h and then concentrated. Chromatography on a Biotage 40+S cartridge using 7:13 v:v EtOAc/hexanes as the eluant afforded the product.

Step B: tert-Butyl 4-[6-(4-chlorophenyl)-7-(2,4-dichlorophenyl)-2,2-dimethyl-3,4-dihydro-2H-pyrano[2,3-b]pyridindin-4-yl]-3-oxopiperazine-1-carboxylate. To a solution of the product of Step A (42 mg, 0.06 mmol) in 5.0 mL of THF at rt was added 60% NaH (4.8 mg, 0.12 mmol). The mixture was allowed to stir at rt for 30 min and then diluted with EtOAc (50 mL). The resulting mixture was washed with brine (50 mL). The organic layer was separated, dried over $MgSO_4$, and concentrated. Chromatography on a Biotage 40+S cartridge using 9:11 v:v EtOAc/hexanes as the eluant afforded the product.

Step C: 1-[6-(4-Chlorophenyl)-7-(2,4-dichlorophenyl)-2,2-dimethyl-3,4-dihydro-2H-pyrano[2,3-b]pyridin-4-yl]piperazin-2-one. A solution of the product of Step B (31 mg, 0.05 mmol) in 5.0 mL of 20% TFA in $CH_2Cl_2$ was stirred at rt for 30 min and then concentrated. HPLC purification afforded the title compound: $^1$H NMR δ 1.47 (s, 3H), 1.59 (s, 3H), 2.10-2.23 (m, 2H), 3.30-3.56 (m, 4H), 3.94-4.07 (m, 2H), 7.10 (d, J=8.5, 2H), 7.23-7.41 (m, 4H), 7.69 (s, 1H).

EXAMPLE 313

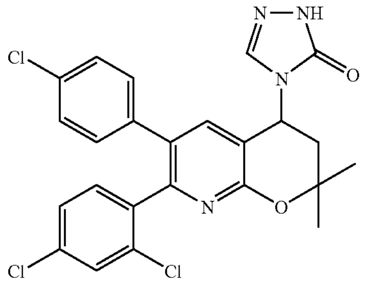

4-[6-(4-Chlorophenyl)-7-(2,4-dichlorophenyl)-2,2-dimethyl-3,4-dihydro-2H-pyrano[2,3-b]pyridin-4-yl] 2,4-dihydro-3H-1,2,4-triazol-3-one Step A: Phenyl [6-(4-chlorophenyl)-7-(2,4-dichlorophenyl)-2,2-dimethyl-3,4-dihydro-2H-pyrano[2,3-b]pyridin-4-yl]carbamate. To a solution of the product of Example 24 (176 mg, 0.41 mmol) and $NEt_3$ (68 μL, 0.49 mmol) in 10 mL of $CH_2Cl_2$ at 0° C. was added phenyl chloroformate (61 μL, 0.49 mmol). After stirring at rt for 1 h, the reaction mixture was concentrated. Chromatography on a Biotage 40+S cartridges using 1:4 v/v EtOAc/hexanes as the eluant afforded the product: $^1$H NMR δ 1.47 (s, 3H), 1.58 (s, 3H), 1.94 (t, J=12.0, 1H), 2.39 (dd, J=5.7, 13.4, 1H), 5.21-5.26 (m, 2H), 7.04 (8.4, 2H), 7.15-7.40 (m, 9H), 7.79 (s, 1H).

Step B: N-[6-(4-Chlorophenyl)-7-(2,4-dichlorophenyl)-2,2-dimethyl-3,4-dihydro-2H-pyrano[2,3-b]pyridin-4-yl]hydrazinecarboxamide. A solution of the product of Step A (77 mg, 0.14 mmol) and hydrazine (8.7 μL, 0.28 mmol) in 5.0 mL of EtOH was refluxed for 3 h. The reaction mixture was then concentrated to give the product, which was used directly in the next step without further purification.

Step C: 4-[6-(4-Chlorophenyl)-7-(2,4-dichlorophenyl)-2,2-dimethyl-3,4-dihydro-2H-pyrano[2,3-b]pyridin-4-yl]2,4-dihydro-3H-1,2,4-triazol-3-one. A mixture of the product of Step B (0.14 mmol) and formamidine acetate (72 mg, 0.70 mmol) in 5.0 mL of DMF was allowed to stir at rt for 2 h. AcOH (40 μL, 0.70 mmol) was then added. The resulting mixture was stirred at 80° C. for 16 h. After cooling to rt, the reaction mixture was diluted with EtOAc (20 mL) and washed with brine (3×20 mL). The organic phase was separated, dried over $MgSO_4$, and concentrated. Chromatography on a Biotage 40+S cartridges using 1:99 v/v $CH_3OH/CH_2Cl_2$ as the eluant afforded the title compound: $^1$H NMR δ 1.53 (s, 3H), 1.62 (s, 3H), 2.18 (t, J=12.7, 1H), 2.36 (dd, J=6.3, 13.1, 1H), 5.56 (m, 1H), 6.95 (d, J=8.3, 2H), 7.16-7.38 (m, 7H), 10.1 (br. s, 1H).

EXAMPLE 314 tert-Butyl [7-(4-bromo-2-chlorophenyl)-6-(4-chlorophenyl)-2,2-dimethyl-3,4-dihydro-2H-pyrano[2,3-b]pyridin-4-yl]carbamate To a solution of 7-(4-bromo-2-chlorophenyl)-6-(4-chlorophenyl)-2,2-dimethyl-3,4-dihydro-2H-pyrano[2,3-b]pyridin-4-amine (1.4 g, 2.93 mmol) and $NEt_3$ (816 μL, 5.86 mmol) in 10 mL of $CH_2Cl_2$ was added di-tert-butyl dicarbonate (958 mg, 4.39 mmol). After stirring at rt for 16 h, the reaction mixture was concentrated. Chromatography on a Biotage 40+M cartridge using 1:1 v/v EtOAc/hexanes as the eluant afforded the title compound as a white solid: $^1$H NMR δ 1.40 (s, 3H), 1.44 (s, 9H), 1.48 (s, 3H), 1.75 (t, J=12.4, 1H), 2.22 (dd, J=5.8, 13.2, 1H), 5.06 (m, 2H), 6.98 (d, J=8.5, 2H), 7.13-7.34 (m, 5H), 7.68 (s, 1H).

EXAMPLE 315

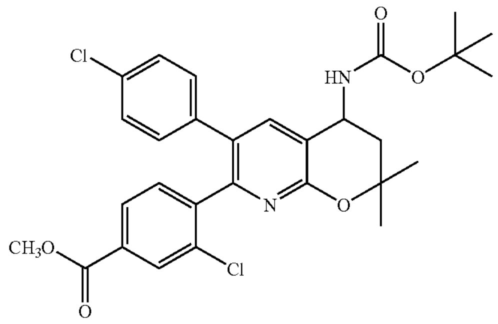

Methyl 3-chloro-4-[6-(4-chlorophenyl)-4-({[(1,1-dimethylethyl)oxy]carbonyl}amino)-2,2-dimethyl-3,4-dihydro-2H-pyrano[2,3-b]pyridin-7-yl]benzoate A solution of Example 314 (840 mg, 1.45 mmol), palladium(II) acetate (16.3 mg, 0.07 mmol), dppf (81 mg, 0.15 mmol), and $NEt_3$ (405 μL, 2.90 mmol) in 20 mL of $CH_3OH$ was stirred at 100° C. under 50 psi of CO for 24 h. After cooling to rt, the reaction mixture was filtered. The filtrate was concentrated and chromatography on a Biotage 25+M cartridge using 1:1 v/v EtOAc/hexanes as the eluant afforded the title compound: $^1$H NMR δ 1.46 (s, 3H), 1.49 (s, 9H), 1.54 (s, 3H), 1.82 (m, 1H), 2.29 (dd, J=6.2, 13.3, 1H), 3.90 (s, 3H), 4.89 (br. s, 1H), 5.12 (m, 1H), 7.01 (d, J=8.5, 2H), 7.16 (d, J=8.4, 2H), 7.40 (m, 1H), 7.73-7.92 (m, 3H).

EXAMPLE 316

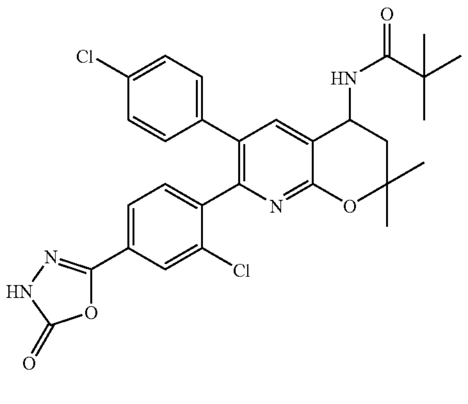

N-[7-[2-Chloro-4-(5-oxo-4,5-dihydro-1,3,4-oxadiazol-2-yl)phenyl]-6-(4-chlorophenyl)-2,2-dimethyl-3,4-dihydro-2H-pyrano[2,3-b]pyridin-4-yl]-2,2-dimethylpropanamide Step A: Methyl 4-[4-amino-6-(4-chlorophenyl)-2,2-dimethyl-3,4-dihydro-2H-pyrano[2,3-b]pyridin-7-yl]-3-chlorobenzoate. To a solution of Example 315 (200 mg, 0.36 mmol) in 5.0 mL of $CH_2Cl_2$ was added 500 μL of TFA. After stirring at rt for 16 h, the reaction mixture was concentrated. The amine TFA salt was taken onto next step without further purification.

Step B: Methyl 3-chloro-4-[6-(4-chlorophenyl)-4-[(2,2-dimethylpropanoyl)amino]-2,2-dimethyl-3,4-dihydro-2H-pyrano[2,3-b]pyridin-7-yl]benzoate. To a solution of the product of Step A (100 mg, 0.22 mmol) in 5.0 mL of $CH_2Cl_2$ was added pivaloyl chloride (32 μL, 0.26 mmol) and $NEt_3$ (46 μL, 0.33 mmol). After stirring at rt for 16 h, the reaction mixture was concentrated. Chromatography on a Biotage 25+M cartridge using 1:1 v/v EtOAc/hexanes as the eluant afforded the product as a white solid.

Step C: N-[7-[2-Chloro-4-(hydrazinocarbonyl)phenyl]-6-(4-chlorophenyl)-2,2-dimethyl-3,4-dihydro-2H-pyrano[2,3-b]pyridin-4-yl]-2,2-dimethylpropanamide. A solution of the product of Step B (22 mmol) and 2.0 mL of hydrazine hydrate in 10 mL of $CH_3OH$ was refluxed for 10 h. After cooling to rt, the reaction mixture was concentrated to give the product, which was taken into the next step without further purification.

Step D: N-[7-[2-Chloro-4-(5-oxo-4,5-dihydro-1,3,4-oxadiazol-2-yl)phenyl]-6-(4-chlorophenyl)-2,2-dimethyl-3,4-dihydro-2H-pyrano[2,3-b]pyridin-4-yl]-2,2-dimethylpropanamide. To a solution of the product of Step C (22 mmol) in 10 mL of $CH_2Cl_2$ at −78° C. was added 300 μL of phosgene (20% in toluene). After stirring at −78° C. for 15 min and at 0° C. for 30 min, the reaction mixture was concentrated. Chromatography on a Biotage 40+S cartridge using 1:1 v/v EtOAc/hexanes as the eluant afforded the title compound: $^1H$ NMR δ 1.27 (s, 9H), 1.48 (s, 3H), 1.56 (s, 3H), 1.86 (t, J=12.2, 1H), 2.27 (m, 1H), 5.50 (m, 1H), 5.87 (m, 1H), 6.99 (d, J=8.0, 2H), 7.17 (d, J=8.0, 2H), 7.39 (m, 1H), 7.58-7.72 (m, 3H), 9.87 (br. s, 1H).

EXAMPLE 317

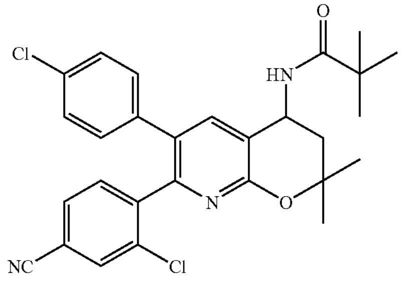

N-[7-(2-Chloro-4-cyanophenyl)-6-(4-chlorophenyl)-2,2-dimethyl-3,4-dihydro-2H-pyrano[2,3-b]pyridin-4-yl]-2,2-dimethylpropanamide Step A: N-[7-(4-Bromo-2-chlorophenyl)-6-(4-chlorophenyl)-2,2-dimethyl-3,4-dihydro-2H-pyrano[2,3-b]pyridin-4-yl]-2,2-dimethylpropanamide. To a solution of the 7-(4-bromo-2-chlorophenyl)-6-(4-chlorophenyl)-2,2-dimethyl-3,4-dihydro-2H-pyrano[2,3-b]pyridin-4-amine (536.2 mg, 1.12 mmol) in 10 mL of $CH_2Cl_2$ at 0° C. was added pivaloyl chloride (166 μL, 1.34 mmol) and $NEt_3$ (313 μL, 2.24 mmol). After stirring at rt for 1 h, the reaction mixture was concentrated. Chromatography on a Biotage 40+M cartridge using 1:3 v/v EtOAc/hexanes as the eluant afforded the product: $^1H$ NMR δ 1.26 (s, 9H), 1.47 (s, 3H), 1.55 (s, 3H), 1.82 (t, J=12.3, 1H), 2.26 (dd, J=6.2, 13.3, 1H), 5.48 (m, 1H), 5.81 (br. s, 1H), 6.97 (d, J=8.5, 2H), 7.16-7.20 (m, 3H), 7.33-7.42 (m, 2H), 7.55 (s, 1H).

Step B: N-[7-(2-Chloro-4-cyanophenyl)-6-(4-chlorophenyl)-2,2-dimethyl-3,4-dihydro-2H-pyrano[2,3-b]pyridin-4-yl]-2,2-dimethylpropanamide. To a suspension of the product of Step A (141 mg, 0.25 mmol), $Zn(CN)_2$ (29.4 mg, 0.25 mmol), tris(dibenzylideneacetone)dipalladium(0) chloroform adduct (5.2 mg, 0.005 mmol), and dppf (6.9 mg, 0.01 mmol) in 5.0 mL of DMF was added one drop of $H_2O$. The solution was degassed and stirred at 120° C. for 16 h, the reaction mixture was cooled to rt and diluted with EtOAc (20 mL). The solid was filtered off and washed with EtOAc. The filtrate was concentrated and chromatography on a Biotage 40+M cartridge using 2:3 v/v EtOAc/hexanes as the eluant afforded the title compound: $^1H$ NMR δ 1.27 (s, 9H), 1.48 (s, 3H), 1.56 (s, 3H), 1.84 (m, 1H), 2.26 (m, 1H), 5.50 (m, 1H), 5.82 (br. s, 1H), 6.95 (d, J=8.2, 2H), 7.19 (d, J=8.3, 2H), 7.41-7.58 (m, 4H).

EXAMPLE 318

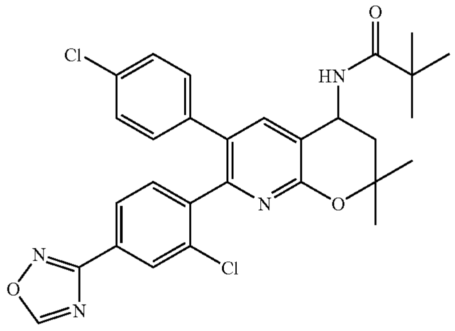

N-[7-[2-Chloro-4-(1,2,4-oxadiazol-3-yl)phenyl]-6-(4-chlorophenyl)-2,2-dimethyl-3,4-dihydro-2H-pyrano[2,3-b]pyridin-4-yl]-2,2-dimethylpropanamide Step A: N-[7-{2-Chloro-4-[(hydroxyamino)(imino)methyl]phenyl}-6-(4-chlorophenyl)-2,2-dimethyl-3,4-dihydro-2H-pyrano[2,3-b]pyridin-4-yl]-2,2-dimethylpropanamide. A solution of Example 317 (120 mg, 0.24 mmol), hydroxylamine hydrochloride (65.6 mg, 0.94 mmol), and $NaHCO_3$ (119 mg, 1.42 mmol) in 10 mL of EtOH was refluxed for 16 h. The reaction mixture was partitioned between brine (50 mL) and $CH_2Cl_2$ (50 mL). The aq layer was separated and extracted with $CH_2Cl_2$ (2×50 mL). The organic layers were combined, dried over $MgSO_4$, and concentrated to give the product, which was taken into the next step without further purification.

Step B: N-[7-[2-Chloro-4-(1,2,4-oxadiazol-3-yl)phenyl]-6-(4-chlorophenyl)-2,2-dimethyl-3,4-dihydro-2H-pyrano[2,3-b]pyridin-4-yl]-2,2-dimethylpropanamide. To a suspension of the product of Step A (61 mg, 0.11 mmol) in 5.0 mL of triethyl orthoformate was added one drop of $BF_3.Et_2O$. After stirring at 110° C. for 1 h, the reaction mixture was diluted with EtOAc (20 mL) and washed with saturated aq $NaHCO_3$ (2×50 mL) and brine (50 mL). The organic layer was separated, dried over $MgSO_4$, and concentrated. Chromatography on a Biotage 40+S cartridge using 7:13 v/v EtOAc/hexanes as the eluant afforded the title compound: $^1H$ NMR δ 1.27 (s, 9H), 1.48 (s, 3H), 1.56 (s, 3H), 1.84 (t, J=11.4, 1H), 2.27 (dd, J=6.2, 13.0, 1H), 5.50 (m, 1H), 5.84 (br. s, 1H), 7.01 (d, J=8.3, 2H), 7.16 (d, J=8.2, 2H), 7.45 (m, 1H), 7.58 (s, 1H), 7.96-8.04 (m, 2H), 8.77 (s, 1H).

EXAMPLE 319

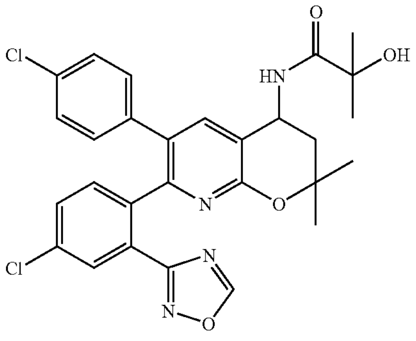

N-[7-[4-Chloro-2-(1,2,4-oxadiazol-3-yl)phenyl]-6-(4-chlorophenyl)-2,2-dimethyl-3,4-dihydro-2H-pyrano[2,3-b]pyridin-4-yl]-2-hydroxy-2-methylpropanamide This example was prepared using procedures analogous to those described for Example 318 substituting Example 237 for N-[7-(2-chloro-4-cyanophenyl)-6-(4-chlorophenyl)-2,2-dimethyl-3,4-dihydro-2H-pyrano[2,3-b]pyridin-4-yl]-2,2-dimethylpropanamide in Step A. (LC-2) HPLC/MS: 553.1 (M+1), 555.1 (M+3); $R_t$=3.45 min.

EXAMPLE 320

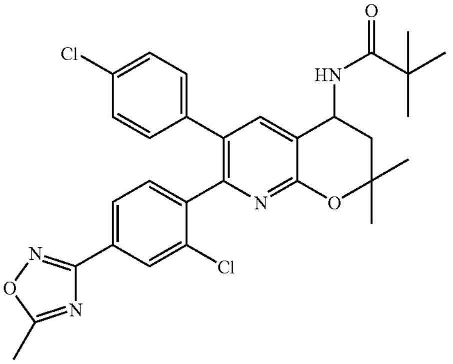

N-[7-[2-Chloro-4-(5-methyl-1,2,4-oxadiazol-3-yl)phenyl]-6-(4-chlorophenyl)-2,2-dimethyl-3,4-dihydro-2H-pyrano[2,3-b]pyridin-4-yl]-2,2-dimethylpropanamide This example was prepared using procedures analogous to those described for Example 318 substituting triethyl orthoacetate for triethyl orthoformate in Step B: $^1H$ NMR δ 1.27 (s, 9H), 1.51 (s, 3H), 1.59 (s, 3H), 2.82 (m, 1H), 2.28 (m, 1H), 2.68 (s, 3H), 5.50 (m, 1H), 5.83 (br. s, 1H), 7.02 (d, J=8.5, 2H), 7.18 (d, J=8.4, 2H), 7.44 (m, 1H), 7.60 (s, 1H), 7.93 (m, 1H), 8.00 (s, 1H).

EXAMPLES 321, 322, 323, AND 324

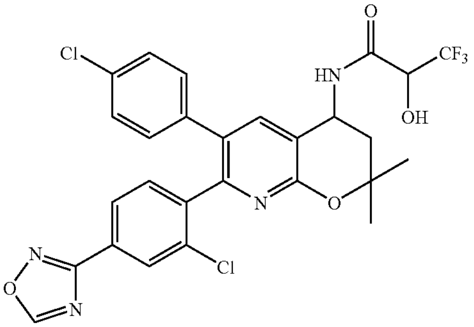

(2R/S)-N-[(4R/S)-7-[2-Chloro-4-(1,2,4-oxadiazol-3-yl)phenyl]-6-(4-chlorophenyl)-2,2-dimethyl-3,4-dihydro-2H-pyrano[2,3-b]pyridin-4-yl]-3,3,3-trifluoro-2-hydroxypropanamide Step A: tert-Butyl [7-(2-chloro-4-(1,2,4-oxadiazol-3-yl)phenyl)-6-(4-chlorophenyl)-2,2-dimethyl-3,4-dihydro-2H-pyrano[2,3-b]pyridin-4-yl]carbamate. The product was prepared using procedures analogous to those described for Example 318 substituting tert-butyl [7-(2-chloro-4-cyanophenyl)-6-(4-chlorophenyl)-2,2-dimethyl-2H-pyrazo[2,3-b]pyridine-4-yl]carbamate for N-[7-(2-chloro-4-cyanophenyl)-6-(4-chlorophenyl)-2,2-dimethyl-2H-pyrazo[2,3-b]pyridine-4-yl]-2,2-dimethylpropan-amide in Step A: $^1H$ NMR δ 1.51 (s, 3H), 1.58 (s, 3H), 1.91 (m, 1H), 2.31 (m, 1H), 4.59 (m, 1H), 4.61 (br. s, 1H), 5.56 (m, 1H), 6.65 (m, 1H), 7.02 (d, J=8.4, 2H), 7.18 (d, J=8.5, 2H), 7.46 (m, 1H), 7.61 (s, 1H), 8.0 (m, 1H), 8.05 (s, 1H), 8.80 (s, 1H).

Step B: 7-(2-Chloro-4-(1,2,4-oxadiazol-3-yl)phenyl)-6-(4-chlorophenyl)-2,2-dimethyl-3,4-dihydro-2H-pyrano[2,3-b]pyridine-4-amine. To a solution of the product of Step A (130 mg, 0.23 mmol) in 5.0 mL of $CH_2Cl_2$ was added TFA (200 μL, 2.60 mmol). After stirring at rt for 16 h, the mixture was concentrated to give the title compound, which was taken into the next step without further purification.

Step C: N-[7-[2-Chloro-4-(1,2,4-oxadiazol-3-yl)phenyl]-6-(4-chlorophenyl)-2,2-dimethyl-3,4-dihydro-2H-pyrano[2,3-b]pyridin-4-yl]-3,3,3-trifluoro-2-hydroxypropanamide. To a solution of the product of Step B (107 mg, 0.23 mmol), 3,3,3-trifluoro-2-hydroxypropionic acid (39 mg, 0.27 mmol), and $NEt_3$ (63 μL, 0.45 mmol) in 10 mL of $CH_2Cl_2$ was added PyBOP (140 mg, 0.27 mmol). After stirring at rt for 16 h, the mixture was concentrated. Chromatography on a Biotage 25+M cartridge using 1:1 v/v EtOAc/hexanes as the eluant afforded two enantiomeric mixtures, which were subsequently resolved (the one having higher $R_f$ value on TLC was resolved by AD using 13% EtOH/hex, and the other by AD using 20% IPA/hept) to afford the title compounds.

EXAMPLE 325

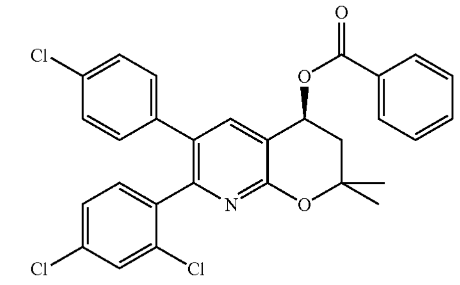

(4S)-6-(4-Chlorophenyl)-7-(2,4-dichlorophenyl)-2,2-dimethyl-3,4-dihydro-2H-pyrano[2,3-b]pyridin-4-yl benzoate Step A: (4S)-6-(4-Chlorophenyl)-7-(2,4-dichlorophenyl)-2,2-dimethyl-3,4-dihydro-2H-pyrano[2,3-b]pyridin-4-ol. A solution of Example 1 (14.1 g, 32.5 mmol) and the (S,S) catalyst described by Noyori in *Angew. Chem. Int. Ed. Engl.* 1997, 36, 285 (998 mg, 1.62 mmol) in IPA (20 mL) and $CH_2Cl_2$ (10 mL) was stirred at rt. After 16 h, the reaction mixture was concentrated to give the product, which was taken into the next step without further purification: $^1$H NMR δ 1.43 (s, 3H), 1.56 (s, 3H), 1.96 (dd, J=9.7, 13.4, 1H), 2.06 (d, J=7.3, 1H), 2.28 (dd, J=6.2, 13.5, 1H), 5.00 (m, 1H), 7.03 (d, J=8.5, 2H), 7.18-7.26 (m, 5H), 7.90 (s, 1H).

Step B: (4S)-6-(4-Chlorophenyl)-7-(2,4-dichlorophenyl)-2,2-dimethyl-3,4-dihydro-2H-pyrano[2,3-b]pyridin-4-yl benzoate. To a solution of the product of Step A (21.6 mg, 0.05 mmol), $NEt_3$ (21 μL, 0.15 mmol), and catalytic amount of DMAP in 10 mL of $CH_2Cl_2$ at rt was added benzoyl chloride (11.5 μL, 0.10 mmol). After stirring for 2 h, the reaction was quenched by adding saturated aq $NaHCO_3$ (5 mL) and the resulting mixture was stirred at rt for 30 min. The reaction mixture was partitioned between $CH_2Cl_2$ (50 mL) and saturated aq $NaHCO_3$ (50 mL). The aq layer was separated and extracted with $CH_2Cl_2$ (3×10 mL). The organic layers were combined, dried over $MgSO_4$, and concentrated. Chromatography on Biotage 40+S cartridges using 3:17 v/v EtOAc/hexanes as the eluant afforded the title compound: $^1$H NMR δ 1.57 (s, 3H), 1.65 (s, 3H), 2.24 (dd, J=6.7, 14.2, 1H), 2.46 (dd, J=5.9, 14.3, 1H), 6.40 (t, J=6.2, 1H), 7.00 (d, J=8.4, 2H), 7.16-7.28 (m, 5H), 7.45-7.60 (m, 3H), 7.77 (s, 1H), 8.07 (d, J=7.5, 2H).

EXAMPLE 326

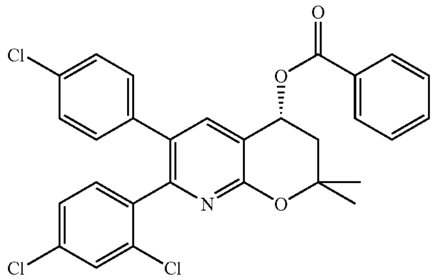

(4R)-6-(4-Chlorophenyl)-7-(2,4-dichlorophenyl)-2,2-dimethyl-3,4-dihydro-2H-pyrano[2,3-b]pyridin-4-yl benzoate This example was prepared using procedures analogous to those described for Example 325 substituting the (R,R) catalyst described by Noyori in *Angew. Chem. Int. Ed. Engl.* 1997, 36, 285 in Step A: $^1$H NMR δ 1.57 (s, 3H), 1.65 (s, 3H), 2.24 (dd, J=6.7, 14.2, 1H), 2.46 (dd, J=5.9, 14.3, 1H), 6.40 (t, J=6.2, 1H), 7.00 (d, J=8.4, 2H), 7.16-7.28 (m, 5H), 7.45-7.60 (m, 3H), 7.77 (s, 1H), 8.07 (d, J=7.5, 2H).

EXAMPLE 327

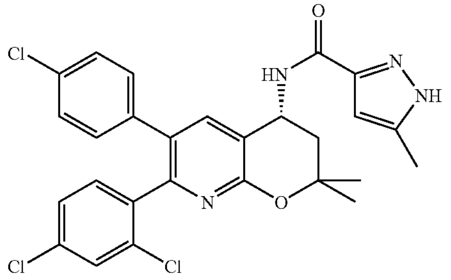

N-[(4R)-6-(4-Chlorophenyl)-7-(2,4-dichlorophenyl)-2,2-dimethyl-3,4-dihydro-2H-pyrano[2,3-b]pyridin-4-yl]-5-methyl-1H-pyrazole-3-carboxamide Step A: (4R)-4-Azido-6-(4-chlorophenyl)-7-(2,4-dichlorophenyl)-2,2-dimethyl-3,4-dihydro-2H-pyrano[2,3-b]pyridine. To a mixture of the product of Example 325, Step A (9.8 g, 22.5 mmol), $Zn(N_3)_2$/bis-pyridine complex (Synthesis 1990, 130) (13.9 g, 45.1 mmol), triphenylphosphine (11.8 g, 45.1 mmol), and imidazole (6.1 g, 90 mmol) in 100 mL of $CH_2Cl_2$ was added diisopropyl azodicarboxylate (8.8 mL, 45.1 mmol) dropwise at rt. The mixture was allowed to stir at rt for 16 h. The supernatant was separated and washed with diluted HCl (1.0 N, 3×50 mL), saturated aq $NaHCO_3$ (3×50 mL) and brine (50 mL). The organic layer was separated, dried over $MgSO_4$, and concentrated. Chromatography on Biotage 40+M cartridges using 3:17 v/v EtOAc/hexanes as the eluant afforded the product: $^1$H NMR δ 1.47 (s, 3H), 1.59 (s, 3H), 2.11 (dd, J=9.6, 13.5, 1H), 2.32 (dd, J=6.1, 13.6, 1H), 4.75 (dd, J=6.0, 9.6, 1H), 7.04 (d, J=8.5, 2H), 7.19-7.28 (m, 5H), 7.78 (s, 1H).

Step B: (4R)-6-(4-Chlorophenyl)-7-(2,4-dichlorophenyl)-2,2-dimethyl-3,4-dihydro-2H-pyrano-[2,3-b]pyridin-4-amine. To a solution of the product of Step A (9.5 g, 20.7 mmol) in 50 mL of THF was added 2.5 mL of $H_2O$ and 31.0 mL of trimethylphosphine in THF (1.0 M, 31.0 mmol). After stirring at rt for 3 h, the solvent was evaporated. Chromatography on a Biotage 40+M cartridge using 1:19 v/v $CH_3OH$/$CH_2Cl_2$ as the eluant afforded the product: $^1$H NMR δ 1.42 (s, 3H), 1.54 (s, 3H), 1.78 (t, J=12.5, 1H), 2.18 (dd, J=5.9, 13.4, 1H), 4.16 (dd, J=6.0, 11.7, 1H), 7.04 (d, J=8.5, 2H), 7.17-7.26 (m, 5H), 7.93 (s, 1H).

Step C: N-[(4R)-6-(4-Chlorophenyl)-7-(2,4-dichlorophenyl)-2,2-dimethyl-3,4-dihydro-2H-pyrano[2,3-b]pyridin-4-yl]-5-methyl-1H-pyrazole-3-carboxamide. A mixture of the product of Step B (300 mg, 0.69 mmol), 5-methylpyrazole-3-carboxylic acid (105 mg, 0.83 mmol), PyBOP (540 mg, 1.04 mmol), and $NEt_3$ (0.19 mL, 1.38 mmol) in 20 mL of $CH_2Cl_2$ was stirred at rt. After 16 h, the reaction mixture was diluted with $Et_2O$ (50 mL), washed with saturated aq $NaHCO_3$ (3×50 mL) and brine (3×50 mL). The organic layer was separated, dried over $MgSO_4$ and concentrated. Chromatography on a Biotage 40+S cartridge using 1:1 v/v EtOAc/Hexanes as the eluant afforded the title compound: $^1$H NMR δ 1.44 (s, 3H), 1.51 (s, 3H), 1.94 (t, J=12.5, 1H), 2.26-2.30 (m, 4H), 5.62 (m, 1H), 6.58 (s, 1H), 6.96 (d, J=8.5, 2H), 7.12-7.29 (m, 5H), 7.69 (s, 1H).

The following examples were prepared using procedures analogous to those described for Example 327 substituting the appropriate amine for (4R)-6-(4-chlorophenyl)-7-(2,4-dichlorophenyl)-2,2-dimethyl-3,4-dihydro-2H-pyrano-[2,3-b]pyridin-4-amine and the appropriate carboxylic acid for 5-methylpyrazole-3-carboxylic acid, respectively, in Step C.

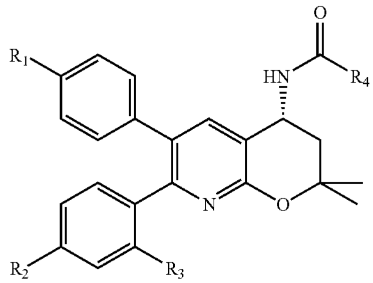

| Example | $R_1$, $R_2$, $R_3$ | $R_4$ | HPLC $R_t$ (min) | MS (M + H/M + 3H) |
|---|---|---|---|---|
| 328 | Cl, Cl, Cl | 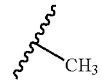 | 3.66 (LC-2) | 475.1/477.1 |
| 329 | Cl, Cl, Cl | 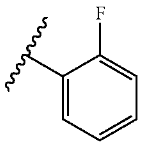 | 2.60 | 555.0/557.0 |
| 330 | Cl, Cl, Cl | 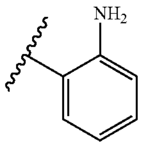 | 2.49 | 552.8/554.8 |
| 331 | Cl, Cl, Cl | 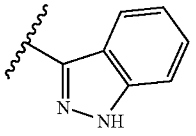 | 2.63 | 577.0/579.0 |
| 332 | Cl, Cl, Cl | 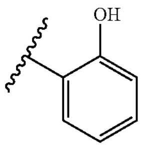 | 2.69 | 553.0/555.0 |

-continued
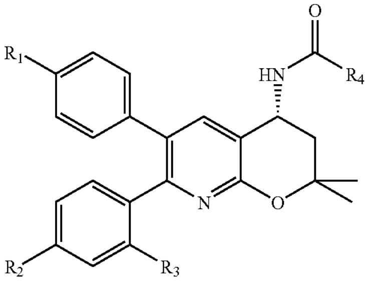
| Example | $R_1$, $R_2$, $R_3$ | $R_4$ | HPLC $R_t$ (min) | MS (M + H/M + 3H) |
|---|---|---|---|---|
| 333 | Cl, Cl, Cl | 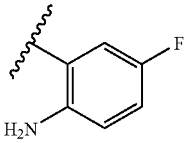 | 2.53 | 570.0/572.1 |
| 334 | Cl, Cl, Cl | 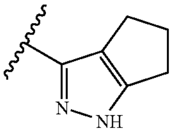 | 2.46 | 567.1/569.1 |
| 335 | Cl, Cl, Cl | 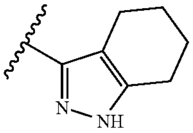 | 2.57 | 581.1/583.1 |
| 336 | Cl, Cl, Cl | 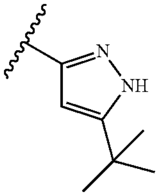 | 2.59 | 583.1/585.1 |
| 337 | Cl, Cl, Cl | 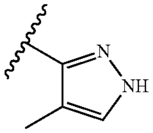 | 2.43 | 541.0/543.0 |
| 338 | Cl, Cl, Cl | 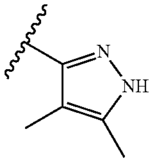 | 2.49 | 555.1/557.1 |
| 339 | Cl, Cl, Cl | 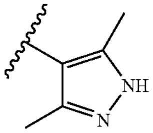 | 3.63 | 557.1/559.1 |
| 340 | Cl, Cl, Cl | 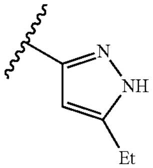 | 2.45 | 555.0/557.1 |

-continued
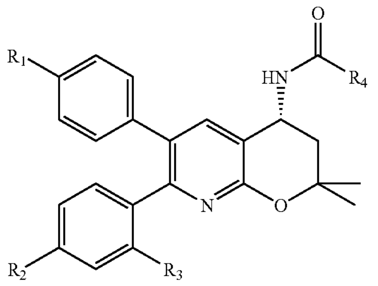
| Example | $R_1$, $R_2$, $R_3$ | $R_4$ | HPLC $R_t$ (min) | MS (M + H/M + 3H) |
|---|---|---|---|---|
| 341 | Cl, Cl, Cl | 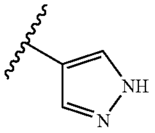 | 2.23 | 527.0/529.0 |
| 342 | Cl, Cl, Cl | 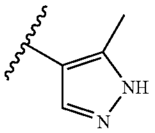 | 2.29 | 541.0/543.0 |
| 343 | Cl, Cl, Cl | 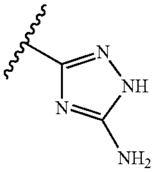 | 3.27 (LC-2) | 543.0/545.0 |
| 344 | Cl, Cl, Cl | 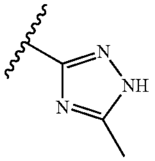 | 3.54 (LC-2) | 542.1/544.1 |
| 345 | Cl, Cl, Cl | 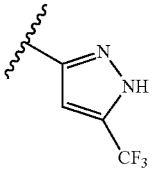 | 4.01 (LC-2) | 595.0/597.0 |
| 346 | Cl, Cl, Cl | 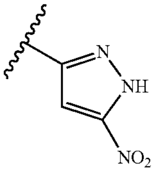 | 3.74 (LC-2) | 570.1/572.1 |
| 347 | Cl, Cl, Cl | 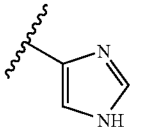 | 3.14 (LC-2) | 525.0/527.0 |

-continued
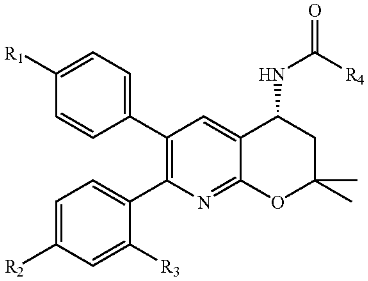
| Example | $R_1$, $R_2$, $R_3$ | $R_4$ | HPLC $R_t$ (min) | MS (M + H/M + 3H) |
|---|---|---|---|---|
| 348 | Cl, Cl, Cl | 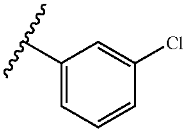 | 2.74 | 570.9/572.9 |
| 349 | Cl, Cl, Cl | 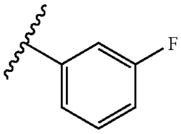 | 2.64 | 555.0/557.0 |
| 350 | Cl, Cl, Cl | 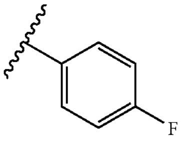 | 2.62 | 555.0/557.0 |
| 351 | Cl, Cl, Cl | 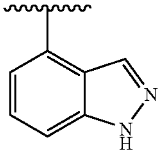 | 3.78 (LC-2) | 579.1/581.0 |
| 352 | Cl, Cl, Cl | 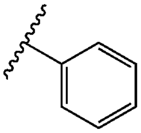 | 2.59 | 537.0/539.0 |
| 353 | Cl, Cl, Cl | 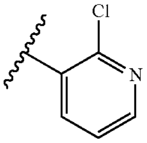 | 2.46 | 572.0/574.0 |
| 354 | Cl, Cl, Cl | 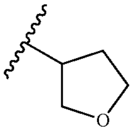 | 2.33 | 531.0/533.0 |
| 355 | Cl, Cl, Cl | 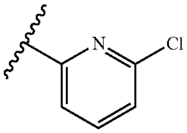 | 2.71 | 572.0/574.0 |

-continued
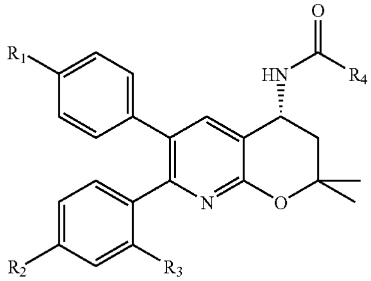
| Example | $R_1$, $R_2$, $R_3$ | $R_4$ | HPLC $R_t$ (min) | MS (M + H/M + 3H) |
|---|---|---|---|---|
| 356 | Cl, Cl, Cl | 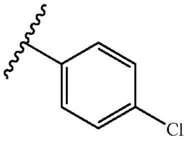 | 2.72 | 570.9/572.9 |
| 357 | Cl, Cl, Cl | 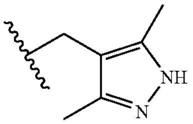 | 3.00 (LC-2) | 571.1/573.1 |
| 358 | Cl, Cl, Cl | 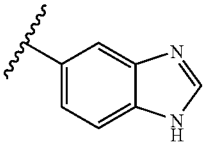 | 3.16 (LC-2) | 579.1/581.0 |
| 359 | $CF_3$, Br, Cl | 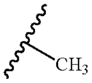 | 2.38 | 553.0/555.0 |
| 360 | $CF_3$, Br, Cl | 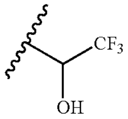 | 2.45, 2 isomers 8.93, 17.06, AD 5% Et/hex | 636.9/638.9 |
| 361 | $OCF_3$, Cl, Cl | 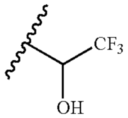 | 3.89 (LC-2), 2 isomers isolated | 609.1/611.1 |
| 362 | $OCF_3$, Cl, Cl | 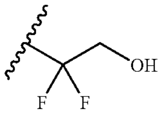 | 3.72 (LC-2) | 591.1/593.1 |
| 363 | $OCF_3$, Cl, Cl | 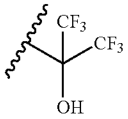 | 4.02 (LC-2) | 677.2/679.1 |
| 364 | $OCF_3$, Cl, Cl | 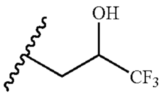 | 3.80 (LC-2), 2 isomers isolated | 623.1/625.1 |
| 365 | $OCF_3$, Cl, Cl | 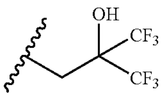 | 4.15 (LC-2) | 691.0/693.0 |

-continued
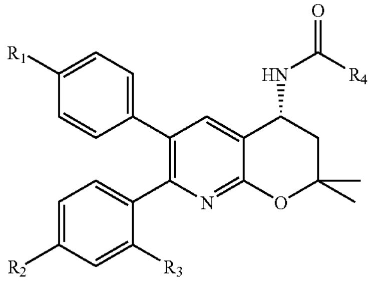
| Example | $R_1$, $R_2$, $R_3$ | $R_4$ | HPLC $R_t$ (min) | MS (M + H/M + 3H) |
|---|---|---|---|---|
| 366 | $OCF_3$, Cl, Cl | 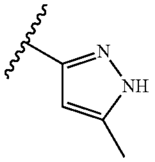 | 2.44 | 591.1/593.1 |
| 367 | $OCH_2CF_3$, Cl, Cl | 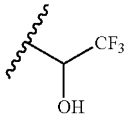 | 2.44, 2 isomers isolated | 623.1/625.1 |
| 368 | Cl, Br, Cl | 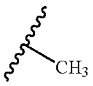 | 2.33 | 518.9/520.9 |
| 369 | Cl, Br, Cl | 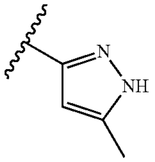 | 3.80 (LC-2) | 587.0/589.0 |
| 370 | Cl, CN, Cl | 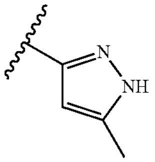 | 3.45 (LC-2) | 532.0/534.0 |
| 371 | Cl, CN, Cl | 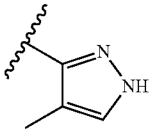 | 3.56 (LC-2) | 532.0/534.0 |
| 372 | Cl, $OCH_2CF_3$, Cl | 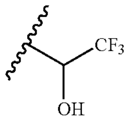 | 3.75 (LC-2), 2 isomers isolated | 623.1/625.1 |
| 373 | Cl, $OCH_2CF_3$, Cl | 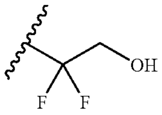 | 3.58 (LC-2) | 605.2/607.2 |
| 374 | Cl, $OCH_2CF_3$, Cl | 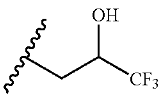 | 3.63 (LC-2), 2 isomers isolated | 637.1/639.1 |

-continued

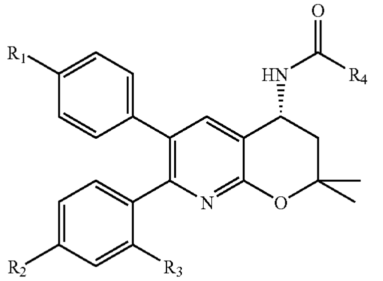

| Example | $R_1$, $R_2$, $R_3$ | $R_4$ | HPLC $R_t$ (min) | MS (M + H/M + 3H) |
|---|---|---|---|---|
| 375 | Cl, H, Cl | 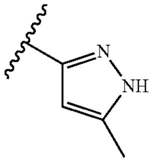 | 2.15 | 507.0/509.0 |
| 376 | Cl, H, Cl | 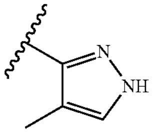 | 2.21 | 507.0/509.0 |
| 377 | Cl, H, Cl | 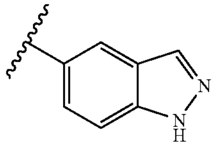 | 3.75 (LC-2) | 577.0/579.0 |

EXAMPLES 378, 379

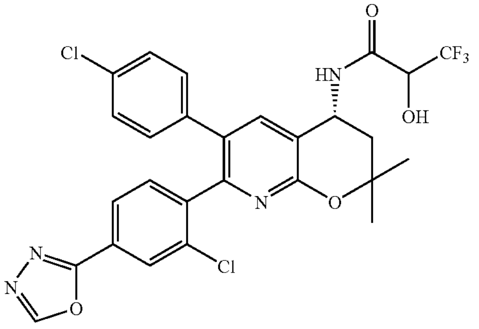

(2R/S)-N-[(4R)-7-[2-Chloro-4-(1,3,4-oxadiazol-2-yl) phenyl]-6-(4-chlorophenyl)-2,2-dimethyl-3,4-dihydro-2H-pyrano[2,3-b]pyridin-4-yl]-3,3,3-trifluoro-2-hydroxypropanamide Step A: Methyl 3-chloro-4-[(4R)-6-(4-chlorophenyl)-4({[(1,1-dimethylethyl)oxy]carbonyl}amino)-2,2-dimethyl-3,4-dihydro-2H-pyrano[2,3-b]pyridin-7-yl]benzoate. The product was prepared using the procedures analogous to those described for Example 325, Example 327 and Example 315 substituting 7-(4-bromo-2-chlorophenyl)-6-(4-chlorophenyl)-2,2-dimethyl-3,4-dihydro-2H-pyrazo[2,3-b]pyridin-4-one for 6-(4-chlorophenyl)-7-(2,4-dichlorophenyl)-2,2-dimethyl-3,4-dihydro-2H-pyrazo[2,3-b]pyridin-4-one in Step A of Example 325.

Step B: tert-Butyl [(4R)-7-[2-chloro-4-(hydrazinocarbonyl)phenyl]-6-(4-chlorophenyl)-2,2-dimethyl-3,4-dihydro-2H-pyrano[2,3-b]pyridin-4-yl]carbamate. The product was prepared using the procedures analogous to those described for Example 316 substituting methyl 3-chloro-4-[(4R)-6-(4-chlorophenyl)-4({[(1,1-dimethylethyl)oxy]carbonyl}amino)-2,2-dimethyl-3,4-dihydro-2H-pyrano[2,3-b]pyridin-7-yl]benzoate for methyl 3-chloro-4-{6-(4-chlorophenyl)-4[(2,2-dimethylpropanoyl)amino]-2,2-dimethyl-3,4-dihydro-2H-pyrano[2,3-b]pyridin-7-yl]benzoate in Step C.

Step C: tert-Butyl [(4R)-7-[2-chloro-4-(1,3,4-oxadiazol-2-yl)phenyl]-6-(4-chlorophenyl)-2,2-dimethyl-3,4-dihydro-2H-pyrano[2,3-b]pyridin-4-yl]carbamate. The product was prepared using the procedures analogous to those described for Example 318 substituting tert-butyl [(4R)-7-[2-chloro-4-(hydrazinocarbonyl)phenyl]-6-(4-chlorophenyl)-2,2-dimethyl-3,4-dihydro-2H-pyrano[2,3-b]pyridin-4-yl]carbamate for N-[7-{2-chloro-4-[(hydroxyamino)(imino)methyl]phenyl}-6-(4-chlorophenyl)-2,2-dimethyl-3,4-dihydro-2H-pyrano[2,3-b]pyridin-4-yl]-2,2-dimethylpropanamide in Step B except without addition of boron trifluoride-diethyl etherate.

Step D: N-[(4R)-7-[2-Chloro-4-(1,3,4-oxadiazol-2-yl)phenyl]-6-(4-chlorophenyl)-2,2-dimethyl-3,4-dihydro-2H-pyrano[2,3-b]pyridin-4-yl]-3,3,3-trifluoro-2-hydroxypropanamide. The title compound was prepared using the procedures analogous to those described for Examples 321, 322, 323, and 324 substituting the product of Step C for tert-butyl [7-(2-chloro-4-(1,2,4-oxadiazol-3-yl)phenyl)-6-(4-chlorophenyl)-2,2-dimethyl-3,4-dihydro-2H-pyrano[2,3-b]pyridin-4-yl]carbamate in Step B.

EXAMPLES 380, AND 381

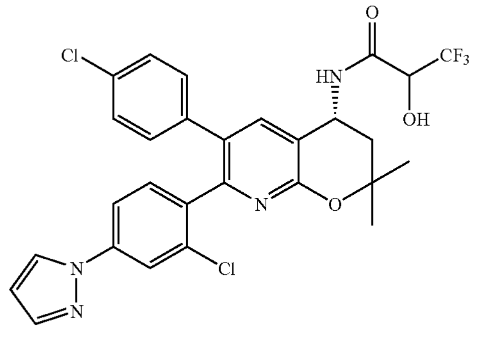

(2R/S)-N-[(4R)-6-(4-Chlorophenyl)-7-[2-chloro-4-(1H-pyrazol-1-yl)phenyl]-2,2-dimethyl-3,4-dihydro-2H-pyrano[2,3-b]pyridin-4-yl]-3,3,3-trifluoro-2-hydroxypropanamide Step A: tert-butyl {(4R)-6-(4-chlorophenyl)-7-[2-chloro-4-(1H-pyrazol-1-yl)phenyl]-2,2-dimethyl-3,4-dihydro-2H-pyrano[2,3-b]pyridin-4-yl}carbamate. A solution of Example 314(280 mg, 0.48 mmol), pyrazole (65.8 mg, 0.97 mmol), copper(I) oxide (3.5 mg, 0.02 mmol), 2-hydroxybenzaldehyde oxime (33.1 mg, 0.24 mmol), and $Cs_2CO_3$ (315 mg, 0.97 mmol) in 10 mL of $CH_3CN$ was degassed and stirred at 85° C. for 16 h. The reaction mixture was cooled and diluted with $CH_2Cl_2$ (50 mL) and filtered through a cake of Celite. The filtrate was washed with $H_2O$ (50 mL) and brine (50 mL). After the phases separated, the organic layer was dried over $MgSO_4$ and concentrated. Chromatography on a Biotage 40+S cartridge using 3:7 v/v EtOAc/hexanes as the eluant afforded the product: $^1$H NMR δ 1.46 (s, 3H), 1.50 (s, 9H), 1.55 (s, 3H), 1.18 (m, 1H), 2.29 (m, 1H), 4.76 (br. s, 1H), 5.13 (m, 1H), 6.38 (m, 1H), 6.47 (m, 1H), 7.05 (d, J=8.5, 2H), 7.18 (d, J=8.5, 2H), 7.39-7.72 (m, 5H), 7.90 (m, 1H).

Step B: (2R/S)-N-[(4R)-6-(4-Chlorophenyl)-7-[2-chloro-4-(1H-pyrazol-1-yl)phenyl]-2,2-dimethyl-3,4-dihydro-2H-pyrano[2,3-b]pyridin-4-yl]-3,3,3-trifluoro-2-hydroxypropanamide. The title compounds were prepared using procedures analogous to those described in Examples 321, 322, 323, and 324 substituting the product of Step A for tert-butyl [7-(2-chloro-4-(1,2,4-oxadiazol-3-yl)phenyl)-6-(4-chlorophenyl)-2,2-dimethyl-3,4-dihydro-2H-pyrano[2,3-b]pyridine-4-yl]carbamate in Step B.

EXAMPLE 382

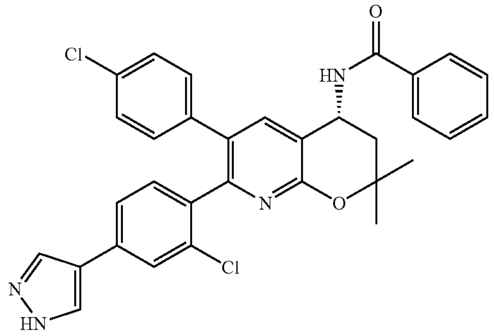

N-{(4R)-6-(4-Chlorophenyl)-7-[2-chloro-4-(1H-pyrazol-4-yl)phenyl]-2,2-dimethyl-3,4-dihydro-2H-pyrano[2,3-b]pyridin-4-yl}benzamide Step A: tert-Butyl {(4R)-6-(4-chlorophenyl)-7-[2-chloro-4-(1H-pyrazol-4-yl)phenyl]-2,2-dimethyl-3,4-dihydro-2H-pyrano[2,3-b]pyridin-4-yl}carbamate. To a solution of Example 314 (1.5 g, 2.59 mmol) in a mixed solvent of 9.0 mL of DMF, 1.0 mL of $H_2O$, and 2.0 mL of EtOH was added tert-butyl 4-(4,4,5,5-tetramethyl-1,3,2-dioxaborolan-2-yl)-1H-pyrazole-1-carboxylate (1.53 g, 5.19 mmol), $Na_2CO_3$ (830 mg, 7.78 mmol), and tetrakis(triphenylphosphino)palladium(0) (150 mg, 0.13 mmol). The mixture was stirred at 120° C. under microwave irradiation for 30 min. After cooling, the mixture was diluted with EtOAc (200 mL) and washed with $H_2O$ (50 mL) and brine (50 mL). The organic layer was separated, dried over $MgSO_4$, and concentrated. Chromatography on a Biotage 40+M cartridge using 1:1 v/v EtOAc/hexanes as the eluant afforded the product: $^1$H NMR δ 1.49 (s, 3H), 1.52 (s, 9H), 1.58 (s, 3H), 1.84 (t, J=12.7, 1H), 2.33 (dd, J=6.2, 13.2, 1H), 4.78 (m, 1H), 5.15 (m, 1H), 7.09 (d, J=8.4, 2H), 7.20 (d, J=8.5, 2H), 7.26-7.41 (m, 3H), 7.74 (s, 1H), 7.85 (s, 2H).

Step B: (4R)-6-(4-Chlorophenyl)-7-[2-chloro-4-(1H-pyrazol-4-yl)phenyl]-2,2-dimethyl-3,4-dihydro-2H-pyrano[2,3-b]pyridin-4-amine. A solution of the product of Step A (364 mg, 0.64 mmol) in 10 mL of 20% TFA in $CH_2Cl_2$ was stirred at rt for 2 h. The reaction mixture was concentrated to give the product, which was used in the next step without further purification.

Step C: N-{(4R)-6-(4-Chlorophenyl)-7-[2-chloro-4-(1H-pyrazol-4-yl)phenyl]-2,2-dimethyl-3,4-dihydro-2H-pyrano[2,3-b]pyridin-4-yl}benzamide. To a solution of the product of Step B (35.6 mg, 0.08 mmol) and $NEt_3$ (43 μL, 0.31 mmol) in 10 mL of $CH_2Cl_2$ was added benzoyl chloride (20 μL, 0.17 mmol). After stirring at rt for 1 h, 2.0 mL of $CH_3OH$ and 100 μL of 5.0 N NaOH was added to the reaction mixture. After stirring for 30 min, the reaction mixture was partitioned between EtOAc (20 mL) and saturated aq $NaHCO_3$ (20 mL). The organic layer was separated and washed with brine (20 mL). After the phases separated, the organic layer was dried over $MgSO_4$ and concentrated. Chromatography on a Biotage 40+S cartridge using 7:3 v/v EtOAc/hexanes as the eluant afforded the title compound: $^1$H NMR δ 1.50 (s, 3H), 1.56 (s, 3H), 1.96 (t, J=12.4, 1H), 2.36 (dd, J=6.4, 13.2, 1H), 5.73 (m, 2H), 6.61 (d, J=8.7, 1H), 7.02 (d, J=8.5, 2H), 7.13 (d, J=8.5, 2H), 7.14-7.55 (m, 6H), 7.72-7.83 (m, 5H).

The following examples were prepared using procedures analogous to those described for Example 382 substituting the appropriate boronic acids or boronic esters for tert-butyl 4-(4,4,5,5-tetramethyl-1,3,2-dioxaborolan-2-yl)-1H-pyrazole-1-carboxylate in Step A and substituting appropriate acyl chlorides or acids for benzoyl chloride in Step C.

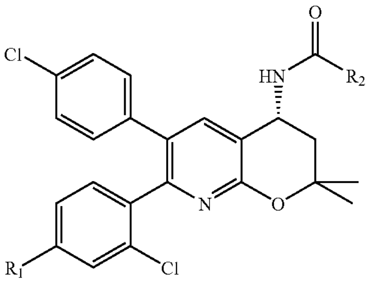

| Example | $R_1$ | $R_2$ | HPLC $R_t$ (min) | MS (M + 1H/M + 3H) |
|---|---|---|---|---|
| 383 | 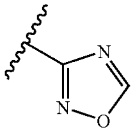 | 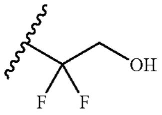 | 3.47 (LC-2) | 575.3/577.3 |
| 384 | 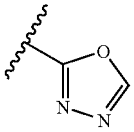 | 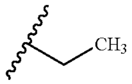 | 3.52 (LC-2) | 539.1/541.1 |
| 385 | 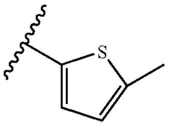 | 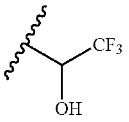 | 3.97 (LC-2), 2 isomers isolated | 621.1/623.1 |
| 386 | 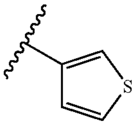 | 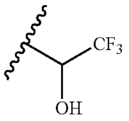 | 3.92 (LC-2), 2 isomers isolated | 607.1/609.1 |
| 387 | 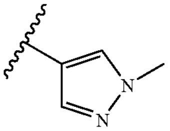 | 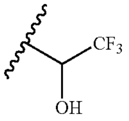 | 3.35 (LC-2), 2 isomers isolated | 605.2/607.2 |
| 388 | 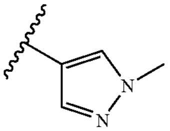 | 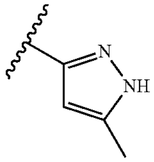 | 3.29 (LC-2) | 587.1/589.1 |
| 389 | 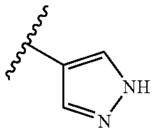 | 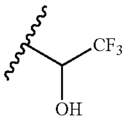 | 3.17 (LC-2), 2 isomers isolated | 591.1/593.1 |
| 390 | 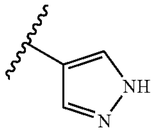 | 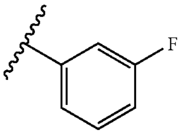 | 3.55 (LC-2) | 587.1/589.1 |

-continued
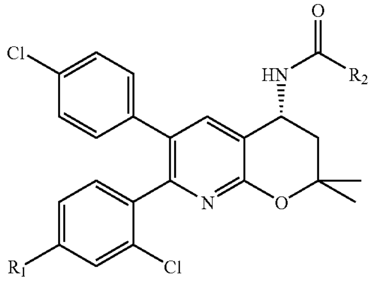
| Example | $R_1$ | $R_2$ | HPLC $R_t$ (min) | MS (M + 1H/M + 3H) |
|---|---|---|---|---|
| 391 | 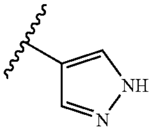 | 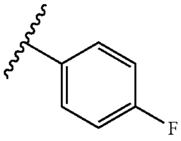 | 3.53 (LC-2) | 587.1/589.1 |
| 392 | 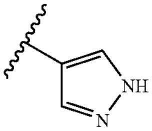 | 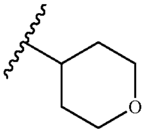 | 3.04 (LC-2) | 577.1/579.1 |
| 393 | 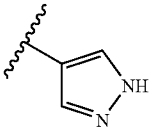 | 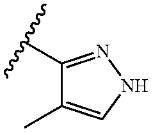 | 2.04 | 573.1/575.1 |
| 394 | 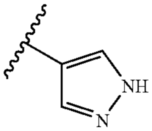 | 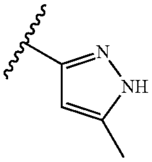 | 3.06 (LC-2) | 573.1/575.1 |
| 395 | 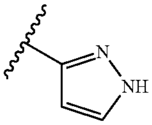 | 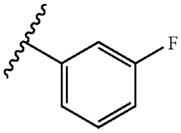 | 3.63 (LC-2) | 587.2/589.2 |
| 396 | 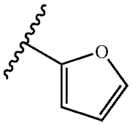 | 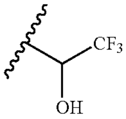 | 3.87 (LC-2), 2 isomers isolated | 591.1/593.1 |
| 397 | 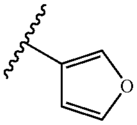 | 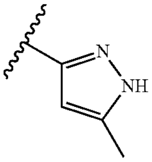 | 3.62 (LC-2) | 573.1/575.1 |
| 398 | 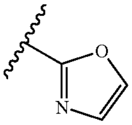 | 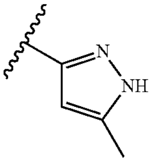 | 3.49 (LC-2) | 574.1/576.1 |

The following examples were prepared utilizing the appropriate amine and carboxylic acid or acid chloride in procedures similar to those described for Example 26 and Example 88.

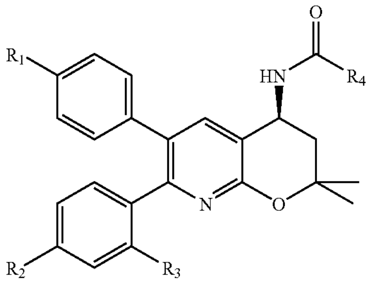

| Example | $R_1$, $R_2$, $R_3$ | $R_4$ | HPLC $R_t$ (min) | MS (M + H/ M + 3H) |
|---|---|---|---|---|
| 399 | Cl, Cl, Cl | 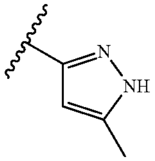 | 3.74 (LC-2) | 541.0/543.0 |
| 400 | $CF_3$, Br, Cl | 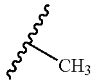 | 2.37 | 553.0/555.0 |
| 401 | $CF_3$, Br, Cl | 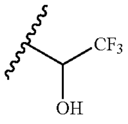 | 2.44, 2 isomers isolated, AD 5% Et/Hex | 637.0/639.1 |

The following examples were prepared utilizing the appropriate amine and carboxylic acid or acid chloride in procedures similar to those described for Example 26 and Example 88.

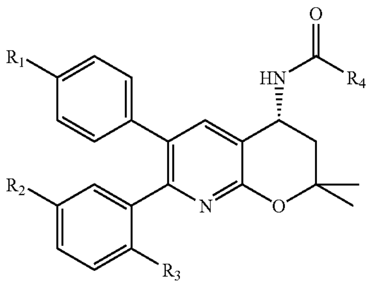

| Example | $R_1$, $R_2$, $R_3$ | $R_4$ | HPLC $R_t$ (min) | ESI-MS (M + H/ M + 3H) |
|---|---|---|---|---|
| 402 | Cl, $OCF_3$, Cl | 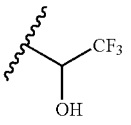 | 3.83 (LC-2), 2 isomers isolated | 609.2/611.2 |

-continued

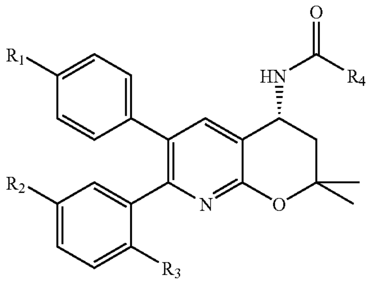

| Example | $R_1$, $R_2$, $R_3$ | $R_4$ | HPLC $R_t$ (min) | ESI-MS (M + H/ M + 3H) |
|---|---|---|---|---|
| 403 | Cl, $OCF_3$, Cl | 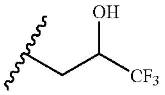 | 3.75 (LC-2), 2 isomers isolated | 623.1/625.1 |
| 404 | Cl, $OCF_3$, Cl | 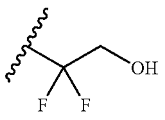 | 3.70 (LC-2) | 591.1/593.1 |
| 405 | Cl, $OCF_3$, Cl | 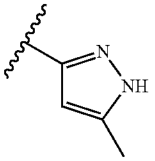 | 3.83 (LC-2) | 591.1/593.1 |

The following examples were prepared using procedures analogous to those described for Example 245 substituting (4R)-6-(4-chlorophenyl)-7-(2,4-dichlorophenyl)-2,2-dimethyl-3,4-dihydro-2H-pyrano-[2,3-b]pyridin-4-amine for the corresponding racemic amine and the appropriate aryl halide for 2-bromopyridine, respectively, in Step A.

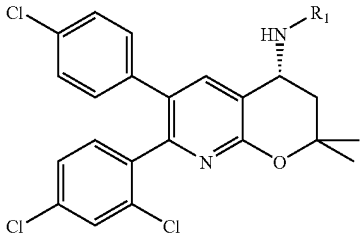

| Example | $R_1$ | HPLC $R_t$ (min) | MS (M + H/M + 3H) |
|---|---|---|---|
| 406 | 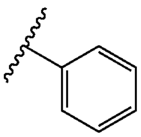 | 2.86 | 509.1/511.0 |

-continued

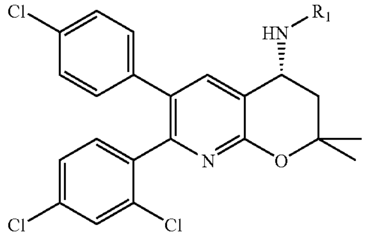

| Example | $R_1$ | HPLC $R_t$ (min) | MS (M + H/M + 3H) |
|---|---|---|---|
| 407 | 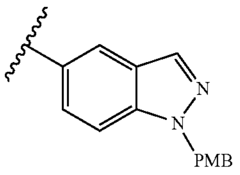 | 2.81 | 670.0/672.0 |
| 408 | 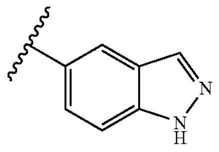 | 2.44 | 549.1/551.1 |
| 409 | 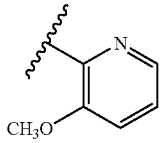 | 2.10 | 540.0/542.0 |
| 410 | 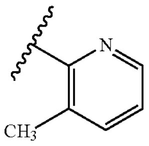 | 2.01 | 524.0/526.0 |
| 411 | 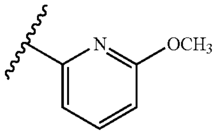 | 2.69 | 540.0/542.0 |

EXAMPLE 412

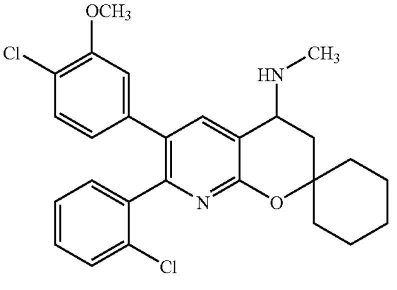

6'-[4-Chloro-3-(methyloxy)phenyl]-7'-(2-chlorophenyl)-N-methyl-3',4'-dihydrospiro[cyclohexane-1,2'-pyrano[2,3-b]pyridine]-4'-amine Step A: 2-[4-Chloro-3-(methyloxy)phenyl]-1-(2-chlorophenyl)-ethanone. A mixture of 1-(2-chlorophenyl)ethanone (1.4 mL, 10.8 mmol), 4-bromo-1-chloro-2-(methyloxy)benzene (2.0 g, 9.0 mmol), sodium tert-butoxide (2.2 g, 22.6 mmol), palladium(II) acetate (20.3 mg, 0.1 mmol), and 2-(dicyclohexylphosphino)-2'-methylbiphenyl (65.8 mg, 0.2 mmol) in 30 mL of toluene was degassed and stirred at 80° C. for 16 h. The reaction mixture was cooled and a mixture of $Et_2O$ (100 mL) and $H_2O$ (100 mL) was added. The aq layer was separated and extracted with $Et_2O$ (3×50 mL). Organic layers were combined, dried over $MgSO_4$, and concentrated. Chromatography on a Biotage 40+M cartridge using 1:9 v/v EtOAc/hexanes as the eluant afforded the product: $^1$H NMR δ 3.87 (s, 3H), 4.22 (s, 2H), 6.75 (dd, J=1.7, 8.2, 1H), 6.81 (d, J=1.6, 1H), 7.26-7.31 (m, 2H), 7.37-7.43 (m, 3H).

Step B: 6'-(4-Chloro-3-methoxyphenyl)-7'-(2-chlorophenyl)spiro[cyclohexane-1,2'-pyrano[2,3-b]pyridin]-4'(3'H)-one. Starting with the product of Step A this example and using procedures similar to those of Example 1 (Steps A and B) followed by that of Example 4 the product was obtained.

Step C: 6'-[4-Chloro-3-(methyloxy)phenyl]-7'-(2-chlorophenyl)-N-methyl-3',4'-dihydrospiro[cyclohexane-1,2'-pyrano[2,3-b]pyridine]-4'-amine. The title compound was prepared using procedures analogous to those described for Example 311 substituting the product of Step B for 6-(4-chloro-phenyl)-7-(2,4-dichlorophenyl)-2,2-dimethyl-2,3-dihydro-4H-pyrano[2,3-b]pyridin-4-one and methylamine for tert-butyl (2-aminoethyl)carbamate, respectively, in Step A: $^1$H NMR δ 1.38-1.98 (m, 12H), 2.37 (m, 1H), 2.54 (s, 3H), 3.56 (s, 3H), 3.96 (m, 1H), 6.56 (d, J=1.2, 1H), 6.77 (d, J=8.0, 1H), 7.20-7.27 (m, 5H), 7.98 (s, 1H).

The following examples were prepared utilizing the appropriate amine and carboxylic acid or acid chloride in procedures similar to those described for Example 26 or Example 88.

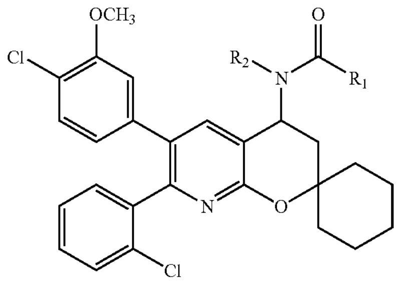

| Example | $R_1$ | $R_2$ | HPLC $R_t$ (min) | MS (M + H/M + 3H) |
|---|---|---|---|---|
| 413 | 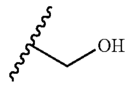 | 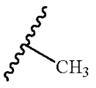 | 3.76 (LC-2) | 541.2/543.3 |
| 414 | 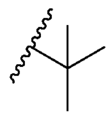 | 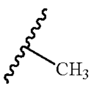 | 4.22 (LC-2) | 567.4/569.3 |

-continued

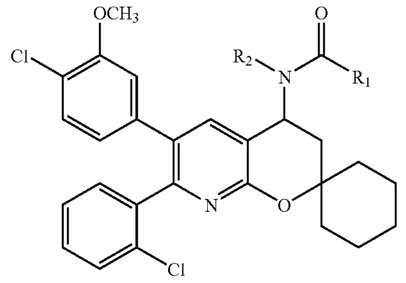

| Example | $R_1$ | $R_2$ | HPLC $R_t$ (min) | MS (M + H/M + 3H) |
|---|---|---|---|---|
| 415 | 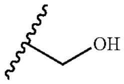 | 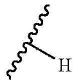 | 3.57 (LC-2) | 527.24/529.2 |
| 416 | 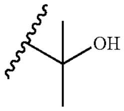 | 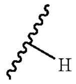 | 3.78 (LC-2) | 555.3/557.3 |

EXAMPLE 417

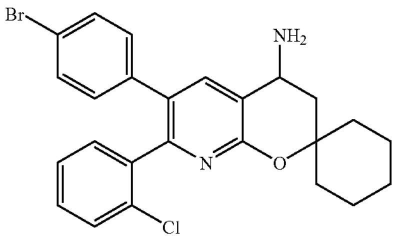

6'-(4-Bromophenyl)-7'-(2-chlorophenyl)-3',4'-dihydrospiro[cyclohexane-1,2'-pyrano[2,3-b]pyridine]-4'-amine The title compound was prepared from 6'-(4-bromophenyl)-7'-(2-chlorophenyl)spiro[cyclohexane-1,2'-pyrano[2,3-b]pyridin]-4'(3'H)-one oxime using a procedure similar to that of Example 23. HPLC/MS: 483.1 (M+1), 485.1 (M+3); $R_t$=3.39 min.

EXAMPLE 418

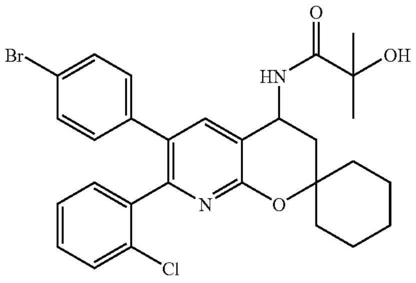

N-[6'-(4-Bromophenyl)-7'-(2-chlorophenyl)-3',4'-dihydrospiro[cyclohexane-1,2'-pyrano[2,3-b]pyridine]-4'-yl]-2-hydroxy-2-methylpropanamide The title compound was prepared using the product of Example 417 and the appropriate carboxylic acid in a procedure similar to that described for Example 88. HPLC/MS: 571.2 (M+1), 573.2 (M+3); $R_t$=3.82 min.

The following examples were prepared by the resolution of enantiomers from Example 418 using chiral chromatographyon an AD column eluting with 10% EtOH/Hexane.

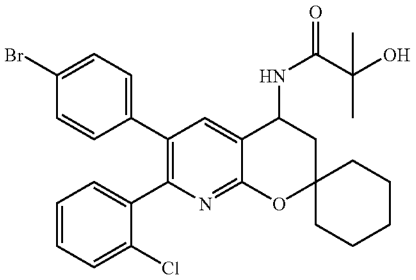

| Example | HPLC $R_t$ (min) | MS (M + H/M + 3H) |
|---|---|---|
| 419 | 3.82 (LC-2) (6.56, AD 10% Et/Hex) | 571.2/573.2 |
| 420 | 3.81 (LC-2) (17.38, AD 10% Et/Hex) | 571.2/573.2 |

EXAMPLE 421

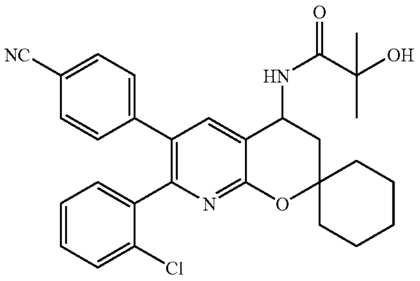

N-[7'-(2-Chlorophenyl)-6'-(4-cyanophenyl)-3',4'-dihydrospiro[cyclohexane-1,2'-pyrano[2,3-b]pyridine]-4'-yl]-2-hydroxy-2-methylpropanamide The product of Example 418 was treated under conditions similar to that of Example 317 Step B to afford the title compound: HPLC/MS: 516.4 (M+1), 518.4 (M+3); $R_t$=3.62 min.

The following examples were prepared utilizing the appropriate amine and carboxylic acid following the general procedure of Example 88.

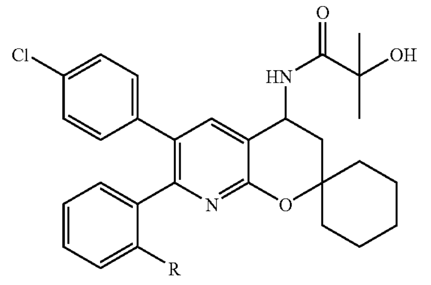

| Example | R | HPLC $R_t$ (min) | MS (M + H/M + 3H) |
|---|---|---|---|
| 422 | 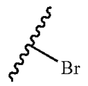 | 3.85 (LC-2) | 571.3/573.2 |
| 423 | 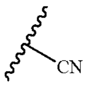 | 3.58 (LC-2) | 516.3/518.3 |

EXAMPLE 424

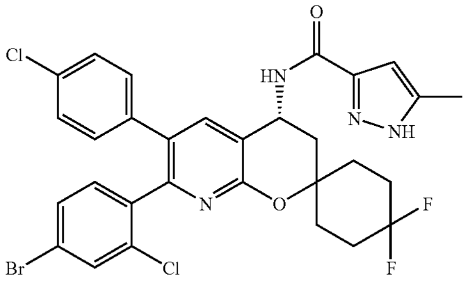

N-[(4'R)-7'-(4-Bromo-2-chlorophenyl)-6'-(4-chlorophenyl)-4,4-difluoro-3',4'-dihydrospiro[cyclohexane-1,2'-pyrano[2,3-b]pyridine]-4'-yl]-5-methyl-1H-pyrazole-3-carboxamide Step A: 7"-(4-Bromo-2-chlorophenyl)-6"-(4-chlorophenyl)dispiro[1,3-dioxolane-2,1'-cyclohexane-4',2"-pyrano[2,3-b]pyridine]-4"(3"H)-one. Starting with 3-acetyl-6-(4-bromo-2-chlorophenyl)-5-(4-chlorophenyl)pyridin-2(1H)-one and utilizing a procedure similar to that of Example 4 step B substituting 1,4-dioxaspiro[4,5]decan-8-one for cyclohexanone the product was prepared.

Step B: (4"R)-4"-Azido-7"-(4-bromo-2-chlorophenyl)-6"-(4-chlorophenyl)-3",4"-dihydrodispiro[1,3-dioxolane-2,1'-cyclohexane-4',2"-pyrano[2,3-b]pyridine]. The product was prepared using procedures analogous to those described for Example 325 and Example 327 substituting the product of Step A for 6-(4-chlorophenyl)-7-(2,4-dichlorophenyl)-2,2-dimethyl-2,3-dihydro-4H-pyrano[2,3-b]pyridine-4-one in Step A of Example 325.

Step C: (4'R)-4'-Azido-7'-(4-bromo-2-chlorophenyl)-6'-(4-chlorophenyl)-3',4'-dihydro-4H-spiro[cyclohexane-1,2'-pyrano[2,3-b]pyridine]-4-one. A solution of the product of Step B (300 mg, 0.54 mmol) and p-toluenesulfonic acid monohydrate (5.1 mg, 0.03 mmol) in 10 mL of acetone was allowed to stir at rt for 16 h. The reaction mixture was diluted with $Et_2O$ (50 mL), washed with saturated aq $NaHCO_3$ (2×50 mL) and brine (50 mL). The organic layer was separated, dried over $MgSO_4$, and concentrated. Chromatography on a Biotage 40+S cartridge using 3:7 v/v EtOAc/hexanes as the eluant afforded the product: $^1$H NMR δ 1.93-2.07 (m, 2H), 2.21-2.53 (m, 6H), 2.86-3.03 (m, 2H), 4.82 (m, 1H), 7.04 (d, J=8.4, 2H), 7.15-7.24 (m, 3H), 7.37 (dd, J=2.1, 8.3, 1H), 7.46 (d, J=1.8, 1H), 7.81 (s, 1H).

Step D: (4'R)-4'-Azido-7'-(4-bromo-2-chlorophenyl)-6'-(4-chlorophenyl)-4,4-difluoro-3',4'-dihydro-4H-spiro[cyclohexane-1,2'-pyrano[2,3-b]pyridine]. A mixture of [bis(2-methoxyethyl)amino]sulfur trifluoride (65 μL, 0.35 mmol) and $BF_3.Et_2O$ (3.2 μL, 0.03 mmol) in 5.0 mL of toluene was allowed to stir for 45 min at 0° C. A solution of the product of Step C (129 mg, 0.25 mmol) in 5.0 mL of toluene was added. The resulting mixture was stirred at 55° C. for 2 days. After cooling, the mixture was partitioned between 2N NaOH (50 mL) and $Et_2O$ (40 mL) at 0° C. and stirred for 30 min. After the phases separated, the organic layer was washed with saturated aq $NaHCO_3$ (50 mL) and brine (50 mL). The organic layer was separated, dried over $MgSO_4$, and concentrated. Chromatography on a Biotage 40+S cartridge using 3:17 v/v EtOAc/hexanes as the eluant afforded the product: $^1$H NMR δ 1.82-2.33 (m, 10H), 4.78 (m, 1H), 7.02 (d, J=8.5, 2H), 7.14-7.45 (m, 5H), 7.78 (s, 1H).

Step E: (4'R)-7'-(4-Bromo-2-chlorophenyl)-6'-(4-chlorophenyl)-4,4-difluoro-3',4'-dihydro-4H-spiro[cyclohexane-1,2'-pyrano[2,3-b]pyridin]-4'-amine. The product was prepared using procedures analogous to those described for Example 327 substituting the product of Step D this example for (4R)-4-azido-6-(4-chlorophenyl)-7-(2,4-dichlorophenyl)-2,2-dimethyl-3,4-dihdyro-2H-pyrano[2,3-b]pyridine in Step B.

Step F: N-[(4'R)-7'-(4-Bromo-2-chlorophenyl)-6'-(4-chlorophenyl)-4,4-difluoro-3',4'-dihydrospiro[cyclohexane-1,2'-pyrano[2,3-b]pyridine]-4'-yl]-5-methyl-1H-pyrazole-3-carboxamide The title compound was prepared using procedures analogous to those described for Example 327 substituting the product of Step E for (4R)-6-(4-chlorophenyl)-7-(2,4-dichlorophenyl)-2,2-dimethyl-3,4-dihdyro-2H-pyrano[2,3-b]pyridine-4-amine in Step C: $^1$H NMR δ 1.82-2.46 (m, 13H), 5.65 (m, 1H), 6.64 (s, 1H), 6.97 (d, J=8.4, 2H), 7.14-7.45 (m, 5H), 7.70 (s, 1H).

EXAMPLE 425

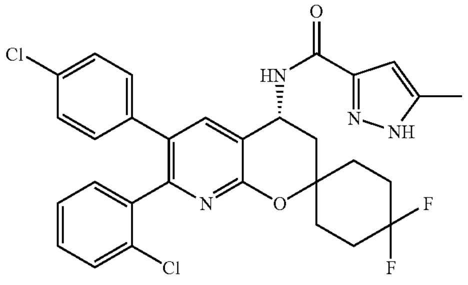

N-[(4'R)-7'-(2-Chlorophenyl)-6'-(4-chlorophenyl)-4,4-difluoro-3',4'-dihydrospiro[cyclohexane-1,2'-pyrano[2,3-b]pyridine]-4'-yl]-5-methyl-1H-pyrazole-3-carboxamide A mixture of Example 425 (68 mg, 0.110 mmol), $NEt_3$ (29 μL, 0.21 mmol), 11 mg of 5% Pd/C in 5.0 mL of EtOAc was degassed and stirred under 1 atm of $H_2$ for 5 h. The solids were filtered and washed with EtOAc. The filtrate was concentrated and chromatography on a Biotage 40+S cartridge using 9:11 v/v EtOAc/hexanes as the eluant afforded the title compound: $^1$H NMR δ 1.81-2.49 (m, 13H), 5.64 (m, 1H), 6.61 (s, 1H), 6.97 (d, J=8.5, 2H), 7.11-7.30 (m, 6H), 7.71 (s, 1H).

EXAMPLE 426

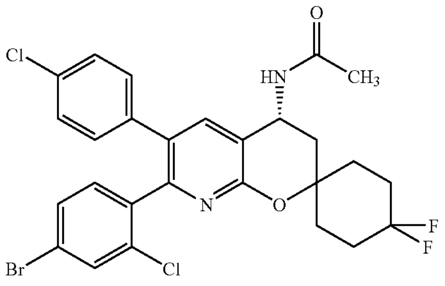

N-[(4'R)-7'-(4-Bromo-2-chlorophenyl)-6'-(4-chlorophenyl)-4,4-difluoro-3',4'-dihydrospiro[cyclohexane-1,2'-pyrano[2,3-b]pyridine]-4'-yl]-5-methyl-1H-pyrazole-3-acetamide The title compound was prepared from the product of Step E Example 424 and acetic anhydride. HPLC/MS: 594.9 (M+1), 596.9 (M+3); $R_t$=2.51 min.

BIOLOGICAL EXAMPLE 1

Cannabinoid Receptor-1 (CB1) Binding Assay

Binding affinity determination is based on recombinant human CB1 receptor expressed in Chinese Hamster Ovary (CHO) cells (Felder et al, Mol. Pharmacol. 48: 443-450, 1995). Total assay volume is 250 μl (240 μl CB1 receptor membrane solution plus 5 μl test compound solution plus 5 μl [3H]CP-55940 solution). Final concentration of [3H]CP-55940 is 0.6 nM. Binding buffer contains 50 mM Tris-HCl, pH7.4, 2.5 mM EDTA, 5 mM $MgCl_2$, 0.5 mg/mL fatty acid free bovine serum albumin and protease inhibitors (Cat#P8340, from Sigma). To initiate the binding reaction, 5 μl of radioligand solution is added, the mixture is incubated with gentle shaking on a shaker for 1.5 h at 30° C. The binding is terminated by using 96-well harvester and filtering through GF/C filter presoaked in 0.05% polyethylenimine. The bound radiolabel is quantitated using scintillation counter. Apparent binding affinities for various compounds are calculated from $IC_{50}$ values (DeBlasi et al., Trends Pharmacol Sci 10: 227-229, 1989). Compounds of the present invention have IC50s of less than 5 micromolar in the CB1 binding assay. In particular, compounds of Examples 1 to 22 and 24-439 were assayed in the CB1 Binding assay and found to have $IC_{50}$ values for the human CB1 receptor less than 1 micromolar.

The binding assay for CB2 receptor is done similarly with recombinant human CB2 receptor expressed in CHO cells. The compounds of the present invention are selective CB1 antagonist/inverse agonist compounds having $IC_{50}$s greater in the CB2 binding assay than in the CB1 assay.

CB1 Receptor Binding Activity for Selected Compounds

| Example No. | CB1 binding $IC_{50}$ (nM) |
|---|---|
| Example 4 | 8 |
| Example 12 | 2 |
| Example 96 | 3 |
| Example 66 | 2 |
| Example 245 | 2 |
| Example 246 | 10 |
| Example 327 | 1 |
| Example 111 | 2 |

BIOLOGICAL EXAMPLE 2

Cannabinoid Receptor-1 (CB1) Functional Activity Assay

The functional activation of CB1 receptor is based on recombinant human CB1 receptor expressed in CHO cells (Felder et al, Mol. Pharmacol. 48: 443-450, 1995). To determine the agonist activity or inverse agonist activity of any test compound, 50 ul of CB1-CHO cell suspension are mixed with test compound and 70 ul assay buffer containing 0.34 mM 3-isobutyl-1-methylxanthine and 5.1 uM of forskolin in 96-well plates. The assay buffer is comprised of Earle's Balanced Salt Solution supplemented with 5 mM $MgCl_2$, 1 mM glutamine, 10 mM HEPES, and 1 mg/mL bovine serum albumin. The mixture is incubated at room temperature for 30 minutes, and terminated by adding 30 ul/well of 0.5M HCl. The total intracellular cAMP level is quantitated using the New England Nuclear Flashplate and cAMP radioimmunoassay kit.

The compounds of Examples 4, 12, 66, 96, 111, 245, 246, and 327 were all tested in the CB1 functional activity assay and found to have EC50s less than 20 nM.

BIOLOGICAL EXAMPLE 3

Cannabinoid Receptor-1 (CB1) Functional Antagonist Assay

To determine the antagonist activity of test compound, the reaction mixture also contains 0.5 nM of the agonist CP55940 (or 50 nM of methanandamide), and the reversal of the CP55940 (or methanandamide) effect is quantitated with increasing concentration of the test compound. Intracellular cAMP is determined as described above. An IC50 value for the test compound is calculated from the titration curve.

Alternatively, a series of dose response curves for the agonist CP55940 (or methanandamide) is performed with increasing concentration of the test compound in each of the dose response curves, and a Schild analysis is carried to calculate the Kb value which is an estimation of test compound binding affinity.

The compounds of Examples 4, 12, 66, 96, 111, 245, 246, and 327 were all tested in the CB1 functional activity assay and were functional inverse agonists.

BIOLOGICAL EXAMPLE 4

Cannabinoid Receptor-2 (CB2) Functional Activity Assay

The functional assay for the CB2 receptor is done similarly with recombinant human CB2 receptor expressed in CHO cells.

BIOLOGICAL EXAMPLE 5

Acute Food Intake Studies in Rats or Mice

General Procedure

Adult rats or mice are used in these studies. After at least 2 days of acclimation to the vivarium conditions (controlled humidity and temperature, lights on for 12 hours out of 24 hours) food is removed from rodent cages. Experimental compounds or their vehicles are administered orally, intraperitoneally, subcutaneously or intravenously before the return of a known amount of food to cage. The optimal interval between dosing and food presentation is based on the half-life of the compound based on when brain concentrations of the compound is the highest. Food remaining is measured at several intervals. Food intake is calculated as grams of food eaten per gram of body weight within each time interval and the appetite-suppressant effect of the compounds are compared to the effect of vehicle. In these experiments many strains of mouse or rat, and several standard rodent chows can be used.

BIOLOGICAL EXAMPLE 6

Chronic Weight Reduction Studies in Rats or Mice

General Procedure

Adult rats or mice are used in these studies. Upon or soon after weaning, rats or mice are made obese due to exclusive access to diets containing fat and sucrose in higher proportions than in the control diet. The rat strains commonly used include the Sprague Dawley bred through Charles River Laboratories. Although several mouse strains may be used, c57B1/6 mice are more prone to obesity and hyperinsulinemia than other strains. Common diets used to induce obesity include: Research Diets D12266B (32% fat) or D12451 (45% fat) and BioServ S3282 (60% fat). The rodents ingest chow until they are significantly heavier and have a higher proportion of body fat than control diet rats, often 9 weeks. The rodents receive injections (1 to 4 per day) or continuous infusions of experimental compounds or their vehicles either orally, intraperitoneally, subcutaneously or intravenously. Food intake and body weights are measured daily or more frequently. Food intake is calculated as grams of food eaten per gram of body weight within each time interval and the appetite-suppressant and weight loss effects of the compounds are compared to the effects of vehicle.

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of structural formula I:

I

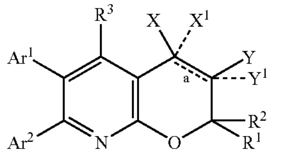

or a pharmaceutically acceptable salt thereof, wherein:

"a" is:

(1) a single bond and $X^1$ and $Y^1$ are present, or (2) a double bond and $X^1$ and $Y^1$ are absent;

X is selected from:

(1) —$C_{1-6}$alkyl, unsubstituted or substituted with one, two or three substituents independently selected from $R^a$, (2) aryl-, unsubstituted or substituted with one, two or three substituents independently selected from $R^b$, (3) cycloalkyl, unsubstituted or substituted with one, two or three substituents independently selected from $R^b$, (4) heteroaryl-, unsubstituted or substituted with one, two, or three substituents independently selected from $R^b$, (5) heterocycloalkyl-, unsubstituted or substituted with one, two or three substituents independently selected from $R^b$, (6) heteroaryl-$C_{1-3}$alkyl, unsubstituted or substituted on heteroaryl with one, two, or three substituents independently selected from $R^b$, (7) —$CO_2R^d$, (8) —CO—$NR^cR^d$, (9) —$OR^d$,

(10) —O—C(O)$R^d$,

(11) —$NR^cR^d$,

(12) —$NR^c$C(═O)$R^d$,

(13) —$NR^c$C(═O)$OR^d$,

(14) —$NR^c$C(═O)—C(═O)$NR^cR^d$, and

(15) —NH—$SO_2$—$R^f$, $X^1$, when present, is selected from hydrogen, halogen and $C_{1-6}$alkyl, or together X and $X^1$ form ═O, ═$NR^g$, or ═CH—C(O)—O—$R^d$;

Y is selected from: hydrogen, halogen, $C_{1-6}$alkyl, and —C(O)—$R^e$;

$Y^1$, when present, is selected from: hydrogen, halogen, and $C_{1-6}$alkyl;

provided that, when "a" is a single bond, X, $X^1$, Y, and $Y^1$ are not simultaneously hydrogen;

$Ar^1$ is:

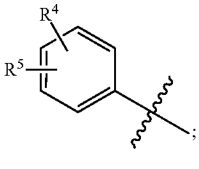

;

$Ar^2$ is:

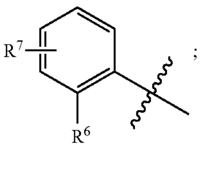

;

$R^1$ is selected from:

(1) hydrogen, (2) $C_{1-6}$alkyl, unsubstituted or substituted with hydroxy, fluoro, or methylsulfonylmethyl, (3) bicyclo[2.2.1]hept-5-en-2-yl, (4) cycloheteroalkyl, (5) cycloheteroalkyl-$C_{1-4}$alkyl, and (6) phenyl, unsubstituted or substituted with fluoro;

$R^2$ is selected from:

(1) $C_{1-6}$alkyl, unsubstituted or substituted with hydroxy, fluoro, or methylsulfonyl, (2) bicyclo[2.2.1]hept-5-en-2-yl, (3) cycloheteroalkyl, (4) cycloheteroalkyl-$C_{1-4}$alkyl, and (5) phenyl, unsubstituted or substituted with fluoro;

or $R^1$ and $R^2$ together with the carbon to which the are attached form a carbonyl group (C═O) or a spiroannulated ring system selected from:

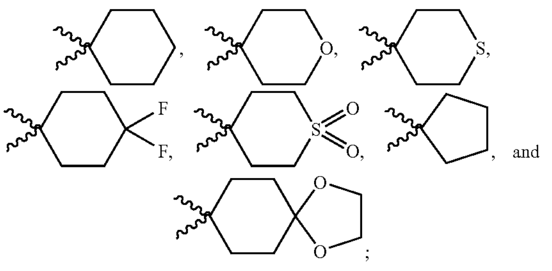

$R^3$ is selected from:

(1) hydrogen, (2) $C_{1-6}$alkyl, (3) $C_{1-6}$alkyloxy, (4) trifluoromethyl, (5) trifluoromethoxy, (6) halo, and (7) $C_{3-7}$cycloalkyl, wherein alkyl, and cycloalkyl are optionally substituted with one, two, or three substituents independently selected from $R^a$;

$R^4$ and $R^5$ are each independently selected from:

(1) —H, (2) halo-, (3) —CN, (4) $C_{1-3}$alkyl-, unsubstituted or substituted with one, two or three $R^h$ substitutents, (5) —$CF_3$, (6) —$OR^d$, and (7) —$OCF_3$, provided that $R^4$ and $R^5$ are not both simultaneously hydrogen;

$R^6$ is selected from:

(1) halo-, (2) —CN, (3) —$C_{1-3}$alkyl, unsubstituted or substituted with one, two, or three $R^h$ substitutents, (4) —$CFI_3$, (5) cycloheteroalkyl, unsubstituted or substituted with one or two $R^h$ substitutents, (6) heteroaryl, unsubstituted or substituted with one or two $R^K$ substitutents, (7) —OH, (8) —$OCH_3$, (9) —$OCF_3$,

(10) —$OCH_2CF_3$, and

(11) —$CO_2R^d$;

$R^7$ is selected from:

(1) —H, (2) halo-, (3) —CN, (4) —$C_{1-3}$alkyl-, unsubstituted or substituted with one, two, or three $R^h$ substitutents, (5) —$CF_3$, (6) cycloheteroalkyl, unsubstituted or substituted with one or two $R^h$ substitutents, (7) heteroaryl, unsubstituted or substituted with one or two $R^K$ substitutents, (8) —OH, (9) —$OCH_3$,

(10) —$OCF_3$,

(11) —$OCH_2CF_3$, and

(12) —$CO_2R^d$;

each $R^a$ is independently selected from:

(1) —$OR^d$, (2) —$NR^cS(O)_mR^d$, (3) halogen, (4) —$SR^d$, (5) —$S(O)_mNR^cR^d$ (6) —$NR^cR^d$, (7) —$C(O)R^d$, (8) —$CO_2R^d$, (9) —CN,

(10) —$C(O)NR^cR^d$,

(11) —$NR^cC(O)R^d$,

(12) —$NR^cC(O)OR^d$,

(13) —$NR^cC(O)NR^cR^d$,

(14) —$CF_3$, and

(15) —$OCF_3$;

each $R^b$ is independently selected from:

(1) $R^a$, (2) oxo, (3) $C_{1-10}$alkyl, (4) $C_{2-10}$alkenyl, (5) cycloalkyl, (6) cycloalkyl-$C_{1-10}$alkyl;

(7) cycloheteroalkyl, (8) cycloheteroalkyl-$C_{1-10}$ alkyl, (9) aryl,

(10) heteroaryl,

(11) aryl-$C_{1-10}$alkyl, and

(12) heteroaryl-$C_{1-10}$ alkyl, wherein alkyl and alkenyl moieties are unsubstituted or substituted with one, two, three or four $R^k$ substituents, and cycloalkyl, cycloheteroalkyl, aryl and heteroaryl moieties are unsubstituted or substituted with one, two, or three $R^k$ substituents;

$R^c$ and $R^d$ are each independently selected from:

(1) hydrogen, (2) $C_{1-10}$alkyl, (3) $C_{2-10}$alkenyl, (4) cycloalkyl, (5) cycloalkyl-$C_{1-10}$alkyl-, (6) cycloheteroalkyl, (7) cycloheteroalkyl-$C_{1-10}$alkyl-, (8) aryl, (9) heteroaryl,

(10) aryl-$C_{1-10}$alkyl-, and

(11) heteroaryl-$C_{1-10}$alkyl-, wherein each $R^c$ and $R^d$ moiety, other than hydrogen, may be unsubstituted or substituted with one to three substituents selected from $R^h$;

each $R^e$ is independently selected from:
(1) $C_{1-10}$alkyl,
(2) aryl,
(3) heteroaryl,
(4) cycloalkyl, and
(5) cycloheteroaryl;
wherein alkyl and aryl are unsubstituted or substituted with one, two, or three substituents independently selected from $R^h$;
each $R^f$ is independently selected from:
(1) halogen,
(2) $C_{1-16}$alkyl, unsubstituted or substituted with one, two, or three $R^i$ substituents,
(3) $C_{2-6}$ alkenyl, unsubstituted or substituted with one, two, or three $R^i$ substituents,
(4) cycloalkyl, unsubstituted or substituted with one, two, or three $R^h$ substituents,
(5) cycloalkyl-$C_{1-4}$alkyl-, unsubstituted or substituted with one, two, or three $R^h$ substituents,
(6) cycloheteroalkyl, unsubstituted or substituted with one, two, or three $R^h$ substituents,
(7) cycloheteroalkyl-$C_{1-4}$alkyl-, unsubstituted or substituted with one, two, or three $R^h$ substituents,
(8) aryl, unsubstituted or substituted with one, two, or three $R^h$ substituents,
(9) heteroaryl, unsubstituted or substituted with one, two, or three $R^h$ substituents,
(10) aryl-$C_{1-4}$alkyl-, unsubstituted or substituted with one, two, or three $R^h$ substituents,
(11) heteroaryl-$C_{1-4}$alkyl-, unsubstituted or substituted with one, two, or three $R^h$ substituents, and
(12) —$N(CH_3)_2$;
each $R^g$ is independently selected from:
(1) hydrogen,
(2) —OH,
(3) $C_{1-3}$alkyl,
(4) aryl,
(5) heteroaryl,
(6) cycloalkyl, and
(7) cycloheteroaryl;
wherein alkyl and aryl are unsubstituted or substituted with one, two, or three substituents independently selected from $R^h$;
each $R^h$ is independently selected from:
(1) halogen,
(2) $C_{1-6}$alkyl,
(3) 4-methylbenzyl-,
(4) —OH,
(5) —O—$C_{1-4}$alkyl,
(6) benzyloxy-,
(7) -oxo,
(8) —OC(O)—$C_{1-6}$alkyl,
(9) —C(O)O—$C_{1-6}$alkyl,
(10) —S—$C_{1-4}$alkyl,
(11) —$NH_2$,
(12) —$NH(CH_3)$,
(13) —$N(CH_3)_2$,
(14) —$NO_2$,
(15) —CN,
(16) —$CF_3$, and
(17) —$OCF_3$,
wherein alkyl may be unsubstituted or substituted with one, two, or three substituents selected from $R^i$;
each $R^i$ is independently selected from:
(1) halogen,
(2) —O—$C_{1-4}$alkyl,
(3) —OH,
(4) —S—$C_{1-4}$alkyl,
(5) —CN,
(6) —$CF_3$, and
(7) —$OCF_3$;
each $R^k$ is independently selected from:
(1) halogen,
(2) oxo,
(3) amino,
(4) hydroxy,
(5) $C_{1-4}$alkyl,
(6) —O—$C_{1-4}$alkyl,
(7) —S—$C_{1-4}$alkyl,
(8) —CN,
(9) —$CF_3$, and
(10) —$OCF_3$;
each m is independently selected from 1 and 2.

2. The compound according to claim 1, wherein:
X is selected from:
(1) methyl, ethyl, isopropyl or t-butyl, substituted with one, two or three substituents independently selected from $R^a$,
(2) phenyl-, unsubstituted or substituted with one, two or three substituents independently selected from $R^b$,
(3) heteroaryl-, unsubstituted or substituted with one, two, or three substituents independently selected from $R^b$,
(4) heterocycloalkyl-, unsubstituted or substituted with one, two or three substituents independently selected from $R^b$,
(5) heteroaryl-methyl-, unsubstituted or substituted on heteroaryl with one, two, or three substituents independently selected from $R^b$,
(6) —$CO_2R^d$,
(7) —CO—$NR^cR^d$,
(8) —$OR^d$,
(9) —O—C(O)$R^d$,
(10) —$NR^cR^d$,
(11) —$NR^cC$(=O)$R^d$,
(12) —NHC(=O)$OR^d$,
(13) —NHC(=O)—C(=O)$NHR^d$, and
(14) —NH—$SO_2$—$R_f$,
X1 is hydrogen, or
X and $X^1$ together form =O, =N—OH, or =CH—C(O)—O—$CH_2CH_3$;
$Ar^1$ is:

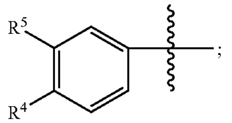

$R^3$ is hydrogen;
$R^6$ is selected from:
(1) —F,
(2) —Cl,
(3) —Br,
(4) —I,
(5) —CN,
(6) —$CH_3$,
(7) —$CF_3$,
(8) oxadiazolyl, unsubstituted or substituted with one or two $R^h$ substitutents,
(9) pyrazolyl,
(10) thienyl,
(11) furyl,

(12) oxazolyl,
(13) —OH,
(14) —$OCH_3$,
(15) —$OCF_3$,
(16) —$OCH_2CF_3$, and
(17) —$CO_2CH_3$;

$R^7$ is selected from:
(1) —H,
(2) —F,
(3) —Cl,
(4) —Br,
(5) —I,
(6) —CN,
(7) —$CH_3$,
(8) —$CF_3$,
(9) oxadiazolyl, unsubstituted or substituted with one or two $R^h$ substitutents,
(10) pyrazolyl,
(11) thienyl,
(12) furyl,
(13) oxazolyl,
(14) —OH,
(15) —$OCH_3$,
(16) —$OCF_3$,
(17) —$OCH_2$CF3, and
(18) —$CO_2$CH3;

each $R^a$ is independently selected from:
(1) —OH,
(2) —F,
(3) —$SO_2CH_3$,
(4) —$CO_2$—$C_{1-6}$alkyl, and
(5) —$CF_3$;

each $R^b$ is independently selected from:
(1) —OH,
(2) —$OCH_3$,
(3) halogen,
(4) —$N(CH_3)_2$,
(5) —CH(O)
(6) —C(O)$R^d$,
(7) —$CO_2CH_3$,
(8) —$CO_2CH_2C_6H_5$,
(9) —CN,
(10) —$CF_3$,
(11) —$OCF_3$,
(12) oxo,
(13) $C_{1-3}$alkyl,
(14) $C_{2-3}$ alkenyl,
(15) cyclopropyl,
(16) oxadiazolyl,
(17) pyrazolyl,
(18) tetrazolyl, and
(19) phenyl, wherein alkyl and alkenyl moieties are unsubstituted or substituted with one, two, or three $R^k$ substituents, and cycloalkyl, cycloheteroalkyl, aryl and heteroaryl moieties are unsubstituted or substituted with one, two or three $R^k$ substituents;

each $R^c$ is independently selected from:
(1) hydrogen, and
(2) $C_{1-3}$alkyl, unsubstituted or substituted with one to three substituents selected from $R^h$;

each $R^d$ is independently selected from:
(1) hydrogen,
(2) $C_{1-6}$alkyl,
(3) $C_{2-6}$alkenyl,
(4) cycloalkyl,
(5) cycloalkyl-$C_{1-10}$alkyl-,
(6) cycloheteroalkyl,
(7) cycloheteroalkyl-$C_{1-10}$alkyl-,
(8) aryl,
(9) heteroaryl,
(10) aryl-$C_{1-3}$alkyl-, and
(11) heteroaryl-$C_{1-3}$alkyl-, wherein each $R^d$ moiety, other than hydrogen, may be unsubstituted or substituted with one, two or three substituents selected from $R^h$;

each $R^f$ is independently selected from:
(1) halogen,
(2) $C_{1-6}$alkyl, unsubstituted or substituted with one or two $R^i$ substituents, and
(3) —$N(CH_3)_2$;

each $R^g$ is independently selected from:
(1) hydrogen,
(2) —OH, and
(3) methyl;

or a pharmaceutically acceptable salt thereof.

3. The compound according to claim 1, selected from:
(1) 6-(4-chlorophenyl)-7-(2,4-dichlorophenyl)-2,2-dimethyl-2,3-dihydro-4H-pyrano[2,3-b]pyridin-4-one,
(2) 6-(4-chlorophenyl)-7-(2,4-dichlorophenyl)-2-methyl-2,3-dihydro-4H-pyrano[2,3-b]pyridin-4-one,
(3) 7-(2-chlorophenyl)-6-(4-chlorophenyl)-2,2-dimethyl-2,3-dihydro-4H-pyrano[2,3-b]pyridin-4-one,
(4) 7'-(2-chlorophenyl)-6'-(4-chlorophenyl)spiro[cyclohexane-1,2'-pyrano[2,3-b]pyridin]-4'(3'H)-one,
(5) 7'-(2-chlorophenyl)-6'-(4-chlorophenyl)spiro[cyclopentane-1,2'-pyrano[2,3-b]pyridin]-4'(3'H)-one,
(6) 7-(2-chlorophenyl)-6-(4-chlorophenyl)-2',3',5',6'-tetrahydrospiro[pyrano[2,3-b]pyridine-2,4'-thiopyran]-4(3H)-one,
(7) 7'-(2-chlorophenyl)-6'-(4-chlorophenyl)-2,3,5,6-tetrahydrospiro[pyran-4,2'-pyrano[2,3-b]pyridin]-4'(3'H)-one,
(8) 7"-(2-chlorophenyl)-6"-(4-chlorophenyl)dispiro[1,3-dioxolane-2,1'-cyclohexane-4',2"-pyrano[2,3-b]pyridin]-4"(3"H)-one,
(9) 7-(2-chlorophenyl)-6-(4-chlorophenyl)-2,2-diethyl-2,3-dihydro-4H-pyrano[2,3-b]pyridin-4-one,
(10) 7-(2-chlorophenyl)-6-(4-chlorophenyl)-2-isopropyl-2-methyl-2,3-dihydro-4H-pyrano[2,3-b]pyridin-4-one,
(11) 7-(2-chlorophenyl)-6-(4-chlorophenyl)-2-ethyl-2-methyl-2,3-dihydro-4H-pyrano[2,3-b]pyridin-4-one,
(12) 2-tert-butyl-7-(2-chlorophenyl)-6-(4-chlorophenyl)-2,3-dihydro-4H-pyrano[2,3-b]pyridin-4-one,
(13) 7-(2-chlorophenyl)-6-(4-chlorophenyl)-2-isopropyl-2,3-dihydro-4H-pyrano[2,3-b]pyridin-4-one,
(14) 2-bicyclo[2.2.1]hept-5-en-2-yl-7-(2-chlorophenyl)-6-(4-chlorophenyl)-2,3-dihydro-4H-pyrano[2,3-b]pyridin-4-one,
(15) 7-(4-bromo-2-chlorophenyl)-2-tert-butyl-6-(4-chlorophenyl)-2,3-dihydro-4H-pyrano[2,3-b]pyridin-4-one,
(16) 7-(2-chlorophenyl)-6-(4-chlorophenyl)-2-isopropyl-3-methyl-2,3-dihydro-4H-pyrano[2,3-b]pyridin-4-one,
(17) (4'E)-7'-(2-chlorophenyl)-6'-(4-chlorophenyl)spiro[cyclohexane-1,2'-pyrano[2,3-b]pyridin]-4'(3'H)-one oxime,
(18) (4E)-6-(4-chlorophenyl)-7-(2,4-dichlorophenyl)-2,2-dimethyl-2,3-dihydro-4H-pyrano[2,3-b]pyridin-4-one oxime,
(19) (4E)-7-(2-chlorophenyl)-6-(4-chlorophenyl)-2',3',5',6'-tetrahydrospiro[pyrano[2,3-b]pyridine-2,4'-thiopyran]-4(3H)-one oxime,

(20) (4'E)-7'-(2-chlorophenyl)-6'-(4-chlorophenyl)spiro[cyclopentane-1,2'-pyrano[2,3-b]pyridin]-4'(3'H)-one oxime,

(21) (4E)-2-tert-butyl-7-(2-chlorophenyl)-6-(4-chlorophenyl)-2,3-dihydro-4H-pyrano[2,3-b]pyridin-4-one oxime,

(22) (4E)-6-(4-chlorophenyl)-7-(2,4-dichlorophenyl)-2-methyl-2,3-dihydro-4H-pyrano[2,3-b]pyridin-4-one oxime,

(23) 7'-(2-chlorophenyl)-6'-(4-chlorophenyl)-3',4'-dihydrospiro[cyclohexane-1,2'-pyrano[2,3-b]pyridin]-4'-amine,

(24) 6-(4-chlorophenyl)-7-(2,4-dichlorophenyl)-2,2-dimethyl-3,4-dihydro-2H-pyrano[2,3-b]pyridin-4-amine,

(25) 2-tert-butyl-7-(2-chlorophenyl)-6-(4-chlorophenyl)-3,4-dihydro-2H-pyrano[2,3-b]pyridin-4-amine,

(26) N-[7'-(2-chlorophenyl)-6'-(4-chlorophenyl)-3',4'-dihydrospiro[cyclohexane-1,2'-pyrano[2,3-b]pyridin]-4'-yl]acetamide,

(27) N-[6-(4-chlorophenyl)-7-(2,4-dichlorophenyl)-2,2-dimethyl-3,4-dihydro-2H-pyrano[2,3-b]pyridin-4-yl]acetamide,

(28) N-[7'-(2-chlorophenyl)-6'-(4-chlorophenyl)-3',4'-dihydrospiro[cyclohexane-1,2'-pyrano[2,3-b]pyridin]-4'-yl]-2-hydroxyacetamide,

(29) N-[7'-(2-chlorophenyl)-6'-(4-chlorophenyl)-3',4'-dihydrospiro[cyclohexane-1,2'-pyrano[2,3-b]pyridin]-4'-yl] isoxazole-5-carboxamide,

(30) N-[7-(2-chlorophenyl)-6-(4-chlorophenyl)-2',3,3',4,5',6'-hexahydrospiro[pyrano[2,3-b]pyridine-2,4'-thiopyran]-4-yl]-2-hydroxyacetamide,

(31) N-[7'-(2-chlorophenyl)-6'-(4-chlorophenyl)-3',4'-dihydrospiro[cyclopentane-1,2'-pyrano[2,3-b]pyridin]-4'-yl]-2-hydroxyacetamide,

(32) ethyl [7'-(2-chlorophenyl)-6'-(4-chlorophenyl)-3',4'-dihydrospiro[cyclohexane-1,2'-pyrano[2,3-b]pyridin]-4'-yl]carbamate,

(33) 3-chloro-N-[7'-(2-chlorophenyl)-6'-(4-chlorophenyl)-3',4'-dihydrospiro[cyclohexane-1,2'-pyrano[2,3-b]pyridin]-4'-yl]-2,2-dimethylpropanamide,

(34) N-[7'-(2-chlorophenyl)-6'-(4-chlorophenyl)-3',4'-dihydrospiro[cyclohexane-1,2'-pyrano[2,3-b]pyridin]-4'-yl]cyclopropanecarboxamide,

(35) 4-bromo-N-[7'-(2-chlorophenyl)-6'-(4-chlorophenyl)-3',4'-dihydrospiro[cyclohexane-1,2'-pyrano[2,3-b]pyridin]-4'-yl]butanamide,

(36) N-[6-(4-chlorophenyl)-7-(2,4-dichlorophenyl)-2,2-dimethyl-3,4-dihydro-2H-pyrano[2,3-b]pyridin-4-yl]-2-hydroxyacetamide,

(37) N-[7-(2-chlorophenyl)-6-(4-chlorophenyl)-2,2-dimethyl-3,4-dihydro-2H-pyrano[2,3-b]pyridin-4-yl]-2-hydroxyacetamide,

(38) (2R)-N-[2-tert-butyl-7-(2-chlorophenyl)-6-(4-chlorophenyl)-3,4-dihydro-2H-pyrano[2,3-b]pyridin-4-yl]-2-hydroxypropanamide,

(39) N-[6-(4-chlorophenyl)-7-(2,4-dichlorophenyl)-2,2-dimethyl-3,4-dihydro-2H-pyrano[2,3-b]pyridin-4-yl]-4,4,4-trifluoro-3-hydroxybutanamide,

(40) 3-(benzyloxy)-N-[6-(4-chlorophenyl)-7-(2,4-dichlorophenyl)-2,2-dimethyl-3,4-dihydro-2H-pyrano[2,3-b]pyridin-4-yl]-2,2-dimethylpropanamide,

(41) 1-[7'-(2-chlorophenyl)-6'-(4-chlorophenyl)-3',4'-dihydrospiro[cyclohexane-1,2'-pyrano[2,3-b]pyridin]-4'-yl]-3,3-dimethylazetidin-2-one,

(42) N-[6-(4-chlorophenyl)-7-(2,4-dichlorophenyl)-2,2-dimethyl-3,4-dihydro-2H-pyrano[2,3-b]pyridin-4-yl]-3-hydroxy-2,2-dimethylpropanamide,

(43) N-[7'-(2-chlorophenyl)-6'-(4-chlorophenyl)spiro[cyclohexane-1,2'-pyrano[2,3-b]pyridin]-4'-yl]acetamide,

(44) N-[2-tert-butyl-7-(2-chlorophenyl)-6-(4-chlorophenyl)-2H-pyrano[2,3-b]pyridin-4-yl]acetamide,

(45) 2-{[6-(4-chlorophenyl)-7-(2,4-dichlorophenyl)-2-methyl-2H-pyrano[2,3-b]pyridin-4-yl]amino}-2-oxoethyl acetate,

(46) 2-{[6-(4-chlorophenyl)-7-(2,4-dichlorophenyl)-2,2-dimethyl-2H-pyrano[2,3-b]pyridin-4-yl]amino}-2-oxoethyl acetate,

(47) N-[6-(4-chlorophenyl)-7-(2,4-dichlorophenyl)-2-methyl-2H-pyrano[2,3-b]pyridin-4-yl]-2-hydroxyacetamide,

(48) N-[6-(4-chlorophenyl)-7-(2,4-dichlorophenyl)-2,2-dimethyl-3,4-dihydro-2H-pyrano[2,3-b]pyridin-4-yl]-N'-methylethanediamide,

(49) 2-tert-butyl-7-(2-chlorophenyl)-6-(4-chlorophenyl)-3,4-dihydro-2H-pyrano[2,3-b]pyridin-4-ol,

(50) 6-(4-chlorophenyl)-7-(2,4-dichlorophenyl)-2,2-dimethyl-3,4-dihydro-2H-pyrano[2,3-b]pyridin-4-ol,

(51) ethyl {[6-(4-chlorophenyl)-7-(2,4-dichlorophenyl)-2,2-dimethyl-3,4-dihydro-2H-pyrano[2,3-b]pyridin-4-yl]oxy}acetate,

(52) 6-(4-chlorophenyl)-7-(2,4-dichlorophenyl)-2,2-dimethyl-3,4-dihydro-2H-pyrano[2,3-b]pyridin-4-yl acetate,

(53) 6-(4-chlorophenyl)-7-(2,4-dichlorophenyl)-2,2,3-trimethyl-3,4-dihydro-2H-pyrano[2,3-b]pyridin-4-ol,

(54) 3-bromo-6-(4-chlorophenyl)-7-(2,4-dichlorophenyl)-2,2-dimethyl-2,3-dihydro-4H-pyrano[2,3-b]pyridin-4-one,

(55) ethyl (2E)-[6-(4-chlorophenyl)-7-(2,4-dichlorophenyl)-2,2-dimethyl-2,3-dihydro-4H-pyrano[2,3-b]pyridin-4-ylidene]acetate,

(56) ethyl [6-(4-chlorophenyl)-7-(2,4-dichlorophenyl)-2,2-dimethyl-2H-pyrano[2,3-b]pyridin-4-yl]acetate,

(57) ethyl 2-[6-(4-chlorophenyl)-7-(2,4-dichlorophenyl)-2,2-dimethyl-2H-pyrano[2,3-b]pyridin-4-yl]-2-methylpropanoate,

(58) ethyl [6-(4-chlorophenyl)-7-(2,4-dichlorophenyl)-2,2-dimethyl-3,4-dihydro-2H-pyrano[2,3-b]pyridin-4-yl]acetate,

(59) 5-{[6-(4-chlorophenyl)-7-(2,4-dichlorophenyl)-2,2-dimethyl-3,4-dihydro-2H-pyrano[2,3-b]pyridin-4-yl]methyl}-1,3,4-oxadiazol-2(3H)-one,

(60) 7'-(2-chlorophenyl)-8'-(4-chlorophenyl)-1'H-spiro[cyclohexane-1,4'-pyrazolo[3',4':4,5]pyrano[2,3-b]pyridine],

(61) 7-(2-chlorophenyl)-6-(4-chlorophenyl)-2',3',5',6'-tetrahydrospiro[pyrano[2,3-b]pyridine-2,4'-thiopyran]-4(3H)-one 1',1'-dioxide,

(62) N-[7-(2-chlorophenyl)-6-(4-chlorophenyl)-1',1'-dioxido-2',3,3',4,5',6'-hexahydrospiro[pyrano[2,3-b]pyridine-2,4'-thiopyran]-4-yl]-2-hydroxyacetamide,

(63) 7-(2-chlorophenyl)-6-(4-chlorophenyl)-3-(piperidin-1-ylcarbonyl)-2H-pyrano[2,3-b]pyridin-2-one,

(64) 6-(4-chlorophenyl)-7-(2,4-dichlorophenyl)-4-ethoxy-2,2-dimethyl-3,4-dihydro-2H-pyrano[2,3-b]pyridine,

(65) 6-(4-chlorophenyl)-7-(2,4-dichlorophenyl)-4-methoxy-2,2-dimethyl-3,4-dihydro-2H-pyrano[2,3-b]pyridine,

(66) (2S)-N-[7'-(2-chlorophenyl)-6'-(4-chlorophenyl)-3',4'-dihydrospiro[cyclohexane-1,2'-pyrano[2,3-b]pyridin]-4'-yl]-2-hydroxypropanamide,

(67) (2R)-N-[7'-(2-chlorophenyl)-6'-(4-chlorophenyl)-3',4'-dihydrospiro[cyclohexane-1,2'-pyrano[2,3-b]pyridin]-4'-yl]-2-hydroxypropanamide,

(68) N-[7'-(2-chlorophenyl)-6'-(4-chlorophenyl)-3',4'-dihydrospiro[cyclohexane-1,2'-pyrano[2,3-b]pyridin]-4'-yl]-2-hydroxy-2-methylpropanamide,

(69) N-[6-(4-chlorophenyl)-7-(2,4-dichlorophenyl)-2,2-dimethyl-3,4-dihydro-2H-pyrano[2,3-b]pyridin-4-yl]-2-hydroxy-2-methylpropanamide,

(70) (2S)-N-[6-(4-chlorophenyl)-7-(2,4-dichlorophenyl)-2,2-dimethyl-3,4-dihydro-2H-pyrano[2,3-b]pyridin-4-yl]-2-hydroxypropanamide,

(71) (2R)-N-[6-(4-chlorophenyl)-7-(2,4-dichlorophenyl)-2,2-dimethyl-3,4-dihydro-2H-pyrano[2,3-b]pyridin-4-yl]-2-hydroxypropanamide,

(72) N-[7'-(2-chlorophenyl)-6'-(4-chlorophenyl)-3',4'-dihydrospiro[cyclohexane-1,2'-pyrano[2,3-b]pyridin]-4'-yl]-2-methylpropanamide,

(73) N-[7'-(2-chlorophenyl)-6'-(4-chlorophenyl)-3',4'-dihydrospiro[cyclohexane-1,2'-pyrano[2,3-b]pyridin]-4'-yl]propanamide,

(74) N-[7'-(2-chlorophenyl)-6'-(4-chlorophenyl)-3',4'-dihydrospiro[cyclohexane-1,2'-pyrano[2,3-b]pyridin]-4'-yl]propane-1-sulfonamide,

(75) 3-chloro-N-[7'-(2-chlorophenyl)-6'-(4-chlorophenyl)-3',4'-dihydrospiro[cyclohexane-1,2'-pyrano[2,3-b]pyridin]-4'-yl]propane-1-sulfonamide,

(76) N-[6-(4-chlorophenyl)-7-(2,4-dichlorophenyl)-2,2-dimethyl-3,4-dihydro-2H-pyrano[2,3-b]pyridin-4-yl]methanesulfonamide,

(77) N'-[6-(4-chlorophenyl)-7-(2,4-dichlorophenyl)-2,2-dimethyl-3,4-dihydro-2H-pyrano[2,3-b]pyridin-4-yl]-N,N-dimethylsulfamide,

(78) N'-[6-(4-chlorophenyl)-7-(2,4-dichlorophenyl)-2,2-dimethyl-3,4-dihydro-2H-pyrano[2,3-b]pyridin-4-yl]-N,N-dimethylurea,

(79) 7'-(2-chlorophenyl)-6'-(4-chlorophenyl)-4'-(1,1-dioxidoisothiazolidin-2-yl)-3',4'-dihydrospiro[cyclohexane-1,2'-pyrano[2,3-b]pyridine],

(80) 1-[6-(4-chlorophenyl)-7-(2,4-dichlorophenyl)-2,2-dimethyl-3,4-dihydro-2H-pyrano[2,3-b]pyridin-4-yl]imidazolidine-2,4-dione,

(81) 7-(2-chlorophenyl)-6-(4-chlorophenyl)-2,2-dimethyl-4-pyridin-4-yl-2H-pyrano[2,3-b]pyridine,

(82) 7-(2-chlorophenyl)-6-(4-chlorophenyl)-2,2-dimethyl-4-(1-methyl-1H-pyrazol-4-yl)-2H-pyrano[2,3-b]pyridine,

(83) 7-(2-chlorophenyl)-6-(4-chlorophenyl)-4-(4-fluorophenyl)-2,2-dimethyl-2H-pyrano[2,3-b]pyridine,

(84) 6-(4-chlorophenyl)-7-(2,4-dichlorophenyl)-2,2-dimethyl-4-(1H-pyrazol-4-yl)-2H-pyrano[2,3-b]pyridine,

(85) 6-(4-chlorophenyl)-7-(2,4-dichlorophenyl)-2,2-dimethyl-4-(1H-pyrazol-3-yl)-2H-pyrano[2,3-b]pyridine,

(86) 7-(2-chlorophenyl)-6-(4-chlorophenyl)-2,2-dimethyl-2H-pyrano[2,3-b]pyridine-4-carboxylic acid,

(87) methyl 7-(2-chlorophenyl)-6-(4-chlorophenyl)-2,2-dimethyl-3,4-dihydro-2H-pyrano[2,3-b]pyridine-4-carboxylate,

(88) methyl 6-(4-chlorophenyl)-7-(2,4-dichlorophenyl)-2,2-dimethyl-2H-pyrano[2,3-b]pyridine-4-carboxylate,

(89) 7-(2-chlorophenyl)-6-(4-chlorophenyl)-N-(2-hydroxyethyl)-2,2-dimethyl-3,4-dihydro-2H-pyrano[2,3-b]pyridine-4-carboxamide,

(90) 6-(4-chlorophenyl)-7-(2,4-dichlorophenyl)-N-(2-hydroxy-1,1-dimethylethyl)-2,2-dimethyl-3,4-dihydro-2H-pyrano[2,3-b]pyridine-4-carboxamide,

(91) 6-(4-chlorophenyl)-7-(2,4-dichlorophenyl)-N-isopropyl-2,2-dimethyl-3,4-dihydro-2H-pyrano[2,3-b]pyridine-4-carboxamide,

(92) 6-(4-chlorophenyl)-7-(2,4-dichlorophenyl)-2,2-dimethyl-N-(3,3,3-trifluoro-2-hydroxypropyl)-3,4-dihydro-2H-pyrano[2,3-b]pyridine-4-carboxamide,

(93) 7'-(2-chlorophenyl)-6'-(4-chlorophenyl)-3'-methylspiro[cyclohexane-1,2'-pyrano[2,3-b]pyridin]-4'(3'H)-one,

(94) 7'-(2-chlorophenyl)-6'-(4-chlorophenyl)-3',3'-dimethylspiro[cyclohexane-1,2'-pyrano[2,3-b]pyridin]-4'(3'H)-one,

(95) 7-(2-chlorophenyl)-6-(4-chlorophenyl)-2-isopropyl-2-methyl-3,4-dihydro-2H-pyrano[2,3-b]pyridin-4-ol,

(96) 7-(2-chlorophenyl)-6-(4-chlorophenyl)-2-ethyl-2-methyl-3,4-dihydro-2H-pyrano[2,3-b]pyridin-4-ol,

(97) N-{7-(2-chlorophenyl)-6-(4-chlorophenyl)-2-methyl-2-[(methylsulfonyl)methyl]-3,4-dihydro-2H-pyrano[2,3-b]pyridin-4-yl}acetamide,

(98) 7-(2-chlorophenyl)-6-(4-chlorophenyl)-2-(3-fluorophenyl)-2,3-dihydro-4H-pyrano[2,3-b]pyridin-4-one,

(99) N-[7-(2-chlorophenyl)-6-(4-chlorophenyl)-2-(hydroxymethyl)-2-methyl-3,4-dihydro-2H-pyrano[2,3-b]pyridin-4-yl]acetamide, (100) (2S)-N-[6-(4-chlorophenyl)-7-(2,4-dichlorophenyl)-2-(hydroxymethyl)-2-methyl-3,4-dihydro-2H-pyrano[2,3-b]pyridin-4-yl]-2-hydroxypropanamide, (101) 6-(4-chlorophenyl)-7-(2,4-dichlorophenyl)-2,2-dimethyl-4-(5-methyl-1,3,4-oxadiazol-2-yl)-3,4-dihydro-2H-pyrano[2,3-b]pyridine, (102) 6-(4-chlorophenyl)-7-(2,4-dichlorophenyl)-4-(5-isopropyl-1,3,4-oxadiazol-2-yl)-2,2-dimethyl-3,4-dihydro-2H-pyrano[2,3-b]pyridine, (103) 6-(4-chlorophenyl)-7-(2,4-dichlorophenyl)-4-(5-isopropyl-1,3,4-oxadiazol-2-yl)-2,2-dimethyl-2H-pyrano[2,3-b]pyridine, (104) (3S)-1-[6-(4-chlorophenyl)-7-(2,4-dichlorophenyl)-2,2-dimethyl-3,4-dihydro-2H-pyrano[2,3-b]pyridin-4-yl]-3-hydroxypyrrolidine-2,5-dione, (105) N-[6-(4-chlorophenyl)-7-(2,4-dichlorophenyl)-2,2-dimethyl-3,4-dihydro-2H-pyrano[2,3-b]pyridin-4-yl]glycinamide, (106) N-[6-(4-chlorophenyl)-7-(2,4-dichlorophenyl)-2,2-dimethyl-3,4-dihydro-2H-pyrano[2,3-b]pyridin-4-yl]-N-2-methylglycinamide, (107) N-[6-(4-chlorophenyl)-7-(2,4-dichlorophenyl)-2,2-dimethyl-3,4-dihydro-2H-pyrano[2,3-b]pyridin-4-yl]-2-methylalaninamide, (108) ethyl 4-{[6-(4-chlorophenyl)-7-(2,4-dichlorophenyl)-2,2-dimethyl-3,4-dihydro-2H-pyrano[2,3-b]pyridin-4-yl]amino}-3,3-dimethyl-4-oxobutanoate, (109) ethyl [6-(4-chlorophenyl)-7-(2,4-dichlorophenyl)-2,2-dimethyl-3,4-dihydro-2H-pyrano[2,3-b]pyridin-4-yl]carbamate, (110) N-[6-(4-chlorophenyl)-7-(2,4-dichlorophenyl)-2,2-dimethyl-3,4-dihydro-2H-pyrano[2,3-b]pyridin-4-yl]-3,3,3-trifluoro-2-hydroxy-2-methylpropanamide, (111) N-[6-(4-chlorophenyl)-7-(2,4-dichlorophenyl)-2,2-dimethyl-3,4-dihydro-2H-pyrano[2,3-b]pyridin-4-yl]-3,3,3-trifluoro-2-hydroxypropanamide, (112) N-[6-(4-chlorophenyl)-7-(2,4-dichlorophenyl)-2,2-dimethyl-3,4-dihydro-2H-pyrano[2,3-b]pyridin-4-yl]-3,3,3-trifluoroalaninamide, (113) N-[6-(4-chlorophenyl)-7-(2,4-dichlorophenyl)-2,2-dimethyl-3,4-dihydro-2H-pyrano[2,3-b]pyridin-4-yl]-2,2-difluoro-3-hydroxypropanamide, (114) N-[6-(4-chlorophenyl)-7-(2,4-dichlorophenyl)-2,2-dimethyl-3,4-dihydro-2H-pyrano[2,3-b]pyridin-4-yl]-3,3,3-trifluoro-2-hydroxy-2-(trifluoromethyl)propanamide,
(115) N-[6-(4-chlorophenyl)-7-(2,4-dichlorophenyl)-2,2-dimethyl-3,4-dihydro-2H-pyrano[2,3-b]pyridin-4-yl]-4,4,4-trifluoro-3-hydroxy-3-(trifluoromethyl)butanamide,
(116) N-[6-(4-chlorophenyl)-7-(2,4-dichlorophenyl)-2,2-dimethyl-3,4-dihydro-2H-pyrano[2,3-b]pyridin-4-yl]-1-hydroxycyclopropanecarboxamide,
(117) N-[6-(4-bromophenyl)-7-(2,4-dichlorophenyl)-2,2-dimethyl-3,4-dihydro-2H-pyrano[2,3-b]pyridin-4-yl]-2-hydroxy-2-methylpropanamide,
(118) N-[6-(4-cyanophenyl)-7-(2,4-dichlorophenyl)-2,2-dimethyl-3,4-dihydro-2H-pyrano[2,3-b]pyridin-4-yl]-2-hydroxy-2-methylpropanamide,
(119) N-[7-(2,4-dichlorophenyl)-2,2-dimethyl-6-(4-methylphenyl)-3,4-dihydro-2H-pyrano[2,3-b]pyridin-4-yl]-2-hydroxy-2-methylpropanamide,
(120) N-[7-(2,4-dichlorophenyl)-2,2-dimethyl-6-(4-methylphenyl)-3,4-dihydro-2H-pyrano[2,3-b]pyridin-4-yl]-2-hydroxyacetamide,
(121) N-{7-(2,4-dichlorophenyl)-2,2-dimethyl-6-[4-(trifluoromethyl)phenyl]-3,4-dihydro-2H-pyrano[2,3-b]pyridin-4-yl}-2-hydroxy-2-methylpropanamide,
(122) N-{7-(2,4-dichlorophenyl)-2,2-dimethyl-6-[4-(trifluoromethyl)phenyl]-3,4-dihydro-2H-pyrano[2,3-b]pyridin-4-yl}-3,3,3-trifluoro-2-hydroxypropanamide,
(123) N-{7-(2,4-dichlorophenyl)-2,2-dimethyl-6-[4-(trifluoromethyl)phenyl]-3,4-dihydro-2H-pyrano[2,3-b]pyridin-4-yl}-5-methyl-1H-pyrazole-3-carboxamide,
(124) N-[7-(2,4-dichlorophenyl)-6-(4-methoxyphenyl)-2,2-dimethyl-3,4-dihydro-2H-pyrano[2,3-b]pyridin-4-yl]-2-hydroxy-2-methylpropanamide,
(125) N-[7-(2-chloro-4-methoxyphenyl)-6-(4-chlorophenyl)-2,2-dimethyl-3,4-dihydro-2H-pyrano[2,3-b]pyridin-4-yl]-2-hydroxyacetamide,
(126) N-[7-(2,4-dichlorophenyl)-6-(4-methoxyphenyl)-2,2-dimethyl-3,4-dihydro-2H-pyrano[2,3-b]pyridin-4-yl]-3,3,3-trifluoro-2-hydroxypropanamide,
(127) N-[7-(4-bromo-2-chlorophenyl)-6-(4-chlorophenyl)-2,2-dimethyl-3,4-dihydro-2H-pyrano[2,3-b]pyridin-4-yl]-2-hydroxy-2-methylpropanamide,
(128) (2S)-N-[7-(4-bromo-2-chlorophenyl)-6-(4-chlorophenyl)-2,2-dimethyl-3,4-dihydro-2H-pyrano[2,3-b]pyridin-4-yl]-2-hydroxypropanamide,
(129) N-[7-(4-bromo-2-chlorophenyl)-6-(4-chlorophenyl)-2,2-dimethyl-3,4-dihydro-2H-pyrano[2,3-b]pyridin-4-yl]glycinamide,
(130) N-[7-(4-bromo-2-chlorophenyl)-6-(4-chlorophenyl)-2,2-dimethyl-3,4-dihydro-2H-pyrano[2,3-b]pyridin-4-yl]-2-methylalaninamide,
(131) N-[7-(2-chloro-4-cyanophenyl)-6-(4-chlorophenyl)-2,2-dimethyl-3,4-dihydro-2H-pyrano[2,3-b]pyridin-4-yl]-2-hydroxy-2-methylpropanamide,
(132) tert-butyl [7-(2-chloro-4-cyanophenyl)-6-(4-chlorophenyl)-2,2-dimethyl-3,4-dihydro-2H-pyrano[2,3-b]pyridin-4-yl]carbamate,
(133) (2S)-N-[7-(2-chloro-4-cyanophenyl)-6-(4-chlorophenyl)-2,2-dimethyl-3,4-dihydro-2H-pyrano[2,3-b]pyridin-4-yl]-2-hydroxypropanamide,
(134) N-[7-(2-chloro-4-cyanophenyl)-6-(4-chlorophenyl)-2,2-dimethyl-3,4-dihydro-2H-pyrano[2,3-b]pyridin-4-yl]-3,3,3-trifluoro-2-hydroxypropanamide,
(135) N-[(4R)-7-(2-chloro-4-cyanophenyl)-6-(4-chlorophenyl)-2,2-dimethyl-3,4-dihydro-2H-pyrano[2,3-b]pyridin-4-yl]-4-methyl-1H-pyrazole-3-carboxamide,
(136) N-[7-(2-chloro-4-methylphenyl)-6-(4-chlorophenyl)-2,2-dimethyl-3,4-dihydro-2H-pyrano[2,3-b]pyridin-4-yl]-2-hydroxy-2-methylpropanamide,
(137) N-[7-(2-chloro-4-methoxyphenyl)-6-(4-chlorophenyl)-2,2-dimethyl-3,4-dihydro-2H-pyrano[2,3-b]pyridin-4-yl]-2-hydroxy-2-methylpropanamide,
(138) N-[7-(2-chloro-4-methoxyphenyl)-6-(4-chlorophenyl)-2,2-dimethyl-3,4-dihydro-2H-pyrano[2,3-b]pyridin-4-yl]-2-hydroxy-4-methylpentanamide,
(139) N-[7-(2-chloro-4-hydroxyphenyl)-6-(4-chlorophenyl)-2,2-dimethyl-3,4-dihydro-2H-pyrano[2,3-b]pyridin-4-yl]-2,2-dimethylpropanamide,
(140) N-[7-(2-bromo-4-chlorophenyl)-6-(4-chlorophenyl)-2,2-dimethyl-3,4-dihydro-2H-pyrano[2,3-b]pyridin-4-yl]-2-hydroxy-2-methylpropanamide,
(141) methyl 4-{[7-(2-bromo-4-chlorophenyl)-6-(4-chlorophenyl)-2,2-dimethyl-3,4-dihydro-2H-pyrano[2,3-b]pyridin-4-yl]amino}-4-oxobutanoate,
(142) N-[7-(4-chloro-2-cyanophenyl)-6-(4-chlorophenyl)-2,2-dimethyl-3,4-dihydro-2H-pyrano[2,3-b]pyridin-4-yl]-2-hydroxy-2-methylpropanamide,
(143) N-[7-(4-chloro-2-methylphenyl)-6-(4-chlorophenyl)-2,2-dimethyl-3,4-dihydro-2H-pyrano[2,3-b]pyridin-4-yl]-2-hydroxy-2-methylpropanamide,
(144) N-[7-[2,4-bis(trifluoromethyl)phenyl]-6-(4-chlorophenyl)-2,2-dimethyl-3,4-dihydro-2H-pyrano[2,3-b]pyridin-4-yl]-2-hydroxy-2-methylpropanamide,
(145) tert-butyl [6-(4-chlorophenyl)-7-(2,4-dicyanophenyl)-2,2-dimethyl-3,4-dihydro-2H-pyrano[2,3-b]pyridin-4-yl]carbamate,
(146) 6-(4-chlorophenyl)-7-(2,4-dichlorophenyl)-2,2-dimethyl-N-pyridin-2-yl-3,4-dihydro-2H-pyrano[2,3-b]pyridin-4-amine,
(147) 6-(4-chlorophenyl)-7-(2,4-dichlorophenyl)-2,2-dimethyl-N-(5-methyl-1H-pyrazol-3-yl)-3,4-dihydro-2H-pyrano[2,3-b]pyridin-4-amine,
(148) N-[6'-(4-bromophenyl)-7'-(2-chlorophenyl)-3',4'-dihydrospiro[cyclohexane-1,2'-pyrano[2,3-b]pyridin]-4'-yl]-2-hydroxy-2-methylpropanamide,
(149) N-[6-(4-chlorophenyl)-7-(2,5-dichlorophenyl)-2,2-dimethyl-3,4-dihydro-2H-pyrano[2,3-b]pyridin-4-yl]-2-hydroxy-2-methylpropanamide,
(150) N-[6-(4-chlorophenyl)-7-(2,5-dichlorophenyl)-2,2-dimethyl-3,4-dihydro-2H-pyrano[2,3-b]pyridin-4-yl]-2-methylalaninamide,
(151) N-[6-(4-chlorophenyl)-7-(2,5-dichlorophenyl)-2,2-dimethyl-3,4-dihydro-2H-pyrano[2,3-b]pyridin-4-yl]-3,3,3-trifluoro-2-hydroxypropanamide,
(152) N-[6-(4-chlorophenyl)-7-(2,5-dichlorophenyl)-2,2-dimethyl-3,4-dihydro-2H-pyrano[2,3-b]pyridin-4-yl]-5-methyl-1H-pyrazole-3-carboxamide,
(153) N-[7-(5-bromo-2-chlorophenyl)-6-(4-chlorophenyl)-2,2-dimethyl-3,4-dihydro-2H-pyrano[2,3-b]pyridin-4-yl]-2-hydroxy-2-methylpropanamide,
(154) (2S)-N-[7-(5-bromo-2-chlorophenyl)-6-(4-chlorophenyl)-2,2-dimethyl-3,4-dihydro-2H-pyrano[2,3-b]pyridin-4-yl]-2-hydroxypropanamide,
(155) N-[7-(5-bromo-2-chlorophenyl)-6-(4-chlorophenyl)-2,2-dimethyl-3,4-dihydro-2H-pyrano[2,3-b]pyridin-4-yl]-2-hydroxy-3-methylbutanamide,
(156) tert-butyl [7-(5-bromo-2-chlorophenyl)-6-(4-chlorophenyl)-2,2-dimethyl-3,4-dihydro-2H-pyrano[2,3-b]pyridin-4-yl]carbamate, (157) N-[7-(5-bromo-2-chlorophenyl)-6-(4-chlorophenyl)-2,2-dimethyl-3,4-dihydro-2H-pyrano[2,3-b]pyridin-4-yl]-5-methyl-1H-pyrazole-3-carboxamide, (158) N-[7-(2-chloro-5-cyanophenyl)-6-(4-chlorophenyl)-2,2-dimethyl-3,4-dihydro-2H-pyrano[2,3-b]pyridin-4-yl]-2-hydroxy-2-methylpropanamide, (159) N-[7-(2-chloro-5-methylphenyl)-6-(4-chlorophenyl)-2,2-dimethyl-3,4-dihydro-2H-pyrano[2,3-b]pyridin-4-yl]-2-hydroxy-2-methylpropanamide, (160) N-[7-(2-chloro-5-methylphenyl)-6-(4-chlorophenyl)-2,2-dimethyl-3,4-dihydro-2H-pyrano[2,3-b]pyridin-4-yl]-2-methylalaninamide, (161) N-{6-(4-chlorophenyl)-7-[2-chloro-5-(trifluoromethyl)phenyl]-2,2-dimethyl-3,4-dihydro-2H-pyrano[2,3-b]pyridin-4-yl}-2-hydroxy-2-methylpropanamide, (162) N-{6-(4-chlorophenyl)-7-[2-chloro-5-(trifluoromethyl)phenyl]-2,2-dimethyl-3,4-dihydro-2H-pyrano[2,3-b]pyridin-4-yl}-3,3,3-trifluoro-2-hydroxypropanamide, (163) N-{6-(4-chlorophenyl)-7-[2-chloro-5-(trifluoromethyl)phenyl]-2,2-dimethyl-3,4-dihydro-2H-pyrano[2,3-b]pyridin-4-yl}-5-methyl-1H-pyrazole-3-carboxamide, (164) N-[7-(2-bromo-5-chlorophenyl)-6-(4-chlorophenyl)-2,2-dimethyl-3,4-dihydro-2H-pyrano[2,3-b]pyridin-4-yl]-3,3,3-trifluoro-2-hydroxypropanamide, (165) N-[7-(5-chloro-2-cyanophenyl)-6-(4-chlorophenyl)-2,2-dimethyl-3,4-dihydro-2H-pyrano[2,3-b]pyridin-4-yl]-3,3,3-trifluoro-2-hydroxypropanamide, (166) N-{6-(4-chlorophenyl)-7-[5-chloro-2-(trifluoromethyl)phenyl]-2,2-dimethyl-3,4-dihydro-2H-pyrano[2,3-b]pyridin-4-yl}-2-hydroxy-2-methylpropanamide, (167) N-[6-(4-chloro-3-methoxyphenyl)-7-(2,4-dichlorophenyl)-2,2-dimethyl-3,4-dihydro-2H-pyrano[2,3-b]pyridin-4-yl]-2-hydroxy-2-methylpropanamide, (168) (2S)-N-[6-(4-chloro-3-methoxyphenyl)-7-(2,4-dichlorophenyl)-2,2-dimethyl-3,4-dihydro-2H-pyrano[2,3-b]pyridin-4-yl]-2-hydroxypropanamide, (169) N-[6-(4-chloro-3-methoxyphenyl)-7-(2,4-dichlorophenyl)-2,2-dimethyl-3,4-dihydro-2H-pyrano[2,3-b]pyridin-4-yl]-2-hydroxy-3-methylbutanamide, (170) N-[6-(4-chloro-3-methoxyphenyl)-7-(2,4-dichlorophenyl)-2,2-dimethyl-3,4-dihydro-2H-pyrano[2,3-b]pyridin-4-yl]-2-hydroxybenzamide, (171) N-[6-(4-chloro-3-methoxyphenyl)-7-(2,4-dichlorophenyl)-2,2-dimethyl-3,4-dihydro-2H-pyrano[2,3-b]pyridin-4-yl]-2-cyclohexyl-2-hydroxyacetamide, (172) 1-[7-(4-bromo-2-chlorophenyl)-6-(4-chlorophenyl)-2,2-dimethyl-3,4-dihydro-2H-pyrano[2,3-b]pyridin-4-yl]pyrrolidin-2-one, (173) 1-[6-(4-chlorophenyl)-7-(2,4-dichlorophenyl)-2,2-dimethyl-3,4-dihydro-2H-pyrano[2,3-b]pyridin-4-yl]piperidin-2-one, (174) (3R)-1-[7-(4-bromo-2-chlorophenyl)-6-(4-chlorophenyl)-2,2-dimethyl-3,4-dihydro-2H-pyrano[2,3-b]pyridin-4-yl]-3-hydroxypyrrolidin-2-one, (175) 1-[6-(4-chlorophenyl)-7-(2,4-dichlorophenyl)-2,2-dimethyl-3,4-dihydro-2H-pyrano[2,3-b]pyridin-4-yl]imidazolidin-2-one, (176) 1-[6-(4-chlorophenyl)-7-(2,4-dichlorophenyl)-2,2-dimethyl-3,4-dihydro-2H-pyrano[2,3-b]pyridin-4-yl]piperazin-2-one, (177) 4-[6-(4-chlorophenyl)-7-(2,4-dichlorophenyl)-2,2-dimethyl-3,4-dihydro-2H-pyrano[2,3-b]pyridin-4-yl]-2,4-dihydro-3H-1,2,4-triazol-3-one, (178) tert-butyl [7-(4-bromo-2-chlorophenyl)-6-(4-chlorophenyl)-2,2-dimethyl-3,4-dihydro-2H-pyrano[2,3-b]pyridin-4-yl]carbamate, (179) methyl 4-[4-[(tert-butoxycarbonyl)amino]-6-(4-chlorophenyl)-2,2-dimethyl-3,4-dihydro-2H-pyrano[2,3-b]pyridin-7-yl]-3-chlorobenzoate, (180) N-[7-[2-chloro-4-(5-oxo-4,5-dihydro-1,3,4-oxadiazol-2-yl)phenyl]-6-(4-chlorophenyl)-2,2-dimethyl-3,4-dihydro-2H-pyrano[2,3-b]pyridin-4-yl]-2,2-dimethylpropanamide, (181) N-[7-(2-chloro-4-cyanophenyl)-6-(4-chlorophenyl)-2,2-dimethyl-3,4-dihydro-2H-pyrano[2,3-b]pyridin-4-yl]-2,2-dimethylpropanamide, (182) N-[7-[2-chloro-4-(1,2,4-oxadiazol-3-yl)phenyl]-6-(4-chlorophenyl)-2,2-dimethyl-3,4-dihydro-2H-pyrano[2,3-b]pyridin-4-yl]-2,2-dimethylpropanamide, (183) N-[7-[4-chloro-2-(1,2,4-oxadiazol-3-yl)phenyl]-6-(4-chlorophenyl)-2,2-dimethyl-3,4-dihydro-2H-pyrano[2,3-b]pyridin-4-yl]-2-hydroxy-2-methylpropanamide, (184) N-[7-[2-chloro-4-(5-methyl-1,2,4-oxadiazol-3-yl)phenyl]-6-(4-chlorophenyl)-2,2-dimethyl-3,4-dihydro-2H-pyrano[2,3-b]pyridin-4-yl]-2,2-dimethylpropanamide, (185) N-[7-[2-chloro-4-(1,2,4-oxadiazol-3-yl)phenyl]-6-(4-chlorophenyl)-2,2-dimethyl-3,4-dihydro-2H-pyrano[2,3-b]pyridin-4-yl]-3,3,3-trifluoro-2-hydroxypropanamide, (186) (4S)-6-(4-chlorophenyl)-7-(2,4-dichlorophenyl)-2,2-dimethyl-3,4-dihydro-2H-pyrano[2,3-b]pyridin-4-yl benzoate, (187) N-[(4R)-6-(4-chlorophenyl)-7-(2,4-dichlorophenyl)-2,2-dimethyl-3,4-dihydro-2H-pyrano[2,3-b]pyridin-4-yl]-5-methyl-1H-pyrazole-3-carboxamide, (188) N-[(4R)-6-(4-chlorophenyl)-7-(2,4-dichlorophenyl)-2,2-dimethyl-3,4-dihydro-2H-pyrano[2,3-b]pyridin-4-yl]acetamide, (189) N-[(4R)-6-(4-chlorophenyl)-7-(2,4-dichlorophenyl)-2,2-dimethyl-3,4-dihydro-2H-pyrano[2,3-b]pyridin-4-yl]-2-fluorobenzamide, (190) 2-amino-N-[(4R)-6-(4-chlorophenyl)-7-(2,4-dichlorophenyl)-2,2-dimethyl-3,4-dihydro-2H-pyrano[2,3-b]pyridin-4-yl]benzamide, (191) N-[(4R)-6-(4-chlorophenyl)-7-(2,4-dichlorophenyl)-2,2-dimethyl-3,4-dihydro-2H-pyrano[2,3-b]pyridin-4-yl]-2H-indazole-3-carboxamide, (192) N-[(4R)-6-(4-chlorophenyl)-7-(2,4-dichlorophenyl)-2,2-dimethyl-3,4-dihydro-2H-pyrano[2,3-b]pyridin-4-yl]-2-hydroxybenzamide, (193) 2-amino-N-[(4R)-6-(4-chlorophenyl)-7-(2,4-dichlorophenyl)-2,2-dimethyl-3,4-dihydro-2H-pyrano[2,3-b]pyridin-4-yl]-5-fluorobenzamide, (194) N-[(4R)-6-(4-chlorophenyl)-7-(2,4-dichlorophenyl)-2,2-dimethyl-3,4-dihydro-2H-pyrano[2,3-b]pyridin-4-yl]-1,4,5,6-tetrahydrocyclopenta[c]pyrazole-3-carboxamide, (195) N-[(4R)-6-(4-chlorophenyl)-7-(2,4-dichlorophenyl)-2,2-dimethyl-3,4-dihydro-2H-pyrano[2,3-b]pyridin-4-yl]-4,5,6,7-tetrahydro-1H-indazole-3-carboxamide, (196) 5-tert-butyl-N-[(4R)-6-(4-chlorophenyl)-7-(2,4-dichlorophenyl)-2,2-dimethyl-3,4-dihydro-2H-pyrano[2,3-b]pyridin-4-yl]-1H-pyrazole-3-carboxamide, (197) N-[(4R)-6-(4-chlorophenyl)-7-(2,4-dichlorophenyl)-2,2-dimethyl-3,4-dihydro-2H-pyrano[2,3-b]pyridin-4-yl]-4-methyl-1H-pyrazole-3-carboxamide, (198) N-[(4R)-6-(4-chlorophenyl)-7-(2,4-dichlorophenyl)-2,2-dimethyl-3,4-dihydro-2H-pyrano[2,3-b]pyridin-4-yl]-4,5-dimethyl-1H-pyrazole-3-carboxamide, (199) N-[(4R)-6-(4-chlorophenyl)-7-(2,4-dichlorophenyl)-2,2-dimethyl-3,4-dihydro-2H-pyrano[2,3-b]pyridin-4-yl]-3,5-dimethyl-1H-pyrazole-4-carboxamide, (200) N-[(4R)-6-(4-chlorophenyl)-7-(2,4-dichlorophenyl)-2,2-dimethyl-3,4-dihydro-2H-pyrano[2,3-b]pyridin-4-yl]-5-ethyl-1H-pyrazole-3-carboxamide, (201) N-[(4R)-6-(4-chlorophenyl)-7-(2,4-dichlorophenyl)-2,2-dimethyl-3,4-dihydro-2H-pyrano[2,3-b]pyridin-4-yl]-1H-pyrazole-4-carboxamide, (202) N-[(4R)-6-(4-chlorophenyl)-7-(2,4-dichlorophenyl)-2,2-dimethyl-3,4-dihydro-2H-pyrano[2,3-b]pyridin-4-yl]-3-methyl-1H-pyrazole-4-carboxamide, (203) 3-amino-N-[(4R)-6-(4-chlorophenyl)-7-(2,4-dichlorophenyl)-2,2-dimethyl-3,4-dihydro-2H-pyrano[2,3-b]pyridin-4-yl]-1H-1,2,4-triazole-5-carboxamide, (204) N-[(4R)-6-(4-chlorophenyl)-7-(2,4-dichlorophenyl)-2,2-dimethyl-3,4-dihydro-2H-pyrano[2,3-b]pyridin-4-yl]-3-methyl-1H-1,2,4-triazole-5-carboxamide, (205) N-[(4R)-6-(4-chlorophenyl)-7-(2,4-dichlorophenyl)-2,2-dimethyl-3,4-dihydro-2H-pyrano[2,3-b]pyridin-4-yl]-3-(trifluoromethyl)-1H-pyrazole-5-carboxamide, (206) N-[(4R)-6-(4-chlorophenyl)-7-(2,4-dichlorophenyl)-2,2-dimethyl-3,4-dihydro-2H-pyrano[2,3-b]pyridin-4-yl]-5-nitro-1H-pyrazole-3-carboxamide, (207) N-[(4R)-6-(4-chlorophenyl)-7-(2,4-dichlorophenyl)-2,2-dimethyl-3,4-dihydro-2H-pyrano[2,3-b]pyridin-4-yl]-1H-imidazole-4-carboxamide, (208) 3-chloro-N-[(4R)-6-(4-chlorophenyl)-7-(2,4-dichlorophenyl)-2,2-dimethyl-3,4-dihydro-2H-pyrano[2,3-b]pyridin-4-yl]benzamide, (209) N-[(4R)-6-(4-chlorophenyl)-7-(2,4-dichlorophenyl)-2,2-dimethyl-3,4-dihydro-2H-pyrano[2,3-b]pyridin-4-yl]-3-fluorobenzamide, (210) N-[(4R)-6-(4-chlorophenyl)-7-(2,4-dichlorophenyl)-2,2-dimethyl-3,4-dihydro-2H-pyrano[2,3-b]pyridin-4-yl]-4-fluorobenzamide, (211) N-[(4R)-6-(4-chlorophenyl)-7-(2,4-dichlorophenyl)-2,2-dimethyl-3,4-dihydro-2H-pyrano[2,3-b]pyridin-4-yl]-1H-indazole-4-carboxamide, (212) 2-chloro-N-[(4R)-6-(4-chlorophenyl)-7-(2,4-dichlorophenyl)-2,2-dimethyl-3,4-dihydro-2H-pyrano[2,3-b]pyridin-4-yl]nicotinamide, (213) N-[(4R)-6-(4-chlorophenyl)-7-(2,4-dichlorophenyl)-2,2-dimethyl-3,4-dihydro-2H-pyrano[2,3-b]pyridin-4-yl]tetrahydrofuran-3-carboxamide, (214) 6-chloro-N-[(4R)-6-(4-chlorophenyl)-7-(2,4-dichlorophenyl)-2,2-dimethyl-3,4-dihydro-2H-pyrano[2,3-b]pyridin-4-yl]pyridine-2-carboxamide, (215) 4-chloro-N-[(4R)-6-(4-chlorophenyl)-7-(2,4-dichlorophenyl)-2,2-dimethyl-3,4-dihydro-2H-pyrano[2,3-b]pyridin-4-yl]benzamide, (216) N-[(4R)-6-(4-chlorophenyl)-7-(2,4-dichlorophenyl)-2,2-dimethyl-3,4-dihydro-2H-pyrano[2,3-b]pyridin-4-yl]-2-(3,5-dimethyl-1H-pyrazol-4-yl)acetamide, (217) N-[(4R)-6-(4-chlorophenyl)-7-(2,4-dichlorophenyl)-2,2-dimethyl-3,4-dihydro-2H-pyrano[2,3-b]pyridin-4-yl]-1H-benzimidazole-5-carboxamide, (218) N-{(4R)-7-(4-bromo-2-chlorophenyl)-2,2-dimethyl-6-[4-(trifluoromethyl)phenyl]-3,4-dihydro-2H-pyrano[2,3-b]pyridin-4-yl}acetamide, (219) N-{(4R)-7-(4-bromo-2-chlorophenyl)-2,2-dimethyl-6-[4-(trifluoromethyl)phenyl]-3,4-dihydro-2H-pyrano[2,3-b]pyridin-4-yl}-3,3,3-trifluoro-2-hydroxypropanamide, (220) N-{(4R)-7-(2,4-dichlorophenyl)-2,2-dimethyl-6-[4-(trifluoromethoxy)phenyl]-3,4-dihydro-2H-pyrano[2,3-b]pyridin-4-yl}-2,2-difluoro-3-hydroxypropanamide, (221) N-{(4R)-7-(2,4-dichlorophenyl)-2,2-dimethyl-6-[4-(trifluoromethoxy)phenyl]-3,4-dihydro-2H-pyrano[2,3-b]pyridin-4-yl}-3,3,3-trifluoro-2-hydroxy-2-(trifluoromethyl)propanamide, (222) N-{(4R)-7-(2,4-dichlorophenyl)-2,2-dimethyl-6-[4-(trifluoromethoxy)phenyl]-3,4-dihydro-2H-pyrano[2,3-b]pyridin-4-yl}-4,4,4-trifluoro-3-hydroxybutanamide, (223) N-{(4R)-6-(4-chlorophenyl)-7-[2-chloro-5-(trifluoromethoxy)phenyl]-2,2-dimethyl-3,4-dihydro-2H-pyrano[2,3-b]pyridin-4-yl}-4,4,4-trifluoro-3-hydroxybutanamide, (224) N-{(4R)-7-(2,4-dichlorophenyl)-2,2-dimethyl-6-[4-(trifluoromethoxy)phenyl]-3,4-dihydro-2H-pyrano[2,3-b]pyridin-4-yl}-4,4,4-trifluoro-3-hydroxy-3-(trifluoromethyl)butanamide, (225) N-{(4R)-7-(2,4-dichlorophenyl)-2,2-dimethyl-6-[4-(trifluoromethoxy)phenyl]-3,4-dihydro-2H-pyrano[2,3-b]pyridin-4-yl}-5-methyl-1H-pyrazole-3-carboxamide, (226) (2S)-N-{(4R)-7-(2,4-dichlorophenyl)-2,2-dimethyl-6-[4-(2,2,2-trifluoroethoxy)phenyl]-3,4-dihydro-2H-pyrano[2,3-b]pyridin-4-yl}-3,3,3-trifluoro-2-hydroxypropanamide, (227) N-[(4R)-7-(4-bromo-2-chlorophenyl)-6-(4-chlorophenyl)-2,2-dimethyl-3,4-dihydro-2H-pyrano[2,3-b]pyridin-4-yl]acetamide, (228) N-[(4R)-7-(4-bromo-2-chlorophenyl)-6-(4-chlorophenyl)-2,2-dimethyl-3,4-dihydro-2H-pyrano[2,3-b]pyridin-4-yl]-5-methyl-1H-pyrazole-3-carboxamide, (229) N-[(4R)-7-(2-chloro-4-cyanophenyl)-6-(4-chlorophenyl)-2,2-dimethyl-3,4-dihydro-2H-pyrano[2,3-b]pyridin-4-yl]-5-methyl-1H-pyrazole-3-carboxamide, (230) N-[(4R)-7-(2-chloro-4-cyanophenyl)-6-(4-chlorophenyl)-2,2-dimethyl-3,4-dihydro-2H-pyrano[2,3-b]pyridin-4-yl]-4-methyl-1H-pyrazole-3-carboxamide, (231) (2S)-N-{(4R)-6-(4-chlorophenyl)-7-[2-chloro-4-(2,2,2-trifluoroethoxy)phenyl]-2,2-dimethyl-3,4-dihydro-2H-pyrano[2,3-b]pyridin-4-yl}-3,3,3-trifluoro-2-hydroxypropanamide, (232) N-{(4R)-6-(4-chlorophenyl)-7-[2-chloro-4-(2,2,2-trifluoroethoxy)phenyl]-2,2-dimethyl-3,4-dihydro-2H-pyrano[2,3-b]pyridin-4-yl}-2,2-difluoro-3-hydroxypropanamide, (233) N-{(4R)-6-(4-chlorophenyl)-7-[2-chloro-4-(2,2,2-trifluoroethoxy)phenyl]-2,2-dimethyl-3,4-dihydro-2H-pyrano[2,3-b]pyridin-4-yl}-4,4,4-trifluoro-3-hydroxybutanamide, (234) N-[(4R)-7-(2-chlorophenyl)-6-(4-chlorophenyl)-2,2-dimethyl-3,4-dihydro-2H-pyrano[2,3-b]pyridin-4-yl]-3-methyl-1H-pyrazole-5-carboxamide, (235) N-[(4R)-7-(2-chlorophenyl)-6-(4-chlorophenyl)-2,2-dimethyl-3,4-dihydro-2H-pyrano[2,3-b]pyridin-4-yl]-4-methyl-1H-pyrazole-5-carboxamide, (236) N-[(4R)-7-(2-chlorophenyl)-6-(4-chlorophenyl)-2,2-dimethyl-3,4-dihydro-2H-pyrano[2,3-b]pyridin-4-yl]-1H-indazole-5-carboxamide, (237) (2S)-N-[(4R)-7-[2-chloro-4-(1,3,4-oxadiazol-2-yl)phenyl]-6-(4-chlorophenyl)-2,2-dimethyl-3,4-dihydro-2H-pyrano[2,3-b]pyridin-4-yl]-3,3,3-trifluoro-2-hydroxypropanamide, (238) (2S)-N-{(4R)-6-(4-chlorophenyl)-7-[2-chloro-4-(1H-pyrazol-1-yl)phenyl]-2,2-dimethyl-3,4-dihydro-2H-pyrano[2,3-b]pyridin-4-yl}-3,3,3-trifluoro-2-hydroxypropanamide, (239) N-{(4R)-6-(4-chlorophenyl)-7-[2-chloro-4-(1H-pyrazol-4-yl)phenyl]-2,2-dimethyl-3,4-dihydro-2H-pyrano[2,3-b]pyridin-4-yl}benzamide, (240) N-[(4R)-7-[2-chloro-4-(1,2,4-oxadiazol-3-yl)phenyl]-6-(4-chlorophenyl)-2,2-dimethyl-3,4-dihydro-2H-pyrano[2,3-b]pyridin-4-yl]-2,2-difluoro-3-hydroxypropanamide, (241) ethyl [(4R)-7-[2-chloro-4-(1,3,4-oxadiazol-2-yl)phenyl]-6-(4-chlorophenyl)-2,2-dimethyl-3,4-dihydro-2H-pyrano[2,3-b]pyridin-4-yl]carbamate, (242) (2S)-N-[(4R)-7-[2-chloro-4-(5-methyl-2-thienyl)phenyl]-6-(4-chlorophenyl)-2,2-dimethyl-3,4-dihydro-2H-pyrano[2,3-b]pyridin-4-yl]-3,3,3-trifluoro-2-hydroxypropanamide, (243) (2S)-N-{(4R)-6-(4-chlorophenyl)-7-[2-chloro-4-(3-thienyl)phenyl]-2,2-dimethyl-3,4-dihydro-2H-pyrano[2,3-b]pyridin-4-yl}-3,3,3-trifluoro-2-hydroxypropanamide, (244) (2S)-N-[(4R)-7-[2-chloro-4-(1-methyl-1H-pyrazol-4-yl)phenyl]-6-(4-chlorophenyl)-2,2-dimethyl-3,4-dihydro-2H-pyrano[2,3-b]pyridin-4-yl]-3,3,3-trifluoro-2-hydroxypropanamide, (245) N-[(4R)-7-[2-chloro-4-(1-methyl-1H-pyrazol-4-yl)phenyl]-6-(4-chlorophenyl)-2,2-dimethyl-3,4-dihydro-2H-pyrano[2,3-b]pyridin-4-yl]-5-methyl-1H-pyrazole-3-carboxamide, (246) (2S)-N-{(4R)-6-(4-chlorophenyl)-7-[2-chloro-4-(1H-pyrazol-4-yl)phenyl]-2,2-dimethyl-3,4-dihydro-2H-pyrano[2,3-b]pyridin-4-yl}-3,3,3-trifluoro-2-hydroxypropanamide, (247) N-{(4R)-6-(4-chlorophenyl)-7-[2-chloro-4-(1H-pyrazol-4-yl)phenyl]-2,2-dimethyl-3,4-dihydro-2H-pyrano[2,3-b]pyridin-4-yl}-3-fluorobenzamide, (248) N-{(4R)-6-(4-chlorophenyl)-7-[2-chloro-4-(1H-pyrazol-4-yl)phenyl]-2,2-dimethyl-3,4-dihydro-2H-pyrano[2,3-b]pyridin-4-yl}-4-fluorobenzamide, (249) N-{(4R)-6-(4-chlorophenyl)-7-[2-chloro-4-(1H-pyrazol-4-yl)phenyl]-2,2-dimethyl-3,4-dihydro-2H-pyrano[2,3-b]pyridin-4-yl}tetrahydro-2H-pyran-4-carboxamide, (250) N-{(4R)-6-(4-chlorophenyl)-7-[2-chloro-4-(1H-pyrazol-4-yl)phenyl]-2,2-dimethyl-3,4-dihydro-2H-pyrano[2,3-b]pyridin-4-yl}-4-methyl-1H-pyrazole-3-carboxamide, (251) N-{(4R)-6-(4-chlorophenyl)-7-[2-chloro-4-(1H-pyrazol-4-yl)phenyl]-2,2-dimethyl-3,4-dihydro-2H-pyrano[2,3-b]pyridin-4-yl}-5-methyl-1H-pyrazole-3-carboxamide, (252) N-{(4R)-6-(4-chlorophenyl)-7-[2-chloro-4-(1H-pyrazol-3-yl)phenyl]-2,2-dimethyl-3,4-dihydro-2H-pyrano[2,3-b]pyridin-4-yl}-3-fluorobenzamide, (253) (2S)-N-[(4R)-7-[2-chloro-4-(2-furyl)phenyl]-6-(4-chlorophenyl)-2,2-dimethyl-3,4-dihydro-2H-pyrano[2,3-b]pyridin-4-yl]-3,3,3-trifluoro-2-hydroxypropanamide, (254) N-[(4R)-7-[2-chloro-4-(3-furyl)phenyl]-6-(4-chlorophenyl)-2,2-dimethyl-3,4-dihydro-2H-pyrano[2,3-b]pyridin-4-yl]-5-methyl-1H-pyrazole-3-carboxamide, (255) N-[(4R)-7-[2-chloro-4-(1,3-oxazol-2-yl)phenyl]-6-(4-chlorophenyl)-2,2-dimethyl-3,4-dihydro-2H-pyrano[2,3-b]pyridin-4-yl]-5-methyl-1H-pyrazole-3-carboxamide, (256) (2S)-N-{(4R)-6-(4-chlorophenyl)-7-[2-chloro-5-(trifluoromethoxy)phenyl]-2,2-dimethyl-3,4-dihydro-2H-pyrano[2,3-b]pyridin-4-yl}-3,3,3-trifluoro-2-hydroxypropanamide, (257) N-{(4R)-6-(4-chlorophenyl)-7-[2-chloro-5-(trifluoromethoxy)phenyl]-2,2-dimethyl-3,4-dihydro-2H-pyrano[2,3-b]pyridin-4-yl}-4,4,4-trifluoro-3-hydroxybutanamide, (258) N-{(4R)-6-(4-chlorophenyl)-7-[2-chloro-5-(trifluoromethoxy)phenyl]-2,2-dimethyl-3,4-dihydro-2H-pyrano[2,3-b]pyridin-4-yl}-2,2-difluoro-3-hydroxypropanamide, (259) N-{(4R)-6-(4-chlorophenyl)-7-[2-chloro-5-(trifluoromethoxy)phenyl]-2,2-dimethyl-3,4-dihydro-2H-pyrano[2,3-b]pyridin-4-yl}-5-methyl-1H-pyrazole-3-carboxamide, (260) (4R)-6-(4-chlorophenyl)-7-(2,4-dichlorophenyl)-2,2-dimethyl-N-phenyl-3,4-dihydro-2H-pyrano[2,3-b]pyridin-4-amine, (261) (4R)-6-(4-chlorophenyl)-7-(2,4-dichlorophenyl)-N-[1-(4-methoxybenzyl)-1H-indazol-6-yl]-2,2-dimethyl-3,4-dihydro-2H-pyrano[2,3-b]pyridin-4-amine, (262) (4R)-6-(4-chlorophenyl)-7-(2,4-dichlorophenyl)-N-1H-indazol-6-yl-2,2-dimethyl-3,4-dihydro-2H-pyrano[2,3-b]pyridin-4-amine, (263) (4R)-6-(4-chlorophenyl)-7-(2,4-dichlorophenyl)-N-(3-methoxypyridin-2-yl)-2,2-dimethyl-3,4-dihydro-2H-pyrano[2,3-b]pyridin-4-amine, (264) (4R)-6-(4-chlorophenyl)-7-(2,4-dichlorophenyl)-2,2-dimethyl-N-(3-methylpyridin-2-yl)-3,4-dihydro-2H-pyrano[2,3-b]pyridin-4-amine, (265) (4R)-6-(4-chlorophenyl)-7-(2,4-dichlorophenyl)-N-(6-methoxypyridin-2-yl)-2,2-dimethyl-3,4-dihydro-2H-pyrano[2,3-b]pyridin-4-amine, (266) 6'-(4-chloro-3-methoxyphenyl)-7'-(2-chlorophenyl)-N-methyl-3',4'-dihydrospiro[cyclohexane-1,2'-pyrano[2,3-b]pyridin]-4'-amine, (267) N-[6'-(4-chloro-3-methoxyphenyl)-7'-(2-chlorophenyl)-3',4'-dihydrospiro[cyclohexane-1,2'-pyrano[2,3-b]pyridin]-4'-yl]-2-hydroxy-N-methylacetamide, (268) N-[6'-(4-chloro-3-methoxyphenyl)-7'-(2-chlorophenyl)-3',4'-dihydrospiro[cyclohexane-1,2'-pyrano[2,3-b]pyridin]-4'-yl]-N,2,2-trimethylpropanamide (269) N-[6'-(4-chloro-3-methoxyphenyl)-7'-(2-chlorophenyl)-3',4'-dihydrospiro[cyclohexane-1,2'-pyrano[2,3-b]pyridin]-4'-yl]-2-hydroxyacetamide, (270) N-[6'-(4-chloro-3-methoxyphenyl)-7'-(2-chlorophenyl)-3',4'-dihydrospiro[cyclohexane-1,2'-pyrano[2,3-b]pyridin]-4'-yl]-2-hydroxy-2-methylpropanamide, (271) 6'-(4-bromophenyl)-7'-(2-chlorophenyl)-3',4'-dihydrospiro[cyclohexane-1,2'-pyrano[2,3-b]pyridin]-4'-amine, (272) N-[6'-(4-bromophenyl)-7'-(2-chlorophenyl)-3',4'-dihydrospiro[cyclohexane-1,2'-pyrano[2,3-b]pyridin]-4'-yl]-2-hydroxy-2-methylpropanamide, (273) N-[6'-(4-bromophenyl)-7'-(2-chlorophenyl)-3',4'-dihydrospiro[cyclohexane-1,2'-pyrano[2,3-b]pyridin]-4'-yl]-2-hydroxy-2-methylpropanamide, (274) N-[7'-(2-chlorophenyl)-6'-(4-cyanophenyl)-3',4'-dihydrospiro[cyclohexane-1,2'-pyrano[2,3-b]pyridin]-4'-yl]-2-hydroxy-2-methylpropanamide, (275) N-[7'-(2-bromophenyl)-6'-(4-chlorophenyl)-3',4'-dihydrospiro[cyclohexane-1,2'-pyrano[2,3-b]pyridin]-4'-yl]-2-hydroxy-2-methylpropanamide, (276) N-[6'-(4-chlorophenyl)-7'-(2-cyanophenyl)-3',4'-dihydrospiro[cyclohexane-1,2'-pyrano[2,3-b]pyridin]-4'-yl]-2-hydroxy-2-methylpropanamide, (277) N-[(4'R)-7'-(4-bromo-2-chlorophenyl)-6'-(4-chlorophenyl)-4,4-difluoro-3',4'-dihydrospiro[cyclohexane-1,2'-pyrano[2,3-b]pyridin]-4'-yl]-5-methyl-1H-pyrazole-3-carboxamide, (278) N-[(4'R)-7'-(2-chlorophenyl)-6'-(4-chlorophenyl)-4,4-difluoro-3',4'-dihydrospiro[cyclohexane-1,2'-pyrano[2,3-b]pyridin]-4'-yl]-5-methyl-1H-pyrazole-3-carboxamide, and (279) N-[(4'R)-7'-(4-bromo-2-chlorophenyl)-6'-(4-chlorophenyl)-4,4-difluoro-3',4'-dihydrospiro[cyclohexane-1,2'-pyrano[2,3-b]pyridin]-4'-yl]acetamide, or a pharmaceutically acceptable salt thereof.

4. The compound according to claim 1 of structural formula ID:

ID

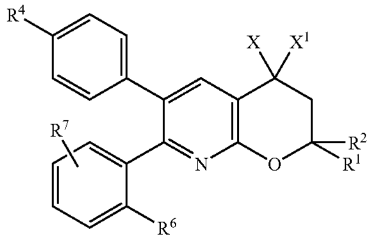

or a pharmaceutically acceptable salt thereof, wherein:

X is selected from:

(1) —$C_{1-6}$alkyl, unsubstituted or substituted with one, two or three substituents independently selected from $R^a$, (2) aryl-, unsubstituted or substituted with one, two or three substituents independently selected from $R^b$, (3) cycloalkyl, unsubstituted or substituted with one, two or three substituents independently selected from $R^b$, (4) heteroaryl-, unsubstituted or substituted with one, two, or three substituents independently selected from $R^b$, (5) heterocycloalkyl-, unsubstituted or substituted with one, two or three substituents independently selected from $R^b$, (6) heteroaryl-$C_{1-3}$alkyl, unsubstituted or substituted on heteroaryl with one, two, or three substituents independently selected from $R^b$, (7) —$CO_2R^d$, (8) —CO—$NR^cR^d$, (9) —$OR^d$,

(10) —O—C(O)$R^d$,

(11) —$NR^cR^d$,

(12) —$NR^c$C(═O)$R^d$,

(13) —$NR^c$C(═O)$OR^d$,

(14) —$NR^c$C(═O)—C(═O)$NR^cR^d$, and

(15) —NH—$SO_2$—$R^f$, $X^1$ is selected from hydrogen, halogen and $C_{1-6}$alkyl, or together X and $X^1$ form ═O, ═$NR^g$, or ═CH—C(O)—O—$R^d$;

$R^1$ selected from:

(1) hydrogen, (2) $C_{1-6}$alkyl, unsubstituted or substituted with hydroxy, fluoro, or methylsulfonylmethyl, (3) bicyclo[2.2.1]hept-5-en-2-yl, (4) cycloheteroalkyl, (5) cycloheteroalkyl-$C_{1-4}$alkyl, and (6) phenyl, unsubstituted or substituted with fluoro;

$R^2$ is selected from:

(1) $C_{1-6}$alkyl, unsubstituted or substituted with hydroxy, fluoro, or methylsulfonyl, (2) bicyclo[2.2.1]hept-5-en-2-yl, (3) cycloheteroalkyl, (4) cycloheteroalkyl-$C_{1-4}$alkyl, and (5) phenyl, unsubstituted or substituted with fluoro;

or $R^1$ and $R^2$ together with the carbon to which they are attached form a carbonyl group (C═O) or a spiroannulated ring system selected from;

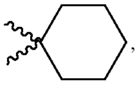, 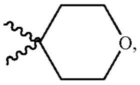, 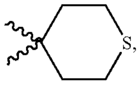,

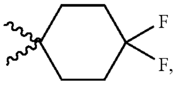, 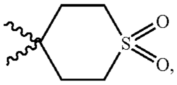, 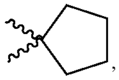, and

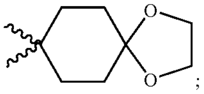;

$R^4$ is selected from:

(1) halo-, (2) —CN, (3) $C_{1-3}$alkyl-, unsubstituted or substituted with one, two or three $R^h$ substitutents, (4) —$CF_3$, (5) —$OR^d$, and (6) —$OCF_3$;

$R^6$ is selected from:

(1) —F, (2) —Cl, (3) —Br, (4) —I, (5) —CN, (6) —$CH_3$, (7) —$CF_3$, (8) oxadiazolyl, unsubstituted or substituted with one or two $R^h$ substitutents, (9) pyrazolyl,

(10) thienyl,

(11) furyl,

(12) oxazolyl,

(13) —OH,

(14) —$OCH_3$,

(15) —$OCF_3$,

(16) —$OCH_2CF_3$, and

(17) —$CO_2CH_3$, $R^7$ is selected from:

(1) —H, (2) —F, (3) —Cl, (4) —Br, (5) —I, (6) —CN, (7) —$CH_3$, (8) —$CF_3$, (9) oxadiazolyl, unsubstituted or substituted with one or two $R^h$ substitutents,

(10) pyrazolyl,

(11) thienyl,
(12) furyl,
(13) oxazolyl,
(14) —OH,
(15) —$OCH_3$,
(16) —$OCF_3$,
(17) —$OCH_2CF_3$, and
(18) —$CO_2CH_3$, each $R^a$ is independently selected from:
(1) —OH,
(2) —$OCH_3$,
(3) halogen,
(4) —SH,
(5) —$SO_2R^d$,
(6) —$NH_2$,
(7) —CN,
(8) —$CO_2R^d$,
(9) —C(O)$NR^cR^d$,
(10) —$CF_3$, and
(11) —$OCF_3$;

each $R^b$ is independently selected from:
(1) —$R^a$,
(2) oxo,
(3) $C_{1-10}$alkyl,
(4) $C_{2-10}$alkenyl,
(5) cycloalkyl,
(6) cycloalkyl-$C_{1-10}$ alkyl,
(7) cycloheteroalkyl,
(8) cycloheteroalkyl-$C_{1-10}$alkyl,
(9) aryl,
(10) heteroaryl,
(11) aryl-$C_{1-10}$alkyl, and
(12) heteroaryl-$C_{1-10}$ alkyl, wherein alkyl and alkenyl moieties are unsubstituted or substituted with one, two, three or four $R^k$ substituents, and cycloalkyl, cycloheteroalkyl, aryl and heteroaryl moieties are unsubstituted or substituted with one, two or three $R^k$ substituents;

$R^c$ and $R^d$ are each independently selected from:
(1) hydrogen,
(2) $C_{1-10}$alkyl,
(3) $C_{2-10}$ alkenyl,
(4) cycloalkyl,
(5) cycloalkyl-$C_{1-10}$ alkyl-,
(6) cycloheteroalkyl,
(7) cycloheteroalkyl-$C_{1-10}$ alkyl-,
(8) aryl,
(9) heteroaryl,
(10) aryl-$C_{1-10}$alkyl-, and
(11) heteroaryl-$C_{1-10}$alkyl-, wherein each $R^c$ and $R^d$ moiety, other than hydrogen, may be unsubstituted or substituted with one to three substituents selected from $R^h$;

each $R^f$ is independently selected from:
(1) halogen,
(2) $C_{1-6}$alkyl, unsubstituted or substituted with one or two $R^i$ substituents, and
(3) —$N(CH_3)_2$;

each $R^g$ is independently selected from: hydrogen, —OH, and methyl;

each $R^h$ is independently selected from:
(1) halogen,
(2) $C_{1-6}$alkyl,
(3) 4-methylbenzyl-,
(4) —OH,
(5) —O—$C_{1-4}$alkyl,
(6) benzyloxy-,
(7) -oxo,
(8) —OC(O)—$C_{1-6}$alkyl,
(9) —C(O)O—$C_{1-6}$alkyl,
(10) —S—$C_{1-4}$alkyl,
(11) —$NH_2$,
(12) —$NH(CH_3)$,
(13) —$N(CH_3)_2$,
(14) —$NO_2$,
(15) —CN,
(16) —$CF_3$, and
(17) —$OCF_3$, wherein alkyl may be unsubstituted or substituted with one, two or three substituents selected from $R^i$;

each $R^i$ is independently selected from: halogen, —O—$C_{1-4}$ alkyl, —OH, —S—$C_{1-4}$alkyl, —CN, —$CF_3$, and —$OCF_3$;

each $R^k$ is independently selected from: halogen, oxo, amino, hydroxy, $C_{1-4}$alkyl, —O—$C_{1-4}$alkyl, —S—$C_{1-4}$ alkyl, —CN, —$CF_3$, and —$OCF_3$.

5. The compound according to claim 4, wherein:

X is selected from:
(1) methyl, ethyl, isopropyl or t-butyl, substituted with one, two or three substituents independently selected from $R^a$,
(2) phenyl-, unsubstituted or substituted with one, two or three substituents independently selected from $R^b$,
(3) heteroaryl-, unsubstituted or substituted with one, two, or three substituents independently selected from $R^b$,
(4) heterocycloalkyl-, unsubstituted or substituted with one, two or three substituents independently selected from $R^b$,
(5) heteroaryl-methyl-, unsubstituted or substituted on heteroaryl with one, two, or three substituents independently selected from $R^b$,
(6) —$CO_2R^d$,
(7) —CO—$NR^cR^d$,
(8) —$OR^d$,
(9) —O—C(O)$R^d$,
(10) —$NR^cR^d$,
(11) —$NR^c$C(=O)$R^d$,
(12) —NHC(=O)$OR^d$,
(13) —NHC(=O)—C(=O)$NHR^d$, and
(14) —NH—$SO_2$—$R^f$, $X^1$ is hydrogen, or X and $X^1$ together form =O, =N—OH, or =CH—C(O)—O—$CH_2CH_3$;

$R^1$ is selected from:
(1) hydrogen,
(2) $C_{1-6}$alkyl, unsubstituted or substituted with hydroxy, fluoro, or methylsulfonylmethyl,
(3) bicyclo[2.2.1]hept-5-en-2-yl,
(4) cycloheteroalkyl,
(5) cycloheteroalkyl-$C_{1-4}$alkyl, and
(6) phenyl, unsubstituted or substituted with fluoro;

$R^2$ is selected from:
(1) $C_{1-6}$alkyl, unsubstituted or substituted with hydroxy, fluoro, or methylsulfonyl,
(2) bicyclo[2.2.1]hept-5-en-2-yl,
(3) cycloheteroalkyl,
(4) cycloheteroalkyl-$C_{1-4}$alkyl, and
(5) phenyl, unsubstituted or substituted with fluoro;

or $R^1$ and $R^2$ together with the carbon to which they are attached form a carbonyl group (C=O) or a spiroannulated ring system selected from:

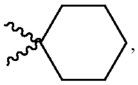, 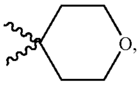 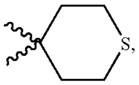
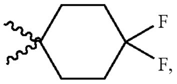 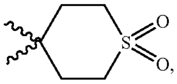 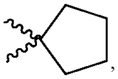, and
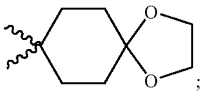;

$R^4$ is selected from:
(1) halo-,
(2) —CN,
(3) —$CH_3$,
(4) —$CF_3$,
(5) —$OCH_3$,
(6) —$OCH_2CF_3$, and
(7) —$OCF_3$;

$R^6$ is selected from:
(1) —Cl,
(2) —Br,
(3) —CN,
(4) —$CH_3$,
(5) —$CF_3$, and
(6) 1,2,4-oxadiazolyl;

$R^7$ is selected from:
(1) —F,
(2) —Ci,
(3) —Br,
(4) —I,
(5) —CN,
(6) —$CH_3$,
(7) —$CF_3$,
(8) oxadiazolyl, unsubstituted or substituted with one or two $R^h$ substitutents,
(9) pyrazolyl,
(10) thienyl,
(11) furyl,
(12) oxazolyl,
(13) —OH,
(14) —$OCH_3$,
(15) —$OCF_3$,
(16) —$OCH_2CF_3$, and
(17) —$CO_2CH_3$;

each $R^a$ is independently selected from:
(1) —OH,
(2) —F,
(3) —$SO_2CH_3$,
(4) —$CO_2$—$C_{1-16}$alkyl, and
(5) —$CF_3$;

each $R^b$ is independently selected from:
(1) —OH,
(2) —$OCH_3$,
(3) halogen,
(4) —$N(CH_3)_2$,
(5) —CH(O)
(6) —$C(O)R^d$,
(7) —$CO_2CH_3$,
(8) —$CO_2CH_2C_6H_5$,
(9) —CN,
(10) —$CF_3$,
(11) —$OCF_3$,
(12) oxo,
(13) $C_{1-3}$alkyl,
(14) $C_{2-3}$ alkenyl,
(15) cyclopropyl,
(16) oxadiazolyl,
(17) pyrazolyl,
(18) tetrazolyl, and
(19) phenyl, wherein alkyl and alkenyl moieties are unsubstituted or substituted with one, two, or three $R^k$ substituents, and cycloalkyl, cycloheteroalkyl, aryl and heteroaryl moieties are unsubstituted or substituted with one, two or three $R^k$ substituents;

each $R^c$ is independently selected from:
(1) hydrogen, and
(2) methyl;

each $R^d$ is independently selected from:
(1) hydrogen,
(2) $C_{1-6}$alkyl,
(3) $C_{2-6}$alkenyl,
(4) cycloalkyl,
(5) cycloalkyl-$C_{1-10}$ alkyl-,
(6) cycloheteroalkyl,
(7) cycloheteroalkyl-$C_{1-10}$ alkyl-,
(8) aryl,
(9) heteroaryl,
(10) aryl-$C_{1-3}$alkyl-, and
(11) heteroaryl-$C_{1-3}$alkyl-, wherein each $R^d$ moiety, other than hydrogen, may be unsubstituted or substituted with one, two or three substituents selected from $R^h$;

each $R^f$ is independently selected from:
(1) chloro,
(2) ethyl,
(3) n-propyl,
(4) chloropropyl, and
(5) —$N(CH_3)_2$;

$R^g$, $R^h$, $R^i$ and $R^k$ are as defined in claim 1,
or a pharmaceutically acceptable salt thereof.

6. The compound according to claim 5, of structural formula ID-1:

ID-1

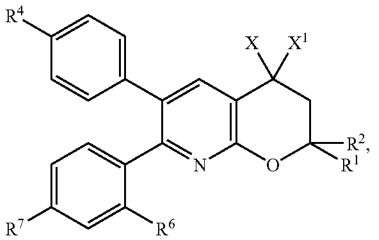

wherein X, $X^1$, $R^1$, $R^2$, $R^4$, $R^6$ and $R^7$ are as defined in claim 5, or a pharmaceutically acceptable salt thereof.

7. The compound according to claim 6, wherein:
$R^1$ and $R^2$ are each methyl or together form:

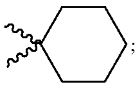;

$R^4$ is chloro,
$R^6$ is chloro,
$R^7$ is hydrogen or chloro,
and X and $X^1$ are as according to claim 6,
or a pharmaceutically acceptable salt thereof.

8. The compound according to claim 7, wherein:

X is selected from:

(1) oxadiazolyl, unsubstituted or substituted on a carbon atom with methyl, (2) piperidinyl, unsubstituted or substituted on carbon with oxo, (3) oxadiazolyl-methyl-, unsubstituted or substituted on an oxadiazolyl carbon atom with methyl or oxo, (4) —NH-pyridyl, (5) —NH(pyrazolyl), wherein the pyrazole is unsubstituted or substituted on a carbon atom with methyl, (6) —NH—C(O)—$CH_2$—OH, (7) —NH—C(O)—$CH(CH_3)$—OH, (8) —NH—C(O)—$C(CH_3)_2$—OH, (9) —NH—C(O)—$N(CH_3)_2$,

(10) isoxazolyl-carboxamide,

(11) pyrazolylcarboxamide, wherein the pyrazole is unsubstituted or substituted on a carbon atom with methyl,

(12) triazolyl-carboxamide, wherein the triazole is unsubstituted or substituted on a carbon atom with methyl,

(13) imidazolyl-carboxamide,

(14) cyclopropylcarboxamide, wherein the cyclopropyl group is unsubstituted or substituted with hydroxy,

(15) —NH—C(O)—C(O)—$NH(CH_3)$, and $X^1$ is hydrogen, or

X and $X^1$ together form ═O;

or a pharmaceutically acceptable salt thereof.

9. The compound according to claim 4, selected from:

(1) 7'-(2-chlorophenyl)-6'-(4-chlorophenyl)spiro[cyclohexane-1,2'-pyrano[2,3-b]pyridin]-4'(3'H)-one;

(2) 2-tert-butyl-7-(2-chlorophenyl)-6-(4-chlorophenyl)-2,3-dihydro-4H-pyrano[2,3-b]pyridin-4-one;

(3) N-[7'-(2-chlorophenyl)-6'-(4-chlorophenyl)-3',4'-dihydrospiro[cyclohexane-1,2'-pyrano[2,3-b]pyridin]-4'-yl]-2-hydroxyacetamide;

(4) N-[7'-(2-chlorophenyl)-6'-(4-chlorophenyl)-3',4'-dihydrospiro[cyclohexane-1,2'-pyrano[2,3-b]pyridin]-4'-yl]isoxazole-5-carboxamide;

(5) N-[7'-(2-chlorophenyl)-6'-(4-chlorophenyl)-3',4'-dihydrospiro[cyclohexane-1,2'-pyrano[2,3-b]pyridin]-4'-yl]-2-hydroxy-2-methylpropanamide;

(6) N-[6-(4-chlorophenyl)-7-(2,4-dichlorophenyl)-2,2-dimethyl-3,4-dihydro-2H-pyrano[2,3-b]pyridin-4-yl]-2-hydroxyacetamide;

(7) (2S)-N-[6-(4-chlorophenyl)-7-(2,4-dichlorophenyl)-2,2-dimethyl-3,4-dihydro-2H-pyrano[2,3-b]pyridin-4-yl]-2-hydroxypropanamide;

(8) (2R)-N-[6-(4-chlorophenyl)-7-(2,4-dichlorophenyl)-2,2-dimethyl-3,4-dihydro-2H-pyrano[2,3-b]pyridin-4-yl]-2-hydroxypropanamide;

(9) N-[6-(4-chlorophenyl)-7-(2,4-dichlorophenyl)-2,2-dimethyl-3,4-dihydro-2H-pyrano[2,3-b]pyridin-4-yl]-2-hydroxy-2-methylpropanamide;

(10) N-[6-(4-chlorophenyl)-7-(2,4-dichlorophenyl)-2,2-dimethyl-3,4-dihydro-2H-pyrano[2,3-b]pyridin-4-yl]-N'-methylethanediamide;

(11) 6-(4-chlorophenyl)-7-(2,4-dichlorophenyl)-2,2-dimethyl-4-(5-methyl-1,3,4-oxadiazol-2-yl)-3,4-dihydro-2H-pyrano[2,3-b]pyridine;

(12) 5-{[6-(4-chlorophenyl)-7-(2,4-dichlorophenyl)-2,2-dimethyl-3,4-dihydro-2H-pyrano[2,3-b]pyridin-4-yl]methyl}-1,3,4-oxadiazol-2(3H)-one;

(13) 6-(4-chlorophenyl)-7-(2,4-dichlorophenyl)-2,2-dimethyl-N-pyridin-2-yl-3,4-dihydro-2H-pyrano[2,3-b]pyridin-4-amine;

(14) 6-(4-chlorophenyl)-7-(2,4-dichlorophenyl)-2,2-dimethyl-N-(5-methyl-1H-pyrazol-3-yl)-3,4-dihydro-2H-pyrano[2,3-b]pyridin-4-amine;

(15) 1-[6-(4-chlorophenyl)-7-(2,4-dichlorophenyl)-2,2-dimethyl-3,4-dihydro-2H-pyrano[2,3-b]pyridin-4-yl]piperidin-2-one;

(16) N-[6-(4-chlorophenyl)-7-(2,4-dichlorophenyl)-2,2-dimethyl-3,4-dihydro-2H-pyrano[2,3-b]pyridin-4-yl]-5-methyl-1H-pyrazole-3-carboxamide;

(17) N-[6-(4-chlorophenyl)-7-(2,4-dichlorophenyl)-2,2-dimethyl-3,4-dihydro-2H-pyrano[2,3-b]pyridin-4-yl]-3-methyl-1H-1,2,4-triazole-5-carboxamide;

(18) N-[6-(4-chlorophenyl)-7-(2,4-dichlorophenyl)-2,2-dimethyl-3,4-dihydro-2H-pyrano[2,3-b]pyridin-4-yl]-1H-imidazole-4-carboxamide;

(19) N-[6-(4-chlorophenyl)-7-(2,4-dichlorophenyl)-2,2-dimethyl-3,4-dihydro-2H-pyrano[2,3-b]pyridin-4-yl]-1-hydroxycyclopropanecarboxamide; and

(20) N'-[6-(4-chlorophenyl)-7-(2,4-dichlorophenyl)-2,2-dimethyl-3,4-dihydro-2H-pyrano[2,3-b]pyridin-4-yl]-N,N-dimethylurea;

or a pharmaceutically acceptable salt thereof.

10. A composition comprising a compound according to claim 1 and a pharmaceutically acceptable carrier.

11. A composition comprising a compound according to claim 9 and a pharmaceutically acceptable carrier.

12. The compound according to claim 1 which is: 7'-(2-chlorophenyl)-6'-(4-chlorophenyl)spiro[cyclohexane-1,2'-pyrano[2,3-b]pyridin]-4'(3'H)-one; or a pharmaceutically acceptable salt thereof.

13. The compound according to claim 1 which is: 2-tert-butyl-7-(2-chlorophenyl)-6-(4-chlorophenyl)-2,3-dihydro-4H-pyrano[2,3-b]pyridin-4-one; or a pharmaceutically acceptable salt thereof.

14. The compound according to claim 1 which is: N-[6-(4-chlorophenyl)-7-(2,4-dichlorophenyl)-2,2-dimethyl-3,4-dihydro-2H-pyrano[2,3-b]pyridin-4-yl]-N'-methylethanediamide; or a pharmaceutically acceptable salt thereof.

15. The compound according to claim 1 which is: N-[6-(4-chlorophenyl)-7-(2,4-dichlorophenyl)-2,2-dimethyl-3,4-dihydro-2H-pyrano[2,3-b]pyridin-4-yl]-5-methyl-1H-pyrazole-3-carboxamide; or a pharmaceutically acceptable salt thereof.

16. The compound according to claim 1 which is: N-[6-(4-chlorophenyl)-7-(2,4-dichlorophenyl)-2,2-dimethyl-3,4-dihydro-2H-pyrano[2,3-b]pyridin-4-yl]-3-methyl-1H-1,2,4-triazole-5-carboxamide; or a pharmaceutically acceptable salt thereof.

* * * * *